(12) United States Patent
Leumann et al.

(10) Patent No.: US 11,028,117 B2
(45) Date of Patent: Jun. 8, 2021

(54) BICYCLIC NUCLEOSIDES AND OLIGOMERS PREPARED THEREFROM

(71) Applicant: UNIVERSITÄT BERN, Bern (CH)

(72) Inventors: Christian Leumann, Bern (CH); Damien Evéquoz, Vétroz (CH)

(73) Assignee: UNIVERSITÄT BERN, Bern (CH)

( * ) Notice: Subject to any disclaimer, the term of this patent is extended or adjusted under 35 U.S.C. 154(b) by 0 days.

(21) Appl. No.: 16/465,127

(22) PCT Filed: Nov. 29, 2017

(86) PCT No.: PCT/EP2017/080769
§ 371 (c)(1),
(2) Date: May 29, 2019

(87) PCT Pub. No.: WO2018/099946
PCT Pub. Date: Jun. 7, 2018

(65) Prior Publication Data
US 2019/0345188 A1 Nov. 14, 2019

(30) Foreign Application Priority Data
Nov. 30, 2016 (EP) .................................. 16201350

(51) Int. Cl.
| | | |
|---|---|---|
| *C07H 19/048* | (2006.01) | |
| *C07D 405/04* | (2006.01) | |
| *C07D 473/18* | (2006.01) | |
| *C07H 21/00* | (2006.01) | |
| *C12N 15/113* | (2010.01) | |
| *C07D 473/34* | (2006.01) | |
| *C07F 7/18* | (2006.01) | |
| *C07F 9/6558* | (2006.01) | |
| *C07F 9/6561* | (2006.01) | |
| *C07H 19/16* | (2006.01) | |

(52) U.S. Cl.
CPC ......... *C07H 19/048* (2013.01); *C07D 405/04* (2013.01); *C07D 473/18* (2013.01); *C07D 473/34* (2013.01); *C07F 7/1804* (2013.01); *C07F 9/65586* (2013.01); *C07F 9/65616* (2013.01); *C07H 19/16* (2013.01); *C07H 21/00* (2013.01); *C12N 15/113* (2013.01); *C12N 2310/11* (2013.01); *C12N 2310/315* (2013.01); *C12N 2310/3231* (2013.01); *C12N 2320/33* (2013.01)

(58) Field of Classification Search
CPC .............. C12N 15/113; C12N 2310/11; C12N 2310/315; C12N 2310/3231; C12N 2320/33; C07H 19/048
See application file for complete search history.

(56) References Cited

U.S. PATENT DOCUMENTS 5,792,608 A 8/1998 Swaminathan et al.

FOREIGN PATENT DOCUMENTS

| WO | WO 2009/124295 A2 | 10/2009 | |
|---|---|---|---|
| WO | WO 2011/017521 A2 | 2/2011 | |
| WO | WO-2012170347 A1 * | 12/2012 | ............. C07H 21/00 |
| WO | WO 2014/140348 A1 | 9/2014 | |

OTHER PUBLICATIONS

Ravn et al. J Chem Soc Perkin Trans 1, 1855-1861 (Year: 2001).*
Dugovic et al. Beilstein J. Org. Chem. 10, 1840-1847 (Year: 2014).*
Ravn, Jacob et al., "Bicyclic nucleosides; stereoselective dihydroxylation and 2'-deoxygenation;" "(ESI available: 13C NMR spectra for compounds 7, 8 and 17 as well as 1 HNMR data spectra for compounds 5, 11 and 18." Organic & Biomolecular Chemistry, vol. 1, No. 5, Feb. 27, 2003.
International Search Report and Written Opinion received in PCT Application No. PCT/EP2017/080769, dated Apr. 3, 2018.

* cited by examiner

*Primary Examiner* — Brian Whiteman
(74) *Attorney, Agent, or Firm* — Knobbe Martens Olson & Bear LLP

(57) ABSTRACT

Oligomers can be prepared from bicyclic nucleosides. The nucleosides can be a compound of formula (I)

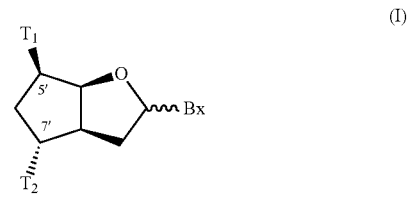

(I)

in which each of $T_1$ and $T_2$ is independently $OR_1$ or $OR_2$; $R_1$ is H or a hydroxyl protecting group, $R_2$ is a phosphorus moiety; and Bx is a nucleobase. The compounds, bicyclic nucleosides and oligomers are useful for the prevention, treatment or diagnosis of muscular dystrophy.

20 Claims, 6 Drawing Sheets
Specification includes a Sequence Listing.

SEQUENCE LISTING

```
<160> NUMBER OF SEQ ID NOS: 29

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: 7',5'-phosphodiester-linked beta anomeric
      thymine nucleotide with a bicyclic sugar  (the bicyclic sugar is
      depicted in formula (V))

<400> SEQUENCE: 1
ggatgttcnc ga                                                        12

<210> SEQ ID NO 2
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: 7',5'-phosphodiester-linked beta anomeric
      thymine nucleotide with a bicyclic sugar  (the bicyclic sugar is
      depicted in formula (V))

<400> SEQUENCE: 2
ggangttctc ga                                                        12

<210> SEQ ID NO 3
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: 7',5'-phosphodiester-linked beta anomeric
      thymine nucleotide with a bicyclic sugar  (the bicyclic sugar is
      depicted in formula (V))

<400> SEQUENCE: 3
ggatgnnctc ga                                                        12

<210> SEQ ID NO 4
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

<222> LOCATION: (8)..(8)
<223> OTHER INFORMATION: 7',5'-phosphodiester-linked beta anomeric
      5'-methylcytosine nucleotide with a bicyclic sugar (the bicyclic
      sugar is depicted in formula (V))

<400> SEQUENCE: 4
ggatgttntc ga                                                       12

<210> SEQ ID NO 5
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: 7',5'-phosphodiester-linked beta anomeric
      5-methylcytosine nucleotide with a bicyclic sugar (the bicyclic
      sugar is depicted in formula (V))

<400> SEQUENCE: 5
ggatgttctn ga                                                       12

<210> SEQ ID NO 6
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: 7',5'-phosphodiester-linked beta anomeric
      adenine nucleotide with a bicyclic sugar (the bicyclic sugar is
      depicted in formula (V))

<400> SEQUENCE: 6
ggntgttctc ga                                                       12

<210> SEQ ID NO 7
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: 7',5'-phosphodiester-linked beta anomeric
      guanine nucleotide with a bicyclic sugar (the bicyclic sugar is
      depicted in formula (V))

<400> SEQUENCE: 7
ggatnttctc ga                                                       12

<210> SEQ ID NO 8
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: 7',5'-phosphodiester-linked beta anomeric
      cytosine nucleotide with a bicyclic sugar (the bicyclic sugar is
      depicted in formula (V))

<400> SEQUENCE: 8
ggatgttntc ga                                                         12

<210> SEQ ID NO 9
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: 7',5'-phosphodiester-linked beta anomeric
      cytosine nucleotide with a bicyclic sugar  (the bicyclic sugar is
      depicted in formula (V))

<400> SEQUENCE: 9
ggatgttctn ga                                                         12

<210> SEQ ID NO 10
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: 7',5'-phosphodiester-linked beta anomeric
      cytosine nucleotide with a bicyclic sugar  (the bicyclic sugar is
      depicted in formula (V))
<220> FEATURE:
<221> NAME/KEY: misc_feature
<222> LOCATION: (10)..(10)
<223> OTHER INFORMATION: 7',5'-phosphodiester-linked beta anomeric
      cytosine nucleotide with a bicyclic sugar  (the bicyclic sugar is
      depicted in formula (V))

<400> SEQUENCE: 10
ggatgttntn ga                                                         12

<210> SEQ ID NO 11
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(8)
<223> OTHER INFORMATION: 7',5'-phosphodiester-linked beta anomeric
      thymine nucleotide with a bicyclic sugar  (the bicyclic sugar is
      depicted in formula (V))

<400> SEQUENCE: 11
gcannnnnac cg                                                         12

<210> SEQ ID NO 12
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 7',5'-phosphodiester-linked beta anomeric
      thymine nucleotide with a bicyclic sugar  (the bicyclic sugar is
      depicted in formula (V))
<220> FEATURE:
<221> NAME/KEY: misc_feature
<222> LOCATION: (5)..(5)
<223> OTHER INFORMATION: 7',5'-phosphodiester-linked beta anomeric 5-methylcytosine nucleotide with a bicyclic sugar (the bicyclic sugar is depicted in formula (V))
<220> FEATURE:
<221> NAME/KEY: misc_feature
<222> LOCATION: (6)..(6)
<223> OTHER INFORMATION: 7',5'-phosphodiester-linked beta anomeric thymine nucleotide with a bicyclic sugar (the bicyclic sugar is depicted in formula (V))
<220> FEATURE:
<221> NAME/KEY: misc_feature
<222> LOCATION: (7)..(8)
<223> OTHER INFORMATION: 7',5'-phosphodiester-linked beta anomeric 5-methylcytosine nucleotide with a bicyclic sugar (the bicyclic sugar is depicted in formula (V))
<220> FEATURE:
<221> NAME/KEY: misc_feature
<222> LOCATION: (9)..(9)
<223> OTHER INFORMATION: 7',5'-phosphodiester-linked beta anomeric thymine nucleotide with a bicyclic sugar (the bicyclic sugar is depicted in formula (V))

<400> SEQUENCE: 12 nnnnnnnnn                                                               9

<210> SEQ ID NO 13
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 7',5'-phosphodiester-linked beta anomeric guanine nucleotide with a bicyclic sugar (the bicyclic sugar is depicted in formula (V))
<220> FEATURE:
<221> NAME/KEY: misc_feature
<222> LOCATION: (3)..(3)
<223> OTHER INFORMATION: 7',5'-phosphodiester-linked beta anomeric adenine nucleotide with a bicyclic sugar (the bicyclic sugar is depicted in formula (V))
<220> FEATURE:
<221> NAME/KEY: misc_feature
<222> LOCATION: (4)..(4)
<223> OTHER INFORMATION: 7',5'-phosphodiester-linked beta anomeric thymine nucleotide with a bicyclic sugar (the bicyclic sugar is depicted in formula (V))
<220> FEATURE:
<221> NAME/KEY: misc_feature
<222> LOCATION: (5)..(5)
<223> OTHER INFORMATION: 7',5'-phosphodiester-linked beta anomeric guanine nucleotide with a bicyclic sugar (the bicyclic sugar is depicted in formula (V))
<220> FEATURE:
<221> NAME/KEY: misc_feature
<222> LOCATION: (6)..(7)
<223> OTHER INFORMATION: 7',5'-phosphodiester-linked beta anomeric thymine nucleotide with a bicyclic sugar (the bicyclic sugar is depicted in formula (V))
<220> FEATURE:
<221> NAME/KEY: misc_feature
<222> LOCATION: (8)..(8)
<223> OTHER INFORMATION: 7',5'-phosphodiester-linked beta anomeric 5-methylcytosine nucleotide with a bicyclic sugar (the bicyclic sugar is depicted in formula (V))
<220> FEATURE:
<221> NAME/KEY: misc_feature
<222> LOCATION: (9)..(9)
<223> OTHER INFORMATION: 7',5'-phosphodiester-linked beta anomeric thymine nucleotide with a bicyclic sugar (the bicyclic sugar is depicted in formula (V))
<220> FEATURE:
<221> NAME/KEY: misc_feature
<222> LOCATION: (10)..(10)
<223> OTHER INFORMATION: 7',5'-phosphodiester-linked beta anomeric 5-methylcytosine nucleotide with a bicyclic

```
      sugar  is depicted in formula (V))
<220> FEATURE:
<221> NAME/KEY: misc_feature
<222> LOCATION: (11)..(11)
<223> OTHER INFORMATION: 7',5'-phosphodiester-linked beta anomeric
      guanine nucleotide with a bicyclic sugar  (the bicyclic sugar  is
      depicted in formula (V))
<220> FEATURE:
<221> NAME/KEY: misc_feature
<222> LOCATION: (12)..(12)
<223> OTHER INFORMATION: 7',5'-phosphodiester-linked beta anomeric
      adenine nucleotide with a bicyclic sugar  (the bicyclic sugar  is
      depicted in formula (V))

<400> SEQUENCE: 13
nnnnnnnnnn nn                                                          12

<210> SEQ ID NO 14
<211> LENGTH: 12
<212> TYPE: DNA
<213> ORGANISM: Artificial Sequence
<220> FEATURE:
<223> OTHER INFORMATION: Sythetic Construct
<220> FEATURE:
<221> NAME/KEY: misc_feature
<222> LOCATION: (1)..(1)
<223> OTHER INFORMATION: 7',5'-phosphodiester-linked beta anomeric
      thymine nucleotide with a bicyclic sugar  (the bicyclic sugar  is
      depicted in formula (V))
<220> FEATURE:
<221> NAME/KEY: misc_feature
<222> LOCATION: (2)..(2)
<223> OTHER INFORMATION: 7',5'-phosphodiester-linked beta anomeric
      5-methylcytosine nucleotide with a bicyclic sugar  (the bicyclic
      sugar  is depicted in formula (V))
<220> FEATURE:
<221> NAME/KEY: misc_feature
<222> LOCATION: (3)..(3)
<223> OTHER INFORMATION: 7',5'-phosphodiester-linked beta anomeric
      guanine nucleotide with a bicyclic sugar  (the bicyclic sugar  is
      depicted in formula (V))
<220> FEATURE:
<221> NAME/KEY: misc_feature
<222> LOCATION: (4)..(4)
<223> OTHER INFORMATION: 7',5'-phosphodiester-linked beta anomeric
      adenine nucleotide with a bicyclic sugar  (the bicyclic sugar  is
      depicted in formula (V))
<220> FEATURE:
<221> NAME/KEY: misc_feature
<222> LOCATION: (5)..(5)
<223> OTHER INFORMATION: 7',5'-phosphodiester-linked beta anomeric
      guanine nucleotide with a bicyclic sugar  (the bicyclic sugar  is
      depicted in formula (V))
<220> FEATURE:
<221> NAME/KEY: misc_feature
<222> LOCATION: (6)..(7)
<223> OTHER INFORMATION: 7',5'-phosphodiester-linked beta anomeric
      adenine nucleotide with a bicyclic sugar  (the bicyclic sugar  is
      depicted in formula (V))
<220> FEATURE:
<221> NAME/KEY: misc_feature
<222> LOCATION: (8)..(8)
<223> OTHER INFORMATION: 7',5'-phosphodiester-linked beta anomeric
      5'-methylcytosine nucleotide with a bicyclic sugar  (the bicyclic
      sugar  is depicted in formula (V))
<220> FEATURE:
<221> NAME/KEY: misc_feature
<222> LOCATION: (9)..(9)
<223> OTHER INFORMATION: 7',5'-phosphodiester-linked beta anomeric
      adenine nucleotide with a bicyclic sugar  (the bicyclic sugar  is
      depicted in formula (V))
<220> FEATURE:
<221> NAME/KEY: misc_feature
<222> LOCATION: (10)..(10)
<223> OTHER INFORMATION: 7',5'-phosphodiester-linked beta anomeric
      thymine nucleotide with a bicyclic sugar  (the bicyclic sugar  is
      depicted in formula (V))
```

```
<220> FEATURE:
<221> NAME/KEY: misc_feature
<222> LOCATION: (11)..(12)
<223> OTHER INFORMATION: 7',5'-phosphodiester-linked beta anomeric
      5-methylcytosine nucleotide with a bicyclic sugar  (the bicyclic
      sugar  is depicted in formula (V))

<400> SEQUENCE: 14
nnnnnnnnnn nn                                                           12

<210> SEQ ID NO 15
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 7',5'-phosphodiester-linked beta anomeric
      5-methylcytosine nucleotide with a bicyclic sugar  (the bicyclic
      sugar  is depicted in formula (V))
<220> FEATURE:
<221> NAME/KEY: misc_feature
<222> LOCATION: (3)..(3)
<223> OTHER INFORMATION: 7',5'-phosphodiester-linked beta anomeric
      thymine nucleotide with a bicyclic sugar  (the bicyclic sugar  is
      depicted in formula (V))
<220> FEATURE:
<221> NAME/KEY: misc_feature
<222> LOCATION: (4)..(4)
<223> OTHER INFORMATION: 7',5'-phosphodiester-linked beta anomeric
      adenine nucleotide with a bicyclic sugar  (the bicyclic sugar  is
      depicted in formula (V))
<220> FEATURE:
<221> NAME/KEY: misc_feature
<222> LOCATION: (5)..(5)
<223> OTHER INFORMATION: 7',5'-phosphodiester-linked beta anomeric
      5-methylcytosine nucleotide with a bicyclic sugar  (the bicyclic
      sugar  is depicted in formula (V))
<220> FEATURE:
<221> NAME/KEY: misc_feature
<222> LOCATION: (6)..(7)
<223> OTHER INFORMATION: 7',5'-phosphodiester-linked beta anomeric
      adenine nucleotide with a bicyclic sugar  (the bicyclic sugar  is
      depicted in formula (V))
<220> FEATURE:
<221> NAME/KEY: misc_feature
<222> LOCATION: (8)..(8)
<223> OTHER INFORMATION: 7',5'-phosphodiester-linked beta anomeric
      guanine nucleotide with a bicyclic sugar  (the bicyclic sugar  is
      depicted in formula (V))
<220> FEATURE:
<221> NAME/KEY: misc_feature
<222> LOCATION: (9)..(9)
<223> OTHER INFORMATION: 7',5'-phosphodiester-linked beta anomeric
      adenine nucleotide with a bicyclic sugar  (the bicyclic sugar  is
      depicted in formula (V))
<220> FEATURE:
<221> NAME/KEY: misc_feature
<222> LOCATION: (10)..(10)
<223> OTHER INFORMATION: 7',5'-phosphodiester-linked beta anomeric
      guanine nucleotide with a bicyclic sugar  (the bicyclic sugar  is
      depicted in formula (V))
<220> FEATURE:
<221> NAME/KEY: misc_feature
<222> LOCATION: (11)..(11)
<223> OTHER INFORMATION: 7',5'-phosphodiester-linked beta anomeric
      5-methylcytosine nucleotide with a bicyclic sugar  (the bicyclic
      sugar  is depicted in formula (V))
<220> FEATURE:
<221> NAME/KEY: misc_feature
<222> LOCATION: (12)..(12)
<223> OTHER INFORMATION: 7',5'-phosphodiester-linked beta anomeric
      thymine nucleotide with a bicyclic sugar  (the bicyclic sugar  is
      depicted in formula (V))
```

```
<400> SEQUENCE: 15
nnnnnnnnnn nn                                                           12

<210> SEQ ID NO 16
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: 7',5'-phosphodiester-linked beta anomeric
      thymine nucleotide with a bicyclic sugar  (the bicyclic sugar  is
      depicted in formula (IV))

<400> SEQUENCE: 16
ggatgttcnc ga                                                           12

<210> SEQ ID NO 17
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: 7',5'-phosphodiester-linked beta anomeric
      thymine nucleotide with a bicyclic sugar  (the bicyclic sugar  is
      depicted in formula (IV))

<400> SEQUENCE: 17
ggangttctc ga                                                           12

<210> SEQ ID NO 18
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: 7',5'-phosphodiester-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (9)..(9)
<223> OTHER INFORMATION: 7',5'-phosphodiester-linked beta anomeric
      thymine nucleotide with a bicyclic sugar  (the bicyclic sugar  is
      depicted in formula (IV))

<400> SEQUENCE: 18
ggangttcnc ga                                                           12

<210> SEQ ID NO 19
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: 7',5'-phosphodiester-linked beta anomeric
      thymine nucleotide with a bicyclic sugar  (the bicyclic sugar  is
      depicted in formula (IV))

<400> SEQUENCE: 19
```
ggatgnnctc ga                                                    12

<210> SEQ ID NO 20
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(8)
<223> OTHER INFORMATION: 7',5'-phosphodiester-linked beta anomeric
      thymine nucleotide with a bicyclic sugar  (the bicyclic sugar  is
      depicted in formula (IV))

<400> SEQUENCE: 20
gcannnnnac cg                                                    12

<210> SEQ ID NO 21
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 7',5'-phosphodiester-linked beta anomeric
      adenine nucleotide with a bicyclic sugar  (the bicyclic sugar  is
      depicted in formula (IV))
<220> FEATURE:
<221> NAME/KEY: misc_feature
<222> LOCATION: (2)..(2)
<223> OTHER INFORMATION: 7',5'-phosphodiester-linked beta anomeric
      guanine nucleotide with a bicyclic sugar  (the bicyclic sugar  is
      depicted in formula (IV))
<220> FEATURE:
<221> NAME/KEY: misc_feature
<222> LOCATION: (3)..(3)
<223> OTHER INFORMATION: 7',5'-phosphodiester-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (4)..(4)
<223> OTHER INFORMATION: 7',5'-phosphodiester-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (5)..(5)
<223> OTHER INFORMATION: 7',5'-phosphodiester-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (6)..(7)
<223> OTHER INFORMATION: 7',5'-phosphodiester-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (8)..(8)
<223> OTHER INFORMATION: 7',5'-phosphodiester-linked beta anomeric
      guanine nucleotide with a bicyclic sugar  (the bicyclic sugar  is
      depicted in formula (IV))
<220> FEATURE:
<221> NAME/KEY: misc_feature
<222> LOCATION: (9)..(9)
<223> OTHER INFORMATION: 7',5'-phosphodiester-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (10)..(10)

```
<223> OTHER INFORMATION: 7',5'-phosphodiester-linked beta anomeric
      adenine nucleotide with a bicyclic sugar  (the bicyclic sugar  is
      depicted in formula (IV))
<220> FEATURE:
<221> NAME/KEY: misc_feature
<222> LOCATION: (11)..(12)
<223> OTHER INFORMATION: 7',5'-phosphodiester-linked beta anomeric
      guanine nucleotide with a bicyclic sugar  (the bicyclic sugar  is
      depicted in formula (IV))

<400> SEQUENCE: 21
nnnnnnnnnn nn                                                          12

<210> SEQ ID NO 22
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 7',5'-phosphodiester-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (3)..(3)
<223> OTHER INFORMATION: 7',5'-phosphodiester-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (4)..(4)
<223> OTHER INFORMATION: 7',5'-phosphodiester-linked beta anomeric
      adenine nucleotide with a bicyclic sugar  (the bicyclic sugar  is
      depicted in formula (IV))
<220> FEATURE:
<221> NAME/KEY: misc_feature
<222> LOCATION: (5)..(5)
<223> OTHER INFORMATION: 7',5'-phosphodiester-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (6)..(7)
<223> OTHER INFORMATION: 7',5'-phosphodiester-linked beta anomeric
      adenine nucleotide with a bicyclic sugar  (the bicyclic sugar  is
      depicted in formula (IV))
<220> FEATURE:
<221> NAME/KEY: misc_feature
<222> LOCATION: (8)..(8)
<223> OTHER INFORMATION: 7',5'-phosphodiester-linked beta anomeric
      guanine nucleotide with a bicyclic sugar  (the bicyclic sugar  is
      depicted in formula (IV))
<220> FEATURE:
<221> NAME/KEY: misc_feature
<222> LOCATION: (9)..(9)
<223> OTHER INFORMATION: 7',5'-phosphodiester-linked beta anomeric
      adenine nucleotide with a bicyclic sugar  (the bicyclic sugar  is
      depicted in formula (IV))
<220> FEATURE:
<221> NAME/KEY: misc_feature
<222> LOCATION: (10)..(10)
<223> OTHER INFORMATION: 7',5'-phosphodiester-linked beta anomeric
      guanine nucleotide with a bicyclic sugar  (the bicyclic sugar  is
      depicted in formula (IV))
<220> FEATURE:
<221> NAME/KEY: misc_feature
<222> LOCATION: (11)..(11)
<223> OTHER INFORMATION: 7',5'-phosphodiester-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (12)..(12)
<223> OTHER INFORMATION: 7',5'-phosphodiester-linked beta anomeric
``` thymine nucleotide with a bicyclic sugar (the bicyclic sugar is
depicted in formula (IV))

<400> SEQUENCE: 22
nnnnnnnnnn nn                                                         12

<210> SEQ ID NO 23
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 7',5'-phosphodiester-linked beta anomeric
      thymine nucleotide with a bicyclic sugar (the bicyclic sugar is
      depicted in formula (IV))
<220> FEATURE:
<221> NAME/KEY: misc_feature
<222> LOCATION: (2)..(2)
<223> OTHER INFORMATION: 7',5'-phosphodiester-linked beta anomeric
      5-methylcytosine nucleotide with a bicyclic sugar (the bicyclic
      sugar is depicted in formula (IV))
<220> FEATURE:
<221> NAME/KEY: misc_feature
<222> LOCATION: (3)..(3)
<223> OTHER INFORMATION: 7',5'-phosphodiester-linked beta anomeric
      guanine nucleotide with a bicyclic sugar (the bicyclic sugar is
      depicted in formula (IV))
<220> FEATURE:
<221> NAME/KEY: misc_feature
<222> LOCATION: (4)..(4)
<223> OTHER INFORMATION: 7',5'-phosphodiester-linked beta anomeric
      adenine nucleotide with a bicyclic sugar (the bicyclic sugar is
      depicted in formula (IV))
<220> FEATURE:
<221> NAME/KEY: misc_feature
<222> LOCATION: (5)..(5)
<223> OTHER INFORMATION: 7',5'-phosphodiester-linked beta anomeric
      guanine nucleotide with a bicyclic sugar (the bicyclic sugar is
      depicted in formula (IV))
<220> FEATURE:
<221> NAME/KEY: misc_feature
<222> LOCATION: (6)..(7)
<223> OTHER INFORMATION: 7',5'-phosphodiester-linked beta anomeric
      adenine nucleotide with a bicyclic sugar (the bicyclic sugar is
      depicted in formula (IV))
<220> FEATURE:
<221> NAME/KEY: misc_feature
<222> LOCATION: (8)..(8)
<223> OTHER INFORMATION: 7',5'-phosphodiester-linked beta anomeric
      5-methylcytosine nucleotide with a bicyclic sugar (the bicyclic
      sugar is depicted in formula (IV))
<220> FEATURE:
<221> NAME/KEY: misc_feature
<222> LOCATION: (9)..(9)
<223> OTHER INFORMATION: 7',5'-phosphodiester-linked beta anomeric
      adenine nucleotide with a bicyclic sugar (the bicyclic sugar is
      depicted in formula (IV))
<220> FEATURE:
<221> NAME/KEY: misc_feature
<222> LOCATION: (10)..(10)
<223> OTHER INFORMATION: 7',5'-phosphodiester-linked beta anomeric
      thymine nucleotide with a bicyclic sugar (the bicyclic sugar is
      depicted in formula (IV))
<220> FEATURE:
<221> NAME/KEY: misc_feature
<222> LOCATION: (11)..(12)
<223> OTHER INFORMATION: 7',5'-phosphodiester-linked beta anomeric
      5-methylcytosine nucleotide with a bicyclic sugar (the bicyclic
      sugar is depicted in formula (IV))

<400> SEQUENCE: 23
nnnnnnnnnn nn                                                         12

<210> SEQ ID NO 24
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 7',5'-phosphorothioate-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (2)..(3)
<223> OTHER INFORMATION: 7',5'-phosphorothioate-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (4)..(4)
<223> OTHER INFORMATION: 7',5'-phosphorothioate-linked beta anomeric
      adenine nucleotide with a bicyclic sugar  (the bicyclic sugar  is
      depicted in formula (IV))
<220> FEATURE:
<221> NAME/KEY: misc_feature
<222> LOCATION: (5)..(6)
<223> OTHER INFORMATION: 7',5'-phosphorothioate-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (7)..(7)
<223> OTHER INFORMATION: 7',5'-phosphorothioate-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (8)..(9)
<223> OTHER INFORMATION: 7',5'-phosphorothioate-linked beta anomeric
      guanine nucleotide with a bicyclic sugar  (the bicyclic sugar  is
      depicted in formula (IV))
<220> FEATURE:
<221> NAME/KEY: misc_feature
<222> LOCATION: (10)..(10)
<223> OTHER INFORMATION: 7',5'-phosphorothioate-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (11)..(11)
<223> OTHER INFORMATION: 7',5'-phosphorothioate-linked beta anomeric
      thymine nucleotide with a bicyclic sugar  (the bicyclic sugar  is
      depicted in formula (IV))
<220> FEATURE:
<221> NAME/KEY: misc_feature
<222> LOCATION: (12)..(13)
<223> OTHER INFORMATION: 7',5'-phosphorothioate-linked beta anomeric
      5-methylcytosine nucleotide with a bicyclic sugar  (the bicyclic
      sugar  is depicted in formula (IV))
<220> FEATURE:
<221> NAME/KEY: misc_feature
<222> LOCATION: (14)..(15)
<223> OTHER INFORMATION: 7',5'-phosphorothioate-linked beta anomeric
      adenine nucleotide with a bicyclic sugar  (the bicyclic sugar  is
      depicted in formula (IV))

<400> SEQUENCE: 24
nnnnnnnnnn nnnnn                                                15

<210> SEQ ID NO 25
<211> LENGTH: 12
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: (4)...(4)
<223> OTHER INFORMATION: n = A,T,C or G

<400> SEQUENCE: 25
tcgngaacat cc                                                              12

<210> SEQ ID NO 26
<211> LENGTH: 12
<212> TYPE: DNA
<213> ORGANISM: Artificial Sequence
<220> FEATURE:
<223> OTHER INFORMATION: Synthetic Construct

<400> SEQUENCE: 26
ggatgttctc ga                                                              12

<210> SEQ ID NO 27
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: n = tricyclo-DNA thymine
<220> FEATURE:
<221> NAME/KEY: misc_feature
<222> LOCATION: (2)...(2)
<223> OTHER INFORMATION: n = tricyclo-DNA methylcytosine
<220> FEATURE:
<221> NAME/KEY: misc_feature
<222> LOCATION: (3)...(3)
<223> OTHER INFORMATION: n = tricyclo-DNA guanine
<220> FEATURE:
<221> NAME/KEY: misc_feature
<222> LOCATION: (4)...(4)
<223> OTHER INFORMATION: n = tricyclo-DNA adenine
<220> FEATURE:
<221> NAME/KEY: misc_feature
<222> LOCATION: (5)...(5)
<223> OTHER INFORMATION: n = tricyclo-DNA guanine
<220> FEATURE:
<221> NAME/KEY: misc_feature
<222> LOCATION: (6)...(6)
<223> OTHER INFORMATION: n = tricyclo-DNA adenine
<220> FEATURE:
<221> NAME/KEY: misc_feature
<222> LOCATION: (7)...(7)
<223> OTHER INFORMATION: n = tricyclo-DNA adenine
<220> FEATURE:
<221> NAME/KEY: misc_feature
<222> LOCATION: (8)...(8)
<223> OTHER INFORMATION: n = tricyclo-DNA methylcytosine
<220> FEATURE:
<221> NAME/KEY: misc_feature
<222> LOCATION: (9)...(9)
<223> OTHER INFORMATION: n = tricyclo-DNA adenine
<220> FEATURE:
<221> NAME/KEY: misc_feature
<222> LOCATION: (10)...(10)
<223> OTHER INFORMATION: n = tricyclo-DNA thymine
<220> FEATURE:
<221> NAME/KEY: misc_feature
<222> LOCATION: (11)...(11)
<223> OTHER INFORMATION: n = tricyclo-DNA methylcytosine
<220> FEATURE:
<221> NAME/KEY: misc_feature
<222> LOCATION: (12)...(12)
<223> OTHER INFORMATION: n = tricyclo-DNA methylcytosine

<400> SEQUENCE: 27
```

```
nnnnnnnnnn nn                                       12

<210> SEQ ID NO 28
<211> LENGTH: 12
<212> TYPE: RNA
<213> ORGANISM: Artificial Sequence
<220> FEATURE:
<223> OTHER INFORMATION: Synthetic Construct

<400> SEQUENCE: 28
ccuacaagag cu                                       12

<210> SEQ ID NO 29
<211> LENGTH: 12
<212> TYPE: DNA
<213> ORGANISM: Artificial Sequence
<220> FEATURE:
<223> OTHER INFORMATION: Synthetic Construct

<400> SEQUENCE: 29
cctacaagag ct                                       12
```

BICYCLIC NUCLEOSIDES AND OLIGOMERS PREPARED THEREFROM

CROSS-REFERENCED TO RELATED APPLICATIONS

This application is the U.S. National Phase under 35 U.S.C. § 371 of International Application No. PCT/EP2017/080769, filed Nov. 29, 2017, designating the U.S., and published in English as WO 2018/099946 A1 on Jun. 7, 2018, which claims priority to EP Application No. 16201350.2, filed Nov. 30, 2016, the entire contents of which are incorporated herein by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is P5164PC00_FINAL_SEQ Protocol ST25t.TXT, the date of creation of the ASCII text file is Jan. 7, 2021, and the size of the ASCII text file is 25.7 KB.

The present invention relates to novel bicyclic nucleosides and oligomers prepared therefrom. In particular, the present invention relates to a compound of formula (I), to an oligomer comprising at least one compound of formula (IV), to the compounds or the oligomer of the invention for use as a medicament in the prevention, treatment or diagnosis of a disease and to a pharmaceutical composition comprising at least one compound or at least one oligomer of the invention. The invention also refers to in vitro uses of the oligomer of the invention for binding to a target nucleic acid sequence and a method for solid-phase synthesis of an oligomer of the invention.

RELATED ART

Antisense therapy has matured as an important platform for the development of innovative drugs. Oligonucleotide analogs displaying strong and sequence specific binding to single-stranded RNA or double-stranded DNA and exhibiting resistance to enzymatic degradation are potential candidates for therapeutic applications as inhibitors or modulators of protein expression. Chemically modified nucleosides are incorporated into antisense compounds to enhance its properties, such as nuclease resistance, pharmacokinetics or affinity for a target RNA.

In the recent years, the field of synthetic biology has evolved with the general aim to develop antisense systems with improved potency and efficacy that do not rely on the known molecular components used in nature. A basic requirement to achieve this goal is the development of artificial genetic polymers, often referred to as xeno-nucleic acids (XNA), that fulfill the function of natural DNA or RNA (Herdewijn et al., Chem. Biodiversity 2009, 6, 791). The availability of such systems and their integration into living organisms is expected to equip them with novel properties that are of interest in the field of biotechnology and medicine.

From the vast repertoire of nucleic acid modifications that appeared over the last 30 years, a handful of candidates has been scrutinized towards their suitability as an alternative genetic material. In an attempt to introduce non-natural components into the natural genetic machinery by minimal chemical alteration, it has been shown that thymidine in the genome of *E. coli* strains can be replaced by 5-chlorouridine in an evolutionary process to a minimum residual thymidine content (Marhère et al., Angewandte Chemie, Int. Edition 2011, 50, 7109). In a different approach, it has been reported that unnatural nucleic acids, such as 1,5-anhydrohexitol nucleic acid (HNA; Hendrix et al., Chem. Eur. J. 1997, 3, 110) and cyclohexene nucleic acid (CeNA; Nauwelaerts et al., Nucleic Acids Res. 2005, 33, 2452), fluoroarabinooligonucleotides (FANA; Wilds et al., J. Nucleic Acids Res. 2000, 28, 3625), arabinonucleic acids (ANA; Damha et al., J. Am. Chem. Soc. 1998, 120, 12976), threose nucleic acid (TNA; Schoning et al., Science 2000, 290, 1347) and locked nucleic acid (LNA; Koshkin et al., J. Am. Chem. Soc. 1998, 120, 13252; Obika et al., Tetrahedron Lett. 1998, 39, 5401) can be transcribed from and reverse transcribed into DNA by DNA-polymerases.

In an alternative approach, backbone structure of RNA and DNA has been altered by changing the point of attachment of the internucleosidic phosphate unit to the sugar from the 3' to the 2' oxygen (2',5'-DNA or 2',5'-RNA). While 2',5'-RNA is a naturally occurring biopolymer, first found in bacteria in the form of 2',5' polyadenylates, 2',5'-DNA is artificial (Trujillo et al., Eur. J. Biochem. 1987, 169, 167). The pairing and replication properties of both polymers have been investigated in the past. It was found that 2',5'-RNA binds to complementary RNA but not to DNA. Duplexes with RNA are slightly less stable as compared to pure RNA duplexes and duplexes in the pure 2',5'-RNA series exist but are even less stable (Wasner et al., J. Biochemistry 1998, 37, 7478). In addition, it was shown in primer template extension experiments that stretches of up to four 2',5'-linked nucleotides on a template can be reverse transcribed into DNA with polymerases or reverse transcriptases even though there is no significant affinity of 2',5'-DNA to natural DNA (Sinha et al., J. Am. Chem. Soc. 2004, 126, 40).

In order to stabilize complex formation with complementary natural nucleic acids entropically, a bicyclic DNA analog that differs from natural DNA by an additional ethylene bridge located between the centers C(3') and C(5') has been designed. The points of attachment of the linking phosphodiester units are the same as in the naturally occurring nucleic acid, i.e. the 3' and 5' terminus. This change in the carbon skeleton results in a locked sugar conformation which causes the bicyclo-deoxynucleosides to exhibit a higher degree of preorganisation of the single strands for duplex formation. Decamers of bicyclo-deoxyadenosine and bicyclo-thymidine bind to their natural RNA and DNA complements as well as with each other, forming double and triple helical structures. Compared with natural DNA, duplex formation is associated with reduced pairing enthalpy and entropy terms, having compensatory effects on the free energy of duplex formation (Bolli et al., Nucleic Acids Res. 1996, 24, 4660).

Nevertheless, after more than three decades of research in the antisense field, clinical applications are still limited by the low biostability, the poor pharmacokinetic properties and the off-target toxicity of this class of compounds.

Thus, there remains a need for antisense compounds that are resistant to enzymatic degradation in vivo and display strong and sequence specific binding to nucleic acids.

SUMMARY OF THE INVENTION

In a first aspect, the invention provides a compound of formula (I):

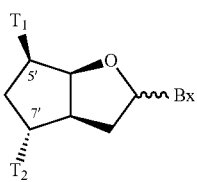

(I)

wherein one of $T_1$ and $T_2$ is $OR_1$ or $OR_2$;
and the other of $T_1$ and $T_2$ is $OR_1$ or $OR_2$; wherein
$R_1$ is H or a hydroxyl protecting group, and
$R_2$ is a phosphorus moiety; and wherein
Bx is a nucleobase.

In a second aspect, the invention provides an oligomer comprising at least one compound of formula (IV)

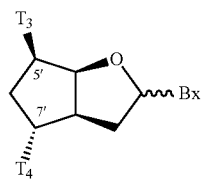

(IV)

wherein independently for each of said at least one compound of formula (IV)
one of $T_3$ or $T_4$ is a nucleosidic linkage group;
the other of $T_3$ and $T_4$ is $OR_1$, $OR_2$, a 5' terminal group, a 7' terminal group or a nucleosidic linkage group, wherein $R_1$ is H or a hydroxyl protecting group, and $R_2$ is a phosphorus moiety; and Bx is a nucleobase.

In a third aspect, the present invention provides for the inventive compound of formula (I), (II) or (III) or the oligomer of the invention for use as a medicament in the prevention or treatment of a disease.

In a further aspect, the present invention provides for the oligomer of the invention, preferably the inventive oligomer of the formula (V), for use as a medicament in the prevention, treatment or diagnosis of a disease, wherein said disease is a muscular dystrophy, and wherein preferably said disease is Duchenne muscular dystrophy.

In a further aspect, the invention provides a pharmaceutical composition comprising at least one compound selected from formula (I), (II) or (III) or at least one oligomer of the invention.

In a further aspect, the oligomer of the invention is used in vitro for binding to a target nucleic acid sequence.

In a further aspect, the invention provides a method for solid-phase synthesis of an oligomer of the invention.

The invention described herein provides for new compounds, wherein the position of the group used for linkage to other entities, such as the nucleosidic linkage group, is shifted as compared to compounds of the prior art. Thus, the compounds of the invention can be or are linked via the 5' terminus and 7' terminus of its bicyclic sugar to other entities such as nucleosides or nucleotides (FIG. 1C and FIG. 1D). In contrast and in the prior art, nucleosides or nucleotides are linked via the 3' and 5' termini, be it for known nucleosides or nucleotides comprising a bicyclic sugar (FIG. 1B) or as in naturally occurring DNA or RNA (FIG. 1A).

As a consequence of that shifted linkage, the backbone geometry of the compounds of the invention within an oligomer is changed. This changed backbone geometry in turn induces a nucleobase stacking of the compounds of the invention that is different from that of naturally occurring nucleic acid helixes. Consequently, oligomers of the invention adopts helix conformations that are distinctly different from that of natural DNA. Furthermore, based on these findings, oligomers of the invention forming duplex structures are expected to have a geometry deviating from conventional canonical duplexes.

Despite of the changes in backbone geometry and nucleobase stacking, we have now surprisingly found that oligomers of the invention cross-pair with natural DNA and RNA, and self-duplexes of oligomers of the invention exhibit thermal stabilities that are in the same range as that of natural DNA duplexes. Consequently, the oligomers of the invention have the structural and base-pairing properties necessary to become a novel xeno-nucleic acid that may fulfill the function of natural DNA. Moreover, the oligomers of the invention show comparable base pairing selectivity and have even a better mismatch discrimination ability compared to its natural DNA counterpart. Increasing the mismatch discrimination typically reduces the potential off-target effects and therefore represents an appealing property for an antisense candidate.

DETAILED DESCRIPTION OF THE INVENTION

Figure 1:
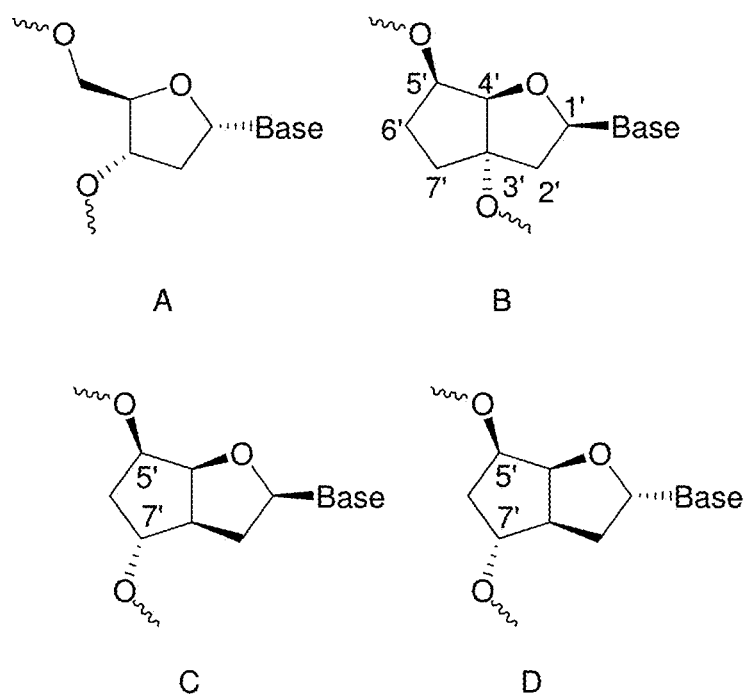
FIG. 1: A) α-monocyclic DNA; B) bicyclic (bc-)DNA; C) 7',5'-β-bc-DNA, i.e. the inventive compound of formula (III); D) 7',5'-α-bc-DNA, i.e. the inventive compound of formula (II).
Figure 2:
FIG. 2: Comparison between 7',5'-β-bc-DNA, i.e. the inventive compound of formula (III) depicted on the left side, and 7',5'-α-bc-DNA, i.e. the inventive compound of formula (II) depicted on the right side.

Unless defined otherwise, all technical and scientific terms used herein have the same meanings as commonly understood by one of ordinary skill in the art to which this invention belongs.

The terms "protecting group for an amino", "protecting group for an amino group", or "amino protecting group" as interchangeably used herein, are well known in the art and include those described in detail in *Protecting Groups in Organic Synthesis*, T. W. Greene and P. G. M. Wuts, 3$^{rd}$ edition, John Wiley & Sons, 1999, Greene's Protective Groups in Organic Synthesis, P. G. M. Wuts, 5th edition, John Wiley & Sons, 2014, and in *Current Protocols in Nucleic Acid Chemistry*, edited by S. L. Beaucage et al. 06/2012, and hereby in particular in Chapter 2. Suitable "amino protecting groups" for the present invention include and are typically and preferably independently at each occurrence selected from methyl carbamate, ethyl carbamate, 9-fluorenylmethyl carbamate (Fmoc), 9-(2-sulfo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1,1-dimethyl-2,2-dibromoethyl carbamate (DB-t-BOC), 1,1-dimethyl-2,2,2-trichloroethyl carbamate (TCBOC), benzyl carbamate (Cbz), p-methoxybenzyl carbamate (Moz) and 2,4,6-trimethylbenzyl carbamate; as well as formamide, acetamide, benzamide.

The terms "protecting group for a hydroxyl", "protecting group for a hydroxyl group", or "hydroxyl protecting group" as interchangeably used herein, are well known in the art and includes those described in detail in *Protecting Groups in Organic Synthesis*, T. W. Greene and P. G. M. Wuts, 3$^{rd}$ edition, John Wiley & Sons, 1999; Greene's Protective Groups in Organic Synthesis, P. G. M. Wuts, 5$^{th}$ edition, John Wiley & Sons, 2014, and in *Current Protocols in Nucleic Acid Chemistry*, edited by S. L. Beaucage et al. 06/2012, and hereby in particular in Chapter 2. In a certain embodiment, the "hydroxyl protecting groups" of the present invention include and, typically and preferably are independently at each occurrence selected from, acetyl, benzoyl, benzyl, β-methoxyethoxymethyl ether (MEM), dimethoxytrityl, [bis-(4-methoxyphenyl)phenylmethyl] (DMTr), methoxymethyl ether (MOM), methoxytrityl [(4-methoxyphenyl)diphenylmethyl] (MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether, such as t-Butyldiphenylsilyl ether (TBDPS), trimethylsilyl (TMS), tert-butyldimethylsilyl (TBDMS), tri-iso-propylsilyloxymethyl (TOM), and tri-isopropylsilyl (TIPS) ethers; methyl ethers, ethoxyethyl ethers (EE).

In a preferred embodiment, the "hydroxyl protecting groups" of the present invention include and, typically and preferably are independently at each occurrence selected from, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl (TBDMS), t-butyldiphenylsilyl (TBDPS), triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, 4-monomethoxytrityl (MMTr), 4,4'dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-y 1 (MOX).

In some embodiments, the hydroxyl protecting group is independently at each occurrence selected from acetyl, benzyl, t-butyldimethylsilyl, t-butyldiphenylsilyl, trityl, 4-monomethoxytrityl, 4,4'-dimethoxytrityl (DMTr), 4,4',4"-trimethoxytrityl (TMTr), 9-phenylxanthin-9-yl (Pixyl) and 9-(p-methoxyphenyl)xanthin-9-yl (MOX). In preferred embodiments, the hydroxyl protecting group is independently at each occurrence selected from triphenylmethyl (trityl), 4-monomethoxytrityl, 4,4'-dimethoxytrityl (DMTr), 4,4',4"-trimethoxytrityl (TMTr), 9-phenylxanthin-9-yl (Pixyl) and 9-(p-methoxyphenyl)xanthin-9-yl (MOX). In further preferred embodiments, the hydroxyl protecting group is independently at each occurrence selected from trityl, 4-monomethoxytrityl and 4,4'-dimethoxytrityl group. In a very preferred embodiment, said hydroxyl protecting group is independently at each occurrence selected from triphenylmethyl (trityl), 4-monomethoxytrityl, 4,4'-dimethoxytrityl (DMTr), 4,4',4"-trimethoxytrityl (TMTr), 9-phenylxanthin-9-yl (Pixyl) and 9-(p-methoxyphenyl)xanthin-9-yl (MOX). In a more preferred embodiment, the hydroxyl protecting groups of the present invention is acetyl, dimethoxytrityl (DMTr), tert-butyldimethylsilyl (TBDMS), tri-iso-propylsilyloxymethyl (TOM), or t-butyldiphenylsilyl ether (TBDPS). In an again very preferred embodiment, said hydroxyl protecting group is independently at each occurrence selected from 4,4'-dimethoxytrityl (DMTr) or 4-monomethoxytrityl. In an again further very preferred embodiment, said hydroxyl protecting group is 4,4'-dimethoxytrityl (DMTr).

The term "phosphorus moiety", as used herein, refers to a moiety comprising a phosphorus atom in the $P^{III}$ or $P^V$ valence state and which is represented by formula (VII)

wherein

W represents O, S or Se or W represents an electron pair;

R$_3$ and R$_4$ are independently of each other H, halogen, OH, OR$_5$, NR$_6$R$_7$, SH, SR$_8$, C$_1$-C$_6$alkyl, C$_1$-C$_6$haloalkyl, $C_1$-$C_6$alkoxy, $C_1$-$C_6$haloalkoxy, $C_1$-$C_6$aminoalkyl; wherein $R_5$ is $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl, each independently of each other optionally substituted with cyano, nitro, halogen, $C_1$-$C_4$alkoxy, $C_1$-$C_4$haloalkyl, $C_1$-$C_4$haloalkoxy, NHC(O)$C_1$-$C_3$alkyl, NHC(O)$C_1$-$C_3$haloalkyl, $C_1$-$C_3$alkylsulfonyl; acetyl; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy; aryl optionally substituted with cyano, nitro, halogen, $C_1$-$C_3$alkyl, $C_1$-$C_3$alkoxy; an amino protecting group; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein $R_8$ is a thiol protecting group; and wherein the wavy line indicates the attachment to the oxygen of said $OR_2$ group. When W represents O, S or Se then said P atom within said phosphorus moiety is in its $P^V$ valence state. When W represents an electron pair then said P atom within said phosphorus moiety is in its $P^{III}$ valence. The moiety of formula (VII) includes any possible stereoisomer. Further included in said moieties represented by formula (VII) are salts thereof, wherein typically and preferably said salts are formed upon treatment with inorganic bases or amines, and are typically and preferably salts derived from reaction with the OH or SH groups being (independently of each other) said $R_3$ and $R_4$. Preferred inorganic bases or amines leading to said salt formation with the OH or SH groups are well known in the art and are typically and preferably trimethylamine, diethylamine, methylamine or ammonium hydroxide. These phosphorus moieties included in the present invention are, if appropriate, also abbreviated as "$O^-HB^+$", wherein said $HB^-$ refers to the counter cation formed.

In a preferred embodiment, in the "phosphorus moiety", $R_3$ and $R_4$ are independently of each other H, OH, $OR_5$, $NR_6R_7$, $C_1$-$C_6$alkyl, $C_1$-$C_6$alkyl, $C_1$-$C_6$haloalkyl, $C_1$-$C_6$alkoxy, $C_1$-$C_6$haloalkoxy, $C_1$-$C_6$aminoalkyl; wherein $R_5$ is $C_1$-$C_9$alkyl optionally substituted with cyano, nitro, halogen; aryl, $C_1$-$C_6$alkylenearyl, each independently of each other optionally substituted with cyano, nitro, halogen; acetyl; a hydroxyl protecting group; wherein $R_6$ and $R_7$ are independently of each other hydrogen, $C_1$-$C_9$alkyl optionally substituted with cyano, nitro, halogen; aryl optionally substituted with cyano, nitro, halogen, $C_1$-$C_3$ alkyl, $C_1$-$C_3$alkoxy; an amino protecting group; and wherein $R_8$ is a thiol protecting group; and wherein the wavy line indicates the attachment to the oxygen of said $OR_2$ group.

The term "phosphorus moiety", as used herein, includes and, typically and preferably is independently at each occurrence selected from a moiety derived from phosphonates, phosphite triester, monophosphate, diphosphate, triphosphate, phosphate triester, phosphate diester, thiophosphate ester, di-thiophosphate ester or phosphoramidites.

Thus, in a preferred embodiment, said $OR_2$ is independently at each occurrence selected from phosphonates, phosphite triester, monophosphate, diphosphate, triphosphate, phosphate triester, phosphate diester, thiophosphate ester, di-thiophosphate ester or phosphoramidites, and wherein preferably said $OR_2$ is a phosphoramidite or a phosphate triester, more preferably a phosphoramidite.

In a preferred embodiment, the phosphorus moiety is derived from a phosphonate represented by formula (VII), wherein W is O, $R_3$ is selected from $C_1$-$C_6$alkyl, $C_1$-$C_6$haloalkyl, $C_1$-$C_6$alkoxy, $C_1$-$C_6$haloalkoxy, $C_1$-$C_6$aminoalkyl, and $R_4$ is OH or $O^-HB^+$; and wherein the wavy line indicates the attachment to the oxygen of said $OR_2$ group. In another embodiment, the phosphorus moiety of formula (VII) is an H-phosphonate, wherein W is O, $R_3$ is hydrogen and $R_4$ is OH or $O^-HB^+$; and wherein preferably said $O^-HB^+$ is $HNEt_3^+$. In a further embodiment, the phosphorus moiety of formula (VII) is an alkyl-phosphonate, wherein W is O, $R_3$ is alkyl, and $R_4$ is OH or $O^-HB^+$; and wherein preferably said $O^-HB^+$ is $HNEt_3^+$. More preferably, the phosphorus moiety of formula (VII) is methyl-phosphonate, wherein W is O, $R_3$ is hydrogen and $R_4$ is OH or $O^-HB^+$; and wherein preferably said $O^-HB^+$ is $HNEt_3^+$). In another embodiment, the phosphorus moiety of formula (VII) is a phosphonocarboxylate, wherein $R_3$ or $R_4$ are independently of each other a carboxylic acid. Preferably, said phosphonocarboxylate is phosphonoacetic acid or phosphonoformic acid. In a further embodiment, the phosphorus moiety of formula (VII) is a 2-aminoethyl-phosphonate.

In a preferred embodiment, $R_3$ and $R_4$ of the phosphorus moiety of formula (VII) are independently of each other H, OH, halogen, $OR_5$, $NR_6R_7$, SH, $SR_8$, $C_1$-$C_4$alkyl, preferably $C_1$-$C_2$alkyl, $C_1$-$C_4$haloalkyl, preferably $C_1$-$C_2$haloalkyl, $C_1$-$C_4$alkoxy, preferably $C_1$-$C_2$alkoxy, $C_1$-$C_4$haloalkoxy, preferably $C_1$-$C_2$haloalkoxy, $C_1$-$C_4$aminoalkyl, preferably $C_1$-$C_2$aminoalkyl; and wherein $R_5$ is $C_1$-$C_6$alkyl, preferably $C_1$-$C_3$alkyl, each independently of each other optionally substituted with cyano, nitro, halogen, NHC(O)$C_1$-$C_3$alkyl, NHC(O)$C_1$-$C_3$haloalkyl, $C_1$-$C_3$alkylsulfonyl; aryl, $C_1$-$C_3$alkylenearyl, $C_1$-$C_3$alkylenediaryl, each independently of each other optionally substituted with cyano, nitro, halogen, $C_1$-$C_4$alkoxy, $C_1$-$C_4$haloalkyl, $C_1$-$C_4$haloalkoxy, NHC(O)$C_1$-$C_3$alkyl, NHC(O)$C_1$-$C_3$haloalkyl, $C_1$-$C_3$alkylsulfonyl; acetyl; a hydroxyl protecting group; and wherein $R_6$ and $R_7$ are independently of each other hydrogen, $C_1$-$C_6$alkyl, preferably $C_1$-$C_4$alkyl, each independently of each other optionally substituted with cyano, nitro, halogen, $C_2$-$C_4$alkenyl, $C_3$-$C_6$cycloalkyl, $C_1$-$C_3$alkoxy; aryl optionally substituted with cyano, nitro, halogen, $C_1$-$C_3$ alkyl, $C_1$-$C_3$alkoxy; an amino protecting group; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein $R_8$ is a thiol protecting group; and wherein the wavy line indicates the attachment to the oxygen of said $OR_2$ group.

In another preferred embodiment, $R_3$ or $R_4$ of the phosphorus moiety of formula (VII) is independently at each occurrence and of each other halogen, preferably chlorine, or $OR_5$, wherein $R_5$ is a hydroxyl protecting group. Additional phosphorus moieties used in the invention are disclosed in Tetrahedron Report Number 309 (Beaucage and Iyer, Tetrahedron, 1992, 48, 2223-2311).

The term "phosphorus moiety", as used herein, preferably refers to a group $R_2$ comprising a phosphorus atom in the $P^{III}$ or $P^V$ valence state and which is represented independently at each occurrence either by formula (VIII), formula (IX) or formula (X),

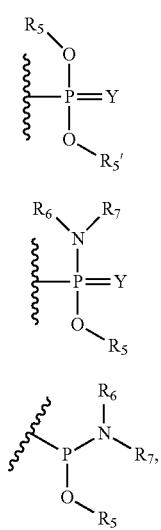

(VIII)

(IX)

(X)

wherein Y is O, S or Se, and wherein Y preferably is O or S, more preferably Y is O; and wherein $R_5$ and $R_{5'}$ are independently at each occurrence and of each other hydrogen, $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy; aryl, preferably phenyl, optionally substituted with cyano, nitro, halogen, $C_1$-$C_3$ alkyl, $C_1$-$C_3$alkoxy; an amino protecting group; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein $R_8$ is a thiol protecting group; and wherein the wavy line indicates the attachment to the oxygen of said $OR_2$ group.

In a preferred embodiment, said phosphorus moiety $R_2$ is represented by formula (VIII)

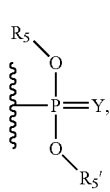

(VIII)

wherein Y is O, S or Se, wherein Y preferably is O or S, most preferably Y is O; and wherein $R_5$ and $R_{5'}$ are independently at each occurrence and of each other hydrogen, $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O) $C_1$-$C_3$alkyl, NHC(O)$C_1$-$C_3$haloalkyl, $C_1$-$C_3$alkylsulfonyl; a hydroxyl protecting group; P(O)(OR$_9$)(OR$_{9'}$), P(O)OP(O)(OR$_9$)(OR$_{9'}$); wherein $R_9$ and $R_{9'}$ are independently at each occurrence and of each other hydrogen, $C_1$-$C_9$alkyl optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; a hydroxyl protecting group; and wherein the wavy line indicates the attachment to the oxygen of said $OR_2$ group.

In a preferred embodiment, $R_5$ and $R_{5'}$ of formula (VIII) are independently at each occurrence and of each other hydrogen, $C_1$-$C_6$alkyl, preferably $C_1$-$C_3$alkyl, $C_1$-$C_4$alkoxy, preferably $C_1$-$C_2$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, preferably phenyl, $C_1$-$C_4$alkylenearyl, $C_1$-$C_4$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; a hydroxyl protecting group.

In a preferred embodiment, $R_5$ and $R_{5'}$ of formula (VIII) are independently of each other $C_1$-$C_4$alkyl or aryl, preferably phenyl. In another preferred embodiment, $R_5$ and $R_{5'}$ of formula (VIII) are independently of each other methyl or ethyl. In a further preferred embodiment, $R_5$ and $R_{5'}$ of formula (VIII) are independently of each other phenyl or benzyl. In another preferred embodiment, $R_5$ and $R_{5'}$ are independently at each occurrence and of each other hydrogen or a hydroxyl protecting group, preferably a hydroxyl protecting group. In a preferred embodiment, in formula (VIII), $R_5$ and $R_{5'}$ are independently at each occurrence and of each other hydrogen, $C_1$-$C_9$alkyl, $C_1$-$C_6$alkoxy, each independently of each other optionally substituted with cyano, nitro, halogen; aryl, $C_1$-$C_6$alkylenearyl, each independently of each other optionally substituted with cyano, nitro, halogen; or a hydroxyl protecting group. Typically and preferably, said phosphorus moiety $R_2$ represented by formula (VIII) is herein referred as "phosphate moiety".

In a preferred embodiment, said phosphorus moiety $R_2$ is represented by formula (IX)

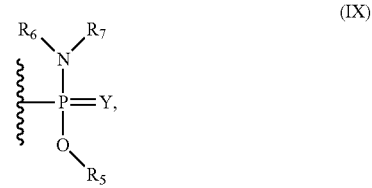

(IX)

wherein wherein

Y is O, S or Se, and wherein Y preferably is O or S, most preferably Y is O; and wherein $R_5$ is independently at each occurrence hydrogen, $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy; aryl, preferably phenyl, optionally substituted with cyano, nitro, halogen, $C_1$-$C_3$ alkyl, $C_1$-$C_3$alkoxy; an amino protecting group; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein the wavy line indicates the attachment to the oxygen of said $OR_2$ group. Typically and preferably, said phosphorus moiety $R_2$ represented by formula (IX) is referred herein as "phosphoramidate moiety" or, interchangeably used, "phosphoroamidate moiety".

In a preferred embodiment, said phosphorus moiety $R_2$ is represented by formula (X)

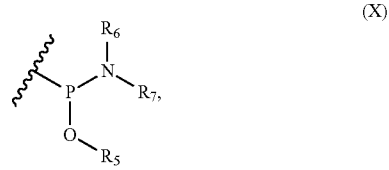

(X)

wherein $R_5$ is hydrogen, $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl, a hydroxyl protecting group; and wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy, aryl, preferably phenyl, optionally substituted with cyano, nitro, halogen, $C_1$-$C_3$ alkyl, $C_1$-$C_3$alkoxy; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl, and wherein the wavy line indicates the attachment to the oxygen of said $OR_2$ group. Typically and preferably, said phosphorus moiety $R_2$ represented by formula (X) is referred herein as "phosphoramidite moiety" or, interchangeably used, "phosphoroamidite moiety".

In a preferred embodiment, in formula (IX) said Y is O; said $R_5$ is independently at each occurrence hydrogen, $C_1$-$C_9$alkyl, $C_1$-$C_6$alkoxy, each independently of each other optionally substituted with cyano, nitro, halogen; aryl, $C_1$-$C_6$alkylenearyl, each independently of each other optionally substituted with cyano, nitro, halogen; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl; aryl optionally substituted with cyano, nitro, halogen, $C_1$-$C_3$ alkyl, $C_1$-$C_3$alkoxy; an amino protecting group; and wherein the wavy line indicates the attachment to the oxygen of said $OR_2$ group.

In a preferred embodiment, in formula (X) said $R_5$ is independently at each occurrence hydrogen, $C_1$-$C_9$alkyl, $C_1$-$C_6$alkoxy, each independently of each other optionally substituted with cyano, nitro, halogen; aryl, $C_1$-$C_6$alkylenearyl, each independently of each other optionally substituted with cyano, nitro, halogen; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl; aryl optionally substituted with cyano, nitro, halogen, $C_1$-$C_3$ alkyl, $C_1$-$C_3$alkoxy; an amino protecting group; and wherein the wavy line indicates the attachment to the oxygen of said $OR_2$ group.

In a very preferred embodiment, said phosphorus moiety $R_2$ is independently at each occurrence selected from a phosphate moiety, phosphoramidate moiety and phosphoramidite moiety.

In a further preferred embodiment, said $R_5$ is independently at each occurrence hydrogen, $C_1$-$C_6$alkyl, preferably $C_1$-$C_4$alkyl, $C_1$-$C_4$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_4$alkylenearyl, $C_1$-$C_4$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; a hydroxyl protecting group; wherein $R_6$ and $R_7$ are independently of each other hydrogen, $C_1$-$C_6$alkyl optionally substituted with cyano, nitro, halogen, $C_2$-$C_4$alkenyl, $C_3$-$C_6$cycloalkyl, $C_1$-$C_3$alkoxy; aryl optionally substituted with cyano, nitro, halogen, $C_1$-$C_3$ alkyl, $C_1$-$C_3$alkoxy; an amino protecting group; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein the wavy line indicates the attachment to the oxygen of said $OR_2$ group.

In a further preferred embodiment, said $R_5$ is $C_1$-$C_3$alkyl optionally substituted with cyano, chlorine, fluorine or bromine; aryl, $C_1$-$C_3$alkylenearyl, $C_1$-$C_3$alkylenediaryl, each independently of each other optionally substituted with cyano, nitro, chlorine, fluorine, bromine, $C_1$-$C_2$alkoxy, $C_1$haloalkyl. In a more preferred embodiment, said $R_5$ is a $C_1$-$C_3$alkyl optionally and preferably substituted with cyano, chlorine, fluorine or bromine; preferably substituted with cyano. In again a more preferred embodiment, said $R_5$ is a cyano substituted $C_2$alkyl, preferably said $R_5$ is —$CH_2CH_2$—CN.

In a further preferred embodiment, said $R_5$ is $C_1$-$C_4$alkyl, preferably methyl or ethyl; aryl, preferably phenyl or benzyl; chloride or a hydroxyl protecting group. In a further preferred embodiment, said $R_5$ is methyl or a hydroxyl protecting group.

In a further preferred embodiment, said $R_5$ is $C_1$-$C_6$alkoxy optionally substituted with cyano, chlorine, fluorine or bromine.

In a further preferred embodiment, said $R_6$ and $R_7$ are independently of each other H or $C_1$-$C_3$alkyl; or together with the nitrogen atom to which they are attached form a heterocyclic ring, wherein said heterocyclic ring is selected from pyrollidinyl, piperidinyl, morpholinyl, piperazinyl wherein said heterocyclic ring is optionally substituted with methyl. In a further preferred embodiment, said $R_6$ and $R_7$ are independently of each other $C_1$-$C_3$alkyl, alkoxy or aryl, wherein the aryl is preferably phenyl or benzyl, optionally substituted with cyano, nitro, chlorine, fluorine, bromine. In a further preferred embodiment, said $R_6$ is hydrogen, and $R_7$ is (i) $C_1$-$C_9$alkyl or (ii) aryl, (i) or (ii) optionally substituted with cyano, nitro, halogen, aryl, wherein preferably $R_7$ is $C_1$-$C_3$alkyl, phenyl or benzyl.

In a further preferred embodiment, said $R_6$ and $R_7$ are independently of each other selected from methyl, ethyl, isopropyl or isobutyl. In a more preferred embodiment, said $R_6$ and $R_7$ are independently of each other isopropyl.

In another very preferred embodiment, said phosphorus moiety $R_2$ is represented by formula (X), wherein said $R_5$ is (i) $C_1$-$C_9$alkyl; (ii) aryl, preferably phenyl; or (iii) said (i) or said (ii) optionally substituted with cyano, nitro, halogen, aryl; and wherein said $R_6$ and $R_7$ are independently of each other $C_1$-$C_9$alkyl, preferably isopropyl.

In another very preferred embodiment, said phosphorus moiety $R_2$ is represented by formula (X), wherein $R_5$ is $C_1$-$C_9$alkyl optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, —NHC(O)$C_1$-$C_3$haloalkyl, $C_1$-$C_3$alkylsulfonyl; and $R_6$ and $R_7$ are independently of each other $C_1$-$C_9$alkyl optionally substituted with cyano, nitro, halogen, $C_2$-$C_6$alkenyl, $C_3$-$C_6$cycloalkyl, $C_1$-$C_3$alkoxy, phenyl optionally substituted with cyano, nitro, halogen, $C_1$-$C_3$ alkyl, $C_1$-$C_3$alkoxy; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein the wavy line indicates the attachment to the oxygen of said $OR_2$ group.

In another very preferred embodiment, said phosphorus moiety $R_2$ is represented by formula (X), wherein said $R_5$ is $C_1$-$C_9$alkyl optionally substituted with cyano, nitro, chlorine, fluorine, bromine, —NHC(O)$C_1$-$C_3$alkyl, —NHC(O)$C_1$-$C_3$haloalkyl; aryl, $C_1$-$C_6$alkylenearyl, $C_1$-$C_6$alkylenediaryl independently of each other optionally substituted with cyano, nitro, chlorine, fluorine, bromine, $C_1$-$C_4$alkoxy, $C_1$-$C_4$haloalkyl.

In another very preferred embodiment, said phosphorus moiety $R_2$ is represented by formula (X), wherein said $R_5$ is $C_1$-$C_3$alkyl optionally substituted with cyano, chlorine, fluorine and bromine; aryl, $C_1$-$C_3$alkylenearyl, $C_1$-$C_3$alkylenediaryl, independently of each other optionally substituted with cyano, nitro, chlorine, fluorine, bromine, $C_1$-$C_2$alkoxy, $C_1$haloalkyl.

In another very preferred embodiment, said phosphorus moiety $R_2$ is represented by formula (X), wherein said $R_5$ is $C_1$-$C_3$alkyl, 2-cyanoethyl, 2,2,2-trichloroethyl, 2,2,2-tribromoethyl, —(CH$_2$)—NHC(O)CF$_3$ wherein n=3-6; phenyl, $C_1$-$C_3$alkylenephenyl, benzhydryl, independently of each other optionally substituted with cyano, nitro, chlorine, fluorine, bromine, $C_1$-$C_2$alkoxy, —CF$_3$.

In another very preferred embodiment, said phosphorus moiety $R_2$ is represented by formula (X), wherein said $R_5$ is methyl, ethyl, 2-cyanoethyl, again preferably 2-cyanoethyl (CH$_2$)$_2$CN).

In another very preferred embodiment, said phosphorus moiety $R_2$ is represented by formula (X), wherein said $R_6$ and $R_7$ are independently of each other $C_1$-$C_3$alkyl or together with the nitrogen atom to which they are attached form a heterocyclic ring, wherein said heterocyclic ring is selected from pyrollidine, piperidine, morpholine, wherein said heterocyclic ring is optionally substituted with $C_1$-$C_3$ alkyl, and wherein again further preferably said heterocyclic ring is optionally substituted with methyl.

In another very preferred embodiment, said phosphorus moiety $R_2$ is represented by formula (X), wherein $R_6$ is equal to $R_7$ and $R_6$ and $R_7$ are iso-propyl or methyl.

In another very preferred embodiment, said phosphorus moiety $R_2$ is represented by formula (X), wherein said $R_5$ is methyl, ethyl, 2-cyanoethyl, preferably 2-cyanoethyl, and wherein $R_6$ is equal to $R_7$ and $R_6$ and $R_7$ are iso-propyl or methyl.

Each alkyl moiety either alone or as part of a larger group such as alkoxy or alkylene is a straight or branched chain and is preferably $C_1$-$C_6$alkyl, more preferably $C_1$-$C_3$alkyl. Examples include methyl, ethyl, n-propyl, prop-2-yl (isopropyl; interchangeably abbreviated herein as iPr or Fri, in particular in the drawn chemical formula), n-butyl, but-2-yl, 2-methyl-prop-1-yl or 2-methyl-prop-2-yl. Examples of an alkoxy include methoxy, ethoxy, propoxy, iso-propoxy, n-butoxy, sec-butoxy, tert-butoxy, n-pentoxy, neo-pentoxy, n-hexoxy. As described herein, alkoxy may include further substituents such as halogen atoms leading to haloalkoxy moieties.

Each alkylene moiety is a straight or branched chain and is, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—.

Each alkenyl moiety either alone or as part of a larger group such as alkenyloxy or alkenylene is a straight or branched chain and is preferably $C_2$-$C_6$alkenyl, more preferably $C_2$-$C_4$alkenyl. Each moiety can be of either the (E)- or (Z)-configuration. Examples include vinyl and allyl. A compound of the present invention comprising an alkenyl moiety thus may include, if applicable, either said compound with said alkenyl moiety in its (E)-configuration, said compound with said alkenyl moiety in its (Z)-configuration and mixtures thereof in any ratio.

Each alkynyl moiety either alone or as part of a larger group such as alkynyloxy is a straight or branched chain and is preferably $C_2$-$C_6$alkynyl, more preferably $C_2$-$C_4$alkynyl. Examples are ethynyl and propargyl.

Halogen is fluorine, chlorine, bromine, or iodine, preferably chlorine. In a preferred embodiment, the halogen substituent is chlorine.

Each haloalkyl moiety either alone or as part of a larger group such as haloalkoxy is an alkyl group substituted by one or more of the same or different halogen atoms. Examples include difluoromethyl, trifluoromethyl, chlorodifluoromethyl and 2,2,2-trifluoro-ethyl.

The term "aryl", as used herein, refers to a monovalent aromatic hydrocarbon radical of 6-14 carbon atoms ($C_6$-$C_{14}$) derived by the removal of one hydrogen atom from a single carbon atom of a parent aromatic ring system as well as said aryl optionally substituted independently with one or more substituents, typically and preferably with one or two substituents as described below. Aryl includes bicyclic radicals comprising an aromatic ring fused to a saturated, partially unsaturated ring, or aromatic carbocyclic or heterocyclic ring. Aryl groups are optionally substituted independently with one or more substituents, typically and preferably with one or two substituents, wherein said substituents are independently at each occurrence selected from $C_1$-$C_4$alkyl, halogen, CF$_3$, OH, $C_1$-$C_3$alkoxy, NR$_{20}$R$_{21}$, $C_6$H$_5$, $C_6$H$_5$ substituted with halogen, $C_1$-$C_3$alkyl, $C_1$-$C_3$alkoxy, NR$_{20}$R$_{21}$, wherein R$_{20}$, R$_{21}$ are independently at each occurrence H, $C_1$-$C_3$alkyl. Typical aryl groups include, but are not limited to, radicals derived from benzene (phenyl), substituted phenyls, naphthalene, anthracene, biphenyl, indenyl, indanyl, 1,2-dihydronapthalene, 1,2,3,4-tetrahydronaphthyl and the like. The term "aryl", as used herein, preferably refers to phenyl optionally substituted with 1 to 3 $R_{22}$, wherein $R_{22}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, $C_3$-$C_6$cycloalkyl, —$NH_2$, $NHCH_3$ or $N(CH_3)_2$.

Where a group is said to be optionally substituted, preferably there are optionally 1-5 substituents, more preferably optionally 1-3 substituents, again more preferably optionally 1 or 2 substituents. Where a group is said to be optionally substituted, and where there are more than one substituents for said optional substitution of said group, said more than one substituents can either be the same or different.

The term "nucleobase", as used herein, and abbreviated as $B_x$, refers to unmodified or naturally occurring nucleobases as well as modified or non-naturally occurring nucleobases and synthetic mimetics thereof. A nucleobase is any heterocyclic base that contains one or more atoms or groups of atoms capable of hydrogen bonding to a heterocyclic base of a nucleic acid.

In one embodiment, the nucleobase is a purine base or a pyrimidine base, wherein preferably said purine base is purine or substituted purine, and said pyrimidine base is pyrimidine or substituted pyrimidine. More preferably, the nucleobase is (i) adenine (A), (ii) cytosine (C), (iii) 5-methylcytosine (MeC), (iv) guanine (G), (v) uracil (U), or (vi) 5-methyluracil (MeU), or to a derivative of (i), (ii), (iii), (iv), (v) or (vi). The terms "derivative of (i), (ii), (iii), (iv), (v) or (vi), and "nucleobase derivative" are used herein interchangeably. Derivatives of (i), (ii), (iii), (iv), (v) or (vi), and nucleobase derivatives, respectively, are known to the skilled person in the art and are described, for example, in Sharma V. K. et al., Med. Chem. Commun., 2014, 5, 1454-1471, and include without limitation 5-hydroxymethyl cytosine, xanthine, hypoxanthine, 2-aminoadenine, alkyl adenine, such as 6-methyl adenine, 2-propyl adenine, alkyl guanine, such as 6-methyl guanine, 2-propyl guanine, 2-thiouracil, 2-thiothymine and 2-thiocytosine, 5-halo uracil, 5-halo cytosine, alkynyl pyrimidine bases, such as 5-propynyl (—C≡C—$CH_3$) uracil, 5-propynyl (—C≡C—$CH_3$) cytosine, 6-azo uracil, 6-azo cytosine, 6-azo thymine, pseudo-uracil, 4-thiouracil; 8-substituted purine bases, such as 8-halo-, 8-amino-, 8-thiol-, 8-thioalkyl-, 8-hydroxyl-adenine or guanine, 5-substituted pyrimidine bases, such as 5-halo-, particularly 5-bromo-, 5-trifluoromethyl-uracil or -cytosine; 7-methylguanine, 7-methyladenine, 2-F-adenine, 2-amino-adenine, 8-azaguanine and 8-azaadenine, 7-deazaguanine, 7-deazaadenine, 3-deazaguanine, 3-deazaadenine, hydrophobic bases, promiscuous bases, size-expanded bases, or fluorinated bases. In certain embodiments, the nucleobase includes without limitation tricyclic pyrimidines, such as 1,3-diazaphenoxazine-2-one, 1,3-diazaphenothiazine-2-one or 9-(2-aminoethoxy)-1,3-diazaphenoxazine-2-one (G-clamp). The term "nucleobase derivative" also includes those in which the purine or pyrimidine base is replaced by other heterocycles, for example 7-deaza-adenine, 7-deazaguanosine, 2-aminopyridine or 2-pyridone. Further nucleobases of the invention include without limitation those known to skilled artisan (e.g. U.S. Pat. No. 3,687,808; Swayze et al., The Medicinal Chemistry of Oligonucleotides, in Antisense a Drug Technology, Chapter 6, pp. 143-182 (Crooke, S. T., ed., 2008); The Concise Encyclopedia Of Polymer Science And Engineering, Kroschwitz, J. I., Ed., John Wiley & Sons, 1990, pp. 858-859; Englisch et al., Angewandte Chemie, International Edition, 1991, Vol. 30 (6), pp. 613-623; Sanghvi, Y. S., Antisense Research and Applications, Crooke, S. T. and Lebleu, B., Eds., CRC Press, 1993, pp. 273-302).

Preferred nucleobase derivatives include methylated adenine, guanine, uracil and cytosine and nucleobase derivatives, preferably of (i), (ii), (iii) or (iv), wherein the respective amino groups, preferably the exocyclic amino groups, are protected by acyl protecting groups or dialkylformamidino, preferably dimethylformamidino (DMF), and further include nucleobase derivatives such as 2-fluorouracil, 2-fluorocytosine, 5-bromouracil, 5-iodouracil, 2,6-diaminopurine, azacytosine and pyrimidine analogs such as pseudoisocytosine and pseudouracil.

In a further preferred embodiment, said nucleobase derivative is selected from methylated adenine, methylated guanine, methylated uracil and methylated cytosine, and from a nucleobase derivative of (i), (ii), (iii) or (iv), wherein the respective amino groups, preferably the exocyclic amino groups, are protected by a protecting group.

In a further preferred embodiment, said nucleobase derivative is selected from methylated adenine, methylated guanine, methylated uracil and methylated cytosine, and from a nucleobase derivative of (i), (ii), (iii) or (iv), wherein the respective amino groups, preferably the exocyclic amino groups, are protected by acyl protecting groups or dialkylformamidino, preferably dimethylformamidino (DMF).

In a further preferred embodiment, said nucleobase derivative is selected from a nucleobase derivative of (i), (ii), (iii) or (iv), wherein the respective amino groups, preferably the exocyclic amino groups, are protected by a protecting group.

In a further preferred embodiment, said nucleobase derivative is a nucleobase derivative of (i), (ii), (iii) or (iv), wherein the exocyclic amino groups, are protected by acyl protecting groups or dialkylformamidino, preferably dimethylformamidino (DMF).

In a further very preferred embodiment, said acyl protecting group of said exocyclic amino group of said nucleobase derivative of (i), (ii), (iii) or (iv) is —C(O)—$R_{11}$, wherein independently of each other $R_{11}$ is selected from $C_1$-$C_{10}$alkyl, $C_6$-$C_{10}$aryl, $C_6$-$C_{10}$aryl$C_1$-$C_{10}$alkylene, or $C_6$-$C_{10}$aryloxy$C_1$-$C_{10}$alkylene and wherein said dialkylformamidino protecting group is =C(H)—$NR_{12}R_{13}$, wherein $R_{12}$ and $R_{13}$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—$R_{14}$, wherein independently of each other $R_{14}$ is selected from $C_1$-$C_4$alkyl; phenyl; phenyl substituted with halogen, $C_1$-$C_6$alkyl, $C_3$-$C_6$cycloalkyl, $C_1$-$C_4$alkoxy; benzyl; benzyl substituted with halogen, $C_1$-$C_6$alkyl, $C_3$-$C_6$cycloalkyl, $C_1$-$C_4$alkoxy; or phenyloxy$C_1$-$C_2$alkylene optionally substituted with halogen, $C_1$-$C_6$alkyl, $C_1$-$C_4$alkoxy; and wherein said dialkylformamidino protecting group is =C(H)—$NR_{12}R_{13}$, wherein $R_{12}$ and $R_{13}$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—$R_{15}$, wherein independently of each other $R_{15}$ is selected from $C_1$-$C_4$alkyl; phenyl; phenyl substituted with halogen, $C_1$-$C_4$alkyl, $C_5$-$C_6$cycloalkyl, $C_1$-$C_4$alkoxy; benzyl; benzyl substituted with halogen, $C_1$-$C_4$alkyl, $C_1$-$C_4$alkoxy; or phenyloxymethylene ($CH_2$—$OC_6H_5$) wherein the phenyl is optionally substituted with halogen, $C_1$-$C_4$alkyl, $C_5$-$C_6$cycloalkyl, $C_1$-$C_4$alkoxy; and wherein said dialkylformamidino protecting group is =C(H)—NR$_{12}$R$_{13}$, wherein R$_{12}$ and R$_{13}$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—R$_{16}$, wherein independently of each other R$_{16}$ is selected from $C_1$-$C_3$alkyl; phenyl; phenyl substituted with $C_1$-$C_3$alkyl, methoxy; benzyl; benzyl substituted with $C_1$-$C_3$alkyl, methoxy; or phenyloxymethylene (CH$_2$—OC$_6$H$_5$) wherein the C$_6$H$_5$ is optionally substituted with $C_1$-$C_3$alkyl, methoxy; and wherein said dialkylformamidino protecting group is =C(H)—NR$_{12}$R$_{13}$, wherein Rig and R$_{13}$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—R$_{17}$, wherein independently of each other R$_{17}$ is selected from $C_1$-$C_3$alkyl; phenyl; phenyl substituted with $C_1$-$C_3$alkyl, methoxy; benzyl; benzyl substituted with $C_1$-$C_3$alkyl, methoxy; or phenyloxymethylene (CH$_2$—OC$_6$H$_5$) wherein the C$_6$H$_5$ is optionally substituted with $C_1$-$C_3$alkyl, methoxy; and wherein said dialkylformamidino protecting group is dimethylformamidino (DMF).

In a further very preferred embodiment, said acyl protecting group of said exocyclic amino group of said nucleobase derivative of (i), (ii), (iii) or (iv) is —C(O)—R$_{18}$, wherein independently of each other Rig is selected from methyl, iso-propyl, phenyl, benzyl, or phenyloxymethylene (CH$_2$—OC$_6$H$_5$) wherein the C$_6$H$_5$ is optionally substituted with $C_1$-$C_3$alkyl, methoxy; and wherein said dialkylformamidino protecting group is dimethylformamidino (DMF).

In a further very preferred embodiment, said acyl protecting group of said exocyclic amino group of said nucleobase derivative of (i), (ii), (iii) or (iv) is —C(O)—R$_{19}$, wherein independently of each other Rig is selected from methyl, iso-propyl, phenyl, benzyl, or phenyloxymethylene (CH$_2$—OC$_6$H$_5$) wherein the C$_6$H$_5$ is optionally substituted with methyl, iso-propyl; and wherein said dialkylformamidino protecting group is dimethylformamidino (DMF).

The term "dialkylformamidino", as used herein refers to =C(H)—NR$_{12}$R$_{13}$, wherein R$_{12}$ and R$_{13}$ are independently of each other selected from $C_1$-$C_4$alkyl. In preferred embodiments, said dialkylformamidino is a protecting group of said exocyclic amino group of said nucleobase derivative of (i), (ii), (iii) or (iv). The resulting compounds may be of either the (E)- or (Z)-configuration and both forms, and mixtures thereof in any ratio, should be included within the scope of the present invention. In a preferred embodiment the inventive compounds comprise the dialkylformamidino, preferably dimethylformamidino (DMF), in the (Z) configuration.

According to one embodiment, Bx is selected from uracil, thymine, cytosine, 5-methylcytosine, adenine and guanine. Preferably, Bx is selected from thymine, 5-methylcytosine, adenine and guanine. According to one embodiment, Bx is an aromatic heterocyclic moiety capable of forming base pairs when incorporated into DNA or RNA oligomers in lieu of the bases uracil, thymine, cytosine, 5-methylcytosine, adenine and guanine.

The term "nucleosidic linkage group", as used herein, refers to any linkage group known in the art that is able to link, preferably links, said inventive compound of formula (IV), (V) or (VI) to a further compound, preferably to a nucleosidic compound including a further inventive compound of formula (IV), (V) or (VI), within the oligomers in accordance with the present invention. Representative patents that teach such possible linkage groups are without limitation U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608. Said further compound is selected from a nucleosidic compound or a non-nucleosidic compound. Said nucleosidic compound includes without limitation, and is typically and preferably selected from, at least one (i) nucleoside, (ii) nucleotide, (iii) oligonucleotide or (iv) modifications of (i), (ii) or (iii). Said non-nucleosidic compound includes, and is typically and preferably selected from, a peptide, protein, silicate compounds or even a solid support. The solid support includes without a limitation surfaces, beads, glass supports, polymers or resins. In a preferred embodiment, the glass is controlled-pore glass, preferably with 500 Å, 1000 Å or 2000 Å pores. The beads include without limitation glass beads, preferably controlled-pore glass, or magnetic beads. The polymer includes without limitation polystyrenes including for example divinylbenzene, styrene, and chloromethylstyrene. In a preferred embodiment, the solid support are highly cross-linked polystyrene beads.

The term "nucleosidic linkage group" includes phosphorus linkage groups and non-phosphorus linkage groups. Non-phosphorus linkage groups do not contain a phosphorus atom and examples of non-phosphorus linkage groups include, and is typically and preferably selected from, alkyl, aryl, preferably, phenyl, benzyl, or benzoyl, cycloalkyl, alkylenearyl, alkylenediaryl, alkoxy, alkoxyalkylene, alkylsulfonyl, alkyne, ether, each independently of each other optionally substituted with cyano, nitro, halogen; carboxyl, amide, amine, amino, imine, thiol, sulfide, sulfoxide, sulfone, sulfamate, sulfonate, sulfonamide, siloxane or mixtures thereof. In a preferred embodiment, the non-phosphorus linkage group is amino propyl, long chain alkyl amine group, inyl, acetylamide, aminomethyl, formacetal, thioformacetal, thioformacetyl, riboacetyl, methyleneimino, methylenehydrazino or a neutral non-ionic nucleoside linkage group, such as amide-3 (3'-CH$_2$—C(=O)—N(H)-5') or amide-4 (3'-CH$_2$—N(H)—C(=O)-5'). In a preferred embodiment, the non-phosphorus linkage group includes a compound selected from alkyl, aryl, preferably phenyl, benzyl, or benzoyl, cycloalkyl, alkylenearyl, alkylenediaryl, alkoxy, alkoxyalkylene, alkylsulfonyl, alkyne, or ether, wherein the compound includes $C_1$-$C_9$, $C_1$-$C_6$, or $C_1$-$C_4$.

In a preferred embodiment, said nucleosidic linkage group is a phosphorus linkage group, and said phosphorus linkage group refers to a moiety comprising a phosphorus atom in the P$^{III}$ or P$^V$ valence state represented by formula (XI):

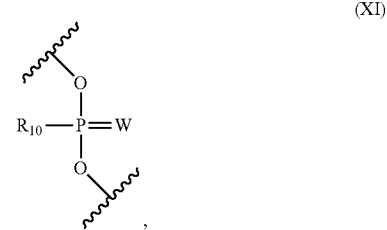

(XI)

wherein

W represents O, S, Se or an electron pair; preferably W represents O or S;

$R_{10}$ is H, halogen, OH, $OR_5$, $NR_6R_7$, SH, $SR_8$, $C_1$-$C_6$alkyl, $C_1$-$C_6$haloalkyl, $C_1$-$C_6$alkoxy, $C_1$-$C_6$haloalkoxy, $C_1$-$C_6$aminoalkyl; wherein $R_5$ is $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl, each independently of each other optionally substituted with cyano, nitro, halogen, $C_1$-$C_4$alkoxy, $C_1$-$C_4$haloalkyl, $C_1$-$C_4$haloalkoxy, NHC(O)$C_1$-$C_3$alkyl, NHC(O)$C_1$-$C_3$haloalkyl, $C_1$-$C_3$alkylsulfonyl; acetyl; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy; aryl optionally substituted with cyano, nitro, halogen, $C_1$-$C_3$alkyl, $C_1$-$C_3$alkoxy; an amino protecting group; or together with the nitrogen atom to which they are attached form a heterocyclic ring, wherein preferably said heterocyclic ring is selected from pyrollidinyl, piperidinyl, morpholinyl, piperazinyl and homopiperazine, wherein said heterocyclic ring is optionally substituted with $C_1$-$C_3$ alkyl; and wherein $R_8$ is a thiol protecting group; and wherein each of the wavy lines indicates the attachment of said phosphorus linkage group of formula (XI) to a further compound, preferably to a nucleosidic compound including a further inventive compound of formula (IV), (V) or (VI), within the oligomers in accordance with the present invention. When W represents O, S or Se then said P atom within said phosphorus moiety is in its $P^V$ valence state. When W represents an electron pair then said P atom within said phosphorus moiety is in its $P^{III}$ valence. The moiety of formula (XI) includes any possible stereoisomer. Further included in said moieties represented by formula (XI) are salts thereof, wherein typically and preferably said salts are formed upon treatment with inorganic bases or amines, and are typically and preferably salts derived from reaction with the OH or SH groups being (independently of each other) said $R_{10}$. Preferred inorganic bases or amines leading to said salt formation with the OH or SH groups are well known in the art and are typically and preferably trimethylamine, diethylamine, methylamine or ammonium hydroxide. These phosphorus moieties included in the present invention are, if appropriate, also abbreviated as "O$^-$HB$^+$", wherein said HB$^+$ refers to the counter cation formed.

In a preferred embodiment, in the phosphorus linkage group of formula (XI), $R_6$ and $R_7$ are independently of each other hydrogen, $C_1$-$C_6$alkyl optionally substituted with cyano, nitro, halogen, $C_2$-$C_6$alkenyl; aryl optionally substituted with cyano, nitro, halogen, $C_1$-$C_3$ alkyl; or an amino protecting group.

In a preferred embodiment, in the phosphorus linkage group of formula (XI), W represents O or S; $R_{10}$ is H, OH, $OR_5$, $NR_6R_7$, $C_1$-$C_6$alkyl, $C_1$-$C_6$alkyl, $C_1$-$C_6$haloalkyl, $C_1$-$C_6$alkoxy, $C_1$-$C_6$haloalkoxy, $C_1$-$C_6$aminoalkyl; wherein $R_5$ is $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; acetyl; or a hydroxyl protecting group; wherein $R_6$ and $R_7$ are independently of each other hydrogen, $C_1$-$C_6$alkyl optionally substituted with cyano, nitro, halogen, $C_2$-$C_6$alkenyl, $C_3$-$C_6$cycloalkyl, $C_1$-$C_3$alkoxy; aryl optionally substituted with cyano, nitro, halogen, $C_1$-$C_3$ alkyl, $C_1$-$C_3$alkoxy; an amino protecting group; and wherein $R_8$ is a thiol protecting group.

In further preferred embodiment, said nucleosidic linkage group is a phosphorus linkage group, and said phosphorus linkage group is selected from a phosphodiester linkage group, a phosphotriester linkage group, a phosphorothioate linkage group, a phosphorodithioate linkage group, a phosphonate linkage group, preferably a H-phosphonate linkage group or a methylphosphonate linkage group; a phosphonothioate linkage group, preferably a H-phosphonothioate linkage group, a methyl phosphonothioate linkage group; a phosphinate linkage group, a phosphorthioamidate linkage, a phosphoramidate linkage group, or a phosphite linkage group. In another very preferred embodiment, said nucleosidic linkage group is a phosphorus linkage group, and wherein said phosphorus linkage group is selected from a phosphodiester linkage group, a phosphotriester linkage group, a phosphorothioate linkage group, or a phosphonate linkage group, wherein the phosphonate is preferably a H-phosphonate linkage group or methylphosphonate linkage group.

In another very preferred embodiment, said nucleosidic linkage group is a phosphorus linkage group, and wherein said phosphorus linkage group is a phosphodiester linkage group. In another very preferred embodiment, said nucleosidic linkage group is a phosphorus linkage group, and wherein said phosphorus linkage group is a phosphorothioate linkage group.

In a preferred embodiment, the phosphorus linkage group is selected from an alkyl phosphodiester linkage group, an alkylene phosphodiester linkage group, a thionoalkyl phosphodiester linkage group or an aminoalkyl phosphodiester linkage group, an alkyl phosphotriester linkage group, an alkylene phosphotriester linkage group, a thionoalkyl phosphotriester linkage group or an aminoalkyl phosphotriester linkage group, an alkyl phosphonate linkage group, an alkylene phosphonate linkage group, an aminoalkyl phosphonate linkage group, a thionoalkyl phosphonate linkage group or a chiral phosphonate linkage group. More preferably, said nucleosidic linkage group is a phosphorus linkage group, and wherein said phosphorus linkage group is a is a phosphodiester linkage group —O—P(=O)(OH)O— or —O—P(=O)(O$^-$)O— with [HB$^+$] as counterion, a phosphorothioate —O—P(=S)(OH)O— or —O—P(=S)(O$^-$)O— with [HB$^+$] as counterion, a methylphosphonate —O—P(=O)(CH$_3$)O—. Various salts, mixed salts and free acid forms of the phosphorus linkage group are included.

In a further embodiment, said nucleosidic linkage group links a nucleoside, nucleotide or oligonucleotide with a further nucleoside, nucleotide or oligonucleotide.

The wavy line within formulas (I) and (IV) symbolizing the bond between the Bx and and the bicyclic core of the inventive compounds indicates that any spatial orientation of the nucleobase Bx are covered by formula (I) or (IV). That means that formulas (I) and (IV) cover either the alpha or the beta conformation or any mixture of alpha and beta anomers of the inventive compounds.

As used herein, the term "nucleoside" refers to a compound comprising a nucleobase and a sugar covalently linked to said nucleobase. The term "nucleotide", as used herein, refers to a nucleoside further comprising a nucleosidic linkage group or phosphorus moiety, wherein said nucleosidic linkage group or said phosphorus moiety is covalently linked to the sugar of said nucleoside.

As used herein the term "nucleoside" or "nucleotide" is meant to include all manner of naturally occurring or modified nucleosides or nucleoside mimetics, or naturally occurring or modified nucleotides or nucleotide mimetics, respectively, that can be incorporated into an oligomer using natural or chemical oligomer synthesis. Typically and preferably, the term "nucleoside", as used herein, refers to a naturally occurring nucleoside, a modified nucleoside or nucleoside mimetic. Typically and preferably, the term "nucleotide", as used herein, refers to a naturally occurring nucleotide, a modified nucleotide or nucleotide mimetic.

The term "modified nucleosides" is intended to include modifications made to the sugar and/or nucleobase of a nucleoside as known to the skilled person in the art and described herein. The term "modified nucleotides" is intended to include modifications made to the sugar and/or nucleobase and/or nucleosidic linkage group or phosphorus moiety of a nucleotide as known to the skilled person in the art and described herein.

The term "nucleoside mimetic" is intended to include those structures used to replace the sugar and the nucleobase. Examples of nucleoside mimetics include nucleosides wherein the nucleobase is replaced with a phenoxazine moiety (for example the 9-(2-aminoethoxy)-1,3-diazaphenoxazine-2-one group) and the sugar moiety is replaced a cyclohexenyl or a bicyclo[3.1.0]hexyl moiety. The term "nucleotide mimetic" as used herein is meant to include nucleotides used to replace the sugar and the nucleosidic linkage group. Examples of nucleotide mimetics include peptide nucleic acids (PNA) or morpholinos.

The term "nucleoside" or "nucleotide" also includes combinations of modifications, such as more than one nucleobase modification, more than one sugar modification or at least one nucleobase and at least one sugar modification.

The sugar of the nucleoside or nucleotide includes without limitation a monocyclic, bicyclic or tricyclic ring system, preferably a tricyclic or bicyclic system or a monocyclic ribose or de(s)oxyribose. Modifications of the sugar further include but are not limited to modified stereochemical configurations, at least one substitution of a group or at least one deletion of a group. A modified sugar is typically and preferably a modified version of the ribosyl moiety as naturally occurring in RNA and DNA (i.e. the furanosyl moiety), such as bicyclic sugars, tetrahydropyrans, 2'-modified sugars, 3'-modified sugars, 4'-modified sugars, 5'-modified sugars, or 4'-substituted sugars. Examples of suitable sugar modifications are known to the skilled person and include, but are not limited to 2', 3' and/or 4' substituted nucleosides (e.g. 4'-S-modified nucleosides); 2'-O-modified RNA nucleotide residues, such as 2'-O-alkyl or 2'-O-(substituted)alkyl e.g. 2'-O-methyl, 2'-O-(2-cyanoethyl), 2'-O-(2-methoxy)ethyl (2'-MOE), 2'-O-(2-thiomethyl)ethyl; 2'-O-(haloalkoxy)methyl e.g. 2'-O-(2-chloroethoxy)methyl (MCEM), 2'-O-(2,2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DMCE), in particular a 2'-O-methyl modification or a 2'-O-methoxyethyl (2'-O-MOE); or other modified sugar moieties, such as morpholino (PMO), cationic morpholino (PMOPlus) or a modified morpholino group, such as PMO-X. The term "PMO-X" refers to a modified morpholino group comprising at least one 3' or 5' terminal modification, such 3'-fluorescent tag, 3' quencher (e.g. 3'-carboxyfluorescein, 3'-Gene Tools Blue, 3'-lissamine, 3'-dabcyl), 3'-affinity tag and functional groups for chemical linkage (e.g. 3'-biotin, 3'-primary amine, 3'-disulfide amide, 3'-pyridyl dithio), 5'-end modifications (5'-primary amine, 5'-dabcyl), 3'-azide, 3'-alkyne, 5'-azide, 5'-alkyne, or as disclosed in WO2011/150408 and US2012/0065169.

"Bicylic sugar moieties" comprise two interconnected ring systems, e.g. bicyclic nucleosides wherein the sugar moiety has a 2'-O—CH(alkyl)-4' or 2'-O—CH2-4' group, locked nucleic acid (LNA), xylo-LNA, alpha-L-LNA, beta-D-LNA, cEt (2'-O,4'-C constrained ethyl) LNA, cMOEt (2'-O,4'-C constrained methoxyethyl) LNA, ethylene-bridged nucleic acid (ENA), hexitol nucleic acid (HNA), fluorinated HNA (F-HNA), pyranosyl-RNA (p-RNA), or 3'-deoxypyranosyl-DNA (p-DNA). Alternatively, the sugar of the nucleoside or nucleotide includes a tricyclic sugar moiety as, for example, described in WO 2013/135900 and WO 2014/140348.

The term "oligomer", as used herein, refers to a compound comprising two or more monomer subunits linked by nucleosidic linkage groups, wherein at least one of said two or more monomer subunits is a compound of the formula (IV), preferably a compound of the formula (V) or a compound of the formula (VI). In a preferred embodiment, the oligomer comprises at least one compound of formula (IV), (V) or (VI) and at least one ribonucleotide or deoxyribonucleotide. More preferably, the oligomer comprises at least one compound of formula (IV), (V) or (VI) and at least one deoxyribonucleotide.

The term "monomer subunit", as used herein, is meant to include all manner of monomer units that are amenable to oligomer synthesis including, and typically and preferably referring to, monomer subunits such as α-D-ribonucleosides, β-D-ribonucleosides, α-D-2'-deoxyribnucleosides, β-D-2'-deoxyribnucleosides, naturally occurring nucleosides, naturally occurring nucleotides, modified nucleosides, modified nucleotides, mimetics of nucleosides, mimetics of nucleotides, and the inventive compounds provided herein including any compounds of any one of the formulas (I) to (VI).

In a preferred embodiment, the oligomer is an oligonucleotide. The term "oligonucleotide", as used herein, refers to a compound comprising at least two nucleosides linked to each other each by a nucleosidic linkage group. Thus, the term "oligonucleotide", as used herein, includes, and typically and preferably refer to, compounds comprising at least two nucleosides linked by nucleosidic linkage groups, wherein said at least two nucleosides are independently selected from naturally occurring nucleosides, modified nucleosides or nucleoside mimetics. Thus, the term "oligonucleotide", as used herein, includes compounds comprising naturally occurring nucleotides, modified nucleotides or nucleotide mimetics and, thus, the term "oligonucleotide", as used herein, includes oligonucleotides with modifications made to the sugar and/or nucleobase and/or nucleosidic linkage group as known to the skilled person in the art and described herein.

The oligomer can be single stranded or double stranded. In one embodiment, the oligomer is double stranded (i.e. a duplex). In a preferred embodiment, the oligomer is single stranded.

In a preferred embodiment the oligomer is coupled to a non-nucleosidic compound, preferably a solid support. The solid support is preferably selected from beads, polymers or resin. In a certain embodiment, the oligomer has a length of up to 40 monomer subunits, preferably up to 30 monomer subunits, more preferably up to 30 monomer subunits, again more preferably up to 20 monomer subunits or up to 15 monomer subunits. In a further embodiment, said oligomer comprises from 5 to 40 monomeric subunits, preferably from 8 to 30 monomer subunits, more preferably from 8 to 25 monomer subunits, again more preferably from 8 to 20 monomer subunits.

In certain embodiments, the oligomer as provided herein is modified by covalent attachment of one or more terminal groups to the 5' or 7' terminus of the oligomer. A terminal group can also be attached at any of the termini of the oligomer.

The term "terminus" refers to the end or terminus of the oligomer, nucleic acid sequence or the compound of formula (IV), (V) or (VI), wherein the integer (3', 5' or 7' etc.) indicates to the carbon atom of the sugar included in the nucleoside of the oligomer, nucleic acid sequence or the compound of formula (IV), (V) or (VI). The term "5' terminal group" or "7' terminal group", as used herein, refers to a group located at the 5' terminus or 7' terminus, respectively, of the sugar included in the compound of formula (IV), (V) or (VI). Examples of the "5' terminal group" or "7' terminal group" include without limitation a capping group, diphosphate, triphosphate, label, such as a fluorescent label (e.g. fluorescein or rhodamine), dye, reporter group suitable for tracking the oligomer, solid support, non-nucleosidic group, antibody or conjugate group. Preferably a "5' terminal group" or "7' terminal group" is selected from a diphosphate, triphosphate, fluorescent label, dye, reporter group that can track the oligomer, solid support, non-nucleosidic group, antibody or conjugate group.

In certain embodiments, the oligomer as provided herein or the compound of formula (IV), (V) or (VI) is modified by covalent attachment of one or more conjugate groups. In general, conjugate groups modify one or more properties of the compound they are attached to. Such properties include without limitation, nuclease stability, binding affinity, pharmacodynamics, pharmacokinetics, binding, absorption, cellular distribution, cellular uptake, delivery, charge and clearance. Conjugate groups are routinely used in the chemical arts and are linked directly or via an optional linkage group to a parent compound such as an oligomer. The term "conjugate group" includes without limitation, and refers preferably to intercalators, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, lipophilic moieties, or coumarins.

The term "nucleic acid" or "nucleic acid sequence", as interchangeably used herein, is understood as oligomeric or polymeric molecule comprising at least two interlinked nucleotides or at least two nucleosides linked by a nucleosidic linkage group. In the context of the present invention, the nucleic acid includes ribonucleic acid (RNA) and deoxyribonucleic acid (DNA) and is preferably selected from naturally occurring RNA, naturally occurring DNA, modified DNA, modified RNA, mixtures thereof, such as RNA-DNA hybrids. The modification may comprise the backbone such as the nucleosidic linkage group and/or the nucleoside and/or the sugar as further described herein. The nucleic acids can be synthesized chemically or enzymatically by polymerases.

The term "natural" or "naturally occurring", as interchangeably used herein, refers to compounds that are of natural origin.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McRaw-Hiff Dictionary of Chemical Terms* (1984), McGraw-Hill Book Company, N.Y. and Eliel, E. and Wilen, S., "Stereochemistry of Organic Compounds", John Wiley & Sons, Inc., New York, 1994.

As used herein, "$T_m$" (melting temperature) is the temperature at which two strands of a duplex nucleic acid separate. The $T_m$ is often used as a measure of duplex stability of an antisense compound toward a complementary nucleic acid.

In a first aspect, the present invention provides a compound of formula (I):

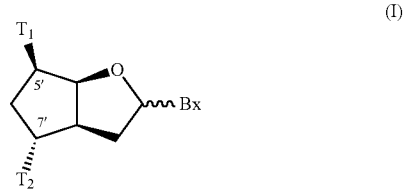

(I)

wherein one of $T_1$ and $T_2$ is $OR_1$ or $OR_2$;

and the other of $T_1$ and $T_2$ is $OR_1$ or $OR_2$; wherein $R_1$ is H or a hydroxyl protecting group, and $R_2$ is a phosphorus moiety; and wherein Bx is a nucleobase.

In a preferred embodiment, said compound of formula (I) of the invention is a compound of formula (II)

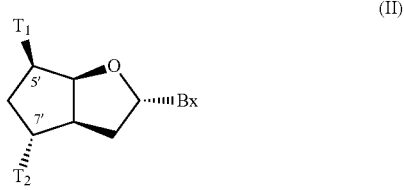

(II)

wherein (i) $T_1$ is $OR_1$, and $T_2$ is $OR_1$ or $OR_2$; or (ii) $T_1$ is $OR_1$ or $OR_2$, $T_2$ is $OR_1$:

wherein preferably $T_1$ is $OR_1$ or $OR_2$, $T_2$ is $OR_1$.

The compound of formula (II) is an alpha anomer or an alpha anomeric monomer that differs from the beta anomer in the spatial configuration of Bx at the chiral center of the first carbon at the 1' terminus.

In another preferred embodiment, said compound of formula (I) is a compound of formula (III)

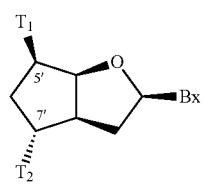

(III)

wherein
(i) T₁ is OR₁, and T₂ is OR₁ or OR₂; or
(ii) T₁ is OR₁ or OR₂, T₂ is OR₁:
wherein preferably T₁ is OR₁, and T₂ is OR₁ or OR₂.

The compound of formula (III) is a beta anomer or a beta anomeric monomer that differs from the alpha anomer in the spatial configuration of Bx at the chiral center of the first carbon at the 1' terminus.

In another preferred embodiment, in the compound of formula (I), said phosphorus moiety $R_2$ is selected from a phosphate moiety, a phosphoramidate moiety and a phosphoramidite moiety. In another preferred embodiment, in the compound of formula (II) said phosphorus moiety $R_2$ is selected from a phosphate moiety, a phosphoramidate moiety and a phosphoramidite moiety. In another preferred embodiment, in the compound of formula (III) said phosphorus moiety $R_2$ is selected from a phosphate moiety, a phosphoramidate moiety and a phosphoramidite moiety.

In another preferred embodiment, in the compound of formula (I), (II) or (III) said Bx is selected from a purine base or pyrimidine base, wherein preferably Bx is selected from (i) adenine (A), (ii) cytosine (C), (iii) 5-methylcytosine (MeC), (iv) guanine (G), (v) uracil (U), or (vi) 5-methyluracil (MeU), or a derivative of (i), (ii), (iii), (iv), (v) or (vi), and wherein further preferably Bx is selected from uracil, thymine, cytosine, 5-methylcytosine, adenine or guanine. Again more preferably, in the compound of formula (I), (II) or (III), Bx is selected from thymine, 5-methylcytosine, adenine or guanine.

In another preferred embodiment, the compound of formula (I), (II) or (III) is linked to a non-nucleosidic compound, preferably a solid-phase.

In a preferred embodiment, the compound of formula (I) is selected from:

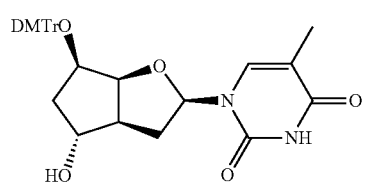

11

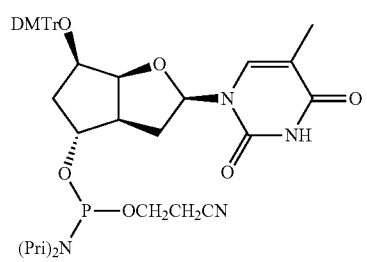

12

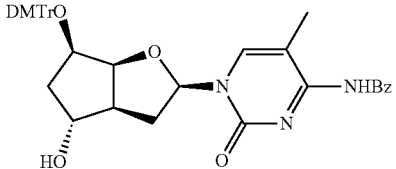

13

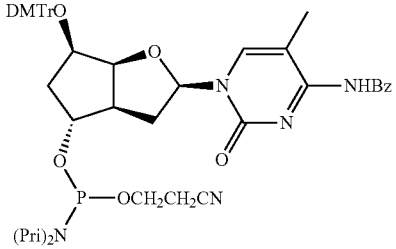

14

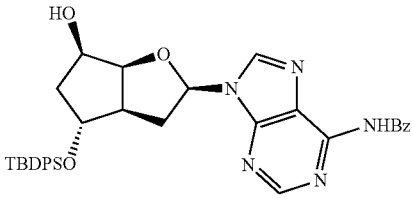

16

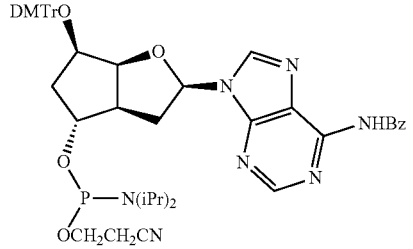

19

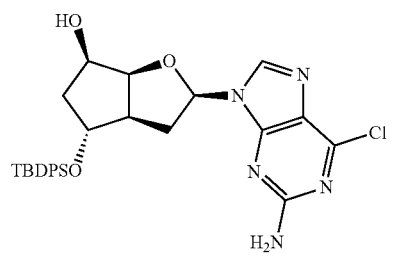

21

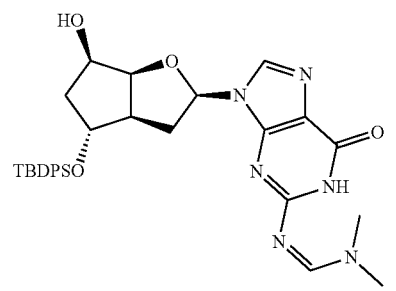

22

27
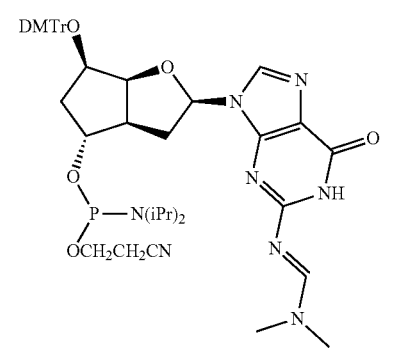
38
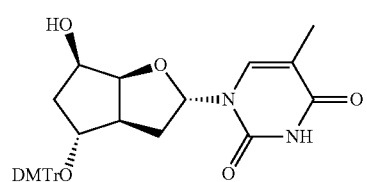
39
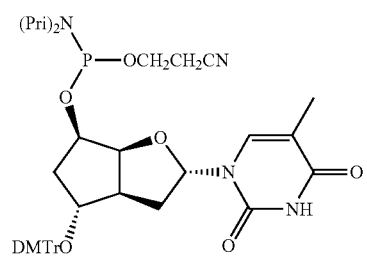
40
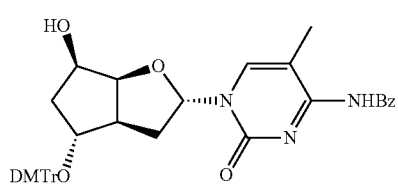
41
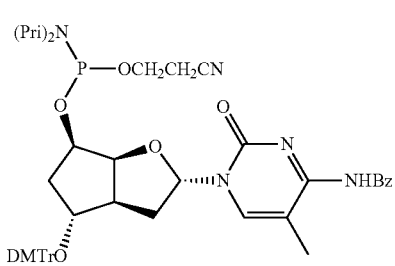
42
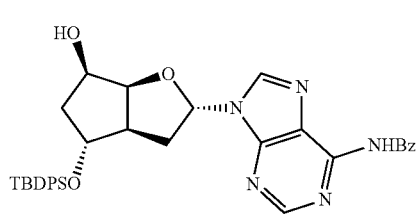
47
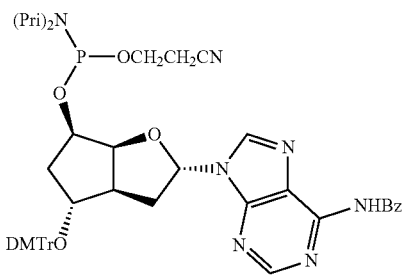
48
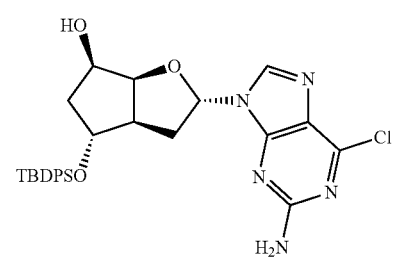
49
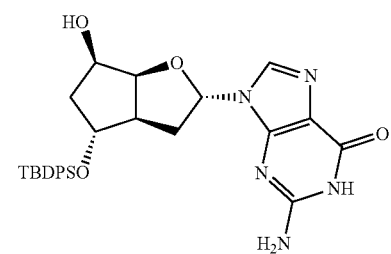
54
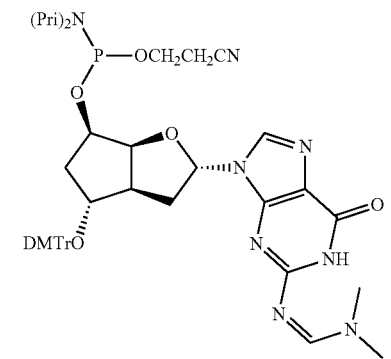
56
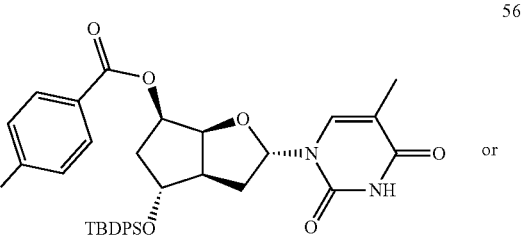
or
57
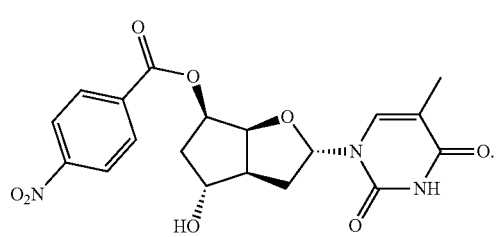

In a second aspect, the invention provides an oligomer comprising at least one compound of formula (IV)

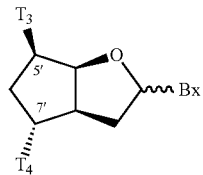

(IV)

wherein independently for each of said at least one compound of formula (IV)
one of $T_3$ or $T_4$ is a nucleosidic linkage group;
the other of $T_3$ and $T_4$ is $OR_1$, $OR_2$, a 5' terminal group, a 7' terminal group or a nucleosidic linkage group, wherein $R_1$ is H or a hydroxyl protecting group, and $R_2$ is a phosphorus moiety; and Bx is a nucleobase.

In a preferred embodiment, the oligomer of the invention comprises at least one compound of formula (IV), wherein said compound of formula (IV) is a compound of formula (V):

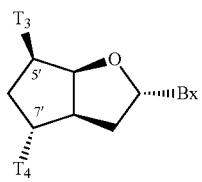

(V)

wherein
(i) $T_3$ is a nucleosidic linkage group, and $T_4$ is a 7' terminal group, $OR_1$, or $OR_2$, preferably $T_4$ is a 7' terminal group or $OR_1$; or
(ii) $T_3$ is a 5' terminal group, $OR_1$, or $OR_2$, preferably $T_3$ is a 5' terminal group or $OR_2$; and $T_4$ is a nucleosidic linkage group; or
(iii) $T_3$ and $T_4$ are independently of each other a nucleosidic linkage group.

In another preferred embodiment, the oligomer of the invention comprises at least one compound of formula (IV), wherein said compound of formula (IV) is a compound of formula (VI):

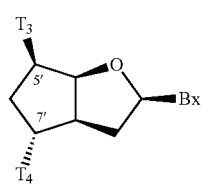

(VI)

wherein
(i) $T_3$ is a nucleosidic linkage group, and $T_4$ is a 7' terminal group, $OR_1$, or $OR_2$, preferably $T_4$ is a 7' terminal group or $OR_2$; or
(ii) $T_3$ is a 5' terminal group, $OR_1$, or $OR_2$, preferably $T_3$ is a 5' terminal group or $OR_1$; and $T_4$ is a nucleosidic linkage group; or
(iii) $T_3$ and $T_4$ are independently of each other a nucleosidic linkage group.

In a preferred embodiment, said oligomer is an oligonucleotide. In a further preferred embodiment, said oligomer is an oligonucleotide, wherein said compound of formula (IV) is a compound of formula (V). In another preferred embodiment, said oligomer is an oligonucleotide, wherein said compound of formula (IV) is a compound of formula (VI). In a more preferred embodiment, the oligomer comprising said least one compound of formula (IV), (V) or (VI) is a DNA.

In another embodiment, the inventive oligomer comprising said least one compound of formula (IV), (V) or (VI) further comprises at least one nucleotide that is different from any one of the compound of formula (IV), (V) or (VI), wherein preferably the at least one different nucleotide is (i) a nucleotide comprising a monocyclic sugar, i.e. a monocyclic nucleotide, or (ii) a nucleotide comprising a bicyclic sugar, i.e. a bicyclic nucleotide, or (iii) a nucleotide comprising a tricyclic sugar, i.e. a tricyclic nucleotide. Preferably, said at least one nucleotide that is different from the compound of formula (IV), (V) or (VI) is a nucleotide comprising a bicyclic sugar. Preferably, said at least one nucleotide that is different from the compound of formula (IV), (V) or (VI) is a nucleotide comprising a tricyclic sugar. More preferably, said at least one nucleotide that is different from the compound of formula (IV), (V) or (VI) is a nucleotide comprising a monocyclic sugar.

In another preferred embodiment of the inventive oligomer, said compound of formula (IV) is a compound of formula (V), and said oligomer further comprises at least one nucleotide that is different from the compound of formula (V), wherein preferably the at least one different nucleotide is (i) a nucleotide comprising a monocyclic sugar, i.e. a monocyclic nucleotide, or (ii) a nucleotide comprising a bicyclic sugar, i.e. a bicyclic nucleotide, or (iii) a nucleotide comprising a tricyclic sugar, i.e. a tricyclic nucleotide. Preferably, said at least one nucleotide that is different from the compound of formula (V) is a nucleotide comprising a bicyclic sugar. Preferably, said at least one nucleotide that is different from the compound of formula (V) is a nucleotide comprising a tricyclic sugar. More preferably, said at least one nucleotide that is different from the compound of formula (V) is a nucleotide comprising a monocyclic sugar.

In another preferred embodiment of the inventive oligomer, said compound of formula (IV) is a compound of formula (VI), and said oligomer further comprises at least one nucleotide that is different from the compound of formula (VI), wherein preferably the at least one different nucleotide is (i) a nucleotide comprising a monocyclic sugar, i.e. a monocyclic nucleotide, or (ii) a nucleotide comprising a bicyclic sugar, i.e. a bicyclic nucleotide, or (iii) a nucleotide comprising a tricyclic sugar, i.e. a tricyclic nucleotide. Preferably, said at least one nucleotide that is different from the compound of formula (VI) is a nucleotide comprising a bicyclic sugar. Preferably, said at least one nucleotide that is different from the compound of formula (VI) is a nucleotide comprising a tricyclic sugar. More preferably, said at least one nucleotide that is different from the compound of formula (VI) is a nucleotide comprising a monocyclic sugar.

In another embodiment, the oligomer comprising the compound of formula (IV), (V) or (VI) further comprises at least two nucleotides that are different from the compound of formula (IV), (V) or (VI), wherein said at least two different nucleotides are linked to each other by a nucleosidic linkage group, wherein each nucleosidic linkage group is independently of each other selected from a phosphodiester linkage group, a phosphotriester linkage group, a phosphorothioate linkage group, a phosphorodithioate linkage group, a phosphonate linkage group, a phosphonothioate linkage group, a phosphinate linkage group, a phosphorthioamidate linkage or a phosphoramidate linkage group, and wherein preferably each nucleosidic linkage group is independently of each other a phosphodiester linkage group or a phosphorothioate linkage group, and wherein further preferably each nucleosidic linkage group is a phosphorothioate linkage group.

In another preferred embodiment of the inventive oligomer, said compound of formula (IV) is a compound of formula (V), and said oligomer further comprises at least two nucleotides that are different from the compound of formula (V), wherein said at least two different nucleotides are linked to each other by a nucleosidic linkage group, wherein each nucleosidic linkage group is independently of each other selected from a phosphodiester linkage group, a phosphotriester linkage group, a phosphorothioate linkage group, a phosphorodithioate linkage group, a phosphonate linkage group, a phosphonothioate linkage group, a phosphinate linkage group, a phosphorthioamidate linkage or a phosphoramidate linkage group, and wherein preferably each nucleosidic linkage group is independently of each other a phosphodiester linkage group or a phosphorothioate linkage group, and wherein further preferably each nucleosidic linkage group is a phosphorothioate linkage group.

In another preferred embodiment of the inventive oligomer, said compound of formula (IV) is a compound of formula (VI), and said oligomer further comprises at least two nucleotides that are different from the compound of formula (VI), wherein said at least two different nucleotides are linked to each other by a nucleosidic linkage group, wherein each nucleosidic linkage group is independently of each other selected from a phosphodiester linkage group, a phosphotriester linkage group, a phosphorothioate linkage group, a phosphorodithioate linkage group, a phosphonate linkage group, a phosphonothioate linkage group, a phosphinate linkage group, a phosphorthioamidate linkage or a phosphoramidate linkage group, and wherein preferably each nucleosidic linkage group is independently of each other a phosphodiester linkage group or a phosphorothioate linkage group, and wherein further preferably each nucleosidic linkage group is a phosphorothioate linkage group.

In another preferred embodiment, in the oligomer of the invention, Bx is selected from a purine base or pyrimidine base, wherein preferably Bx is selected from (i) adenine (A), (ii) cytosine (C), (iii) 5-methylcytosine (MeC), (iv) guanine (G), (v) uracil (U), or (vi) 5-methyluracil (MeU), or a derivative of (i), (ii), (iii), (iv), (v) or (vi), and wherein further preferably Bx is selected from uracil, thymine, cytosine, 5-methylcytosine, adenine or guanine. More preferably, in the oligomer of the invention, Bx is selected from thymine, 5-methylcytosine, adenine or guanine.

In another preferred embodiment, in the oligomer of the invention, each nucleosidic linkage group is independently of each other selected from a phosphodiester linkage group, a phosphotriester linkage group, a phosphorothioate linkage group, a phosphorodithioate linkage group, a phosphonate linkage group, a phosphonothioate linkage group, a phosphinate linkage group, a phosphorthioamidate linkage or a phosphoramidate linkage group, and wherein preferably each nucleosidic linkage group is independently of each other a phosphodiester linkage group or a phosphorothioate linkage group, and wherein further preferably each nucleosidic linkage group is a phosphorothioate linkage group.

In another embodiment, the oligomer of the invention comprises 1 to 5, preferably 1 to 4, more preferably 1 to 2, again more preferably 1 to 2, again more preferably exactly one compound of formula (IV), (V) or (VI). In a preferred embodiment of the inventive oligomer, said compound of formula (IV) is a compound of formula (VI), and wherein said oligomer comprises 1 to 5, preferably 1 to 4, more preferably 1 to 2, again more preferably 1 to 2, again more preferably exactly one compound of formula (VI). It has been found that, in particular, a single incorporation of a compound of formula (VI) within an oligonucleotide, and preferably a single incorporation of a compound of formula (VI), wherein Bx is methylcytosine, inside DNA duplexes has a substantial stabilizing effect. Thus, in a very preferred embodiment of the inventive oligomer, said oligomer comprises exactly one compound of formula (IV), wherein said compound of formula (IV) is a compound of formula (VI) and wherein said Bx is methylcytosine, and wherein said oligomer is an oligonucleotide and further comprises at least one nucleotide that is different from the compound of formula (VI), wherein preferably the at least one different nucleotide is a nucleotide comprising a monocyclic sugar.

In another preferred embodiment of the inventive oligomer, said oligomer comprises at least two compounds of formula (IV) and further comprises at least one nucleotide that is different from the compound of formula (IV), wherein said compound of formula (IV) is a compound of formula (V), and wherein EACH of said compound of formula (V) is linked with its 5' terminus to (i) a 5' terminus of said at least one nucleotide that is different from the compound of formula (IV) or (ii) a 7' terminus of another compound of formula (V); and wherein said compound of formula (V) is linked with its 7' terminus to (i) a 3' terminus of said at least one nucleotide that is different from the compound of formula (IV) or (ii) a 5' terminus of another compound of formula (V).

In another embodiment of the inventive oligomer, said oligomer comprises at least two compounds of formula (IV) and further comprises at least one nucleotide that is different from the compound of formula (IV), wherein said compound of formula (IV) is a compound of formula (VI), and wherein EACH of said compound of formula (VI) is linked with its 5' terminus to (i) a 3' terminus of said at least one nucleotide that is different from the compound of formula (IV) or (ii) a 3' terminus of another compound of formula (VI); and wherein EACH of said compound of formula (VI) is linked with its 3' terminus to (i) a 5' terminus of said at least one nucleotide that is different from the compound of formula (IV) or (ii) a 5' terminus of another compound of formula (VI).

In a preferred embodiment of the inventive oligomer, said oligomer further comprises at least two nucleotides that are different from the compound of formula (IV), and wherein said compound of formula (IV) is a compound of formula (V), and wherein EACH OF said nucleotide that is different from the compound of formula (IV) is linked with its 3' terminus to (i) a 7' terminus of said compound of formula (V) or (ii) a 5' terminus of another nucleotide that is different from the compound of formula (IV), and wherein EACH of said nucleotide that is different from the compound of formula (IV) is linked with its 5' terminus to (i) a 5' terminus of said compound of formula (V) or (ii) a 3' terminus of another nucleotide that is different from the compound of formula (IV).

In a preferred embodiment of the inventive oligomer, said oligomer further comprises at least two nucleotides that are different from the compound of formula (IV), and wherein said compound of formula (IV) is a compound of formula (V), and wherein EACH of said nucleotide that is different from the compound of formula (IV) is linked with its 3' terminus to (i) a 7' terminus of said compound of formula (V) or (ii) a 5' terminus of another nucleotide that is different from the compound of formula (IV), and wherein EACH of said nucleotide that is different from the compound of formula (IV) is linked with its 5' terminus to (i) a 5' terminus of said compound of formula (V) or (ii) a 3' terminus of another nucleotide that is different from the compound of formula (IV).

In a preferred embodiment of the inventive oligomer, said oligomer further comprises at least two nucleotides that are different from the compound of formula (IV), and wherein said compound of formula (IV) is a compound of formula (V), and wherein each of the at least one compound of formula (V) is linked with its 5' terminus and with its 7' terminus to said nucleotide that is different from the compound of formula (IV).

In a preferred embodiment of the inventive oligomer, said oligomer further comprises at least two nucleotides that are different from the compound of formula (IV), and wherein said compound of formula (IV) is a compound of formula (V), and wherein EACH of said nucleotide that is different from the compound of formula (IV) is linked with its 3' terminus to (i) a 7' terminus of said compound of formula (V) or (ii) a 5' terminus of another nucleotide that is different from the compound of formula (IV), and wherein EACH of said nucleotide that is different from the compound of formula (IV) is linked with its 5' terminus to (i) a 5' terminus of said compound of formula (V) or (ii) a 3' terminus of another nucleotide that is different from the compound of formula (IV).

In a preferred embodiment of the inventive oligomer, said oligomer further comprises at least two nucleotides that are different from the compound of formula (IV), and wherein said compound of formula (IV) is a compound of formula (VI), and wherein each of the at least one compound of formula (VI) is linked with its 5' terminus and with its 7' terminus to said nucleotide that is different from the compound of formula (IV).

In another preferred embodiment of the inventive oligomer, said oligomer comprises at least two compounds of formula (IV) and further comprises at least two nucleotides that are different from the compound of formula (IV), and wherein said compound of formula (IV) is a compound of formula (V), and wherein each of the at least one compound of formula (V) is linked with its 7' terminus to a 3' terminus of the nucleotide that is different from the compound of formula (IV); and with its 5' terminus to a 5' terminus of a nucleotide that is different from the compound of formula (IV).

In another preferred embodiment of the inventive oligomer, said oligomer comprises at least two compounds of formula (IV) and further comprises at least two nucleotides that are different from the compound of formula (IV), and wherein said compound of formula (IV) is a compound of formula (VI), and wherein each of the at least one compound of formula (VI) is linked with its 5' terminus to a 3' terminus of the nucleotide that is different from the compound of formula (IV); and with its 7' terminus to a 5' terminus of a nucleotide that is different from the compound of formula (IV).

In a preferred embodiment of the inventive oligomer, said oligomer comprises at least one compound of formula (IV), wherein said compound is a compound of formula (VI), wherein each of the at least one compound of formula (VI) is linked with its 5' terminus and with its 7' terminus to a nucleotide that is different from the compound of formula (IV), and wherein Bx is cytosine or 5-methylcytosine, preferably 5-methylcytosine.

In a further preferred embodiment of the inventive oligomer, said oligomer comprises exactly one compound of formula (IV), wherein said compound is a compound of formula (VI), wherein said compound of formula (VI) is linked with its 5' terminus and with its 7' terminus to a nucleotide that is different from the compound of formula (IV), and wherein Bx is cytosine or 5-methylcytosine, preferably 5-methylcytosine.

In another preferred embodiment, the oligomer of the invention comprises 1 to 5, preferably 1 to 4, more preferably 1 to 2, again more preferably 1 to 2, again more preferably exactly one compound of formula (IV), (V) or (VI), preferably of formula (VI), wherein Bx is a pyrimidine base, more preferably cytosine or 5-methylcytosine, again more preferably 5-methylcytosine. In a more preferred embodiment, the oligomer of the invention comprises exactly one compound of formula (VI), wherein Bx is cytosine or 5-methylcytosine, preferably 5-methylcytosine. Incorporation of exactly one or only few compounds of formula (IV), (V) or (VI), preferably of formula (VI), wherein Bx is a pyrimidine bases, leads only to a small destabilization or even stabilizes duplex formation with oligomers of the invention. Especially, when the nucleobase is a cytosine or cytosine derivative, preferably 5-methylcytosine, significantly stabilize duplexes of the oligomer of the invention including compounds of formula (IV), (V) or (VI), preferably of formula (VI), with complementary DNA. This stabilizing effect is more pronounced for the 5-methyl cytosine nucleosides. In another embodiment, the oligomer of the invention comprises 1 to 5, preferably 1 to 4, more preferably 1 to 2, again more preferably 1 to 2, again more preferably exactly one compound of formula (IV), (V) or (VI), preferably of formula (VI), wherein Bx is a purine base. The nucleobase purine stabilizes duplexes of the oligomers of the invention including compounds of formula (IV), (V) or (VI), preferably of formula (VI), with complementary RNA.

In another preferred embodiment, the oligomer of the invention comprises or preferably consists of at least two contiguous compounds of formula (IV), wherein each of the contiguous compounds of formula (IV) is independently linked to the adjacent contiguous compound of formula (IV) by the nucleosidic linkage group, wherein the nucleosidic linkage group links a 5' terminus and a 7' terminus of two contiguous compounds of formula (IV). In another preferred embodiment, in the oligomer of the invention comprises or preferably consists of at least two contiguous compounds of formula (V), wherein each of the contiguous compounds of formula (V) is independently linked to the adjacent contiguous compound of formula (V) by the nucleosidic linkage group, wherein the nucleosidic linkage group links a 5' terminus and a 7' terminus of two contiguous compounds of formula (V). In another preferred embodiment, in the oligomer of the invention comprises or preferably consists of at least two contiguous compounds of formula (VI), wherein each of the contiguous compounds of formula (VI) is independently linked to the adjacent contiguous compound of formula (VI) by the nucleosidic linkage group, wherein the nucleosidic linkage group links a 5' terminus and a 7' terminus of two contiguous compounds of formula (VI).

In a further preferred embodiment, the oligomer of the invention comprises or preferably consists of 10 to 40 contiguous compounds of formula (IV), preferably 10 to 30 contiguous compounds of formula (IV), more preferably 10 to 25 contiguous compounds of formula (IV), again more preferably 10 to 20 contiguous compounds of formula (IV) or 10 to 15 contiguous compounds of formula (IV). In a further preferred embodiment of the inventive oligomer, said at least one compound of formula (IV) is a compound of formula (V), and wherein said oligomer comprises or preferably consists of 10 to 40 contiguous compounds of formula (V), preferably 10 to 30 contiguous compounds of formula (V), more preferably 10 to 25 contiguous compounds of formula (V), again more preferably 10 to 20 contiguous compounds of formula (V), and again more preferably 10 to 15 contiguous compounds of formula (V). In a further preferred embodiment of the inventive oligomer, said at least one compound of formula (IV) is a compound of formula (VI), and wherein said oligomer comprises or preferably consists of 10 to 40 contiguous compounds of formula (VI), preferably 10 to 30 contiguous compounds of formula (VI), more preferably 10 to 25 contiguous compounds of formula (VI), again more preferably 10 to 20 contiguous compounds of formula (VI), and again more preferably 10 to 15 contiguous compounds of formula (VI).

In a further preferred embodiment of the inventive oligomer, said at least one compound of formula (IV) is a compound of formula (V), and wherein said oligomer comprises or preferably consists of 10 to 40 contiguous compounds of formula (V), preferably 10 to 30 contiguous compounds of formula (V), more preferably 10 to 25 contiguous compounds of formula (V), again more preferably 10 to 20 contiguous compounds of formula (V), and again more preferably 10 to 15 contiguous compounds of formula (V) and wherein each of the contiguous compounds of formula (V) is independently linked to the adjacent contiguous compound of formula (V) by the nucleosidic linkage group, wherein the nucleosidic linkage group links a 5' terminus and a 7' terminus of two contiguous compounds of formula (V), and wherein said nucleosidic linkage group is a phosphorus linkage group, and wherein said phosphorus linkage group is selected from a phosphodiester linkage group, a phosphotriester linkage group and a phosphorothioate linkage group, and wherein preferably said phosphorus linkage group is a phosphodiester linkage group or a phosphorothioate linkage group.

In a further preferred embodiment, the oligomer of the invention comprises or preferably consists of at least one nucleic acid sequence, wherein said nucleic acid sequence comprises said at least one compound of formula (IV), and wherein said nucleic acid sequence is selected from SEQ ID NO: 1 to 24, preferably SEQ ID NO: 24. In a further preferred embodiment, the oligomer of the invention comprises or preferably consists of at least one nucleic acid sequence, wherein said nucleic acid sequence comprises said at least one compound of formula (V), and wherein said nucleic acid sequence is selected from SEQ ID NO: 16 to 24, preferably SEQ ID NO: 21 to 24, more preferably SEQ ID NO: 24. In a further preferred embodiment, the oligomer of the invention comprises or preferably consists of at least one nucleic acid sequence, wherein said nucleic acid sequence comprises said at least one compound of formula (VI), and wherein said nucleic acid sequence is selected from SEQ ID NO: 1 to 15, preferably SEQ ID NO: 13-15. In a more preferred embodiment, the oligomer of the invention consists of a nucleic acid sequence selected from SEQ ID NO: 13 to 15 or 21 to 24, preferably SEQ ID NO: 24. In another preferred embodiment, said oligomer is the nucleic acid sequence selected from SEQ ID NO: 13 to 15 or 21 to 24, and wherein preferably said oligomer is SEQ ID NO: 24.

In a further preferred embodiment of the inventive oligomer, said oligomer comprises a nucleic acid sequence, wherein said nucleic acid sequence consists of at least two contiguous compounds of formula (IV), wherein said nucleic acid sequence is flanked on its 5' terminus or its 7' terminus by at least one nucleotide or nucleoside that is different from the compound of formula (IV). In a further preferred embodiment of the inventive oligomer, said oligomer comprises a nucleic acid sequence, wherein said nucleic acid sequence consists of at least two contiguous compounds of formula (V), wherein said nucleic acid sequence is flanked on its 5' terminus or its 7' terminus by at least one nucleotide or nucleoside that is different from the compound of formula (V), preferably different from the compound of formula (V) or (VI), and further preferably different from the compound of formula (IV). In a further preferred embodiment of the inventive oligomer, said oligomer comprises a nucleic acid sequence, wherein said nucleic acid sequence consists of at least two contiguous compounds of formula (VI), wherein said nucleic acid sequence is flanked on its 5' terminus or its 7' terminus by at least one nucleotide or nucleoside that is different from the compound of formula (VI), preferably different from the compound of formula (V) or (VI), and further preferably different from the compound of formula (IV).

In a further preferred embodiment of the inventive oligomer, said oligomer comprises a nucleic acid sequence, wherein said nucleic acid sequence consists of at least two contiguous compounds of formula (IV), wherein said nucleic acid sequence is flanked on its 5' terminus and its 7' terminus by at least one nucleotide or nucleoside that is different from the compound of formula (IV). In a further preferred embodiment of the inventive oligomer, said oligomer comprises a nucleic acid sequence, wherein said nucleic acid sequence consists of at least two contiguous compounds of formula (V), wherein said nucleic acid sequence is flanked on its 5' terminus and its 7' terminus by at least one nucleotide or nucleoside that is different from the compound of formula (V), preferably different from the compound of formula (V) or (VI), and further preferably different from the compound of formula (IV). In a further preferred embodiment of the inventive oligomer, said oligomer comprises a nucleic acid sequence, wherein said nucleic acid sequence consists of at least two contiguous compounds of formula (VI), wherein said nucleic acid sequence is flanked on its 5' terminus and its 7' terminus by at least one nucleotide or nucleoside that is different from the compound of formula (VI), preferably different from the compound of formula (V) or (VI), and further preferably different from the compound of formula (IV).

In a further preferred embodiment of the inventive oligomer, said oligomer comprises a nucleic acid sequence, wherein said nucleic acid sequence consists of at least two contiguous compounds of formula (V), wherein said nucleic acid sequence is flanked on its 5' terminus or its 7' terminus by at least one nucleotide or nucleoside that is different from the compound of formula (V), preferably different from the compound of formula (V) or (VI), and further preferably different from the compound of formula (IV), wherein the 5' terminus of said nucleic acid sequence is linked to a 5' terminus of the nucleotide that is different from the compound of formula (V), preferably different from the compound of formula (V) or (VI), and further preferably different from the compound of formula (IV); or wherein the 7' terminus of said nucleic acid sequence is linked to a 3' terminus of the nucleotide or nucleoside that is different from the compound of formula (V), preferably different from the compound of formula (V) or (VI), and further preferably different from the compound of formula (IV).

In a further preferred embodiment of the inventive oligomer, said oligomer comprises a nucleic acid sequence, wherein said nucleic acid sequence consists of at least two contiguous compounds of formula (V), wherein said nucleic acid sequence is flanked on its 5' terminus and on its 7' terminus by at least one nucleotide or nucleoside that is different from the compound of formula (V), preferably different from the compound of formula (V) or (VI), and further preferably different from the compound of formula (IV), wherein the 5' terminus of said nucleic acid sequence is linked to a 5' terminus of the nucleotide or nucleoside that is different from the compound of formula (V), preferably different from the compound of formula (V) or (VI), and further preferably different from the compound of formula (IV); and wherein the 7' terminus of said nucleic acid sequence is linked to a 3' terminus of the nucleotide or nucleoside that is different from the compound of formula (V), preferably different from the compound of formula (V) or (VI), and further preferably different from the compound of formula (IV).

In a further preferred embodiment of the inventive oligomer, said oligomer comprises a nucleic acid sequence, wherein said nucleic acid sequence consists of at least two contiguous compounds of formula (VI), wherein said nucleic acid sequence is flanked on its 5' terminus or on its 7' terminus by at least one nucleotide or nucleoside t that is different from the compound of formula (VI), preferably different from the compound of formula (V) or (VI), and further preferably different from the compound of formula (IV), wherein the 5' terminus of said nucleic acid sequence is linked to a 3' terminus of the nucleotide or nucleoside that is different from the compound of formula (VI), preferably different from the compound of formula (V) or (VI), and further preferably different from the compound of formula (IV); or wherein the 7' terminus of said nucleic acid sequence is linked to a 5' terminus of the nucleotide or nucleoside that is different from the compound of formula (VI), preferably different from the compound of formula (V) or (VI), and further preferably different from the compound of formula (IV).

In a further preferred embodiment of the inventive oligomer, said oligomer comprises a nucleic acid sequence, wherein said nucleic acid sequence consists of at least two contiguous compounds of formula (VI), wherein said nucleic acid sequence is flanked on its 5' terminus and on its 7' terminus each by at least one nucleotide or nucleoside that is different from the compound of formula (VI), preferably different from the compound of formula (V) or (VI), and further preferably different from the compound of formula (IV), wherein the 5' terminus of said nucleic acid sequence is linked to a 3' terminus of the nucleotide or nucleoside that is different from the compound of formula (VI), preferably different from the compound of formula (V) or (VI), and further preferably different from the compound of formula (IV); and wherein the 7' terminus of said nucleic acid sequence is linked to a 5' terminus of the nucleotide or nucleoside that is different from the compound of formula (VI), preferably different from the compound of formula (V) or (VI), and further preferably different from the compound of formula (IV).

In a further preferred embodiment of the inventive oligomer, said compound of formula (IV) is selected from

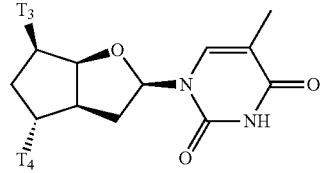
(a)

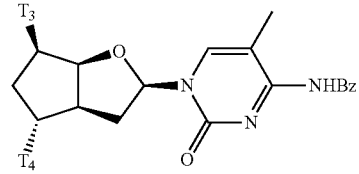
(b)

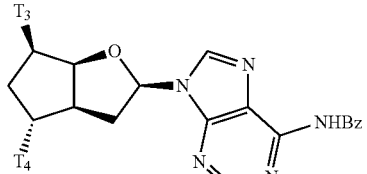
(c)

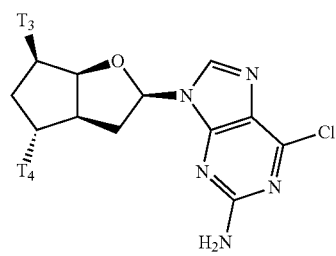
(d)

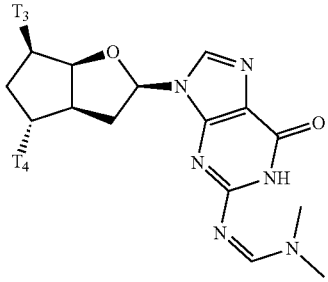
(e)

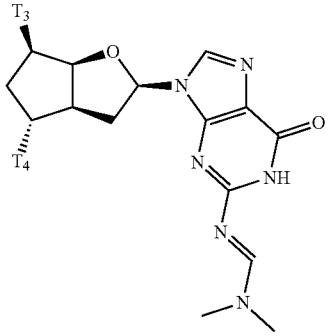
(f)

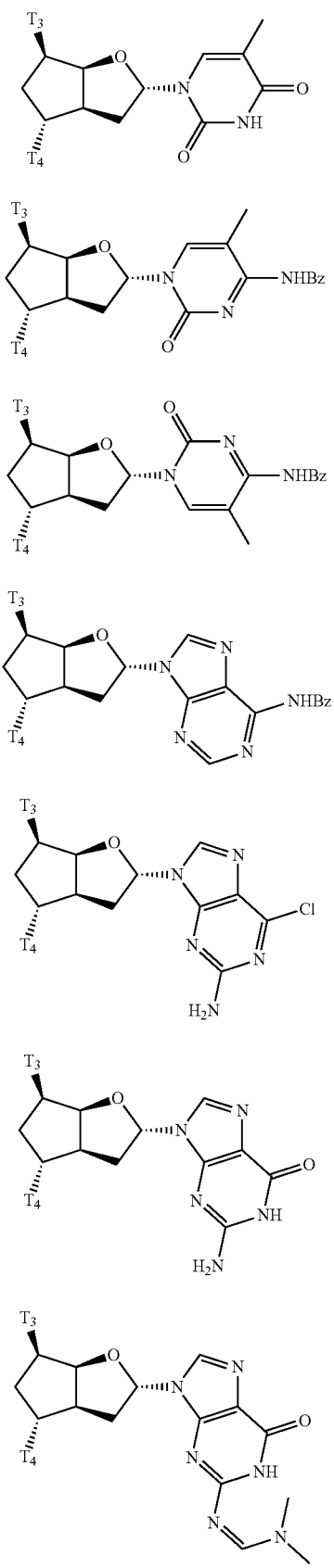
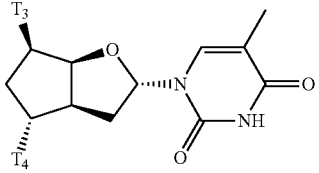

In a further preferred embodiment, the oligomer of the invention is double-stranded. In a certain embodiment, exactly one or both strands of said double stranded oligomer comprise at least one compound of formulae (IV), (V) or (VI).

In a third aspect, the present invention provides the inventive compound of formula (I), (II) or (III) or the oligomer of the invention for use as a medicament in the prevention, treatment or diagnosis of a disease.

In a certain embodiment, the compound of formula (I), (II) or (III) is used as a medicament in the prevention or treatment of a disease. The invention provides a method of preventing a disease in a patient or treating a patient suffering from a disease by administering a therapeutically effective amount of formula (I), (II) or (III) to the patient. In another embodiment, the compound of formula (I), (II) or (III) is used for the manufacture of a medicament for the prevention or treatment of a disease.

In a further embodiment, the oligomer of the invention is used as a medicament in the prevention or treatment of a disease. The invention provides a method of preventing a disease in a patient or treating a patient suffering from a disease by administering a therapeutically effective amount of the oligomer of the invention to the patient. In another preferred embodiment, the oligomer of the invention is used for the manufacture of a medicament for the prevention or treatment of a disease.

The term "patient" as used herein refers to a human or an animal, wherein the animal is preferably a mammal. The term "patient" is not restricted to subjects showing symptoms of a disease or disorder, but includes healthy subjects (i.e. without symptoms) or subjects being at risk for exhibiting a symptom. A "therapeutically effective amount" refers to an amount administered to a subject, either as a single dose or as part of a series of doses, which is effective to produce a desired physiological response or therapeutic effect in the subject. Examples of desired therapeutic effects include, without limitation, improvements in the symptoms or pathology, reducing the progression of symptoms or pathology, and slowing the onset of symptoms or pathology of the disease. The therapeutically effective amount will vary depending on the nature of the formulation used and the type and condition of the recipient. The determination of appropriate amounts for any given composition is within the skill in the art, through standard series of tests designed to assess appropriate therapeutic levels. Typical and preferred therapeutically effective amounts of the antisense oligonucleotide range from about 0.05 to 1000 mg/kg body weight, and in particular from about 5 to 500 mg/kg body weight.

In a further embodiment, the oligomer of the invention is an antisense oligonucleotide. In preferred embodiment the antisense oligonucleotide of the invention is used in the prevention, treatment or diagnosis of a disease. As used herein, the term "antisense oligonucleotide" refers to an oligonucleotide that is capable of hybridizing with a target nucleic acid sequence. In a preferred embodiment, the antisense oligonucleotide is complementary to the target nucleic acid sequence. An oligonucleotide is complementary to a target nucleic acid when a sufficient number of complementary positions in the oligonucleotide and the target nucleic acid are occupied by complementary nucleobases which can form hydrogen bonds with each other such that specific binding occurs between the oligonucleotide and the target nucleic acid. For example, adenine and thymine are complementary nucleobases which pair through the formation of hydrogen bonds. Hybridization can occur under varying circumstances. It is understood in the art that the sequence of an antisense oligonucleotide need not to include nucleotides that are 100% complementary to the nucleotides of the target nucleic acid to be hybridizable. An antisense oligonucleotide may hybridize over one or more nucleotides whereas intervening or adjacent nucleotides are not involved in hybridization. It is preferred that the oligonucleotide portion of the antisense oligonucleotide of the present invention comprise at least 70% sequence complementarity to a target region within the target nucleic acid, more preferably that they comprise 85% or 90% sequence complementarity, and even more preferably comprise 95% sequence complementarity to the target region within the target nucleic acid sequence.

In a certain embodiment, the oligomer of the invention is used in the prevention or treatment of a disease, wherein the oligomer is capable of interfering with replication, translation, transcription, translocation, catalytic activity, complex formation, splicing or integrity of a target nucleic acid. In a certain embodiment, the oligomer of the invention is used in the prevention or treatment of a disease, wherein the oligomer is capable of binding to a target nucleic acid, downregulating expression of a target nucleic acid, sterically blocking a target nucleic acid sequence or inducing nucleic acid interference, gene silencing, degradation or exon skipping in a target nucleic acid. In a preferred embodiment, the oligomer of the invention is used in the prevention or treatment of a disease, wherein the oligomer is capable of binding to a target nucleic acid and downregulating expression of said target nucleic acid. In another preferred embodiment, the oligomer of the invention is used in the prevention or treatment of a disease, wherein the oligomer is capable of binding to a target nucleic acid, sterically blocking said target nucleic acid and inducing exon skipping in said target nucleic acid. In a preferred embodiment, said target nucleic acid is a DNA or RNA. The RNA is preferably a pre-mRNA (pre-processed or precursor messenger RNA) or mature RNA. The RNA can be an mRNA or a functional form of a non-coding RNA, such as a long non-coding RNA, micro RNA, small interfering RNA, small nucleolar RNA, Piwi-interacting RNA, tRNA-derived small RNA, small rDNA-derived RNA, rRNA or tRNA. In a certain embodiment, the oligomer of the invention is used in the prevention or treatment of a disease, wherein the oligomer is capable of altering a splice process in a target nucleic acid, wherein preferably the target nucleic acid is a pre-mRNA. Preferably said oligomer is capable of inducing exon skipping in a target pre-mRNA. An "exon" refers to a defined section of a nucleic acid that encodes for a protein, or a nucleic acid sequence that is represented in the mature form of an RNA molecule after either portions of a pre-mRNA have been removed by splicing.

In a further embodiment, the oligomer of the invention is used as a medicament in the prevention or treatment of a disease, wherein said disease is a genetic disease. In a preferred embodiment, the oligomer of the invention is used as a medicament in the prevention or treatment of a disease, wherein said disease is a muscular dystrophy, preferably Duchenne muscular dystrophy. In another preferred embodiment, the oligomer for use as a medicament in the prevention, treatment or diagnosis of a disease is the nucleic acid sequence of SEQ ID NO: 21 or the nucleic acid sequence of SEQ ID NO: 24, preferably the nucleic acid sequence of SEQ ID NO: 24 and wherein the disease is a muscular dystrophy, preferably Duchenne muscular dystrophy. The oligomers of the invention and in particular SEQ ID NO: 24 maintain a good affinity toward RNA, and oligomers consisting of compounds of formula (V) seem to confer a significantly improved biostability compared to its naturally occurring corresponding DNA. Moreover, the nucleic acid of SEQ ID NO: 24 does not activate complement significantly, and complement activation represents an important toxic response often associated with an in vivo use of antisense oligonucleotides. Therefore, the oligomers of the invention, preferably oligomers comprising or preferably consisting of compounds of formula (V) are promising antisense candidates. Finally, oligomers consisting of compounds of formula (V), preferably the nucleic acid of SEQ ID NO: 24 is able to induce strong exon skipping of exon 23 and double exon skipping of exons 22 and 23. These promising results indicate that the oligomer of the invention, especially oligomers consisting of compounds of formula (V) meet the prerequisites to induce a strong therapeutic effect in patients suffering muscular dystrophies, such as Duchenne.

In another aspect, the present invention provides for the oligomer of the invention for use as a medicament in the prevention or treatment of a disease.

In a further aspect, the oligomer of the invention is used in the diagnosis of a disease. In a further aspect, the oligomer of the invention is used as a medicament in the diagnosis of a disease. In another preferred embodiment, the oligomer of the invention is used for the manufacture of a medicament for the diagnosis of a disease. The invention provides a method of diagnosing a disease in a patient. Said diagnosis or said diagnosing comprises (i) administering an effective amount of the oligomer of the invention to a patient, wherein the oligomer is labelled, and
(ii) non-invasive or invasive, preferably non-invasive in vivo imaging of the labelled oligomer or
(i') obtaining a sample from a patient,
(ii') adding a oligomer of the invention to the sample, wherein the oligomer is labelled, and
(iii') analyzing the sample for binding of the labelled oligomer with nucleic acids included in the sample. In a preferred embodiment, the oligomer of the invention used in the diagnosis of a disease is an oligonucleotide, more preferably an antisense oligonucleotide. The sample obtained from a patient is preferably a blood, serum, liquor or tissue sample. The term "labelled oligomer" as used herein refers to an oligomer comprising a label. Preferably the label is selected from a fluorescent label, dye, reporter group or a radiolabel.

In a further aspect, the invention provides a pharmaceutical composition comprising at least one compound selected from formula (I), (II) or (III). In a further aspect, the invention provides a pharmaceutical composition comprising at least one oligomer of the invention. In a preferred embodiment, said pharmaceutical composition comprises one or more oligomers of the invention, wherein at least one of said one or more oligomers is an oligonucleotide, more preferably an antisense oligonucleotide. In a preferred embodiment, the pharmaceutical composition comprises a therapeutically-effective amount of the at least one compound of formula (I), (II) or (III) or the at least one oligomer of the invention, preferably formulated together with one or more pharmaceutically acceptable carriers. In one embodiment, a unit dose of the pharmaceutical composition of the invention contains about 1 microgram to 20,000 micrograms of the oligomer or the compound of formula (I), (II) or (III) per unit, and preferably from about 10 to 1000 micrograms. For intravenous delivery, a unit dose of the pharmaceutical formulation contains preferably from 0.5 to 500 micrograms per kg body weight, more preferably from 5 to 300 micrograms per kg body weight of the oligomer of the invention. In the pharmaceutical compositions of the invention, the oligomer or the compound of formula (I), (II) or (III) is ordinarily present in an amount of about 0.5-95% by weight based on the total weight of the composition.

In a preferred embodiment, the pharmaceutical composition comprising the at least one compound of formula (I), (II) or (III) or the at least one oligomer of the invention further comprises at least one pharmaceutically acceptable carrier. The term "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material. The pharmaceutically acceptable carrier can be involved in carrying or transporting the subject compound from one organ or portion of the body to another. Methods for the delivery of nucleic acids are described, for example, in Akhtar et al., 1992, Trends Cell Bio., 2:139; and Delivery Strategies for Antisense Oligonucleotide Therapeutics, ed. Akhtar; Sullivan et al., PCT WO 94/02595. These and other protocols can be utilized for the delivery of virtually any nucleotide or nucleic acid molecule, including the compound of formula (I), (II) or (III) and the oligomers of the present invention. The invention also features the pharmaceutical composition of the invention further comprising P-glycoprotein inhibitors (such as Pluronic P85), which can enhance entry of drugs into various tissues; biodegradable polymers, such as poly (DL-lactide-coglycolide) microspheres for sustained release delivery after implantation (Emerich, D F et al., 1999, Cell Transplant, 8, 47-58) Alkermes, Inc. Cambridge, Mass.); nanoparticles, such as those made of polybutylcyanoacrylate, which can deliver drugs across the blood brain barrier and can alter cellular uptake mechanisms (Frog Neuropsychopharmacol Biol Psychiatry, 23, 941-949, 1999); or liposomes containing polyethylene glycol-lipids.

Administration of the pharmaceutical composition, the compound of formula (I), (II) or (III) or the oligomer of the invention can be carried out using the various mechanisms known in the art. In a preferred embodiment, the pharmaceutical composition, the compound of formula (I), (II) or (III) or the oligomer of the invention is administered locally or systemically. In a preferred embodiment, the pharmaceutical composition, the compound of formula (I), (II) or (III) or the oligomer of the invention is administered orally (for example, as an aqueous or non-aqueous solution or suspension, tablet, bolus, powder, granule, paste), parenterally (for example, by subcutaneous, intramuscular, intravenous, intraperitoneal or epidural injection as, for example, a sterile solution or suspension, or sustained-release formulation), topically (for example, as a cream, ointment, or a controlled-release patch or spray), intravaginally or intrarectally (for example, as a pessary, cream or foam), sublingually, ocularly, transdermally, nasally, intracellularly or by direct local tumor injection. In a preferred embodiment, the pharmaceutical composition comprising the oligomer of the invention is used for downregulating expression of a target nucleic acid, sterically blocking a target nucleic acid sequence or inducing nucleic acid interference, gene silencing, degradation or exon skipping in a target nucleic acid.

In a further aspect, the oligomer of the invention is used in vitro for binding to a target nucleic acid sequence. In a preferred embodiment, the oligomer of the invention is used in vitro for downregulating expression of a target nucleic acid, sterically blocking a target nucleic acid sequence or inducing nucleic acid interference, gene silencing, degradation or exon skipping in a target nucleic acid. In a certain embodiment, the oligomer of the invention is used in vitro for interfering with replication, translation, transcription, translocation, catalytic activity, complex formation, splicing or integrity of a target nucleic acid. In a preferred embodiment, oligomer of the invention is used in vitro for binding to a target nucleic acid, wherein exon skipping is induced in said target nucleic acid. In a preferred embodiment, the present invention provides an in vitro method of downregulating the expression of a target gene in the cytosol of a cell by delivering the oligomer of the invention of the invention across a membrane of the cell. In a preferred embodiment, the target nucleic acid is DNA, pre-mRNA or mature mRNA.

In a further aspect, the invention provides a method for solid-phase synthesis of an oligomer of the invention comprising the use of any one of the compounds of formulae (I) to (VI).

EXAMPLES

General Procedures

All reactions were performed in dried glassware and under an inert atmosphere of Argon. Anhydrous solvents for reactions were obtained by filtration through activated alumina or by storage over molecular sieves (4 Å). Colum chromatography (CC) was performed on silica gel (Silia-Flash P60, 40-63 um, 60 Å). Methanol used for CC was of HPLC grade, all other solvents used for CC were of technical grade and distilled prior to use. Thin-layer chromatography was performed on silica gel plates (macherey-nagel, pre-coated TLC-plates sil G-25 UV254). Compounds were visualized under UV-light or by dipping in a p-Anisaldehyde staining solution [p-Anisaldehyde (3.7 mL), glacial acetic acid (3.7 mL), concentrated sulfuric acid (5 mL), ethanol (135 mL)] followed by heating with a heat gun. NMR spectra were recorded at 300 or 400 MHz ($^1$H), at 75 or 101 MHz ($^{13}$C) and at 122 MHz ($^{31}$P) in either CDCl$_3$, CD$_3$OD or CD$_3$CN. Chemical shifts (δ) are reported relative to the residual undertreated solvent peak [CDCl$_3$: 7.26 ppm ($^1$H), 77.16 ppm ($^{13}$C); CD$_3$OD: 3.31 ppm ($^1$H), 49.00 ppm ($^{13}$C)]. Signal assignments are based APT and DEPT and on $^1$H, $^1$H and $^1$H, $^{13}$C correlation experiments (COSY, HSQC, HMBC). High resolution mass detections were performed by electrospray ionization in the positive mode (ion trap, ESI$^+$).

Within this Examples section, for sake of simplicity, nucleotides or nucleosides mentioned in this Examples section refer to beta anomers, unless mentioned specifically as alpha anomers. Furthermore, and consistent hereto, oligomers or oligonucleotides mentioned within this Examples section comprise beta anomers, unless mentioned specifically as alpha anomers.

Temperature of Melting

UV-melting experiments were recorded on a Varian Cary Bio 100 UV/vis spectrophotometer. Experiments were performed at 2 μM duplex concentration, 10 mM NaH$_2$PO$_4$, between 0 M and 150 mM NaCl (alpha anomer) or between 0.05 M and 1.00 M NaCl (beta anomer) and pH adjusted to 7.0. Samples were protected from evaporation by a covering layer of dimethylpolysiloxane. Absorbance was monitored at 260 nm. For every experiment, three cooling-heating cycles were performed with a temperature gradient of 0.5° C./min. The maxima of the curves first derivative were extracted with Varian WinUV software and $T_m$ values were reported as the average of the six ramps.

Circular Dichroism Spectroscopy

CD-spectra were recorded on a Jasco J-715 spectropolarimeter equipped with a Jasco PFO-3505 temperature controller. Sample conditions were the same as for UV-melting experiments. Spectra were recorded between 210 and 320 nm at a 50 nm/min rate and the temperature was measured directly from the sample. For each experiment, a blank containing the same salt concentrations as the sample were recorded. The reported spectra were obtained by taking a smoothed average of three scans and subtracting the corresponding blank spectrum.

Characterizations of Oligonucleotides

Example 1

Syntheses of the Inventive Compounds

General Overview

The bicyclic scaffolds 7 and 10 envisaged for subsequent nucleoside synthesis could be constructed from the previously described intermediate 1 (Tarköy, M.; Bolli, M.; Schweizer, B.; Leumann, C. *Helv. Chim. Acta* 1993, 76, 481) (Scheme 1). The epoxide ring in 1 was efficiently opened by LiHMDS mediated intramolecular elimination at −78° C., yielding the unsaturated ester 2 in good yield. Subsequent nickel-catalyzed NaBH$_4$ reduction of 2 proceeded stereospecifically from the convex side of the bicyclic core structure, resulting in ester 3 as the only identifiable diastereoisomer. The hydroxyl function in 3 was then TBDPS protected, giving 4 in quantitative yield. Intermediate 4 was consequently reduced with DIBAL at −78° C., leading to aldehyde 5. The acetonide protecting group in 5 was then hydrolyzed under mild conditions with In(OTf)$_3$ as catalyst

| Entry | SEQ ID NO | Sequence[a] | Exact mass | Experimental mass |
|---|---|---|---|---|
| ON1 | 1 | d(GGATGTTCtCGA) | 3700.67 | 3701.66 |
| ON2 | 2 | d(GGAtGTTCTCGA) | 3700.67 | 3701.66 |
| ON3 | 3 | d(GGATGttCTCGA) | 3726.68 | 3727.70 |
| ON4 | 4 | d(GGATGTTcTCGA) | 3714.68 | 3715.67 |
| ON5 | 5 | d(GGATGTTCTcGA) | 3714.68 | 3715.67 |
| ON6 | 6 | d(GGaTGTTCTCGA) | 3700.67 | 3701.66 |
| ON7 | 7 | d(GGATgTTCTCGA) | 3700.67 | 3701.66 |
| ON8 | 8 | d(GGATGTTcTCGA) | 3700.67 | 3701.66 |
| ON9 | 9 | d(GGATGTTCTcGA) | 3700.67 | 3701.66 |
| ON10 | 10 | d(GGATGTTcTcGA) | 3726.68 | 3727.67 |
| ON11 | 11 | d(GCAttt ttACCG) | 3739.71 | 3740.72 |
| ON12 | 12 | 5'-(ttt tct cct)-7' | 2905.65 | 2906.64 |
| ON13 | 13 | 5'-(gga tgt tct cga)-7 | 4014.87 | 4015.85 |
| ON14 | 14 | 5'-(tcg aga aca tcc)-7' | 3980.91 | 3981.90 |
| ON15 | 15 | 5'-(cct aca aga gct)-7 | 3980.91 | 3981.90 |
| ON16 | 16 | 5'-d(GGA TGT TCt CGA)-3' | 3700.67 | 3701.64 |
| ON17 | 17 | 5'-d(GGA t GT TCT CGA)-3' | 3700.67 | 3701.64 |
| ON18 | 18 | 5'-d(GGA tGT TCt CGA)-3' | 3726.68 | 3727.66 |
| ON19 | 19 | 5'-d(GGA TGt tCT CGA)-3' | 3726.68 | 3727.66 |
| ON20 | 20 | 5'-d(GCA ttt ttA CCG)-3' | 3739.71 | 3739.65 |
| ON21 | 21 | 5'-d(agc tct tgt agg)-7' | 4014.87 | 4015.86 |
| ON22 | 22 | 5'-d(cct aca aga gct)-7' | 3980.91 | 3981.90 |
| ON23 | 23 | 5'-d(tcg aga aca tcc)-7' | 3980.91 | 3981.90 |
| ON24 | 24 | 5'-d(t*c*c*a*t*t*c*g*g*c*t*c*c*a*a*)-7' | 5185.81 | 5186.81 |

[a]A, G, T, C denote natural 2'-deoxynucleosides; a, g, t, c corresponds to modified adenine, guanine, thymine and methylcytosine respectively, *denotes a phosphorothioate linkage, c stands for the modified 5-methyl cytosine nucleoside.

(Golden, K. C.; Gregg, B. T.; Quinn, J. F. *Tetrahedron Lett.* 2010, 51, 4010), in a mixture of MeCN and H₂O, and the resulting bicyclic hemiacetal converted into the methyl glycoside 6 by simply changing the solvent to MeOH. Compound 6 was then acetylated to afford the protected precursor 7 that was used for the synthesis of the corresponding purine nucleosides via Vorbrüggen chemistry.

Scheme 1:

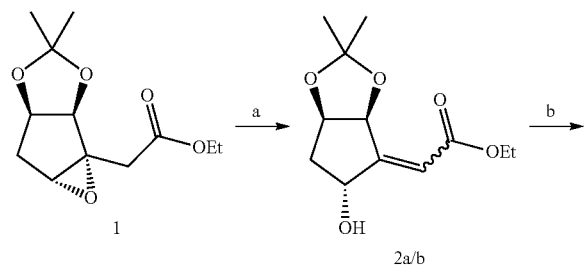

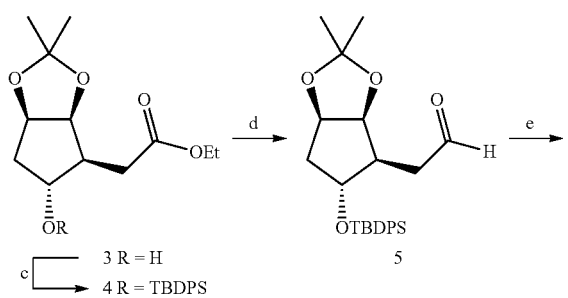

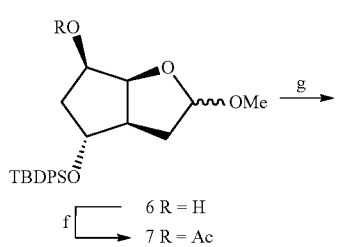

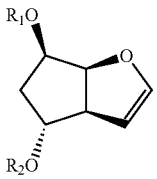

(a) LiHMDS, THF, -78° C., 74%;
(b) NaBH₄, NiCl₂, EtOH, 0° C. → rt, 2 h, 90%;
(c) TBDPSCl, I₂, N-methylimidazole, THF, rt, 3 h, quant;
(d) DiBAL-H, CH₂Cl₂, -78° C., 90 min, 89%;
(e) i) In(OTf)₃, MeCN/H₂O, rt, 48 h, ii) MeOH, 6 h, 81%;
(f) Ac₂O, DMAP, DCM, rt, 2 h, 96%;
(g) i) TMSOTf, 2,6-lutidine, DCM, rt, 60 min, ii) TBAF, THF, 0° C., 20 min, 92%;
(h) DMTr-Cl, AgOTf, DCM/lutidine, rt, 4 h, 93%;
(i) TBAF, THF, rt, 20 h, quant.

The synthesis of the preferred pyrimidine nucleosides of the present invention consisted in the well-established application of the β-stereoselective NIH induced addition of the nucleobases to a corresponding bicyclic glycal (Medvecky, M.; Istrate, A.; Leumann, C. J. *J. Org. Chem.* 2015, 80, 3556; Dugovic, B.; Leumann, C. J. *Journal of Organic Chemistry* 2014, 79, 1271; Lietard, J.; Leumann, C. J. *J. Org. Chem.* 2012, 77, 4566). First, to introduce the thymine nucleobase, the N-iodosuccinimide (NIS) induced nucleosidation was performed on the direct precursor of glycal 8, where R₁=TMS, that was easily obtained from 6 by treatment with TMSOTf only. This approach resulted in the stereoselective formation of the corresponding β-nucleoside, however, with a significant contamination of 7% of the α-anomer that remained inseparable by standard chromatography techniques. It was reasoned that the β-selectivity could be enhanced by increasing steric bulk at R₁ and decreasing it at R₂, as in glycal 10. This would favor initial α-attack of the electrophilic iodine at C(4). To this end compound 6 was converted to glycal 8 with TMSOTf followed by a short treatment with TBAF to remove the newly introduced TMS group selectively. Intermediate 8 was then elaborated into the dimethoxytrityl compound 9 which was finally subjected to removal of the TBDPS protecting group with TBAF to give the desired sugar component 10.

NIS-nucleosidation on the in situ TMS protected glycal 10, followed by radical reduction of the iodide intermediate with Bu₃SnH, yielded the DMTr-protected thymidine derivative 11 in good yield containing only trace amounts (<2% by ¹H-NMR) of the α-anomer (Scheme 2). Final phosphitylation with 2-cyanoethyl N,N,N',N'-tetraisopropylphosphordiamidite lead to the thymidine phosphoramidite building block 12. The synthesis of the 5-methylcytosine nucleoside was achieved by conversion of the base thymine. To this end, nucleoside 11 was TMS protected and converted to the corresponding triazolide by treatment with 1,2,4-triazole and POCl₃. Subsequent treatment of this triazolide in a mixture of ammonia and 1,4-dioxane yielded the corresponding 5-methylcytosine nucleoside, which was directly protected with Bz₂O to give 13 in 88% yield over three steps. The phosphoramidite 14 was obtained by a phosphitylation as described above.

Scheme 2:

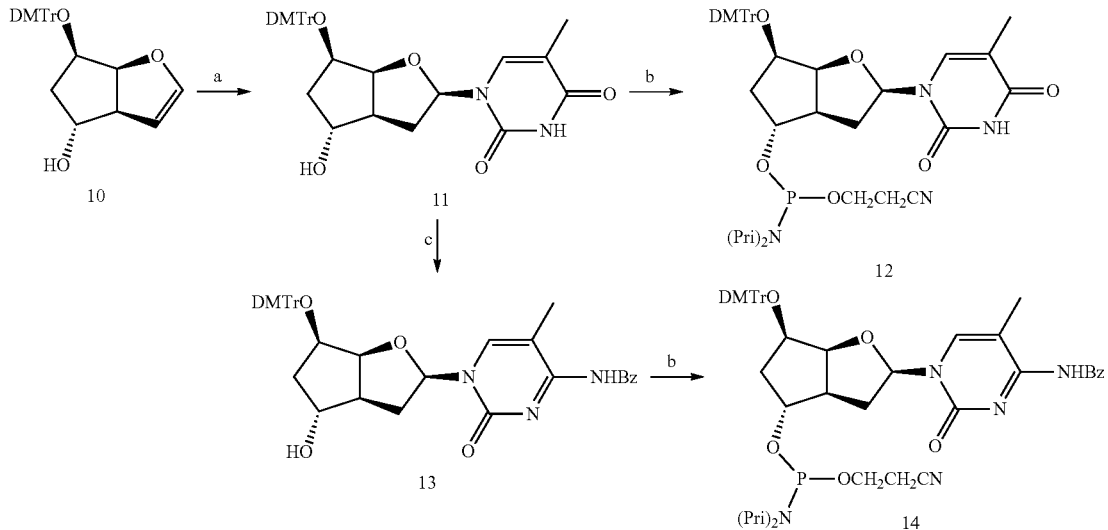

(a) i) Thymine, BSA,NIS, DCM, rt, 7 h; ii) Bu$_3$SnH, AIBN, toluene, 70° C., 30 min, 73%;
(b) 2-Cyanoethyl N,N,N′,N′-tetraisopropylphosphordiamidite, ETT, DCM, rt, 30 min, 70% for 12, 75% for 14;
(c) i) BSA, Triazole, POCl$_3$, CH$_3$CN, rt, 5 h, ii) 1,4-Dioxane/NH$_4$OH, rt, 2 h, iii) Bz$_2$O, Et$_3$N, DMF, rt, 20 h, 88%.

Classical Vorbrüggen nucleosidation was applied for introducing the purine nucleobases resulted generally in the prevalence of the α-nucleosides. The conversion of precursor 7 with either N$^6$-benzoyladenine or 2-amino-6-chloropurine leads to the inseparable anomeric mixtures 15 and 20, resp. in α/β ratios of 4:1 and 7:3 (Scheme 3). Separation of anomers was possible after deacetylation, leading to the pure β-anomers 16 and 21. From here, the adenine building block 19 could be obtained by standard dimethoxytritylation (→17) followed TBAF mediated cleavage of the silyl protecting group (→19) and phosphitylation. The synthesis of the guanine building block required the conversion of the 2-amino-6-chloropurine nucleobase. This was achieved by treatment of 21 with 3-hydroxypropionitrile and TBD and subsequent protection of the 2-amino group with DMF, yielding the protected guanosine derivatives 22. Following the same chemical pathway as above, the synthesis of the guanine building block 25 was achieved by dimethoxytritylation (→23) followed by removal of silyl protecting group (→24) and phosphitylation.

Scheme 3:

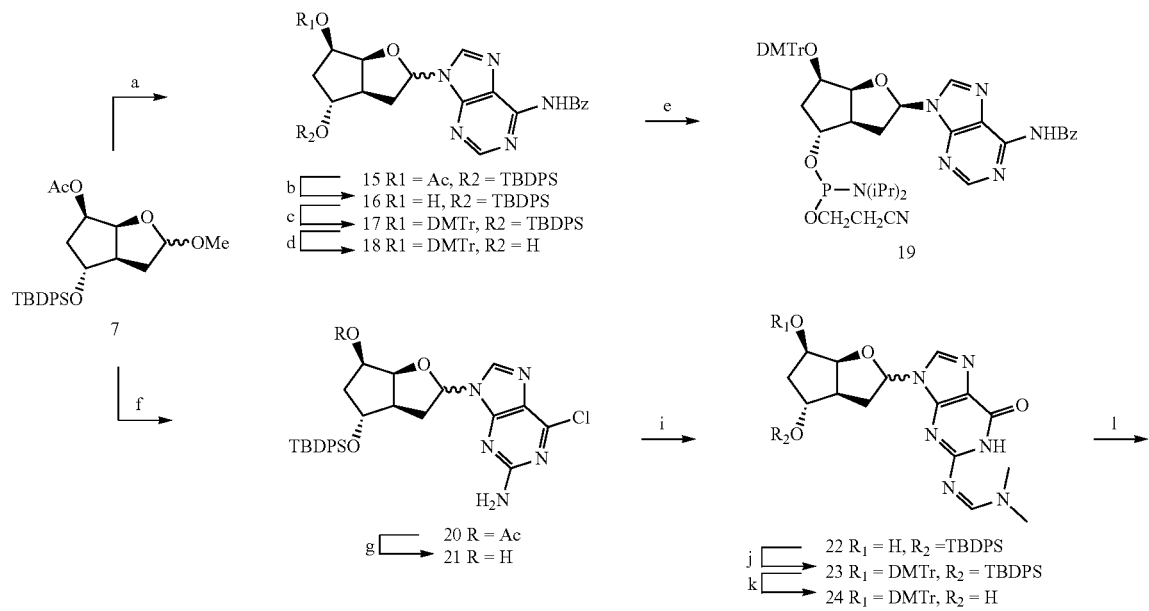

-continued

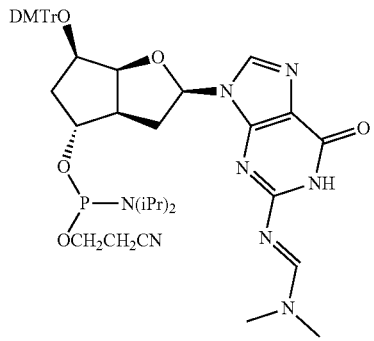

25

(a) N⁶-Benzoyladenine, BSA, TMSOTf, MeCN, 70° C., 20 min, 64%; (b) NaOH, THF/MeOH/H₂O, 0° C., 20 min, 69%; (c)DMTr—Cl, pyridine, rt, 24 h, 87%; (d) TBAF, THF, rt, 48 h, 87%; (e) CEP-Cl, DIPEA, THF, rt, 2 h, 71%; (f) 2-amino-6-chloropurine, BSA, TMSOTf, MeCN, 55° C., 50 min, 77%; (g) NaOH, THF/MeOH/H₂O, 0° C., 20 min, 85%; (i) i) TBD, 3-hydroxypropionitrile, DCM, 48 h, ii) N,N-dimethylformamide dimethylacetal, DMF, 55°C., 2 h, 73%; (j)DMTr—Cl,pyridine, rt, 18 h, 70%; (k) TBAF, THF, rt, 7 h, 87%; (l) 2-Cyanoethyl N,N,N',N'-tetraisopropylphosphordiamidite, ETT, DCM, rt, 50 min, 69%.

Starting from protected sugar 7 the synthesis of four preferred phosphoramidite building blocks of the present invention was developed. Treatment of a mixture of sugar 7 and in situ silylated thymine with TMSOTf resulted in the smooth formation of the nucleoside 35, with a favorable anomeric ratio α/β of approximately 85:15 (determined by ¹H-NMR) (Scheme 4). The chemical pathway leading to the thymidine phosphoramidite bearing the DMTr group on the 5' position does not allow the separation of anomers by standard chromatography. Therefore, and in order to introduce the modification with polarity reversal into DNA strands, the DMTr group was introduced on the 7' position. To this end, the silyl group of 35 was removed by short treatment with TBAF (→36) followed by standard dimethoxytritylation (→37). Separation of the two anomers was possible after standard deacetylation, leading to the pure α-anomer 38. The thymidine building block 39 was finally obtained by phosphitylation with 2-cyanoethyl N,N,N',N'-tetraisopropylphosphordiamidite in the presence of 5-(Ethylthio)-1H-tetrazole. The intermediate 38 also offered us short access to the 5-methylcytosine nucleoside, by conversion of the in situ TMS protected nucleoside 38 to the corresponding triazolide with POCl₃ and 1,2,4-triazole, followed by treatment in a mixture of ammonia and 1,4-dioxane. Direct protection with Bz₂O in DMF resulted in the efficient formation of nucleoside 40, the labile silyl protecting group being cleaved during the process. Final phosphitylation in conditions as described above afforded the 5-methylcytidine phosphoramidite 41.

Scheme 4:

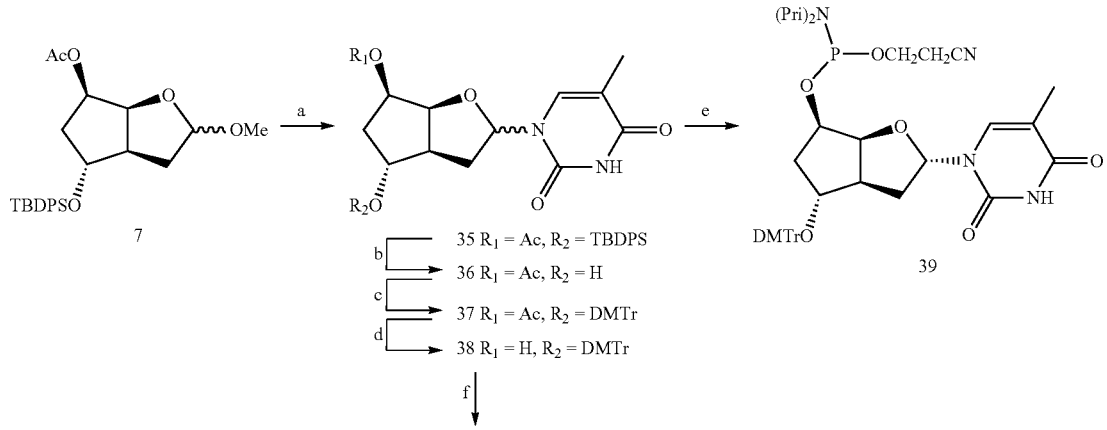

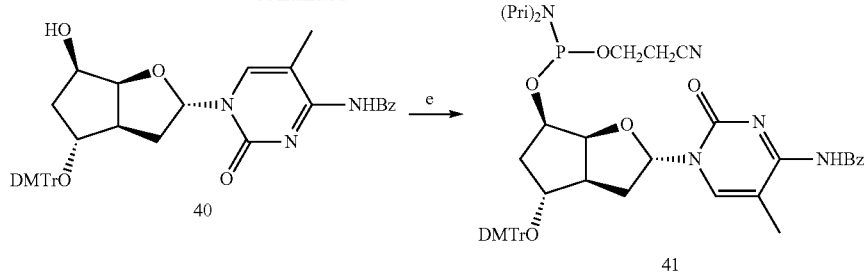

(a) Thymine, BSA, TMSOTf, MeCN, rt, 18 h, 82%;
(b) TBAF, THF, 2 h, 75%;
(c) DMTr-Cl, pyridine, rt, 24 h, 96%;
(d) K₂CO₃, MeOH, 3 h, 86%;
(e) 2-Cyanoethyl N,N,N',N'-tetraisopropylphosphordiamidite, ETT, DCM, rt, 1 h, 81% for 39, 30 min, 80% for 41;
f) i) BSA, 1,2,4-triazole, POCl₃, Et₃N, MeCN, rt, 7 h, ii) 1,4-Dioxane/NH₄OH, rt, 3 h, iii) Bz₂O, Et₃N, DMF, rt, 18 h, 83%.

For the purine nucleobases, the introduction of the purines were performed by a short nucleosidation in slightly elevated temperature with either N⁶-benzoyladenine or 2-amino-6-chloropurine, leading to the nucleoside 15 and 20, resp. in α/β ratios of 4:1 and 7:3 (Scheme 5). To separate the anomers, acetyl groups were removed under mild conditions, yielding the pure α-anomers 42 and 48. The formation of the adenosine building block continues with the reintroduction of the acetyl protecting group (→43), removal of the TPDPS protecting group with TBAF (→44) followed by standard dimethoxytritylation (→45). Selective deprotection of the acetyl group (→46) followed by phosphitylation in conditions as described above yielded the adenine building block 47.

For the guanine building block, after separation of the two anomers, the 6-chloropurine was converted to the guanine nucleobase by treatment with TBD and 3-hydroxypropionitrile yielding the guanosine nucleoside 49. Acetylation over 48 h allowed the concomitant protection of the 5'-hydroxy and 2-amino groups, yielding the protected nucleoside 50. Similarly as above, the DMTr group was introduced by removal of the silyl protecting group with TBAF (→51) followed by dimethoxytritylation (→52). The two acetyl groups were removed by treatment with K₂CO₃ and the resulting polar product was directly protected with DMF to afford the guanosine nucleoside 53. Final phosphitylation yielded building block 54.

Scheme 5:

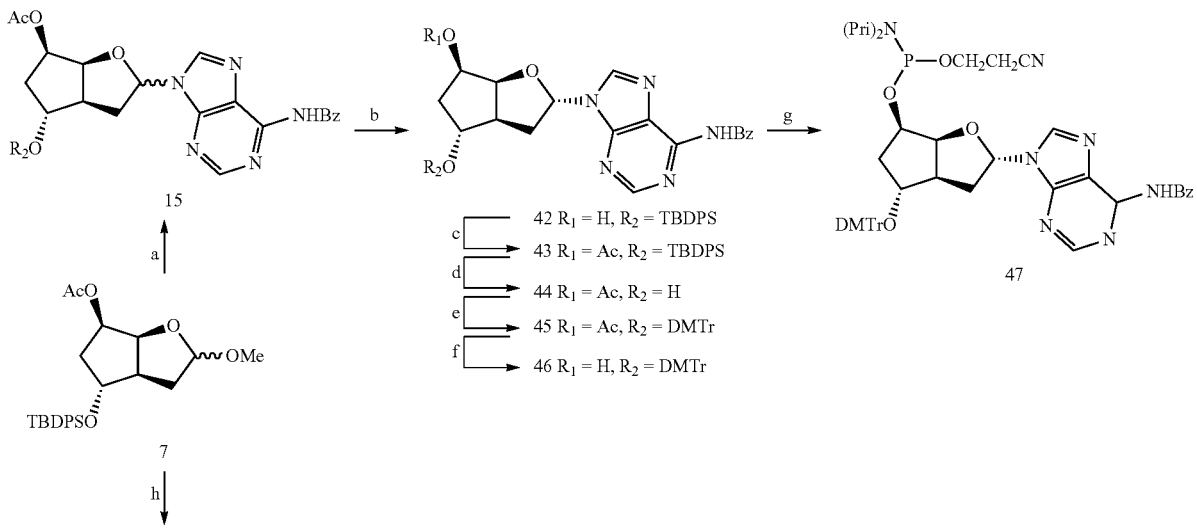

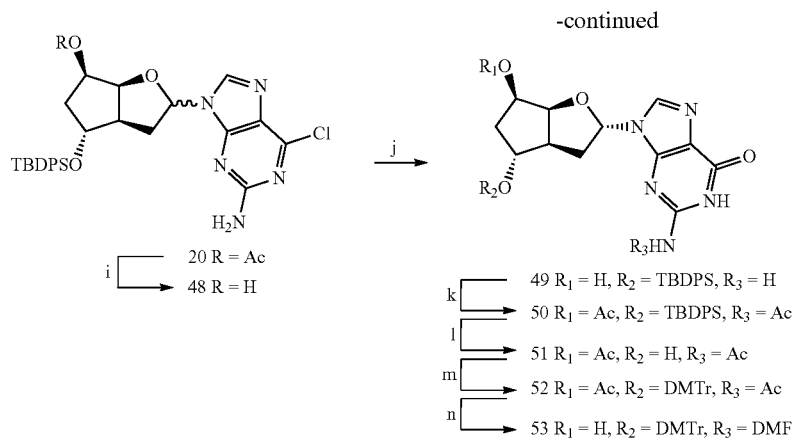

i ⎡ 20 R = Ac
  ⎣ 48 R = H k ⎡ 49 R₁ = H, R₂ = TBDPS, R₃ = H
l ⎢ 50 R₁ = Ac, R₂ = TBDPS, R₃ = Ac
m ⎢ 51 R₁ = Ac, R₂ = H, R₃ = Ac
n ⎢ 52 R₁ = Ac, R₂ = DMTr, R₃ = Ac
  ⎣ 53 R₁ = H, R₂ = DMTr, R₃ = DMF a) N⁶-Benzoyladenine, BSA, TMSOTf, MeCN, 70° C., 20 min, 64%;
(b) NaOH, THF/MeOH/H₂O, 0° C., 20 min, 51% α-anomer, 18% β-anomer;
(c) Ac₂O, DMAP, DCM, rt, 18 h, 90%;
(d) TBAF, THF, rt, 3.5 h, 90%;
(e) DMTr-Cl, pyridine, rt, 24 h, 89%;
(f) NaOH, THF/MeOH/H₂O, 0° C., 30 min, 94%
(g) 2-Cyanoethyl N,N,N',N'-tetraisopropyl-phosphordiamidite, ETT, DCM, rt, 1 h, 77% for 47, 50 min, 77%;
(i) NaOH, THF/MeOH/H₂O, 0° C., 20 min, 85%;
(j) TBD, 3 hydroxypropionitrile, DCM, 48 h 87%
(k) Ac₂O, DMAP, DCM, rt, 48 h 76%;
(l) TBAF, THF, rt, 4 h, 87%;
(m) DMTr-Cl, pyridine, rt, 48 h, 99%;
(n) i) K₂CO₃, MeOH, rt, 7 h, ii) N,N-dimethylformamide dimethylacetal, DMF, 55° C., 2 h 77%.

Example 2

Ethyl (E and Z, 1'R,5'S,7'R)-(7'-hydroxy-3',3'-dimethyl-2',4'-dioxabicyclo[3.3.0]oct-6'-ylidene)acetate (2a/b)

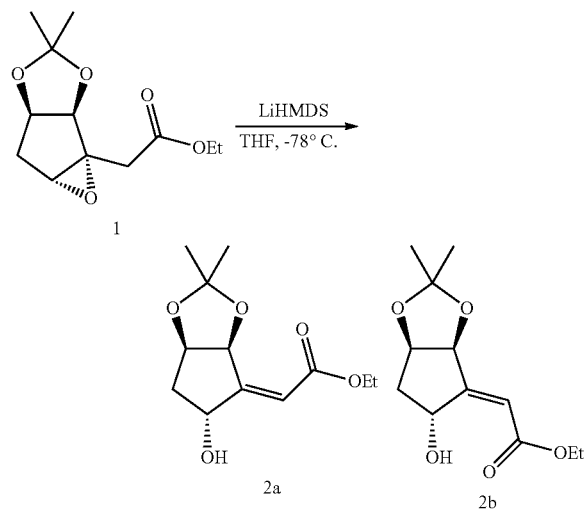

A solution of the epoxide 1 (4.46 g, 18.4 mmol) in dry THF (100 mL) was cooled down to −78° C. Then LiHMDS (1M in THF, 22.1 mL, 22.1 mmol) was slowly added. The solution was stirred for 2 hours at −78° C. before being allowed to warm to rt and neutralized with addition of 1M aqueous HCl (22.1 mL). The mixture was then diluted with EtOAc (100 mL) and THF was removed under reduced pressure. The mixture is then washed with 0.5 M NaH₂PO₄ (50 mL) and aqueous phase extracted with EtOAc (2×50 mL). The combined organic phases were dried over MgSO₄, filtered and evaporated. The crude product was purified by CC (EtOAc/hexane 3:1) to yield the two isomers 2a/b (3.30 g, 74%) as a slightly yellow solid.

Data for 2a: $R_f$=0.37 (EtoAc/hexane 1:1);

$^1$H NMR (300 MHz, CDCl₃) δ 6.07-5.98 (m, 1H, H—C(2)), 5.59 (d, J=6.0 Hz, 1H, H—C(5')), 4.94-4.81 (m, 1H, H—C(1')), 4.65 (t, J=5.6 Hz, 1H, H—C(7')), 4.18 (q, J=7.1 Hz, 2H, CH₃CH₂), 2.67 (br, 1H, OH), 2.37 (dd, J=13.5, 7.5 Hz, 1H, H—C(8')), 1.55-1.42 (m, 1H, H—C(8')), 1.40, 1.33 (2s, 6H, (CH₃)₂C), 1.26 (t, J=7.1 Hz, 3H, CH₂CH₃).

$^{13}$C NMR (75 MHz, CDCl₃) δ 165.75 (C(1)), 161.61 (C(6')), 116.53 (C(2)), 110.69 (C(3')), 76.55 (C(5')), 75.52 (C(1')), 71.63 (C(7')), 60.51 (CH₂CH₃), 37.46 (C(8')), 26.44, 24.11 ((CH₃)₂C), 14.27 (CH₂CH₃).

ESI⁺-HRMS m/z calcd for C₁₂H₁₉O₅ ([M+H]⁺) 243.1227, found 243.1231.

Data for 2b: $R_f$=0.52 (EtoAc/hexane 1:1);

$^1$H NMR (300 MHz, CDCl₃) δ 6.15-6.05 (m, 1H, H—C(2)), 5.37-5.02 (m, 2H, H—C(5'), OH), 4.87 (d, J=3.4 Hz, 1H, H—C(1')), 4.67 (t, J=4.9 Hz, 1H, H—C(7')), 4.20 (qd, J=7.1, 0.9 Hz, 2H, CH₃CH₂), 2.55 (dd, J=14.6, 8.1 Hz, 1H, H—C(8')), 1.94-1.77 (m, 1H, H—C(8')), 1.39-1.25 (m, 9H, (CH₃)₂C, CH₂CH₃).

$^{13}$C NMR (75 MHz, CDCl₃) δ 167.91 (C(1)), 167.43 (C(6')), 120.13 (C(2)), 111.75 (C(3')), 81.62 (C(5')), 78.08 (C(1')), 70.85 (C(7')), 61.25 (CH₂CH₃), 36.53 (C(8')), 27.38, 25.45 ((CH₃)₂C), 14.19 (CH₂CH₃).

ESI⁺-HRMS m/z calcd for C₁₂H₁₉O₅ ([M+H]⁺) 243.1227, found 243.1227.

Example 3

Ethyl (1'R,5'S,6'S,7'R)-(7'-hydroxy-3',3'-dimethyl-2, 4'-dioxabicyclo[3.3.0]oct-6'-yl)acetate (3)

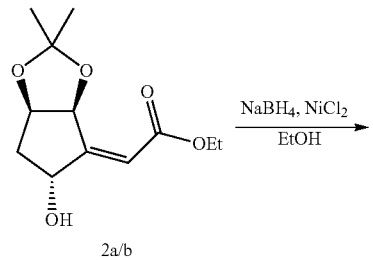

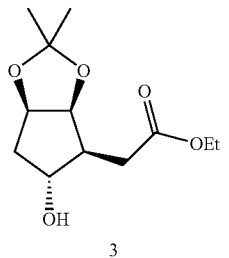
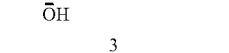

To a solution of the alcohols 2a/b (12.65 g, 52.2 mmol) and nickel chloride hexahydrate (2.48 g, 10.4 mmol) in EtOH (300 mL) was added portion wise sodium borohydride (9.88 g, 261 mmol) at 0° C. The resulting dark solution was stirred for 30 min at 0° C. and 90 min at rt. Then EtOH was carefully concentrated under reduced pressure, the resulting solid diluted with EtOAc (200 mL) and the excess of NaBH$_4$ quenched by addition of water (100 mL) at 0° C. followed by stirring at rt for 30 min. The two phases are then separated. Organic phase was washed with water (100 mL). Aqueous phases are then combined, filtered and extracted with EtOAc (2×100 mL). The combined organic phases were dried over MgSO$_4$, filtered and concentrated. The crude product was purified by CC (EtOAc/hexane 2:1) to yield 3 (11.4 g, 90%) as a white solid.

Data for 3: R$_f$=0.40 (EtOAc/hexane 1:1);

$^1$H NMR (300 MHz, CDCl$_3$) δ 4.65-4.52 (m, 2H, H—C(1'), H—C(5')), 4.15 (qd, J=7.1, 1.4 Hz, 2H, CH$_3$CH$_2$), 4.05 (ddd, J=10.0, 9.99, 6.2 Hz, 1H, H—C(7')), 2.86 (br, s, 1H, OH), 2.65 (qd, J=16.9, 7.1 Hz, 2H, H—C(2)), 2.24 (dd, J=13.7, 6.2 Hz, 1H, H—C(8')), 1.93 (dt, J=12.7, 7.1 Hz, 1H. H—C(6')), 1.56 (ddd, J=13.9, 10.2, 5.5 Hz, 1H, H—C(8')), 1.38 (s, 3H, (CH$_3$)$_2$C), 1.30-1.21 (m, 6H, (CH$_3$)$_2$C, CH$_2$CH$_3$).

$^{13}$C NMR (75 MHz, CDCl$_3$) δ 174.38 (C(1)), 109.06 (C(3')), 79.65 (C(5')), 77.19 (C(1'), 74.32 (C(7'), 60.80 (CH$_2$CH$_3$), 46.66 (C(6')), 40.38 (C(8')), 32.43 (C(2)), 26.00, 23.69 ((CH$_3$)$_2$C), 14.17 (CH$_2$CH$_3$).

ESI$^+$-HRMS m/z calcd for C$_{12}$H$_{21}$O$_5$ ([M+H]$^+$) 245.1384, found 245.1388.

Example 4

Ethyl (1'R,5'S,6'S,7'R)-(7'-(tert-butyldiphenylsilyl) oxy)-3',3'-dimethyl-2,4'-dioxabicyclo[3.3.0]oct-6'-yl) acetate (4)

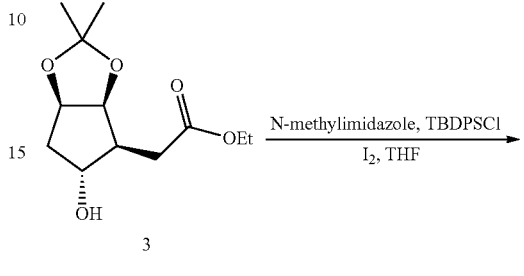

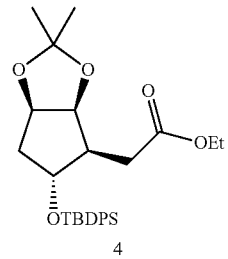

To a solution of the alcohol 3 (2.50 g, 10.2 mmol), N-methylimidazole (12.6 g, 153 mmol) and iodine (7.80 g, 30.6 mmol) in dry THF (60 mL) was added dropwise tert-butyl(chloro)diphenylsilane (3.0 mL, 11.2 mmol) at rt. The solution was stirred for 3 hours at rt and hen THF was evaporated, the mixture diluted with EtOAc (50 mL) and washed with 10% aqueous Na$_2$O$_3$S$_2$ (2×40 mL). Aqueous phases are then combined and extracted with EtOAc (50 mL). The combined organic phases were dried over MgSO$_4$, filtered and evaporated. The crude product was purified by CC (EtOAc/hexane 1:10) to yield 4 (5.01 g, quantitative yield) as a white solid Data for 4: R$_f$=0.87 (DCM/MeOH 10:1);

$^1$H NMR (300 MHz, CDCl$_3$) δ 7.77-7.59 (m, 4H, H-arom), 7.51-7.32 (m, 6H, H-arom), 4.61 (t, J=5.7 Hz, 1H, H—C(5')), 4.49 (t, J=5.7 Hz, 1H, H—C(1')), 4.15 (q, J=6.9 Hz, 2H, CH$_3$CH$_2$), 3.96 (dd, J=15.5, 9.5 Hz, 1H, H—C(7')), 2.64-2.32 (m, 2H, H—C(2)), 2.15 (tt, J=9.0, 4.3 Hz, 1H, H—C(6')), 1.83 (dd, J=12.7, 5.2 Hz, 1H, H—C(8')), 1.61-1.45 (m, 1H, H—C(8')), 1.27 (td, J=7.1, 1.9 Hz, 3H, CH$_2$CH$_3$), 1.18 (s, 6H, (CH$_3$)$_2$C), 1.09, 1.08 (2s, 9H, (CH$_3$)$_3$—C—Si).

$^{13}$C NMR (75 MHz, CDCl$_3$) δ 173.07 (C(1)), 135.87, 135.85 (CH-arom), 134.08, 133.73 (C-arom), 129.80, 129.75, 127.67, 127.58 (CH-arom), 108.82 (C(3')), 77.92 (C(5')), 76.96 (C(1')), 74.93 (C(7')), 60.24 (CH$_2$CH$_3$), 47.27 (C(6')), 40.27 (C(8')), 31.10 (C(2)), 27.04 (CH$_3$)$_3$—C—Si), 25.86 ((CH$_3$)$_2$C), 23.83 ((CH$_3$)$_2$C), 19.23 (CH$_3$)$_3$—C—Si), 14.24 (CH$_2$—CH$_3$).

ESI$^+$-HRMS m/z calcd for C$_{28}$H$_{39}$O$_5$Si ([M+H]$^+$) 483.2561, found 483.2562.

Example 5

(1'R,5'S,6'S,7'R)-(7'-(tert-butyldiphenylsilyl)oxy)-3',3'-dimethyl-2,4'-dioxabicyclo[3.3.0]oct-6'-yl)acetaldehyde (5)

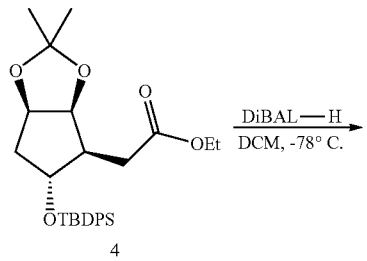

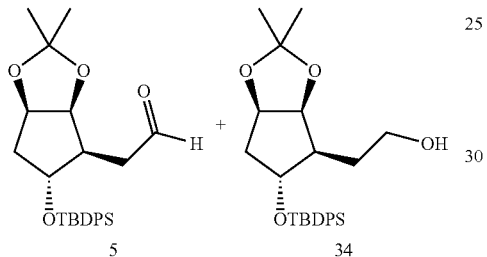

Example 6

(3aR,4R,6R,6aS)-4-((tert-butyldiphenylsilyl)oxy)-2-methoxyhexahydro-2H-cyclopenta[b]furan-6-ol (6)

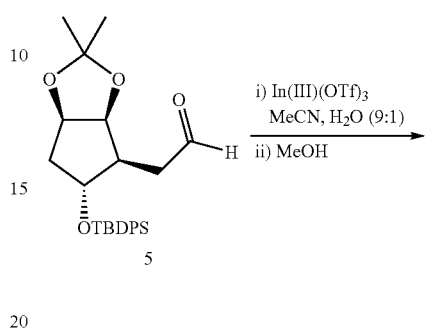

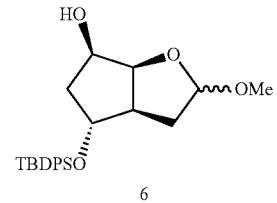

A solution of the ester 4 (8.56 g, 16.3 mmol) in dry DCM (120 mL) was cool down to −78° C. and then DiBAL-H (1M in cyclohexane, 18 mL, 18 mmol) was slowly added. The solution was further stirred at −78° C. for 90 min before being allowed to warm to rt. Reaction was quenched by addition of 0.5 M aqueous $NaH_2PO_4$ (100 mL). The organic phase was separated and aqueous phase was further extracted with DCM (2×100 mL). The combined organic phases were dried over $MgSO_4$, filtered and evaporated. The crude product was purified by CC (EtOAc/hexane 2:10 to 2:1) to yield aldehyde 5 (6.36 g, 89%) and alcohol 34 (0.637 g, 9%).

Data for 5: $R_f$=0.65 (EtOAc/hexane 2:1);

$^1$H NMR (300 MHz, $CDCl_3$) δ 9.72 (s, 1H, H—C(1)), 7.65 (td, J=8.0, 1.6 Hz, 4H, H-arom), 7.47-7.33 (m, 6H, H-arom), 4.57 (t, J=5.7 Hz, 1H, H—C(5')), 4.51 (t, J=5.7 Hz, 1H, H—C(1')), 3.99 (td, J=10.0, 5.9 Hz, 1H, H—C(7')), 2.58-2.43 (m, 2H, H—C(2)), 2.20-2.08 (m, 1H, H—C(6')), 1.87 (dd, J=13.5, 5.9 Hz, 1H, H—C(8')), 1.53 (ddd, J=13.5, 10.1, 5.5 Hz, 1H, H—C(8')), 1.16 (d, J=3.5 Hz, 6H, $((CH_3)_2C)$, 1.05 (s, 9H, $(CH_3)_3$—C—Si).

$^{13}$C NMR (75 MHz, $CDCl_3$) δ 201.87 (C(1)), 135.93, 135.90 (CH-arom), 133.96, 133.73 (C-arom), 129.96, 129.89, 127.79, 127.68 (CH-arom), 108.89 (C(3')), 77.76 (C(5')), 77.17 (C(1')), 74.96 (C(7'), 45.44 (C(6')), 41.31 (C(2)), 40.16 (C(8')), 27.08 $(CH_3)_3$—C—Si), 25.87 $((CH_3)_2C)$, 23.79 $((CH_3)_2C)$, 19.25 $(CH_3)_3$—C—Si).

$ESI^+$-HRMS m/z calcd for $C_{26}H_{35}O_4Si$ $([M+H]^+)$ 439.2299, found 439.2297.

To a solution of the aldehyde 5 (13.73 g, 31.31 mmol) in MeCN (170 mL) and $H_2O$ (19 mL) was added Indium(III) trifluoromethanesulfonate (703 mg, 1.25 mmol). The solution was further stirred for 48 hours, and then solvents were removed under reduced pressure and coevaporated with toluene. The residue was dissolved in dry MeOH and stirred for 6 hours. After evaporation of solvent, the crude product was purified by CC (EtOAc/hexane 3:10) to yield a mixture of 6 (10.50 g, 81%) in an anomeric ratio α/β≈4:1 as a colorless oil.

Data for 6: $R_f$=0.53 (EtOAc/hexane 1:1);

$^1$H NMR (300 MHz, $CDCl_3$) δ 7.63 (dd, J=7.1, 0.6 Hz, 4H, H-arom), 7.46-7.34 (m, 6H, H-arom), 4.98 (d, J=4.8 Hz, 0.8H, H—C(2)), 4.91 (dd, J=5.9, 1.3 Hz, 0.2H, H—C(2)), 4.63-4.54 (m, 1H, H—C(6a)), 4.53-4.37 (m, 1H, H—C(6)), 4.09 (m, 0.2H, H—C(4)), 3.92 (br, 0.8H, H—C(4)), 3.29, 3.27 (2s, 3H, MeO), 2.79 (dd, J=17.0, 8.2 Hz, 0.8H, H—C(3a)), 2.64-2.51 (m, 0.2H, H—C(3a)), 2.29 (d, J=8.1 Hz, 1H, OH), 2.10-1.80 (m, 2.4H, H—C(3), H—C(5)), 1.65 (ddd, J=13.2, 9.1, 4.4 Hz, 0.8H, H—C(5)), 1.44-1.34 (m, 0.2H, H—C(3)), 1.22 (ddd, J=13.2, 8.1, 4.9 Hz, 0.8H, H—C(3)), 1.05 (s, 9H, $(CH_3)_3$—C—Si).

$^{13}$C NMR (75 MHz, $CDCl_3$) δ 135.78, 135.74 (CH-arom), 133.96, 133.84 (C-arom), 129.78, 127.72 (CH-arom), 107.21, 106.50 (C(2)), 85.37, 81.76 (C(6a)), 78.11, 77.19 (C(4)), 73.03, 72.44 (C(6)), 55.30, 54.46 (MeO), 50.91, 49.67 (C(3a)), 41.13, 40.29 (C(3)), 38.16, 37.98 (C(5)), 26.96, 26.92 $(CH_3)_3$—C—Si), 19.07 $(CH_3)_3$—C—Si).

$ESI^+$-HRMS m/z calcd for $C_{26}H_{35}O_4Si$ $([M+H]^+)$ 435.1962, found 435.1950.

Example 7

(3aR,4R,6R,6aS)-4-((tert-butyldiphenylsilyl)oxy)-2-methoxyhexahydro-2H-cyclopenta[b]furan-6-yl acetate (7)

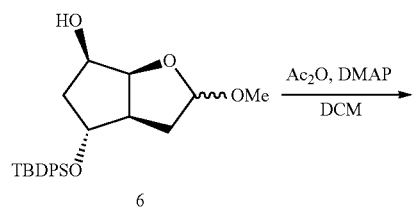

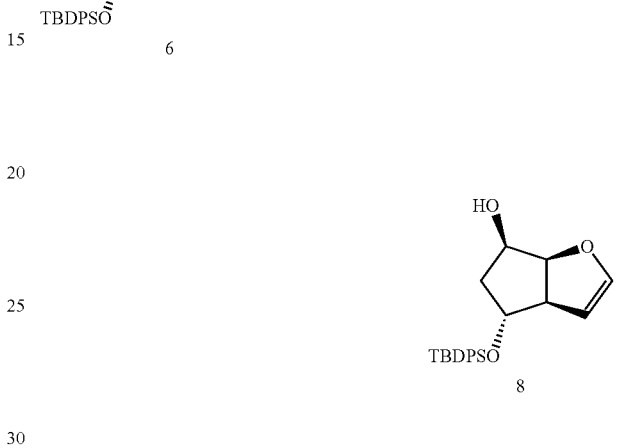

To a solution of sugar 6 (3.35 g, 8.12 mmol) and 4-Dimethylaminopyridine (1.29 g, 10.6 mmol) in dry DCM (100 mL) was added acetic anhydride (3.8 mL, 41 mmol) at rt. After stirring for 2 h, reaction is quenched by slow addition of satd $NaHCO_3$ (10 mL). The mixture is then diluted with satd $NaHCO_3$ (50 mL) and extracted with DCM (3×50 mL). The combined organic phases were dried over $MgSO_4$, filtered and evaporated. The crude product was purified by CC (EtOAc/Hexanne 1:2) to yield a mixture of 7 (3.53 g, 96%) in an anomeric ratio α/β≈4:1 as a colorless oil.

Data for 7: $R_f$=0.42 (EtOAc/hexane 1:2);

$^1$H NMR (400 MHz, $CDCl_3$) δ 7.70-7.59 (m, 4H, H-arom), 7.48-7.34 (m, 6H, H-arom), 5.41 (dt, J=11.0, 5.6 Hz, 0.8H, H—C(6)), 5.28 (ddd, J=11.7, 6.6, 5.2 Hz, 0.2H, H—C(6)), 4.99 (d, J=4.8 Hz, 0.8H, H—C(2)), 4.89-4.81 (m, 0.4H, H—C(2), H—C(6a)), 4.76-4.69 (m, 0.8H, H—C(6a)), 4.11 (d, J=5.1 Hz, 0.2H, H—C(4)), 3.90 (d, J=4.0 Hz, 0.8H, H—C(4)), 3.27, 3.24 (2s, 3H, MeO), 2.81 (dd, J=16.6, 7.6 Hz, 0.8H, H—C(3a)), 2.60 (dd, J=10.1, 7.0 Hz, 0.2H, H—C(3a)), 2.30-2.18 (m, 0.2H, H—C(5)), 2.12, 2.10 (2s, J=4.7 Hz, 3H, $MeCO_2$), 2.07-1.82 (m, 2.8H, H—C(5), H—C(3)), 1.24 (ddd, J=12.9, 7.6, 3.7 Hz, 1H, H—C(3)), 1.07 (s, 9H, $(CH_3)_3$—C—Si).

$^{13}$C NMR (75 MHz, $CDCl_3$) δ 170.75, 170.66 ($MeCO_2$), 135.77, 135.73, 135.72 (CH-arom), 133.75, 133.65 (C-arom), 129.82, 129.74, 127.76, 127.75, 127.71 (CH-arom), 106.19, 106.15 (C(2)), 83.17, 79.80 (C(6a)), 77.49, 76.46 (C(4)), 75.64, 74.41 (C(6)), 54.34, 54.25 (MeO), 51.48, 50.17 (C(3a)), 38.05, 37.98 (C(3)), 36.96, 36.21 (C(5)), 26.95, 26.90 $(CH_3)_3$—C—Si), 21.09, 21.04 ($MeCO_2$), 19.04 $(CH_3)_3$—C—Si).

$ESI^+$-HRMS m/z calcd for $C_{26}H_{34}O_5NaSi$ $([M+Na]^+)$ 477.2068, found 477.2063.

Example 8

(3aR,4R,6R,6aS)-4-((tert-butyldiphenylsilyl)oxy)-3a,5,6,6a-tetrahydro-4H-cyclopenta[b]furan-6-ol (8)

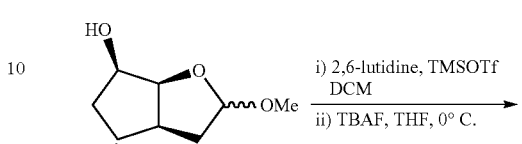

To a solution of the sugar 6 (2.08 g, 5.04 mmol) in dry DCM (35 mL) was added 2,6-lutidine (2.95 mL, 25.2 mmol) at 0° C. After stirring for 20 min at 0° C., TMSOTf (2.73 mL, 15.1 mmol) was added dropwise and then the solution was allowed to warm to rt and stirred for another 60 min. The reaction was then quenched by addition of satd $NaHCO_3$ (40 mL). The organic phase was separated and aqueous phase was further extracted with DCM (3×30 mL). The combined organic phases were dried over $MgSO_4$, filtered and evaporated.

The resulting product was dissolved in dry THF (35 mL), cool down to 0° C., and TBAF (1M in THF, 5.6 mL, 5.6 mmol) was added. The solution was stirred for 10 min and then diluted with satd $NaHCO_3$ (30 mL) and extracted with DCM (4×40 mL). The combined organic phases were dried over $MgSO_4$, filtered and evaporated. The crude product was purified by CC (EtOAc/hexane 1:4) to yield the glycal 8 (1.76 g, 92%).

Data for 8: $R_f$=0.49 (EtOAc/hexane 1:2);

$^1$H NMR (300 MHz, $CDCl_3$) δ 7.66 (m, 4H, H-arom), 7.42 (m, 6H, H-arom), 6.22 (t, J=2.1 Hz, 1H, H—C(2)), 4.91 (dd, J=8.2, 5.3 Hz, 1H, H—C(3)), 4.70 (dt, J=11.1, 5.6 Hz, 1H, H—C(6)), 4.56 (t, J=2.8 Hz, 1H, H—C(6a)), 3.97 (d, J=4.0 Hz, 1H, H—C(4)), 3.24 (d, J=8.2 Hz, 1H, H—C(3a)), 2.30 (br, 1H, OH), 2.03 (dd, J=12.6, 5.4 Hz, 1H, H—C(5)), 1.51 (ddd, J=12.7, 11.2, 4.2 Hz, 1H, H—C(5)), 1.08 (s, 9H, $(CH_3)_3$—C—Si).

$^{13}$C NMR (75 MHz, $CDCl_3$) δ 146.24 (C(2)), 135.72, 135.69 (CH-arom), 134.03, 133.74 (C-arom), 129.80, 129.78, 127.73 (CH-arom), 101.84 (C(3)), 84.59 (C(6a)), 76.79 (C(4)), 74.10 (C(6)), 55.56 (C(3a)), 39.38 (C(5)), 26.93 $(CH_3)_3$—C—Si), 19.08 $(CH_3)_3$—C—Si).

$ESI^+$-HRMS m/z calcd for $C_{23}H_{29}O_3Si$ $([M+H]^+)$ 381.1880, found 381.1893.

Example 9

(((3aR,4R,6R,6aS)-6-(bis(4-methoxyphenyl)(phenyl)methoxy)-3a,5,6,6a-tetrahydro-4H-cyclopenta[b]furan-4-yl)oxy)(tert-butyl)diphenylsilane (9)

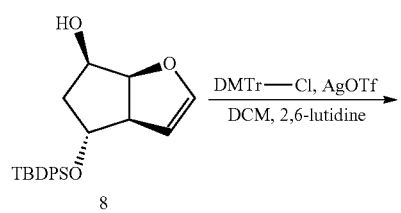

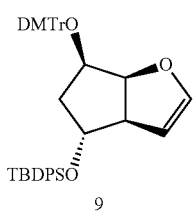

To a solution of glycal 8 (1.34 g, 3.52 mmol) and DMTr-Cl (1.43 g, 4.23 mmol) in a mixture of dry DCM (15 mL) and dry 2,6-lutidine (15 mL) was added portionwise silver triflate (1.13 g, 4.40 mmol), resulting in a deep red suspension. After stirring for 2 hours at rt, an additional portion of DMTr-Cl (239 mg, 0.705 mmol) was added. The suspension was further stirred for 2 hours and then was filtered. The organic phase was washed with satd NaHCO$_3$ (100 mL) and aqueous phase were extracted with DCM (3×30 mL). The combined organic phases were dried over MgSO$_4$, filtered and evaporated. The crude product was purified by CC (EtOAc/hexane 1:7, +0.5% Et$_3$N) to yield the protected glycal 9 (2.24, 93%) as a white foam.

Data for 9: R$_f$=0.59 (EtOAc/hexane 1:2);

$^1$H NMR (400 MHz, CDCl$_3$) δ 7.76 (d, J=7.4 Hz, 2H, H-arom), 7.69-7.60 (m, J=9.3, 5.9, 4.6 Hz, 8H, H-arom), 7.56-7.39 (m, 8H, H-arom), 7.33 (t, J=7.3 Hz, 1H, H-arom), 7.00-6.93 (m, 4H, H-arom), 6.47-6.37 (m, 1H, H—C(2)), 4.67-4.58 (m, 1H, H—C(6)), 4.58-4.50 (m, 2H, H—C(3), H—C(6a)), 3.86, 3.85 (2s, 6H, MeO), 3.82 (d, J=4.0 Hz, 1H, H—C(4)), 3.08 (d, J=8.1 Hz, 1H, H—C(3a)), 1.67 (td, J=12.4, 4.2 Hz, 1H, H—C(5)), 1.28 (dd, J=12.7, 5.4 Hz, 1H, H—C(5)), 1.11 (s, 9H, (CH$_3$)$_3$—C—Si).

$^{13}$C NMR (75 MHz, CDCl$_3$) δ 158.67 (MeO—C-arom), 147.61 (C(2)), 146.26, 137.36, 137.21 (C-arom), 135.81, 135.78 (CH-arom), 134.17, 134.04 (C-arom), 130.48, 129.83, 129.81, 128.37, 127.98, 127.76, 127.73, 126.79, 113.32, 113.28 (CH-arom), 100.29 (C(3)), 86.96 (C(Ph)$_3$), 84.95 (C(6a)), 76.17 (C(6)), 76.07 (C(4)), 55.26 (MeO-DMTr), 55.11 (C(3a)), 37.32 (C(5)), 27.04 (CH$_3$)$_3$—C—Si), 19.21 (CH$_3$)$_3$—C—Si).

ESI$^+$-HRMS m/z calcd for C$_{44}$H$_{46}$O$_5$NaSi ([M+Na]$^+$) 705.3007, found 705.3021.

Example 10

(3aS,4R,6R,6aS)-6-(bis(4-methoxyphenyl)(phenyl)methoxy)-3a,5,6,6a-tetrahydro-4H-cyclopenta[b]furan-4-ol (10)

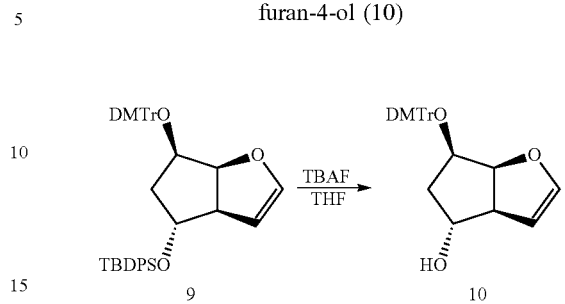

To a solution of glycal 9 (2.23 g, 3.27 mmol) in dry THF (20 mL) was added TBAF (1M in THF, 20 mL, 20 mmol) at rt. The solution was stirred for 20 h and then was diluted with satd NaHCO$_3$ (100 mL) and extracted with DCM (3×80 mL). The combined organic phases were dried over MgSO$_4$, filtered and evaporated. The crude product was purified by CC (0.5% MeOH in DCM, +0.5% Et$_3$N) to yield 10 (1.45 g, quant.) as a white foam.

Data for 10: R$_f$=0.44 (EtOAc/hexane 1:1);

$^1$H NMR (300 MHz, CDCl$_3$) δ 7.53-7.46 (m, 2H, H-arom), 7.43-7.35 (m, 4H, H-arom), 7.21 (dd, J=10.7, 5.3 Hz, 2H, H-arom), 7.16-7.08 (m, 1H, H-arom), 6.80-6.71 (m, 4H, H-arom), 6.30 (t, J=2.1 Hz, 1H, H—C(2)), 4.68 (t, J=2.8 Hz, 1H, H—C(3)), 4.29-4.14 (m, 2H, H—C(6), H—C(6a)), 3.71 (s, 6H, MeO), 3.65 (d, J=3.5 Hz, 1H, H—C(4)), 2.87 (d, J=7.9 Hz, 1H, H—C(3a)), 1.59 (ddd, J=13.2, 11.6, 4.3 Hz, 1H, H—C(5)), 1.05-0.95 (m, 2H, H—C(5), OH).

$^{13}$C NMR (75 MHz, CDCl$_3$) δ 158.54 (MeO—C-arom), 147.64 (C(2)), 145.82, 137.12, 137.08 (C-arom), 130.26, 128.29, 127.81, 126.71, 113.13 (CH-arom), 100.17 (C(3)), 86.75 (C(Ph)$_3$), 84.42 C(6a)), 75.54 (C(6)), 74.59 (C(4)), 55.22 (MeO-DMTr), 54.25 (C(3a)), 37.56 (C(5)).

ESI$^+$-HRMS m/z calcd for C$_{30}$H$_{27}$O$_5$ ([M+H]$^+$) 467.1853, found 467.1844.

Example 11

(3'S,5'R,7'R)-1-{2',3'-Dideoxy-3',5'-ethano-7'-hydroxy-5'-O-[(4,4'-dimethoxytriphenyl)methyl]-β-D-ribofuranosyl} thymine (11)

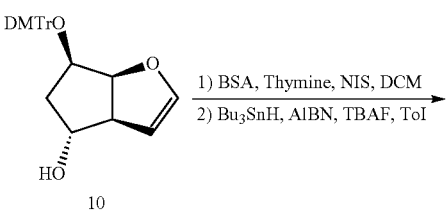

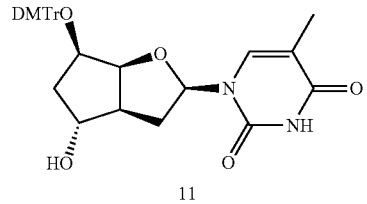

To a solution of glycal 10 (1.45 g, 3.27 mmol) in dry DCM (45 mL), at 0°, was added dropwise BSA (2.0 mL, 8.18 mmol) and then the solution was allowed to warm to rt. After stirring for 45 min, Thymine (595 mg, 4.91 mmol) was added and the reaction was further stirred for 60 min at rt. The mixture was then cooled down to 0° C. and N-iodo-succinimide (875 mg, 3.92 mmol) was added. After stirring for 3 h at 0° C. and for 4 h at rt, the reaction mixture was diluted with EtOAc (100 mL) and subsequently washed with a 10% aq solution of $Na_2S_2O_3$ (100 mL) and satd $NaHCO_3$ (100 mL). Aqueous phases were combined and extracted with DCM (3×50 mL). The combined organic phases were dried over $MgSO_4$, filtered and evaporated.

The crude product was dissolved in dry toluene (45 mL) and then $Bu_3SnH$ (1.32 mL, 4.91 mmol) and azoisobutyronitrile (AIBN, 53 mg, 0.33 mmol) were added at rt. After heating at 70° C. for 30 min, the mixture was cool down to rt and TBAF was added (1M in THF, 6.5 mL, 6.5 mmol). The solution was further stirred for 25 min and was diluted with satd $NaHCO_3$ (100 mL) and extracted with DCM (4×70 mL). The combined organic phases were dried over $MgSO_4$, filtered and evaporated. The crude product was purified by CC (3% MeOH in DCM, +0.5% $Et_3N$) to yield 11 (1.45 g, 73% over two steps) as a white foam.

Data for 11: $R_f$=0.29 (6% MeOH in DCM);

$^1$H NMR (400 MHz, $CDCl_3$) δ 9.37 (br, 1H, H—N(3)), 7.83 (d, J=1.1 Hz, 1H, H—C(6)), 7.58-7.52 (m, 2H, H-arom), 7.48-7.41 (m, 4H, H-arom), 7.28 (t, J=7.7 Hz, 2H, H-arom), 7.21 (t, J=7.2 Hz, 1H, H-arom), 6.84 (dd, J=8.9, 1.2 Hz, 4H, H-arom), 5.91 (dd, J=8.0, 5.5 Hz, 1H, H—C(1')), 4.25 (dt, J=10.8, 6.0 Hz, 1H, H—C(5')), 4.13-4.08 (m, 1H, H—C(4')), 3.86 (d, J=3.4 Hz, 1H, H—C(7')), 3.79 (s, 6H, MeO), 2.70 (ddd, J=12.8, 10.2, 5.5 Hz, 1H, H—C(2')), 2.61 (dd, J=16.9, 8.2 Hz, 1H, H—C(3')), 1.84 (d, J=0.8 Hz, 3H, Me-C(5)), 1.80 (br, 1H, OH), 1.60 (ddd, J=14.2, 10.5, 4.2 Hz, 1H, H—C(6')), 1.33 (dt, J=12.9, 8.0 Hz, 1H, H—C(2')), 1.14 (dd, J=13.7, 6.1 Hz, 1H, H—C(6')).

$^{13}$C NMR (101 MHz, $CDCl_3$) δ 164.17 (C(4)), 158.64 (MeO—C-arom), 150.47 (C(2)), 145.65, 136.85, 136.71 (C-arom), 135.52 (C(6)), 130.20, 128.12, 127.91, 126.90, 113.22, 113.21 (CH-arom), 110.69 (C(5)), 87.21 (C(Ph)$_3$), 86.57 (C(1')), 82.02 (C(4')), 74.19 (C(5')), 74.13 (C(7')), 55.25 (MeO-DMTr), 49.40 (C(3')), 38.51 (C(6')), 37.64 (C(2')), 12.58 (Me-C(5)).

ESI$^+$-HRMS m/z calcd for $C_{33}H_{34}O_7N_2Na$ ([M+NA]$^+$) 593.2258, found 593.2250.

Example 12

(3'R,5'R,7'R)-1-{7'-O-[(2-cyanoethoxy)-diisopropylaminophosphanyl]-2',3'-Dideoxy-3',5'-ethano-5'-O-[(4,4'-dimethoxytriphenyl)methyl]-β-D-ribofuranosyl} Thymine (12)

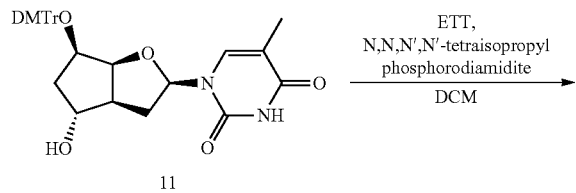

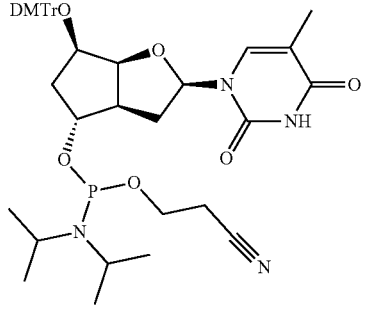

To a solution of the nucleoside 11 (232 mg, 0.406 mmol) and 5-(Ethylthio)-1H-tetrazole (90 mg, 0.69 mmol) in dry DCM (10 mL) was added dropwise 2-Cyanoethyl N,N,N',N'-tetraisopropylphosphordiamidite (0.26 mL, 0.81 mmol) at rt. After stirring for 30 min, the reaction mixture was diluted with DCM (50 mL) and washed with satd $NaHCO_3$ (2×30 mL) and satd NaCl (30 mL). Aqueous phases were combined and extracted with DCM (50 mL). The combined organic phases were dried over $MgSO_4$, filtered and evaporated. The crude product was purified by CC (1.8% MeOH in DCM, +0.5% $Et_3N$) to yield 12 (219 mg, mixture of two isomers, 70%) as a white foam.

Data for 11: $R_f$=0.68 (6% MeOH in DCM);

$^1$H NMR (300 MHz, $CDCl_3$) δ 8.93 (br, 1H, H—N(3)), 7.85 (d, J=1.2 Hz, 1H, H—C(6)), 7.65-7.52 (m, 2H, H-arom), 7.52-7.40 (m, 4H, H-arom), 7.40-7.21 (m, 3H, H-arom), 6.96-6.81 (m, 4H, H-arom), 6.00, 5.94 (2dd, J=8.3, 5.2 Hz, 1H, H—C(1')), 4.29-4.17 (m, 1H, H—C(5')), 4.12-3.89 (m, 2H, H—C(4'), H—C(7')), 3.85, 3.84 (2s, 6H, MeO), 3.81-3.63 (m, 2H, OCH$_2$CH$_2$CN), 3.56-3.41 (m, 2H, (Me$_2$CH)$_2$N), 2.88-2.69 (m, 2H, H—C(3'), H—C(2')), 2.61, 2.56 (dt, J=12.9 6.3 Hz, 2H, OCH$_2$CH$_2$CN), 1.92, 1.82 (2d, J=0.8 Hz, 3H, Me-C(5)), 1.75-1.56 (m, 1H, H—C(6')), 1.52-1.36 (m, 2H, H—C(6'), H—C(2')), 1.22-1.01 (m, 12H, (Me$_2$CH)$_2$N).

$^{13}$C NMR (101 MHz, $CDCl_3$) δ 163.86 (C(4)), 158.66, 158.64 (MeO—C-arom), 150.29, 150.27 (C(2)), 145.58, 145.52, 136.76, 136.71, 136.69, 136.60 (C-arom), 135.49, 135.35 (C(6)), 130.21, 130.16, 128.17, 128.13, 127.88, 126.91, 126.89 (CH-arom), 117.49 (OCH$_2$CH$_2$CN), 113.18 (CH-arom), 110.74 (C(5)), 87.27, 87.25 (C(Ph)$_3$), 86.58, 86.45 (C(1')), 81.79, 81.68 (C(4')), 76.02, 75.50 ($J_{C,P}$=16.5, 15.7 Hz, C(7')), 74.22 (C(5')), 58.26, 58.06, 57.87 (OCH$_2$CH$_2$CN), 55.26, 55.22 (MeO-DMTr), 48.85, 48.62 ($J_{C,P}$=2.6, 5.0 Hz, C(3')), 43.10, 43.04 ($J_{C,P}$=12.3, 12.4 Hz (Me$_2$CH)$_2$N), 37.78 ($J_{C,P}$=5.3 Hz C(6')), 37.62, 37.48 (C(2')), 37.41 ($J_{C,P}$=3.6 Hz C(6')), 24.57, 24.53, 24.50, 24.46, 24.44, 24.39, 24.37 (Me$_2$CH)$_2$N), 20.35, 20.25 ($J_{C,P}$=7.1, 7.0 Hz, OCH$_2$CH$_2$CN), 12.58, 12.41 (7s, Me-C(5)).

$^{31}$P NMR (122 MHz, $CDCl_3$) δ 147.32, 146.98.

ESI$^+$-HRMS m/z calcd for $C_{42}H_{52}O_8N_4P$ ([M+H]$^+$) 771.3517, found 771.3512.

Example 13

(3'S,5'R,7'R)—N4-Benzoyl-1-{2',3'-Dideoxy-3',5'-ethano-7'-hydroxy-5'-O-[(4,4'-dimethoxytriphenyl)methyl]-β-D-ribofuranosyl}-5-methylcytosine (13)

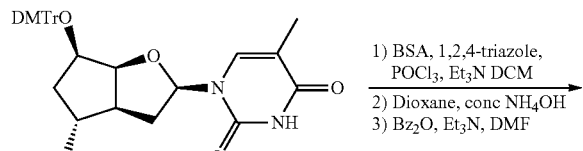

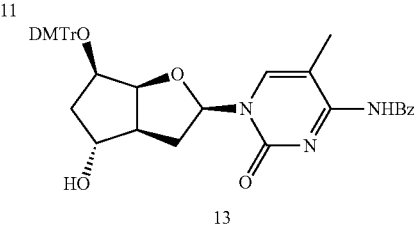

To a solution of the nucleoside 11 (302 mg, 0.530 mmol) in dry MeCN (5 mL) was added dropwise BSA (0.31 mL, 1.27 mmol) at 0°, and then the solution was stirred overnight at rt. In another flask, a suspension of 1,2,4-triazole (1.28 g, 18.55 mmol) in dry MeCN (50 mL) was cool down to 0° C. and POCl₃ (0.40 mL, 4.2 mmol) and Et₃N (2.96 mL, 21.2 mmol) were added. The suspension was stirred for 30 min at 0° C., and then the previous prepared solution of the silylated compound 11 was added to the suspension and the mixture was further stirred for 5 h at rt. Reaction was quenched with addition satd NaHCO₃ (10 mL), MeCN removed under reduced pressure and the resulting mixture diluted with satd NaHCO₃ (35 mL) and extracted with DCM (3×40 mL). The combined organic phases were dried over MgSO₄, filtered and evaporated.

The crude product was then dissolved in a mixture of 1,4-dioxane (10 mL) and concd NH₄OH (10 mL). After stirring for 2 h at rt, the mixture was reduced to half of the volume in vacuo, diluted with satd NaHCO₃ (30 mL) and extracted with DCM (4×30 mL). The combined organic phases were dried over MgSO₄, filtered and evaporated.

The crude product was then dissolved in dry DMF (13 mL), Et₃N (90 µL, 0.64 mmol) followed by Bz₂O (300 mg, 1.33 mmol) were added at rt and the solution was stirred overnight. The resulting brown solution was quenched by careful addition of satd NaHCO₃ (50 mL) and extracted with DCM (4×50 mL). The combined organic phases were dried over MgSO₄, filtered and evaporated. The crude product was purified by CC (hexane/EtOAc 1:2, +0.5% Et₃N) to yield 13 (315 mg, 88%) as a white foam.

Data for 13: $R_f$=0.57 (4% MeOH in DCM);
$^1$H NMR (300 MHz, CDCl₃) δ 13.39 (br, 1H, NH), 8.46-8.26 (m, 2H, H-arom), 8.13 (d, J=0.5 Hz, 1H, C(6)), 7.61 (d, J=7.3 Hz, 2H, H-arom), 7.58-7.43 (m, 7H, H-arom), 7.34 (t, J=7.4 Hz, 2H, H-arom), 7.30-7.23 (m, 1H, H-arom), 6.89 (d, J=8.8 Hz, 4H, H-arom), 5.96 (dd, J=7.5, 5.8 Hz, 1H, H—C(1')), 4.38-4.25 (m, 1H, H—C(5')), 4.22-4.12 (m, 1H, H—C(4')), 3.90 (d, J=3.6 Hz, 1H, H—C(7')), 3.83 (s, 6H, MeO), 2.82 (ddd, J=13.3, 10.2, 5.7 Hz, 1H, H—C(2')), 2.66 (dd, J=17.0, 8.1 Hz, 1H, H—C(3')), 2.08 (s, 3H, Me-C(5)), 1.77 (br, 1H, OH), 1.71-1.57 (m, 1H, H—C(6')), 1.49-1.36 (m, 1H, H—C(2')), 1.21 (dd, J=13.7, 6.2 Hz, 1H, H—C(6')).

$^{13}$C NMR (75 MHz, CDCl₃) δ 179.56 (CONH), 160.01 (C(4)), 158.70 (MeO—C-arom), 147.96 (C(2)), 145.65 (C-arom), 137.26 (C(6)), 136.99, 136.83, 136.71 (C-arom), 132.41, 130.22, 129.89, 128.16, 128.14, 127.95, 126.94, 113.25 (CH-arom), 111.57 (C(5)), 87.34 (C(Ph)₃), 87.32 (C(1')), 82.57 (C(4')), 74.30 (C(5')), 74.16 (C(7')), 55.27 (MeO-DMTr), 49.56 (C(3')), 38.52 (C(6')), 38.00 (C(2')), 13.63 (Me-C(5)).

ESI⁺-HRMS m/z calcd for C₄₀H₄₀O₇N₃ ([M+H]⁺) 674.2861, found 674.2862.

Example 14

(3'R,5'R,7'R)—N4-Benzoyl-1-{7'-O-[(2-cyanoethoxy)-diisopropylaminophosphanyl]-2',3'-Dideoxy-3',5'-ethano-5'-O-[(4,4'-dimethoxytriphenyl)methyl]-β-D-ribofuranosyl}-5-methylcytosine (14)

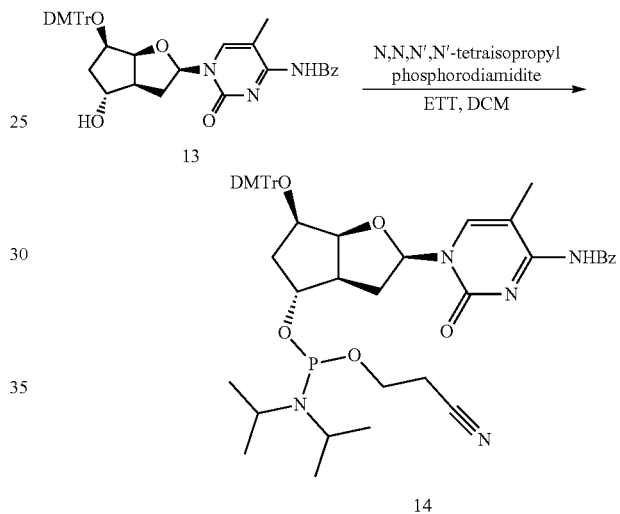

To a solution of the nucleoside 13 (276 mg, 0.409 mmol) and 5-(Ethylthio)-1H-tetrazole (69 mg, 0.53 mmol) in dry DCM (10 mL) was added dropwise 2-Cyanoethyl N,N,N',N'-tetraisopropylphosphordiamidite (0.20 mL, 0.61 mmol) at rt. After stirring for 60 min, the reaction mixture was diluted with DCM (50 mL) and washed with satd NaHCO₃ (2×30 mL) and satd NaCl (30 mL). Aqueous phases were combined and extracted with DCM (50 mL). The combined organic phases were dried over MgSO₄, filtered and evaporated. The crude product was purified by CC (EtOAc/Hexanne 2:3, +0.5% Et₃N) to yield 14 (268 mg, mixture of two isomers, 75%) as a white foam.

Data for 14: $R_f$=0.77 (5% MeOH in DCM);
$^1$H NMR (400 MHz, CDCl₃) δ 13.32 (s, 1H, NH), 8.41-8.28 (m, 2H, H-arom), 8.13-8.04 (m, 1H, C(6)), 7.61-7.51 (m, 3H, H-arom), 7.51-7.40 (m, 6H, H-arom), 7.37-7.29 (m, 2H, H-arom), 7.29-7.20 (m, 1H, H-arom), 6.92-6.82 (m, 4H, H-arom), 6.07-5.87 (m, 1H, H—C(1')), 4.24 (dq, J=11.7, 5.8 Hz, 1H, H—C(5')), 4.13-4.00 (m, 1H, H—C(4')), 3.94 (ddd, J=14.5, 10.5, 2.8 Hz, 1H, H—C(7')), 3.83, 3.82 (2s, 6H, MeO), 3.69 (m, 2H, OCH₂CH₂CN), 3.53-3.40 (m, 2H, (Me₂CH)₂N), 2.91-2.70 (m, 2H, H—C(2'), H—C(3')), 2.57, 2.53 (2t, J=6.3 Hz, 2H, OCH₂CH₂CN), 2.08, 1.99 (2d, J=0.6 Hz, 3H, Me-C(5)), 1.72 1.56 (m, 1H, H—C(6')), 1.54-1.36 (m, 2H, H—C(2'), H—C(6')), 1.10 (m, 12H, (Me₂CH)₂N).

$^{13}$C NMR (101 MHz, CDCl$_3$) δ 179.54 (CONH), 159.98 (C(4)), 158.69 (MeO—C-arom), 147.90 (C(2)), 145.58, 145.54 (C-arom), 137.30, 136.93 (C(6)), 136.81, 136.80, 136.73, 136.70, 136.67, 136.60 (C-arom), 132.37, 132.35, 130.22, 130.17, 129.89, 128.17, 128.15, 128.11, 127.93, 126.94 (CH-arom), 117.49 (OCH$_2$CH$_2$CN), 113.23 (CH-arom), 111.60 (C(5)), 87.36, 87.35 (C(Ph)$_3$), 87.33, 87.25 (C(1')), 82.33, 82.25 (C(4')), 76.05, 75.52 (J$_{C,P}$=16.4, 15.6 Hz, C(7')), 74.32 (C(5')), 58.18, 57.98 (J$_{C,P}$=19.5 Hz OCH$_2$CH$_2$CN), 55.28, 55.24 (MeO-DMTr), 48.93, 48.72 (J$_{C,P}$=2.7, 4.9 Hz, C(3')), 43.11, 43.05 (J$_{C,P}$=12.4 Hz (Me$_2$CH)$_2$N), 38.02, 37.88 (C(2')), 37.74, 37.40 (J$_{C,P}$=5.3, 3.4 Hz, C(6')), 24.58, 24.54, 24.50, 24.47, 24.40, 24.38 (6s, Me$_2$CH)$_2$N), 20.36, 20.26 (J$_{C,P}$=7.1 Hz, OCH$_2$CH$_2$CN,), 13.66, 13.49 (Me-C(5)).

$^{31}$P NMR (122 MHz, CDCl$_3$) δ 147.37, 147.07.

ESI$^+$-HRMS m/z calcd for C$_{49}$H$_{57}$O$_8$N$_5$P ([M+H]$^+$) 874.3939, found 874.3937.

Example 15

(3'R,5'R,7'R)—N6-Benzoyl-9-{5'-O-acetyl-7'-[(tert-butyldiphenylsilyl)oxy]-2',3'-Dideoxy-3',5'-ethano-α,β-D-ribofuranosyl} adenine (15)

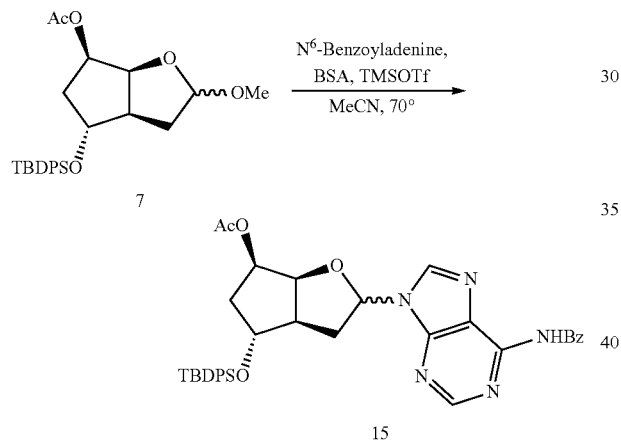

To a suspension of sugar 7 (1.86 g, 4.10 mmol) and N$^6$-Benzoyladenine (1.96 g, 8.20 mmol) in dry MeCN (40 mL) was added BSA (4.00 mL, 16.4 mmol) at rt. After stirring for 25 min, the suspension became a clear solution and then was heated to 70° C. TMSOTf (1.48 mL, 8.20 mmol) was added dropwise and the solution was further stirred for 20 min at 70° C. The solution was then cool down to rt, quenched with addition of satd NaHCO$_3$ (100 mL) and extracted with EtOAc (4×50 mL). The combined organic phases were dried over MgSO$_4$, filtered and evaporated. The crude product was purified by CC (2% MeOH in DCM) to yield a mixture of 15 (1.74 g, 64%) in an anomeric ratio α/β≈4:1 as a white foam.

Data for 15: R$_f$=0.33 (EtOAc/hexane 4:1);

$^1$H NMR (400 MHz, CDCl$_3$) δ 9.33 (br, 1H, NH), 8.68 (d, J=5.4 Hz, 0.8H, H—C(2)), 8.64 (d, J=5.6 Hz, 0.2H, H—C(2)), 8.10 (d, J=1.5 Hz, 0.2H. H—C(8)), 7.99 (d, J=7.3 Hz, 2H, H-arom), 7.95 (s, 0.8H, H—C(8)), 7.63 (t, J=8.7 Hz, 4H, H-arom), 7.55 (t, J=13.0, 6.4 Hz, 1H, H-arom), 7.50-7.34 (m, 8H, H-arom), 6.20 (dd, J=6.3, 2.5 Hz, 0.8H, H—C(1')), 6.05 (t, J=6.5 Hz, 0.2H, H—C(1')), 5.43-5.32 (m, 1H, H—C(5')), 5.03-4.97 (m, 0.8H, H—C(4')), 4.83 (t, J=6.0 Hz, 0.2H, H—C(4')), 4.14 (br, 0.2H, H—C(7')), 4.08 (d, J=3.7 Hz, 0.8H, H—C(7')), 3.02 (dd, J=16.1, 6.6 Hz, 0.8H, H—C(3')), 2.83 (dd, J=16.9, 7.7 Hz, 0.2H, H—C(3')), 2.59-2.39 (m, 1H, H—C(2')), 2.18-2.11 (m, 1H, H—C(6')), 2.07 (d, J=1.6 Hz, 2.4H, MeCO$_2$), 2.02 (d, J=1.9 Hz, 0.6H, MeCO$_2$), 2.01-1.92 (m, 1H, H—C(6')), 1.91-1.80 (m, 1H, H—C(3')), 1.07 (s, 9H, (CH$_3$)$_3$—C—Si).

$^{13}$C NMR (101 MHz, CDCl$_3$) δ 170.57, 170.49 (MeCO$_2$), 164.82 (CONH), 152.50 (C(2)), 151.27 (C(4)), 149.56 (C(6)), 141.37, 141.06 (C(8)), 135.72, 135.68, 135.66 (CH-arom), 133.67, 133.57, 133.24, 133.22 (C-arom), 132.73, 130.03, 129.98, 128.80, 128.78, 127.92, 127.86, 127.85 (CH-arom), 123.61 (C(5)), 87.19, 86.17 (C(1')), 83.22, 80.96 (C(4'), 76.50, 76.04 (C(7')), 74.38 (C(5')), 51.07 (C(3')), 37.29, 37.15, 36.80, 36.60 (C(2'), C(6')), 26.89 (CH$_3$)$_3$—C—Si), 20.97, 20.90 (MeCO$_2$), 19.01 (CH$_3$)$_3$—C—Si).

ESI$^+$-HRMS m/z calcd for C$_{37}$H$_{40}$O$_5$N$_5$Si ([M+H]$^+$) 662.2793, found 662.2787.

Example 16

(3'R,5'R,7'R)—N6-Benzoyl-9-{7'-[(tert-butyldiphenylsilyl)oxy]-2',3'-Dideoxy-3',5'-ethano-β-D-ribofuranosyl} adenine (16)

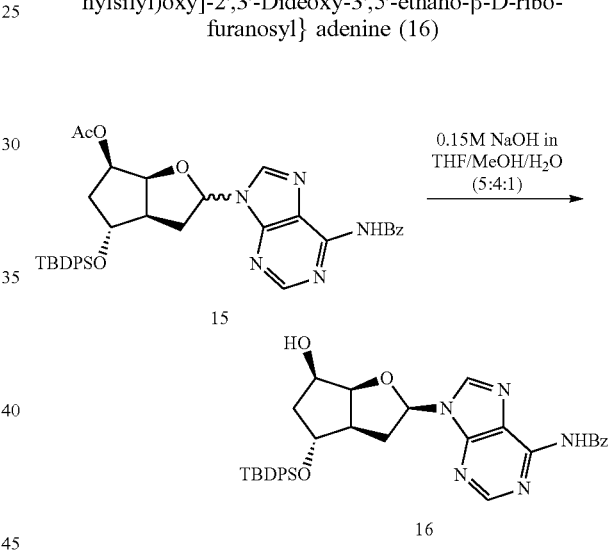

The nucleoside 15 (1.74 g, 2.64 mmol) was dissolved in 0.15 M NaOH in THF/methanol/H$_2$O (5:4:1, 80 mL) at 0° C. The reaction was stirred for 20 min and quenched by addition of NH$_4$Cl (1.06 g). Solvents were then removed under reduced pressure and the product purified by CC (5% isopropanol in DCM) to yield 16 (287 mg, 18%) and its corresponding α anomer (836 mg, 51%) white foams.

Data for 16: R$_f$=0.44 (6% MeOH in DCM);

$^1$H NMR (300 MHz, CDCl$_3$) δ 8.70 (s, 1H, H—C(2)), 8.09-7.98 (m, 2H, H-arom), 7.97 (s, 1H, H—C(8)), 7.63 (ddd, J=7.4, 5.7, 1.5 Hz, 4H, H-arom), 7.59-7.55 (m, 1H, H-arom), 7.51 (m, 2H, H-arom), 7.44-7.33 (m, 6H, H-arom), 6.02 (dd, J=9.4, 5.5 Hz, 1H, H—C(1')), 4.57 (dd, J=8.1, 5.0 Hz, 1H, H—C(4')), 4.43 (dd, J=11.8, 5.3 Hz, 1H, H—C(5')), 4.26 (br, 1H, H—C(7')), 2.78 (q, J=8.9 Hz, 1H, H—C(3')), 2.32-1.80 (m, 5H, H—C(2'), H—C(6'), OH), 1.06 (s, 9H, (CH$_3$)$_3$—C—Si).

$^{13}$C NMR (101 MHz, CDCl$_3$) δ 164.85 (CONH), 152.56 (C(2)), 151.17 (C(4)), 149.86 (C(6)), 141.25 (C(8)), 135.68 (CH-arom), 133.87, 133.39 (C-arom), 132.78, 129.92, 128.78, 128.01, 127.78 (CH-arom), 123.51 (C(5)), 87.65

(C(1')), 82.91 (C(4')), 76.66 (C(7')), 72.54 (C(5')), 50.44 (C(3')), 41.42 (C(6')), 36.17 (C(2')), 26.89 (CH$_3$)$_3$—C—Si), 19.03 (CH$_3$)$_3$—C—Si).

ESI$^+$-HRMS m/z calcd for C$_{35}$H$_{38}$O$_4$N$_5$Si ([M+H]$^+$) 620.2688, found 620.2671.

Example 17

(3'R,5'R,7'R)—N6-Benzoyl-9-{7'-[(tert-butyldiphenylsilyl)oxy]-2',3'-Dideoxy-3',5'-ethano-5'-O-[(4,4'-dimethoxytriphenyl)methyl]-β-D-ribofuranosyl} adenine (17)

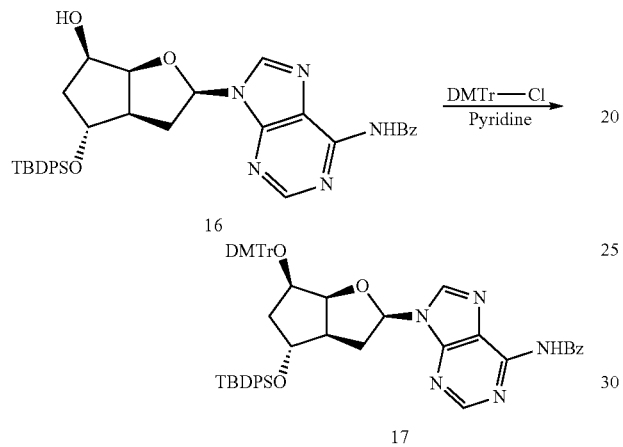

To a solution of nucleoside 16 (307 mg, 0.495 mmol) in dry pyridine (6 mL) was added DMTr-Cl (503 mg, 1.49 mmol) at rt. The solution was stirred for 1 day and then diluted with satd NaHCO$_3$ (50 mL) and extracted with DCM (3×70 mL). The combined organic phases were dried over MgSO$_4$, filtered and evaporated. The crude product was purified by CC (1.5% MeOH in DCM, +0.5% Et$_3$N) to yield 17 (395 mg, 87%) as a yellow foam.

Data for 17: R$_f$=0.65 (5% MeOH in DCM);

$^1$H NMR (300 MHz, MeOD) δ 8.64 (s, 1H, H—C(2)), 8.61 (s, 1H, H—C(8)), 8.08 (d, J=7.2 Hz, 2H, H-arom), 7.68-7.17 (m, 22H, H-arom), 6.86-6.75 (m, 4H, H-arom), 6.14 (dd, J=7.4, 6.3 Hz, 1H, H—C(1')), 4.48-4.31 (m, 1H, H—C(5')), 4.28-4.15 (m, 1H, H—C(4')), 3.88 (d, J=3.8 Hz, 1H, H—C(7')), 3.75, 3.74 (2s, 6H, MeO), 2.67 (dd, J=16.6, 6.7 Hz, 1H, H—C(3')), 2.47 (ddd, J=13.3, 10.2, 6.1 Hz, 1H, H—C(2')), 2.15-1.94 (m, 1H, H—C(6')), 1.71 (dddd, J=13.0, 11.3, 4.4 Hz, 1H, H—C(2')), 1.11 (dd, J=12.2, 4.9 Hz, 1H, H—C(6')), 0.95 (s, 9H, (CH$_3$)$_3$—C—Si).

$^{13}$C NMR (75 MHz, CDCl$_3$) δ 164.69 (CONH), 158.61, 158.60 (MeO—C-arom), 152.42 (C(2)), 151.27 (C(4)), 149.41 (C(6)), 145.81 (C-arom), 141.25 (C(8)), 137.00, 136.85 (C-arom), 135.60, 135.57 (CH-arom), 133.80, 133.69, 133.43 (C-arom), 132.70, 130.28, 130.25, 129.85, 129.81, 128.84, 128.18, 127.89, 127.71, 127.65, 126.78 (CH-arom), 123.52 (C(5)), 113.22, 113.19 (CH-arom), 87.09 (C(Ph)$_3$), 86.41 (C(1')), 83.52 (C(4')), 76.05 (C(7')), 74.78 (C(5')), 55.20 (MeO-DMTr), 50.43 (C(3')), 38.10 (C(2'), C(6')), 26.84 (CH$_3$)$_3$—C—Si), 19.00 (CH$_3$)$_3$—C—Si).

ESI$^+$-HRMS m/z calcd for C$_{56}$H$_{56}$O$_6$N$_5$Si ([M+H]$^+$) 922.3994, found 922.3953.

Example 18

(3'S,5'R,7'R)—N6-Benzoyl-9-{2',3'-Dideoxy-3',5'-ethano-7'-hydroxy-5'-O-[(4,4'-dimethoxytriphenyl)methyl]-β-D-ribofuranosyl} adenine (18)

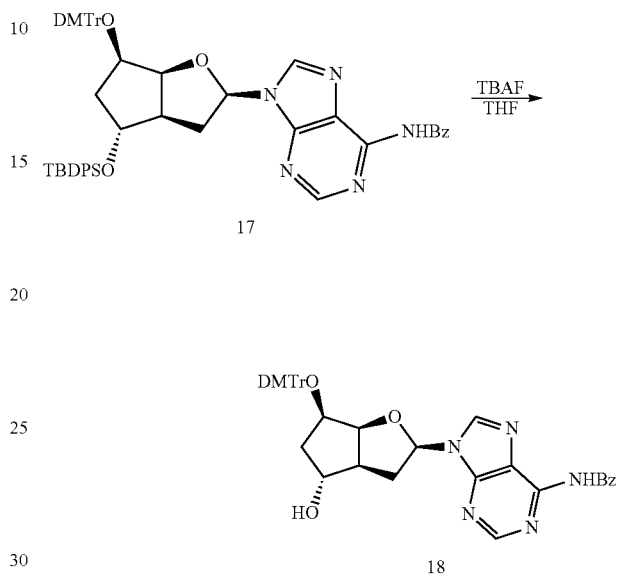

To a solution of nucleoside 17 (376 mg, 0.408 mmol) in dry THF (9 mL) was added TBAF (1M in THF, 1.22 mL, 1.22 mmol) at rt. The solution was stirred for 2 days and was then diluted with satd NaHCO$_3$ (25 mL) and extracted with DCM (4×25 mL). The combined organic phases were dried over MgSO$_4$, filtered and evaporated. The crude product was purified by CC (4% MeOH in DCM, +0.5% Et$_3$N) to yield 18 (242 mg, 87%) as a white foam.

Data for 18: R$_f$=0.33 (5% MeOH in DCM);

$^1$H NMR (300 MHz, CD$_3$CN) δ 9.35 (br, 1H, NH), 8.67 (s, 1H, C(2)), 8.46 (s, 1H, C(8)), 8.01 (d, J=7.4 Hz, 2H, H-arom), 7.54 (m, 5H, H-arom), 7.35 (m, 4H, H-arom), 7.30-7.17 (m, 3H, H-arom), 6.84 (d, J=8.9 Hz, 4H, H-arom), 6.09 (dd, J=7.8, 6.2 Hz, 1H, H—C(1')), 4.12 (dt, J=11.2, 5.8 Hz, 1H, C(5')), 3.87-3.79 (m, 2H, C(4'), C(7')), 3.75 (s, 6H, MeO), 2.83-2.64 (m, 2H, C(2'), OH), 2.58-2.46 (m, 1H, C(3')), 2.21 (dd, J=13.9, 7.1 Hz, 1H, C(2')), 1.92-1.82 (m, 1H, C(6')), 1.29-1.17 (m, 1H, C(6')).

$^{13}$C NMR (75 MHz, CDCl$_3$) δ 165.03 (CONH), 158.57 (MeO—C-arom), 152.40 (C(2)), 151.23 (C(4)), 149.52 (C(6)), 145.68 (C-arom), 141.49 (C(8)), 136.86, 136.84, 133.77 (C-arom), 132.77, 130.22, 128.81, 128.16, 128.02, 127.89, 126.84 (CH-arom), 123.40 (C(5)), 113.19 (CH-arom), 87.06 (C(Ph)$_3$), 86.74 (C(1')), 83.58 (C(4')), 74.62 (C(5')), 74.38 (C(8')), 55.25 (MeO-DMTr), 49.77 (C(3')), 38.55, 38.32 (C(6'), C(2')).

ESI$^+$-HRMS m/z calcd for C$_{40}$H$_{38}$O$_6$N$_5$ ([M+H]$^+$) 684.2817, found 684.2830.

Example 19

(3'R,5'R,7'R)—N6-Benzoyl-9-{7'-O-[(2-cyanoethoxy)-diisopropylaminophosphanyl]-2',3'-Dideoxy-3',5'-ethano-5'-O-[(4,4'-dimethoxytriphenyl)methyl]-β-D-ribofuranosyl} Adenine (19)

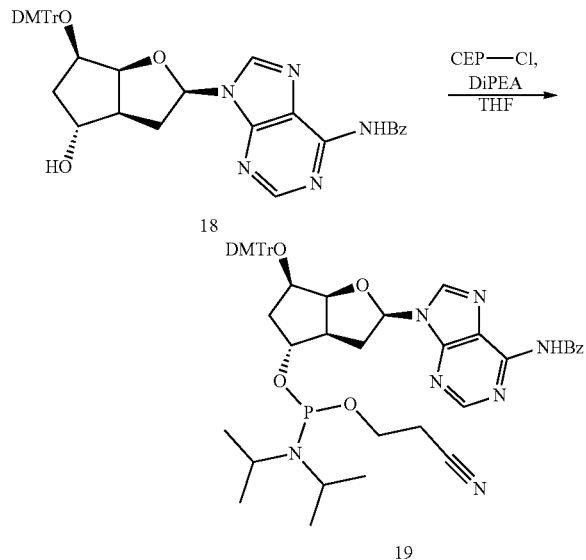

To a solution of the nucleoside 18 (173 mg, 0.253 mmol) and N,N-Diisopropylethylamine (0.18 mL, 1.0 mmol) in dry THF (8 mL) was added N,N-diisopropylchlorophosphoramidite (0.11 mL, 0.50 mmol) at rt. The solution was stirred for 2 hours and then was diluted with satd NaHCO$_3$ (40 mL) and extracted with DCM (4×40 mL). The combined organic phases were dried over MgSO$_4$, filtered and evaporated. The crude product was purified by CC (EtOAc, +0.5% Et$_3$N) to yield 19 (177 mg, mixture of two isomers, 71%) as a white foam.

Data for 19: R$_f$=0.38, 0.44 (EtOAc);
$^1$H NMR (400 MHz, CDCl$_3$) δ 9.05 (br, 1H, NH), 8.70, 8.70 (2s, 1H, H—C(2)), 8.47, 8.46 (2s, 1H, H—C(8)), 7.97 (d, J=7.5 Hz, 2H, H-arom), 7.57-7.50 (m, 1H, H-arom), 7.49-7.41 (m, 4H, H-arom), 7.39-7.31 (m, 4H, H-arom), 7.24-7.17 (m, 5.4 Hz, 2H, H-arom), 7.13 (dt, J=12.5, 6.2 Hz, 1H, H-arom), 6.83-6.70 (m, 4H, H-arom), 6.14-5.97 (m, 1H, H—C(1')), 4.14 (ddd, J=11.1, 7.8, 3.4 Hz, 1H, H—C(5')), 3.91-3.74 (m, 2H, H-(4'), H—C(7')), 3.71, 3.70 (2s, 6H, MeO), 3.65-3.50 (m, 2H, OCH$_2$CH$_2$CN), 3.37 (ddq, J=13.9, 10.2, 6.8 Hz, 2H, (Me$_2$CH)$_2$N), 2.90-2.76 (m, 1H, H—C(2')), 2.75-2.60 (m, 1H, H—C(3')), 2.47, 2.42 (2t, J=6.3 Hz, 2H, OCH$_2$CH$_2$CN), 2.11 (dt, J=12.7, 6.1 Hz, 1H, H—C(2')), 1.73 (ddt, J=13.6, 10.4, 5.1 Hz, 1H, H—C(6')), 1.39 (ddd, J=50.2, 13.4, 6.2 Hz, 1H, H—C(6')), 1.10-0.89 (m, 12H, (Me$_2$CH)$_2$N).
$^{13}$C NMR (101 MHz, CDCl$_3$) δ 164.66 (CONH), 158.57 (MeO—C-arom), 152.46 (C(2)), 151.32, 151.26 (C(4)), 149.45, 149.43 (C(6)), 145.60, 145.59 (C-arom), 141.52, 141.47 (C(8)), 136.88, 136.83, 136.81, 133.78 (C-arom), 132.75, 132.73, 130.22, 130.21, 130.19, 130.17, 128.87, 128.17, 127.87, 126.82, 126.80 (CH-arom), 123.59 (C(5)), 117.53, 117.50 (OCH$_2$CH$_2$CN), 113.17 (CH-arom), 87.10, 87.07 (C(Ph)$_3$), 86.72, 86.68 (C(1')), 83.36, 83.25 (C(4')), 76.55, 75.81 (J$_{C,P}$=16.9, 15.7 Hz, C(7')), 74.63, 74.60 (C(5')), 58.24, 57.86 (J$_{C,P}$=19.1, 19.2 Hz OCH$_2$CH$_2$CN), 55.25, 55.21 (MeO-DMTr), 49.29, 49.08 (J$_{C,P}$=2.6, 4.7 Hz, C(3')), 43.12, 43.00 (J$_{C,P}$=2.4, 2.3 Hz (Me$_2$CH)$_2$N), 38.27, 38.23 (C(2')), 37.41, 37.22 (J$_{C,P}$=5.3, 3.5 Hz, C(6')) 24.56, 24.53, 24.49, 24.47, 24.43, 24.41, 24.36, 24.33 (8s, Me$_2$CH)$_2$N), 20.36, 20.25 (J$_{C,P}$=7.2, 7.0 Hz, OCH$_2$CH$_2$CN).
$^{31}$P NMR (122 MHz, CDCl$_3$) δ 147.64, 146.87.
ESI$^+$-HRMS m/z calcd for C$_{49}$H$_{55}$O$_7$N$_7$ ([M+H]$^+$) 884.3895, found 884.3898.

Example 20

(3'R,5'R,7'R)-2-Amino-6-chloro-9-{5'-O-acetyl-7'-[(tert-butyldiphenylsilyl)oxy]-2',3'-Dideoxy-3',5'-ethano-α,β-D-ribofuranosyl} purine (20)

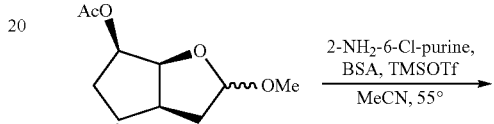

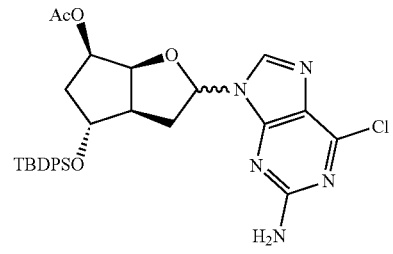

To a suspension of sugar 7 (1.75 g, 3.85 mmol) and 2-amino-6-chloropurine (1.05 g, 6.17 mmol) in dry MeCN (20 mL) was added BSA (3.80 mL, 15.4 mmol) at rt. The suspension was heated to 55° C. and stirred for 30 min. Then TMSOTf (1.05 mL, 5.78 mmol) was added dropwise and the solution was further stirred for 50 min at 55° C. The solution was cool down to rt, quenched with addition of satd NaHCO$_3$ (10 mL), diluted EtOAc (50 mL) and filtered through a short pad of SiO$_2$. The SiO$_2$ was washed with additional EtOAc. The mixture was then washed with satd NaHCO$_3$ (2×80 mL), aqueous phases were combined and extracted with EtOAc (3×50 mL). The combined organic phases were dried over MgSO$_4$, filtered and evaporated. The crude product was purified by CC (2.5% MeOH in DCM) to yield a mixture of 20 (1.77 g, 77%) in an anomeric ratio α/β≈7:3 as a white foam.

Data for 20: R$_f$=0.54 (EtOAc/hexane 5:1);
$^1$H NMR (300 MHz, CDCl$_3$) δ 7.86 (s, 0.3H, H—C(8)), 7.69 (s, 0.7H, H—C(8)), 7.68-7.60 (m, 4H, H-arom), 7.47-7.34 (m, 6H, H-arom), 6.04 (dd, J=6.9, 3.0 Hz, 0.7H, H—C(1')), 5.87 (dd, J=8.0, 6.2 Hz, 0.3H, H—C(1')), 5.37 (dt, J=14.2, 4.6 Hz, 1H, H—C(5')), 5.16 (br, 2H, NH$_2$), 4.91 (dd, J=6.5, 5.1 Hz, 0.7H, H—C(4')), 4.79 (dd, J=6.9, 5.2 Hz, 0.3H, H—C(4')), 4.13 (br, 0.3H, H—C(7')), 4.06 (d, J=4.0 Hz, 0.7H, H—C(7')), 2.95 (dd, J=16.3, 6.6 Hz, 0.7H, H—C(3')), 2.81 (dd, J=17.0, 7.4 Hz, 0.3H, H—C(3')), 2.49-2.30 (m, 1H, H—C(2')), 2.14 (dd, J=13.1, 6.7 Hz, 1H, H—C(6')), 2.08 (s, 2.1H, MeCO$_2$), 2.02 (s, 0.9H, MeCO$_2$), 2.02-1.91

(m, 1H, H—C(6')), 1.80 (td, J=13.4, 6.8 Hz, 1H, H—C(2')), 1.07, 1.06 (2s, 9H, (CH₃)₃—C—Si).

¹³C NMR (75 MHz, CDCl₃) δ 170.55, 170.44 (MeCO₂), 158.98, 158.91 (C(2)), 153.18, 152.95 (C(4)), 151.40, 151.34 (C(6)), 140.38, 140.14 (C(8)), 135.73, 135.70 (CH-arom), 133.78, 133.62, 133.24, 133.17 (C-arom), 130.03, 130.00, 127.88, 127.86 (CH-arom), 125.65, 125.57 (C(5)), 86.59, 85.74 (C(1')), 82.93, 80.99 (C(4')), 76.57, 76.14 (C(7')), 74.34, 74.32 (C(5')), 51.15, 51.10 (C(3')), 37.19, 36.99 (C(6')), 36.70, 36.25 (C(2')), 26.87 (CH₃)₃—C—Si), 20.95, 20.86 (MeCO₂), 19.00 (CH₃)₃—C—Si).

ESI⁺-HRMS m/z calcd for C₃₀H₃₅O₄N₅ClSi ([M+H]⁺) 592.2141, found 592.2158.

Example 21

(3'R,5'R,7'R)-2-Amino-6-chloro-9-{7'-[(tert-butyldiphenylsilyl)oxy]-2',3'-Dideoxy-3,5'-ethano-β-D-ribofuranosyl} purine (22b)

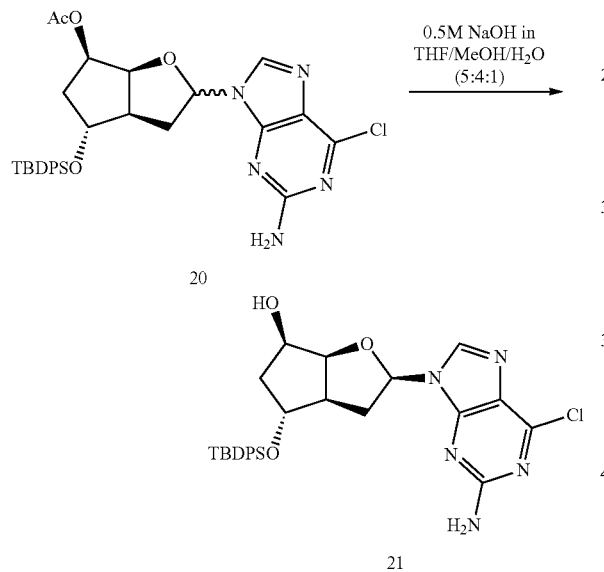

The nucleoside 20 (1.78 g, 3.01 mmol) was dissolved in 0.5 M NaOH in THF/methanol/H₂O (5:4:1, 15 mL) at 0° C. The reaction was stirred for 20 min at 0° C. and quenched by addition of NH₄Cl (484 mg). The suspension was then diluted with satd NaHCO₃ (100 mL) and extracted with DCM (4×75 mL). The combined organic phases were dried over MgSO₄, filtered and evaporated. The crude product was purified by CC (3% MeOH in DCM) to yield 21 (428 mg, 25%) and its corresponding α anomer (992 mg, 60%) as white foams.

Data for 21: $R_f$=0.43 (5% MeOH in DCM);

¹H NMR (300 MHz, CDCl₃) δ 7.71 (s, 1H, H—C(8)), 7.68-7.60 (m, 4H, H-arom), 7.44-7.33 (m, 6H, H-arom), 5.85 (dd, J=9.3, 5.8 Hz, 1H, H—C(1')), 5.33 (br, 2H, NH₂), 4.62 (dd, J=8.4, 4.9 Hz, 1H, H—C(4')), 4.44 (dd, J=10.7, 5.3 Hz, 1H, H—C(5')), 4.40-4.15 (m, 2H, H—C(7'), OH), 2.79 (q, J=8.7 Hz, 1H, H—C(3')), 2.22 (dd, J=15.2, 9.3 Hz, 1H, H—C(6')), 2.11-2.02 (m, 1H, H—C(6')), 2.02-1.85 (m, 2H, H—C(2')), 1.06 (s, 9H, (CH₃)₃—C—Si).

¹³C NMR (75 MHz, CDCl₃) δ 158.73 (C(2)), 152.78 (C(4)), 151.94 (C(6)), 140.70 (C(8)), 135.70 (CH-arom), 133.91, 133.48 (C-arom), 129.90, 127.78 (CH-arom), 125.97 (C(5)), 87.96 (C(1')), 82.88 (C(5')), 76.85 (C(7')), 72.36 (C(5')), 50.41 (C(3')), 41.96 (C(6')), 35.73 (C(2')), 26.90 (CH₃)₃—C—Si), 19.02 (CH₃)₃—C—Si).

ESI⁺-HRMS m/z calcd for C₂₈H₃₃O₃N₅ClSi ([M+H]⁺) 550.2036, found 550.2015.

Example 22

(3'R,5'R,7'R)—N2-(N,N-Dimethylformamidino)-9-{7'-[(tert-butyldiphenylsilyl)oxy]-2',3'-Dideoxy-3',5'-ethano-β-D-ribofuranosyl} guanine (22)

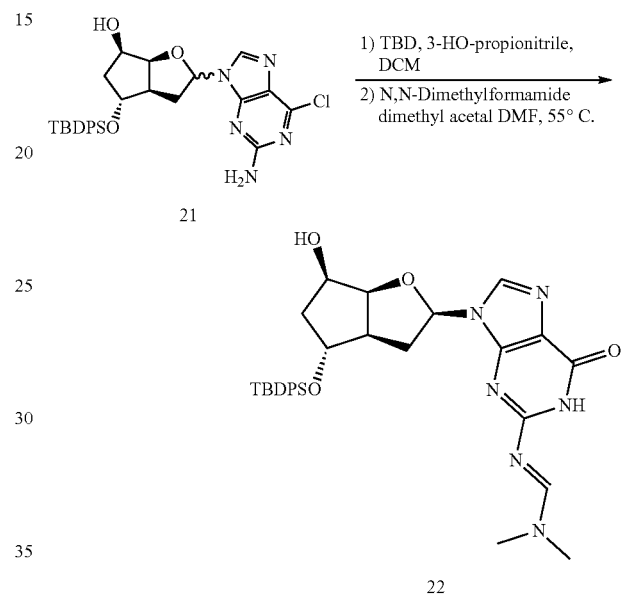

To a solution of 21 (380 mg, 0.645 mmol) and 3-hydroxypropionitrile (0.22 mL, 3.23 mmol) in dry DCM (15 mL) was added 1,5,7-Triazabicyclo[4.4.0]dec-5-ene (400 mg, 2.87 mmol) at 0° C. The solution was stirred for 3 hours at 0° C. and then for 2 days at rt. Reaction was stopped by addition of silica. After evaporation of solvent, the SiO₂ powder was filtered, washed with MeOH and solvent evaporated to yield a brown foam.

The crude product was dissolved in dry DMF (5 mL) and N,N-Dimethylformamide dimethyl acetal (0.43 mL, 3.2 mmol) was added. The solution was stirred for 2 hours at 55° C. and then the solvents were removed under reduced pressure. The crude product was purified by CC (6% MeOH in DCM) to yield 23 (274 mg, 73%) as yellowish foams.

Data for 22: $R_f$=0.45 (12% MeOH in DCM);

¹H NMR (300 MHz, CDCl₃) δ 9.52 (s, 1H, NH), 8.46 (s, 1H, NCHN(CH₃)₂), 7.63 (dd, J=7.7, 1.5 Hz, 4H, H-arom), 7.50 (s, 1H, H—C(8)), 7.44-7.30 (m, 6H, H-arom), 5.83 (dd, J=9.3, 6.0 Hz, 1H, H—C(1')), 4.61 (dd, J=8.7, 5.0 Hz, 1H, H—C(4')), 4.43-4.32 (m, 1H, H—C(5')), 4.29 (dd, J=7.0, 4.8 Hz, 1H, H—C(7')), 3.95 (d, J=5.1 Hz, 1H, OH), 2.98 (s, 6H, NCHN(CH₃)₂), 2.79 (dd, J=18.0, 7.0 Hz, 1H, H—C(3')), 2.20 (dt, J=12.8, 5.4 Hz, 1H, H—C(6')), 2.09-1.88 (m, 3H, H—C(6'), H—C(2')), 1.05 (s, 9H, (CH₃)₃—C—Si)).

¹³C NMR (75 MHz, CDCl₃) δ 158.73 (C(2)), 157.79 (C(6)), 156.91 (NCHN(CH₃)₂), 149.84 (C(4)), 137.00 (C(8)), 135.70, 135.67 (CH-arom), 133.78, 133.60 (C-arom), 129.93, 129.86, 127.78, 127.72 (CH-arom), 121.61 (C(5)), 88.04 (C(1')), 82.21 (C(4')), 77.49 (C(7')), 71.94 (C(5')), 50.13 (C(3')), 42.23 (C(6')), 41.20 (NCHN(CH$_3$)$_2$), 35.50 (C(2')), 34.97 (NCHN(CH$_3$)$_2$), 26.87 (CH$_3$)$_3$—C—Si), 19.02 (CH$_3$)$_3$—C—Si).

ESI$^+$-HRMS m/z calcd for C$_{31}$H$_{38}$O$_4$N$_6$Si ([M+H]$^+$) 586.2718, found 586.2703.

Example 23

(3'R,5'R,7'R)—N2-(N,N-Dimethylformamidino)-9-{7'-[(tert-butyldiphenylsilyl)oxy]-2,3'-Dideoxy-3,5'-ethano-5'-O-[(4,4'-dimethoxytriphenyl)methyl]-β-D-ribofuranosyl} guanine (23)

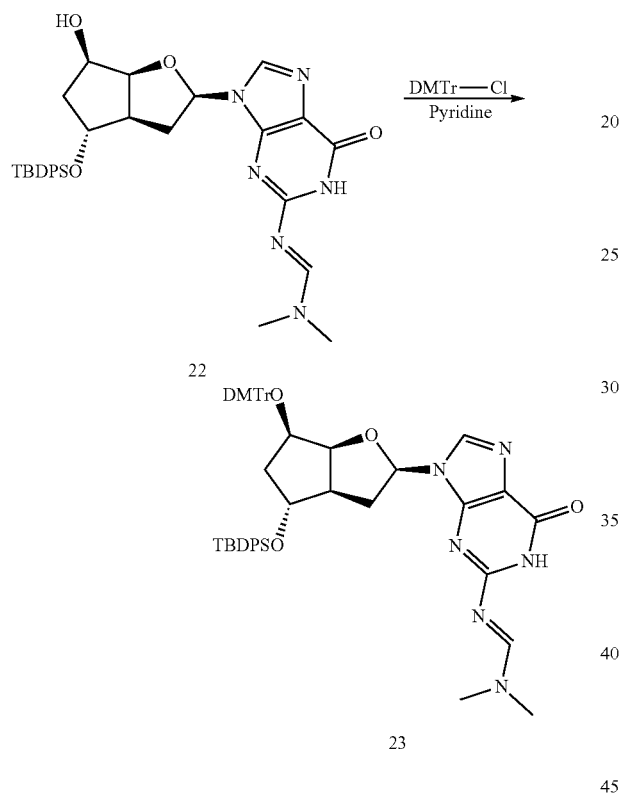

To a solution of 22 (139 mg, 0.237 mmol) in dry pyridine (2 mL) was added DMTr-Cl (240 mg, 0.708 mmol) in six portions over 3 hours at rt. After stirring overnight, the orange solution was diluted with satd NaHCO$_3$ (20 mL) and extracted with DCM (3×20 mL). The combined organic phases were dried over MgSO$_4$, filtered and evaporated. The crude product was purified by CC (4% MeOH in DCM, +0.5% Et$_3$N) to yield 23 (148 mg, 70%) as yellowish foams.

Data for 23: R$_f$=0.52 (10% MeOH in DCM);

$^1$H NMR (400 MHz, CDCl$_3$) δ 9.49 (s, 1H, NH), 8.38 (s, 1H, NCHN(CH$_3$)$_2$), 7.80 (s, 1H, C(8)), 7.50-7.43 (m, 2H, H-arom), 7.42-7.27 (m, 10H, H-arom), 7.26-7.15 (m, 6H, H-arom), 7.14-7.08 (m, 1H, H-arom), 6.77-6.68 (m, 4H, H-arom), 5.78 (dd, J=8.2, 5.9 Hz, 1H, H—C(1')), 4.25 (dt, J=11.0, 5.6 Hz, 1H, H—C(5')), 4.14-4.03 (m, 1H, H—C(4')), 3.70-3.64 (m, 7H, MeO, H—C(7')), 3.00 (s, 3H, NCHN (CH$_3$)$_2$), 2.97 (s, 3H, NCHN(CH$_3$)$_2$), 2.43 (dd, J=16.7, 7.5 Hz, 1H, H—C(3')), 2.24 (ddd, J=13.3, 10.1, 5.8 Hz, 1H, H—C(2')), 1.62 (td, J=13.1, 4.3 Hz, 1H, H—C(6')), 1.43 (dt, J=13.5, 8.0 Hz, 1H, H—C(2')), 0.99 (dd, J=13.3, 6.2 Hz, 1H), 0.86 (s, 9H, (CH$_3$)$_3$—C—Si)).

$^{13}$C NMR (101 MHz, CDCl$_3$) δ 158.51, 158.49 (MeO—C-arom), 158.04 (C(2)), 157.91 (C(6)), 156.60 (NCHN (CH$_3$)$_2$), 149.76 (C(4)), 145.83, 137.12, 136.94 (C-arom), 136.01 (C(8)), 135.60, 135.59 (CH-arom), 133.81, 133.47 (C-arom), 130.32, 130.26, 129.77, 128.24, 127.82, 127.65, 127.62, 126.67 (CH-arom), 120.65 (C(5)), 113.13, 113.09 (CH-arom), 86.82 (C(Ph)$_3$), 85.01 (C(1')), 82.26 (C(4')), 76.14 (C(7')), 74.61 (C(5')), 55.19 (MeO-DMTr), 50.18 (C(3')), 41.29 (NCHN(CH$_3$)$_2$), 38.01 (C(6')), 37.76 (C(2')), 35.14 (NCHN(CH$_3$)$_2$) 26.81 87 (CH$_3$)$_3$—C—Si), 19.01 (CH$_3$)$_3$—C—Si).

ESI$^+$-HRMS m/z calcd for C$_{52}$H$_{57}$O$_6$N$_6$Si ([M+H]$^+$) 889.4103, found 889.4128.

Example 24

(3'S,5'R,7'R)—N2-(N,N-Dimethylformamidino)-9-{2',3'-Dideoxy-3',5'-ethano-7'-hydroxy-5'-O-[(4,4'-dimethoxytriphenyl)methyl]-β-D-ribofuranosyl} guanine (24)

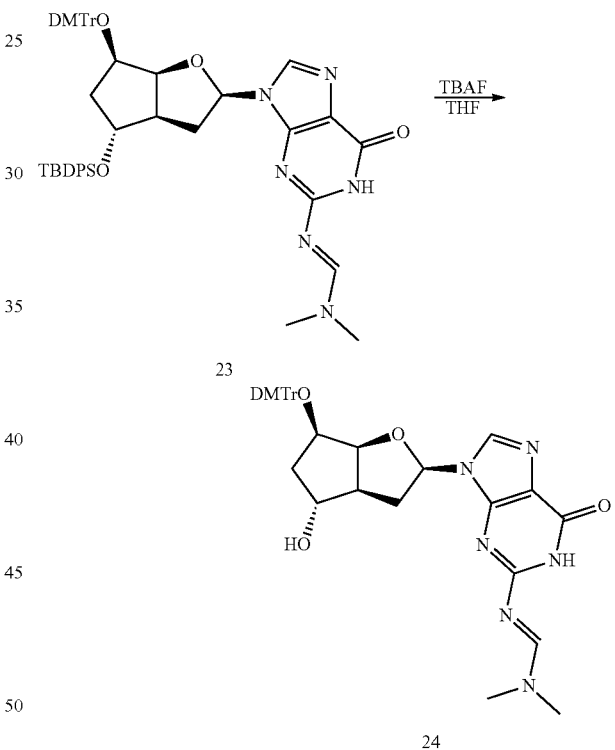

To a solution of 23 (243 mg, 0.273 mmol) in dry THF (2 mL) was added TBAF (1M in THF, 1.65 mL, 1.63 mmol) at rt. The solution was stirred for 7 hours and then was diluted with satd NaHCO$_3$ (30 mL) and extracted with DCM (4×30 mL). The combined organic phases were dried over MgSO$_4$, filtered and evaporated. The crude product was purified by CC (7% MeOH in DCM, +0.5% Et$_3$N) to yield 24 (155 mg, 87%) as a white foam still containing traces of TBAF.

Data for 24: R$_f$=0.44 (10% MeOH in DCM);

$^1$H NMR (400 MHz, CDCl$_3$) δ 9.55 (s, 1H, NH), 8.45 (s, 1H, NCHN(CH$_3$)$_2$), 8.00 (s, 1H, H—C(8)), 7.60-7.50 (m, 2H, H-arom), 7.49-7.39 (m, 4H, H-arom), 7.31-7.23 (m, 2H, H-arom), 7.21-7.12 (m, 1H, H-arom), 6.81 (d, J=8.5 Hz, 4H, H-arom), 5.93 (dd, J=7.5, 6.1 Hz, 1H, H—C(1')), 4.26 (dt, J=11.1, 5.8 Hz, 1H, H—C(5')), 4.07-3.98 (m, 1H, H—C(4')), 3.91 (d, J=4.3 Hz, 1H, H—C(7')), 3.77 (s, 6H, MeO), 3.14 (s, 3H, NCHN(CH$_3$)$_2$), 3.04 (s, 3H, NCHN(CH$_3$)$_2$), 2.73 (ddd, J=13.3, 10.1, 6.0 Hz, 1H, H—C(2')), 2.63-2.48 (m, 1H, H—C(3')), 2.12 (br, 1H, OH), 1.95-1.82 (m, 2H, H—C(6'), H—C(2')), 1.14 (dd, J=13.4, 6.1 Hz, 1H, H—C(6')).

$^{13}$C NMR (101 MHz, CDCl$_3$) δ 158.52 (MeO—C-arom), 158.12 (C(2)), 157.88 (C(6)), 156.65 (NCHN(CH$_3$)$_2$), 149.78 (C(4)), 145.69, 137.02, 136.99 (C-arom), 136.07 (C(8)), 130.26, 128.26, 127.82, 126.74 (CH-arom), 120.53 (C(5)), 113.12 (CH-arom), 86.81 (C(Ph)$_3$), 85.35 (C(1')), 82.64 (C(4')), 74.61 (C(7')), 74.48 (C(5')), 55.23 (MeO-DMTr), 49.63 (C(3')), 41.37 (NCHN(CH$_3$)$_2$), 38.55 (C(6')), 38.23 (C(2')), 35.14 (NCHN(CH$_3$)$_2$).

ESI$^+$-HRMS m/z calcd for C$_{36}$H$_{39}$O$_6$N$_6$Si ([M+H]$^+$) 651.2926, found 651.2912.

Example 25

(3'R,5'R,7'R)—N2-(N,N-Dimethylformamidino)-9-{7'-O-[(2-cyanoethoxy)-diisopropylaminophosphanyl]-2',3'-Dideoxy-3,5'-ethano-5'-O-[(4,4'-dimethoxytriphenyl)methyl]-β-D-ribofuranosyl} guanine (25)

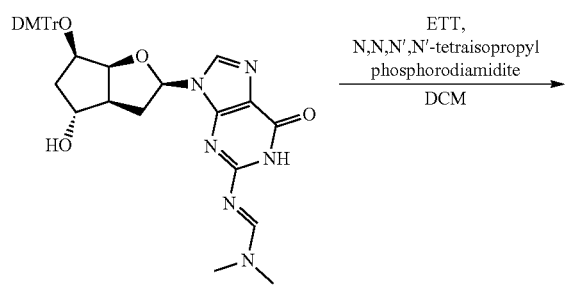

To a solution of the nucleoside 24 (143 mg, 0.220 mmol) and 5-(Ethylthio)-1H-tetrazole (43 mg, 0.33 mmol) in dry DCM (10 mL) was added dropwise 2-Cyanoethyl N,N,N',N'-tetraisopropylphosphordiamidite (0.12 mL, 0.38 mmol) at rt. After stirring for 50 min, the reaction mixture was diluted with satd NaHCO$_3$ (20 mL) and extracted with DCM (3×20 mL). The combined organic phases were dried over MgSO$_4$, filtered and evaporated. The crude product was purified by CC (3.5% MeOH in DCM, +0.5% Et$_3$N) to yield 25 (130 mg, mixture of two isomers, 69%) as a white foam.

Data for 25: R$_f$=0.60 (10% MeOH in DCM);

$^1$H NMR (300 MHz, CDCl$_3$) δ 9.54, 9.47 (2s, 1H, NH), 8.54, 8.52 (2s, 1H, NCHN(CH$_3$)$_2$), 8.02, 8.00 (2s, 1H, H—C(8)), 7.58-7.49 (m, 2H, H-arom), 7.46-7.36 (m, 4H, H-arom), 7.25 (dd, J=11.0, 3.5 Hz, 2H, H-arom), 7.21-7.13 (m, 1H, H-arom), 6.80 (dd, J=8.8, 2.2 Hz, 4H, H-arom), 6.00-5.82 (m, 1H, H—C(1')), 4.16 (dd, J=10.7, 5.4 Hz, 1H, H—C(5')), 4.00-3.82 (m, 2H, H—C(4'), H—C(7')), 3.77, 3.77 (2s, 6H, MeO), 3.62 (dt, J=12.2, 6.1 Hz, 2H, OCH$_2$CH$_2$CN), 3.51-3.33 (m, 2H, (Me$_2$CH)$_2$N), 3.15, 3.14 (2s, 3H, NCHN(CH$_3$)$_2$), 3.07 (s, 3H, NCHN(CH$_3$)$_2$), 2.85-2.61 (m, 2H, C(2'), C(3')), 2.59-2.44 (m, 2H, OCH$_2$CH$_2$CN), 2.00-1.79 (m, 2H, H—(C2'), H—C(6')), 1.53-1.26 (m, 1H, H—C(6')), 1.10, 1.01 (2t, J=6.4 Hz, 12H, (Me$_2$CH)$_2$N).

$^{13}$C NMR (101 MHz, CDCl$_3$) δ 158.50 (MeO—C-arom), 158.04, 158.00 (C(2)), 157.93 (C(6)), 156.61, 156.60 (NCHN(CH$_3$)$_2$), 149.73, 149.72 (C(4)), 145.62, 145.62, 136.97, 136.94 (C-arom), 136.14 (C(8)), 130.27, 130.24, 130.22, 128.26, 127.81, 126.73 (CH-arom), 120.81, 120.76 (C(5)), 117.67, 117.56 (OCH$_2$CH$_2$CN), 113.10 (CH-arom), 86.88, 86.85 (C(Ph)$_3$), 85.58, 85.37 (C(1')), 82.41, 82.07 (C(4')), 77.08, 76.01 (J$_{C,P}$=37.0, 15.1 Hz, C(7')), 74.52, 74.46 (C(5')), 58.19, 57.74 (J$_{C,P}$=18.9, 19.0 Hz OCH$_2$CH$_2$CN), 55.25, 55.21 (MeO-DMTr), 49.10, 48.83 (J$_{C,P}$=2.2, 4.8 Hz, C(3')), 43.12, 43.00 ((Me$_2$CH)$_2$N), 41.34, 41.33 (NCHN(CH$_3$)$_2$), 38.48, 38.41 (C(2')), 37.23, 36.92 (J$_{C,P}$=5.7, 3.3 Hz C(6')), 35.17 ((Me$_2$CH)$_2$N), 24.56, 24.53, 24.48, 24.47, 24.43, 25.36, 24.35 (7s, Me$_2$CH)$_2$N), 20.39, 20.28 (J$_{C,P}$=7.1, 6.9 Hz, OCH$_2$CH$_2$CN).

$^{31}$P NMR (122 MHz, CDCl$_3$) δ 147.69, 146.37.

ESI$^+$-HRMS m/z calcd for C$_{45}$H$_{56}$O$_7$N$_8$P ([M+H]$^+$) 851.4004, found 851.4018.

Example 26

(3'S,5'R,7'R)-1-{7'-[(tert-butyldiphenylsilyl)oxy]-2',3'-Dideoxy-3',5'-ethano-β-D-ribofuranosyl} uracil (26)

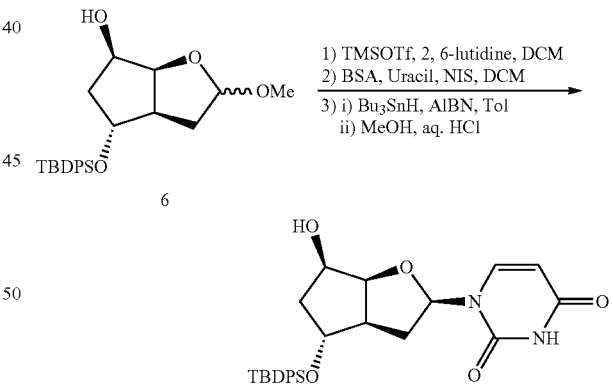

To a solution of the sugar 6 (669 mg, 1.62 mmol) in dry DCM (13 mL) was added 2,6-lutidine (0.94 mL, 8.10 mmol) at 0° C. After stirring for 20 min at 0° C., TMSOTf (0.89 mL, 4.86 mmol) was added dropwise and then the solution was allowed to warm to rt and was stirred for an additional 3 h. The reaction was then quenched by addition of satd NaHCO$_3$ (20 mL). The organic phase was separated and aqueous phase was further extracted with DCM (2×20 mL). The combined organic phases were dried over MgSO$_4$, filtered and evaporated. The crude product was dissolved in dry DCM (12 mL) and then Uracil (545 mg, 4.86 mmol) and BSA (1.8 mL, 7.29 mmol) were added at rt. After stirring for 60 min at rt, the resulting fine suspension was cool down to 0° C. and N-iodosuccinimide (578 mg, 2.52 mmol) was added. After stirring for 30 min at 0° C. and for 4 h at rt, the reaction mixture was diluted with EtOAc (50 mL) and subsequently washed with a 10% aq solution of Na₂S₂O₃ (30 mL) and satd NaHCO₃ (30 mL). Aqueous phases were combined and extracted with DCM (2×20 mL). The combined organic phases were dried over MgSO₄, filtered and evaporated.

The crude product was dissolved in dry toluene (15 mL) and then Bu₃SnH (0.65 mL, 2.43 mmol) and azoisobutyronitrile (AIBN, 13 mg, 0.081 mmol) were added at rt. After heating at 95° C. for 2 h, the mixture was cool down to rt and MeOH (7 mL) and HCl (1M in water, 1.6 mL, 1.6 mmol) were added. The solution was further stirred for 15 min and was then diluted with satd NaHCO₃ (50 mL) and extracted with DCM (3×50 mL). The combined organic phases were dried over MgSO₄, filtered and evaporated. The crude product was purified by CC (EtOAc/hexane 4:1) to yield 26 (490 mg, 61% over three steps) as a white foam.

Data for 26: $R_f$=0.15 (EtOAc/hexane 2:1);
$^1$H NMR (300 MHz, CDCl₃) δ 9.95 (br, 1H, H—N(3)), 7.69 (d, J=6.4 Hz, 4H, H-arom), 7.54-7.39 (m, 7H, H—C(6), H-arom), 5.98 (dd, J=9.3, 5.6 Hz, 1H, H—C(1')), 5.71 (d, J=8.1 Hz, 1H, H—C(5)), 4.51 (dd, J=13.7, 6.3 Hz, 2H, H—C(4'), H—C(5')), 4.14 (br, 1H, H—C(7')), 3.25 (br, 1H, OH), 2.74 (dd, J=17.1, 8.7 Hz, 1H, H—C(3')), 2.26-1.87 (m, 3H, H—C(2'), H—C(6')), 1.49-1.19 (m, 1H, H—C(2')), 1.12 (s, 9H, (CH₃)₃—C—Si).
$^{13}$C NMR (75 MHz, CDCl₃) δ 163.65 (C(4)), 150.46 (C(2)), 139.85 (C(6)), 135.69, 135.66 (CH-arom), 133.71, 133.42 (C-arom), 129.98, 129.93, 127.85, 127.81 (CH-arom), 102.84 (C(5)), 86.17 (C(1')), 81.83 (C(4')), 76.94 (C(7')), 72.45 (C(5')), 50.09 (C(3')), 40.93 (C(6')), 35.83 (C(2')), 26.91 (CH₃)₃—C—Si), 19.03 (CH₃)₃—C—Si).
ESI⁺-HRMS m/z calcd for C₂₇H₃₂O₅N₂NaSi ([M+Na]⁺) 515.1973, found 515.1963.

Example 27

(3'S,5'R,7'R)-1-{7'-[(tert-butyldiphenylsilyl)oxy]-2', 3'-Dideoxy-3',5'-ethano-5'-O-[(4,4'-dimethoxytriphenyl)methyl]-β-D-ribofuranosyl} uracil (27)

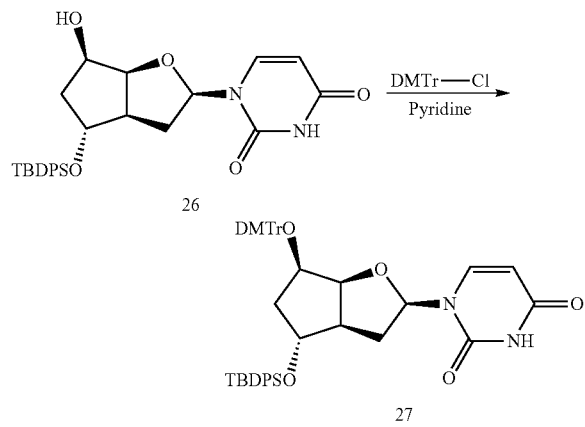

To a solution of nucleoside 26 (438 mg, 0.889 mmol) in dry pyridine (7 mL) was added DMTr-Cl (1.20 g, 3.55 mmol) at rt. The solution was stirred for 1 day at rt and then diluted with satd NaHCO₃ (30 mL) and extracted with DCM (3×40 mL). The combined organic phases were dried over MgSO₄, filtered and evaporated. The crude product was purified by CC (1.5% MeOH in DCM, +0.5% Et₃N) to yield 27 (601 mg, 80%) as a yellow foam.

Data for 27: $R_f$=0.48 (EtOAc/hexane 2:1);
$^1$H NMR (300 MHz, CDCl₃) δ 9.26 (br, 1H, H—N(3)), 7.84 (d, J=8.1 Hz, 1H, H—C(6)), 7.40-7.08 (m, 19H, H-arom), 6.69 (dd, J=8.8, 4.9 Hz, 4H, H-arom), 5.70 (dd, J=7.8, 5.8 Hz, 1H, H—C(1')), 5.49 (dd, J=8.1, 1.5 Hz, 1H, H—C(5)), 4.24-4.11 (m, 1H, H—C(5')), 4.05-3.95 (m, 1H, H—C(4')), 3.65 (d, J=1.7 Hz, 6H, MeO), 3.62 (d, J=3.0 Hz, 1H, H—C(7')), 2.41 (dd, J=17.2, 8.5 Hz, 1H, H—C(3')), 2.24 (ddd, J=13.5, 10.2, 5.7 Hz, 1H, H—C(2')), 1.39-1.24 (m, 1H, H—C(6')), 1.04 (dd, J=13.1, 5.7 Hz, 1H, H—C(6')), 0.89 (dt, J=13.8, 8.3 Hz, 1H, H—C(2')), 0.81 (s, 9H, (CH₃)₃—C—Si).
$^{13}$C NMR (75 MHz, CDCl₃) δ 163.58 (C(4)), 158.66 (MeO—C-arom), 150.38 (C(2)), 145.61 (C-arom), 139.92 (C(6)), 136.71, 136.56 (C-arom), 135.61, 135.55 (CH-arom), 133.55, 133.41 (C-arom), 130.30, 129.92, 129.84, 128.16, 127.90, 127.74, 127.67, 126.90, 113.19, 113.15 (CH-arom), 102.12 (C(5)), 87.41 (C(Ph)₃), 86.80 (C(1')), 82.32 (C4')), 75.54 (C(7')), 74.41 (C(5')), 55.23 (MeO-DMTr), 50.05 (C(3')), 38.49 (C(6')), 37.53 (C(2')), 26.81 (CH₃)₃—C—Si), 18.99 (CH₃)₃—C—Si).
ESI⁺-HRMS m/z calcd for C₄₈H₅₀O₇N₂NaSi ([M+Na]⁺) 817.3279, found 817.3286.

Example 28

(3'S,5'R,7'R)-1-{7'-[(tert-butyldiphenylsilyl)oxy]-2', 3'-Dideoxy-3',5'-ethano-5'-O-[(4,4'-dimethoxytriphenyl)methyl]-β-D-ribofuranosyl} cytosine (28)

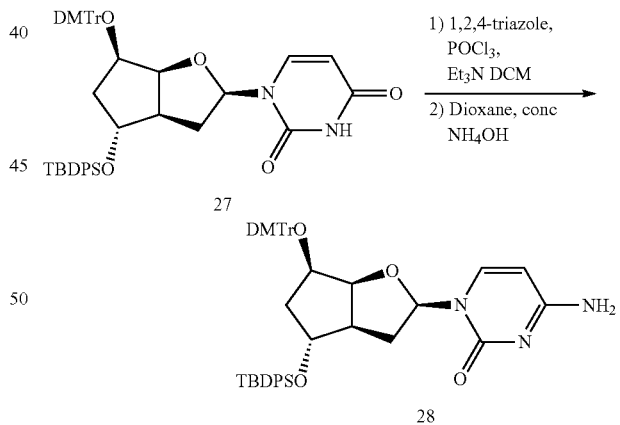

To a suspension of 1,2,4-triazole (1.83 g, 26.5 mmol) in dry MeCN (70 mL), at 0° C., were added POCl₃ (0.57 mL, 6.05 mmol) followed by Et₃N (4.2 mL, 30.2 mmol). The suspension was stirred for 30 min at 0° C. and then a solution of the nucleoside 27 (601 mg, 0.756 mmol) in dry MeCN (4 mL) was added at 0° C. After for 4 h of stirring at rt, the reaction was quenched with addition satd NaHCO₃ (20 mL), MeCN removed under reduced pressure and the resulting mixture diluted with satd NaHCO₃ (30 mL) and extracted with DCM (3×60 mL). The combined organic phases were dried over MgSO₄, filtered and evaporated.

The crude product was then dissolved in a mixture of 1,4-dioxane (18 mL) and concd NH₄OH (18 mL). After stirring for 3 h at rt, the mixture was reduced to half of the volume in vacuo, diluted with satd NaHCO₃ (30 mL) and extracted with DCM (3×30 mL). The combined organic phases were dried over MgSO₄, filtered and evaporated. The crude product was purified by CC (5% MeOH in DCM, +0.5% Et₃N) to yield 28 (520 mg, 87%) as a white foam.

Data for 28: $R_f$=0.41 (10% MeOH in DCM);

¹H NMR (300 MHz, CDCl₃) δ 7.96 (d, J=7.4 Hz, 1H, H—C(6)), 7.45 (d, J=7.4 Hz, 2H, H-arom), 7.38-7.08 (m, 17H, H-arom), 6.73 (dd, J=8.7, 4.7 Hz, 4H, H-arom), 5.73 (t, J=8.6 Hz, 2H, H—C(5), H—C(1')), 4.32-4.16 (m, 1H, H—C(5')), 4.03 (t, J=5.6 Hz, 1H, H—C(4')), 3.66 (d, J=0.9 Hz, 6H, MeO), 3.61 (d, J=2.9 Hz, 1H, H—C(7')), 2.50-2.33 (m, 2H, H—C(2'), H—C(3')), 1.47-1.28 (m, 1H, H—C(6')), 1.03 (dd, J=12.9, 5.6 Hz, 1H, H—C(6')), 0.92-0.75 (m, 10H, H—C(2'), (CH₃)₃—C—Si).

¹³C NMR (75 MHz, CDCl₃) δ 165.78 (C(4)), 158.59 (MeO—C-arom), 155.94 (C(2)), 145.88 (C-arom), 140.68 (C(6)), 136.93, 136.78 (C-arom), 135.59, 135.53 (CH-arom), 133.60, 133.54 (C-arom), 130.31, 129.86, 129.77, 128.15, 127.88, 127.71, 127.64, 126.79, 113.18, 113.14 (CH-arom), 94.53 (C(5)), 87.55 (C(Ph)₃), 87.22 (C(1')), 82.23 (C(4')), 75.76 (C(7')), 74.68 (C(5')), 55.21 (MeO-DMTr), 50.18 (C(3')), 38.25 (C(6')), 38.08 (C(2')), 26.83 (CH₃)₃—C—Si), 19.00 (CH₃)₃—C—Si).

ESI⁺-HRMS m/z calcd for $C_{44}H_{52}O_6N_3Si$ ([M+H]⁺) 794.3620, found 794.3649.

Example 29

(3'S,5'R,7'R)— N4-Benzoyl-1-{7'-[(tert-butyldiphenylsilyl)oxy]-2',3'-Dideoxy-3',5'-ethano-5'-O-[(4,4'-dimethoxytriphenyl)methyl]-β-D-ribofuranosyl} cytosine (29)

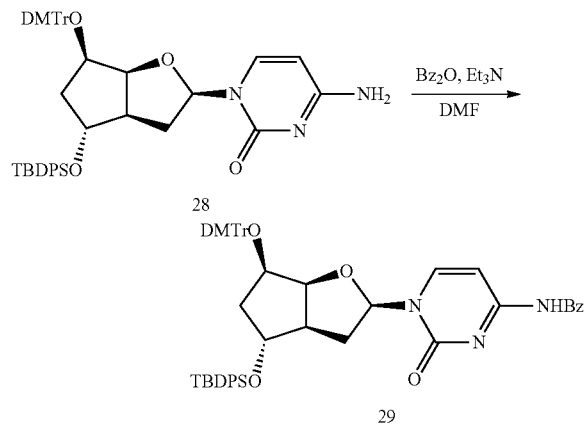

To a solution of nucleoside 28 (519 mg, 0.653 mmol) in dry DMF (15 mL) were added Et₃N (110 μL, 0.784 mmol) followed by Bz₂O (370 mg, 1633 mmol) at rt and the solution was stirred overnight. Then the solution was quenched by careful addition of satd NaHCO₃ (60 mL) and extracted with DCM (3×70 mL). The combined organic phases were dried over MgSO₄, filtered and evaporated. The crude product was purified by CC (hexane/EtOAc 2:3, +0.5% Et₃N) to yield 29 (580 mg, 99%) as a white foam.

Data for 29: $R_f$=0.51 (EtOAc);

¹H NMR (300 MHz, CDCl₃) δ 8.61 (d, J=7.4 Hz, 1H, H—C(6)), 7.81 (d, J=7.5 Hz, 2H, H-arom), 7.49-7.13 (m, 24H, H-arom, H—C(5)), 6.77 (dd, J=8.5, 4.4 Hz, 4H, H-arom), 5.73 (t, J=6.4 Hz, 1H, H—C(1')), 4.39-4.20 (m, 1H, H—C(5')), 4.05 (t, J=6.1 Hz, 1H, H—C(4')), 3.70 (s, 6H, MeO), 3.63 (d, J=2.3 Hz, 1H, H—C(7')), 2.72-2.55 (m, 1H, H—C(2')), 2.48 (dd, J=16.0, 8.4 Hz, 1H, H—C(3')), 1.42-1.29 (m, 1H, H—C(6')), 1.19-1.11 (m, 1H, H—C(6')), 1.07-0.96 (m, 1H, H—C(2')), 0.85 (s, 9H, (CH₃)₃—C—Si).

¹³C NMR (75 MHz, CDCl₃) δ 166.64 (CONH), 162.25 (C(4)), 158.70 (MeO—C-arom), 154.84 (C(2)), 145.71 (C-arom), 144.84 (C(6)), 136.74, 136.67 (C-arom), 135.59, 135.51 (CH-arom), 133.52, 133.42, 133.24 (C-arom), 133.11, 130.30, 129.92, 129.85, 129.02, 128.12, 127.97, 127.76, 127.68, 127.61, 126.94, 113.25, 113.22 (CH-arom), 96.22 (C(5)), 89.07 (C(Ph)₃), 87.53 (C(1')), 83.46 (C(4')), 75.59 (C(7')), 74.71 (C(5')), 55.24 (MeO-DMTr), 50.35 (C(3')), 38.61 (C(6')), 38.15 (C(2')), 26.82 (CH₃)₃—C—Si), 19.00 (CH₃)₃—C—Si).

ESI⁺-HRMS m/z calcd for $C_{55}H_{56}O_7N_3Si$ ([M+H]⁺) 898.3882, found 898.3898.

Example 30

(3'S,5'R,7'R)— N4-Benzoyl-1-{2',3'-Dideoxy-3',5'-ethano-7'-hydroxy-5'-O-[(4,4'-dimethoxytriphenyl)methyl]-β-D-ribofuranosyl} cytosine (30)

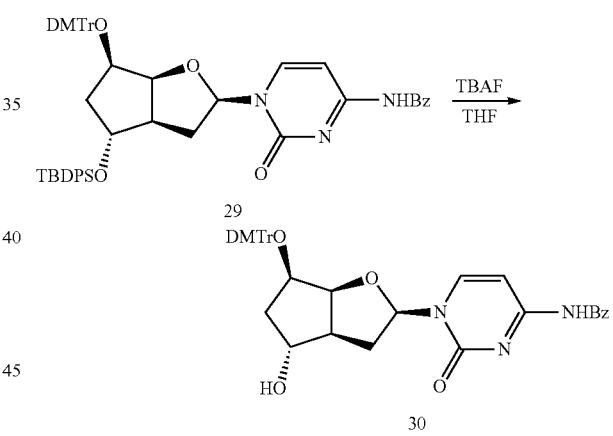

To a solution of 29 (580 mg, 0.648 mmol) in dry THF (14 mL) was added TBAF (1M in THF, 3.25 mL, 3.25 mmol) at rt. The solution was stirred for 1 day and then was diluted with satd NaHCO₃ (50 mL) and extracted with DCM (3×40 mL). The combined organic phases were dried over MgSO₄, filtered and evaporated. The crude product was purified by CC (3% MeOH in DCM, +0.5% Et₃N) to yield 30 (366 mg, 85%) as a white foam.

Data for 30: $R_f$=0.31 (5% MeOH in DCM);

¹H NMR (300 MHz, CDCl₃) δ 8.90 (br, 1H, NH), 8.73 (d, J=7.5 Hz, 1H, H—C(6)), 7.82 (d, J=7.3 Hz, 2H, H-arom), 7.55-7.31 (m, 10H, H-arom, H—C(5)), 7.28-7.09 (m, 3H, H-arom), 6.76 (dd, J=8.8, 1.7 Hz, 4H, H-arom), 5.73 (t, J=6.3 Hz, 1H, H—C(1')), 4.28-4.13 (m, 1H, H—C(5')), 3.83 (t, J=6.0 Hz, 1H, H—C(4')), 3.75 (d, J=3.6 Hz, 1H, H—C (7')), 3.70 (s, 6H, MeO), 2.86 (d, J=14.7 Hz, 1H, H—C-(2')), 2.54 (dd, J=17.4, 7.4 Hz, 1H, H—C(3')), 1.68-1.55 (m, 1H, H—C(6')), 1.45-1.13 (m, 3H, H—C(2'), H—C(6'), OH).

$^{13}$C NMR (75 MHz, CDCl$_3$) δ 166.63 (CONH), 162.34 (C(4)), 158.65 (MeO—C-arom), 155.00 (C(2)), 145.62 (C-arom), 145.11 (C(6)), 136.72, 136.64, 133.16 (C-arom), 130.25, 129.02, 128.12, 127.93, 127.61, 126.95, 113.20 (CH-arom), 96.24 (C(5)), 89.20 (C(Ph)$_3$), 87.48 (C(1')), 83.40 (C(4')), 74.50, (C(5')) 73.90 (C(7')), 55.25 (MeO-DMTr), 50.05 (C(3')), 38.90 (C(6')), 38.40 (C(2')).

ESI$^+$-HRMS m/z calcd for C$_{39}$H$_{38}$O$_7$N$_3$ ([M+H]$^+$) 660.2704, found 660.2707.

Example 31

N4-Benzoyl-1-{7'-O-[(2-cyanoethoxy)-diisopropylaminophosphanyl]-2',3'-Dideoxy-3',5'-ethano-5'-O-[(4,4'-dimethoxytriphenyl)methyl]-β-D-ribofuranosyl} cytosine (31)

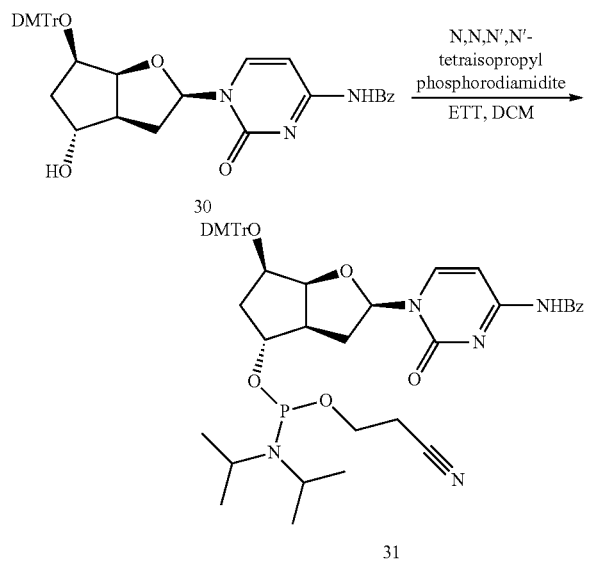

To a solution of the nucleoside 30 (67 mg, 0.101 mmol) and 5-(Ethylthio)-1H-tetrazole (22 mg, 0.17 mmol) in dry DCM (3 mL) was added dropwise 2-Cyanoethyl N,N,N',N'-tetraisopropylphosphordiamidite (65 μL, 0.20 mmol) at rt. After stirring for 40 min, the reaction mixture was diluted with DCM (20 mL) and washed with satd NaHCO$_3$ (2×15 mL) and satd NaCl (15 mL). Aqueous phases were combined and extracted with DCM (20 mL). The combined organic phases were dried over MgSO$_4$, filtered and evaporated. The crude product was purified by CC (EtOAc, +0.5% Et$_3$N) to yield 31 (75 mg, mixture of two isomers, 86%) as a white foam.

Data for 31: R$_f$=0.67 (4% MeOH in DCM);

$^1$H NMR (300 MHz, CDCl$_3$) δ 8.88 (s, 1H, NH), 8.79 (d, J=7.5 Hz, 1H, H—C(6)), 7.93 (d, J=7.5 Hz, 2H, H-arom), 7.67-7.40 (m, 10H, H-arom, H—C(5)), 7.39-7.22 (m, 3H, H-arom), 6.93-6.79 (m, 4H, H-arom), 5.97-5.77 (m, 1H, H—C(1')), 4.22 (dt, J=14.5, 5.6 Hz, 1H, H-(5')), 3.98-3.84 (m, 2H, H—C(4'), H—C(7')), 3.82 (s, 6H, MeO), 3.66 (ddd, J=16.8, 13.5, 6.7 Hz, 2H, OCH$_2$CH$_2$CN), 3.53-3.37 (m, (Me$_2$CH)$_2$N), 3.14-2.93 (m, 1H, H—C(2')), 2.84-2.66 (m, 1H, H—C(3')), 2.53 (dt, J=12.4, 6.3 Hz, 2H, OCH$_2$CH$_2$CN), 1.83-1.56 (m, 2H, H—C(6')), 1.46 (td, J=14.1, 7.0 Hz, 1H, H—C(2')), 1.18-0.97 (m, 12H, (Me$_2$CH)$_2$N).

$^{13}$C NMR (75 MHz, CDCl$_3$) δ 166.70 (CONH), 162.32, 162.28 (C(4)), 158.68 (MeO—C-arom), 154.93 (C(2)), 145.53 (C-arom), 144.95, 144.89 (C(6)), 136.69, 136.63, 136.56, 136.52, 133.24 (C-arom), 133.10, 130.24, 130.20, 129.01, 128.10, 127.94, 127.60, 126.96 (CH-arom), 117.53 (OCH$_2$CH$_2$CN), 113.20 (CH-arom), 96.24 (C(5)), 89.15, 89.10 (C(Ph)$_3$), 87.55, 87.54 (C(1')), 83.11, 83.04 (C(4')), 75.93, 75.37 (J$_{C,P}$=16.7, 15.5 Hz, C(7')), 74.48 (C(5')), 58.25, 57.99 (J$_{C,P}$=17.9, 18.1 Hz OCH$_2$CH$_2$CN), 55.27, 55.24 (MeO-DMTr), 49.27, 49.03 (J$_{C,P}$=3.1, 4.8 Hz, C(3')), 43.15, 42.98 ((Me$_2$CH)$_2$N), 38.89, 38.80 (C(2')), 37.44, 37.24 (J$_{C,P}$=5.2, 3.2 Hz, C(6')), 24.58, 24.54, 24.48, 24.45, 24.35 (5s, Me$_2$CH)$_2$N), 20.33, 20.24 (J$_{C,P}$=5.8, 5.7 Hz, OCH$_2$CH$_2$CN).

$^{31}$P NMR (121 MHz, CDCl$_3$) δ 147.19, 146.94.

ESI$^+$-HRMS m/z calcd for C$_{48}$H$_{55}$O$_8$N$_5$P ([M+H]$^+$) 860.3783, found 860.3791.

Example 32

(3'S,5'R,7'R)-1-{2',3'-Dideoxy-3',5'-ethano-7'-O-(4-nitrobenzoate)-5'-O-[(4,4'-dimethoxytriphenyl)methyl]-β-D-ribofuranosyl} Thymine (32)

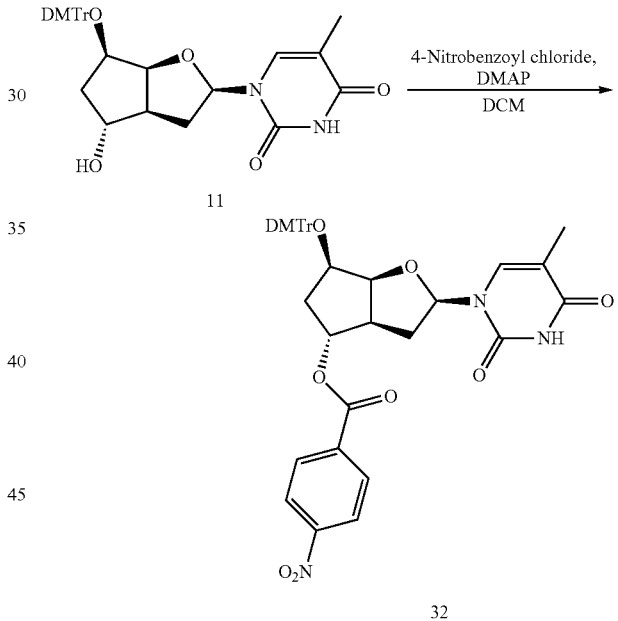

To a solution of nucleoside 11 (100 mg, 0.175 mmol) and 4-Dimethylaminopyridine (26 mg, 0.21 mmol) in dry DCM (8 mL) was added 4-Nitrobenzoyl chloride (59 mg, 0.315 mmol) at rt. After stirring for 6 h, the reaction is quenched by addition of satd NaHCO$_3$ (5 mL). The mixture is then diluted with satd NaHCO$_3$ (15 mL) and extracted with DCM (3×15 mL). The combined organic phases were dried over MgSO$_4$, filtered and evaporated. The crude product was purified by CC (2.5% MeOH in DCM, +0.5% Et$_3$N) to yield 32 (98 mg, 78%) as a white foam, containing traces of Et$_3$N.

Data for 32: R$_f$=0.42 (5% MeOH in DCM);

$^1$H NMR (300 MHz, CDCl$_3$) δ 8.26 (t, J=7.3 Hz, 3H, H-arom, HN(3)), 8.00 (d, J=8.9 Hz, 2H, H-arom), 7.72 (d, J=1.0 Hz, 1H, H—C(6)), 7.55 (d, J=6.9 Hz, 2H, H-arom), 7.44 (dd, J=8.8, 6.6 Hz, 4H, H-arom), 7.35-7.18 (m, 3H, H-arom), 6.83 (dd, J=9.0, 2.6 Hz, 4H, H-arom), 6.01 (dd, J=8.2, 5.2 Hz, 1H, H—C(1')), 4.96 (d, J=3.3 Hz, 1H, H—C(7')), 4.33-4.24 (m, 1H, H—C(4')), 4.24-4.13 (m, 1H, H—C(5')), 3.78 (d, J=0.9 Hz, 6H, MeO), 2.92-2.72 (m, 2H, H—C(3'), H—C(2')), 1.81 (d, J=0.6 Hz, 3H, Me-C(5)), 1.79-1.62 (m, 2H, H—C(6')), 1.22 (d, J=5.9 Hz, 1H, H—C(2')).

$^{13}$C NMR (75 MHz, CDCl$_3$) δ 164.05, 163.84 (C(4), CO$_2$R), 158.81 (MeO—C-arom), 150.64, 150.52 (O$_2$N—C-arom, C(2)), 145.29, 136.43, 136.34 (C-arom), 135.18 (C(6)), 130.62, 130.20, 130.17, 128.16, 128.01, 127.15, 123.58, 113.30, 113.27 (C-arom), 111.17 (C(5)), 87.53 (C(Ph)$_3$), 86.29 (C(1')), 81.59 (C(4')), 78.65 (C(7')), 74.16 (C(5')), 55.26 (MeO-DMTr), 47.07 (C(3')), 37.35 (C(2')), 35.71 (C(6')), 12.51 (Me-C(5)).

ESI$^+$-HRMS m/z calcd for C$_{40}$H$_{37}$O$_{10}$N$_3$Na ([M+Na]$^+$) 742.2371, found 742.2375.

Example 33

((3'S,5'R,7'R)-1-{2',3'-Dideoxy-3',5'-ethano-7'-O-(4-nitrobenzoate)-β-D-ribofuranosyl} Thymine (33)

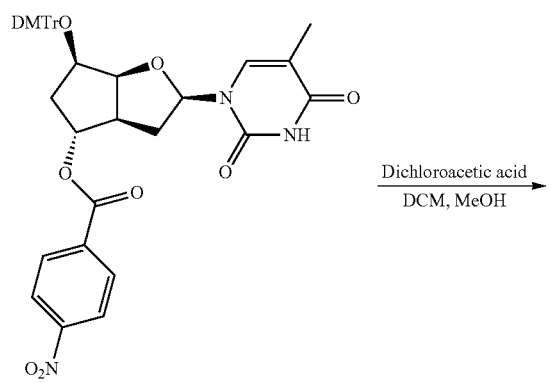

To a solution of 32 (60 mg, 0.083 mmol) in a mixture of dry DCM (1 mL) and MeOH (0.4 mL), was added dropwise dichloroacetic acid (0.2 mL) at rt. After stirring for 3 h, the mixture is then diluted with satd NaHCO$_3$ (15 mL) and extracted with DCM (3×10 mL). The combined organic phases were dried over MgSO$_4$, filtered and evaporated. The crude product was purified by CC (5% MeOH in DCM) to yield 33 (29 mg, 84%) as a white foam. Crystals suitable for X-ray analysis were obtain by recrystallization in a mixture of H$_2$O/MeOH.

Data for 33: R$_f$=0.18 (5% MeOH in DCM);
$^1$H NMR (400 MHz, DMSO) δ 11.33 (s, 1H, H—N(3)), 8.34 (d, J=8.8 Hz, 2H, H-arom), 8.27-8.13 (m, 2H, H-arom), 7.78 (s, 1H, H—C(6)), 5.96 (dd, J=9.3, 5.6 Hz, 1H, H—C(1')), 5.18 (t, J=3.8 Hz, 1H, H—C(7')), 5.12 (d, J=6.0 Hz, 1H, OH), 4.33 (dd, J=7.3, 4.7 Hz, 1H, H—C(4')), 4.27 (td, J=10.5, 5.5 Hz, 1H, H—C(5')), 2.90 (dd, J=17.2, 8.5 Hz, 1H, H—C(3')), 2.58-2.46 (m, 1H, H—C(2')), 2.30 (ddd, J=13.8, 8.8, 5.3 Hz, 1H, H—C(6')), 2.03 (dd, J=9.6, 4.2 Hz, 1H, H—C(6')), 1.92-1.76 (m, 4H, H—C(2'), Me-C(5)).

$^{13}$C NMR (101 MHz, DMSO) δ 164.33, 164.23 (C(4), CO$_2$R), 150.91, 150.75 (O$_2$N—C-arom, C(2)), 136.79 (C-arom), 135.69 (C(6)), 131.20, 124.32 (CH-arom), 109.89 (C(5)), 85.31 (C(1')), 81.48 (C(4')), 80.07 (C(7')), 71.72 (C(5')), 47.18 (C(3')), 37.77 (C(6')), 35.48 (C(2')), 12.66 12.58 (Me-C(5)).

ESI$^+$-HRMS m/z calcd for C$_{19}$H$_{20}$O$_8$N$_3$ ([M+H]$^+$) 418.1245, found 418.1242.

Example 35

(3'R,5'R,7'R)-1-{5'-O-acetyl-7'-[(tert-butyldiphenyl-silyl)oxy]-2',3'-dideoxy-3',5'-ethano-α,β-D-ribofuranosyl} Thymine (35)

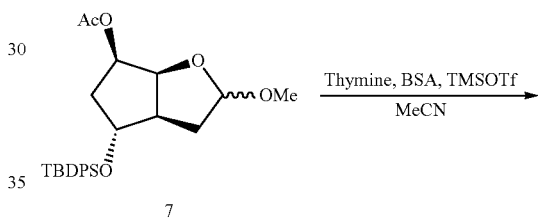

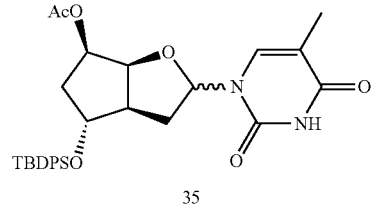

To a solution of the sugar 7 (933 mg, 2.05 mmol) and thymine (372 mg, 3.08 mmol) in dry MeCN (12 mL) was added dropwise BSA (1.5 mL, 6.15 mmol) at rt. After stirring for 50 min at rt, the solution was cooled down to 0° C. and TMSOTf (0.45 mL, 2.5 mmol) was added dropwise. After further stirring for 3 h at 0° C. and for 15 h at rt, the reaction mixture was diluted with satd NaHCO$_3$ (100 mL) and extracted with DCM (4×40 mL). The combined organic phases were dried over MgSO$_4$, filtered and evaporated. The crude product was purified by CC (2.5% isopropanol in DCM) to yield a mixture of 35 (924 mg, 82%) in an anomeric ratio α/β≈85:15 as a white foam.

Data for 35: R$_f$=0.56 (7% MeOH in DCM);
$^1$H NMR (300 MHz, CDCl$_3$) δ 9.14 (br, 1H, H—N(3)), 7.53 (dd, J=7.7, 1.6 Hz, 4H, H-arom), 7.39-7.23 (m, 6H, H-arom), 7.09 (d, J=1.0 Hz, 0.15H, H—C(6)), 6.87 (d, J=1.0 Hz, 0.85H, H—C(6)), 5.83 (t, J=6.2 Hz, 0.85H, H—C(1')), 5.80-5.70 (m, 0.15H, H—C(1')), 5.36-5.04 (m, 1H, H—C(5')), 4.89 (dd, J=6.3, 5.2 Hz, 1H, H—C(4')), 4.62 (dd, J=7.1, 5.6 Hz, 0.15H, H—C(4')), 4.01-3.85 (m, 1H, H—C(7')), 2.76-2.55 (m, 1H, H—C(3')), 2.09-1.91 (m, 4H, H—C(6', MeCO$_2$), 1.90-1.58 (m, 6H, H—C(6'), H—C(2'), Me-C(5)), 0.96 (s, 9H, (CH$_3$)$_3$—C—Si).

$^{13}$C NMR (75 MHz, CDCl$_3$) δ 170.70 (MeCO$_2$), 163.87 (C(4)), 150.29 (C(2)), 135.69, 135.67 (CH-arom), 134.99 (C(6)), 133.58, 133.18 (C-arom), 130.03, 127.87 (CH-arom), 111.05 (C(5)), 87.56 (C(1')), 82.85 (C(4')), 76.50 (C(7')), 74.76 (C(5')), 50.72 (C(3')), 37.79 (C(6')), 36.94 (C(2')), 26.88 ((CH$_3$)$_3$—C—Si), 20.95 (MeCO$_2$), 19.01 ((CH$_3$)$_3$—C—Si), 12.63 (Me-C(5)).

ESI$^+$-HRMS m/z calcd for C$_{30}$H$_{37}$O$_6$N$_2$Si ([M+H]$^+$) 549.2415, found 549.2401.

Example 36

(3'S,5'R,7'R)-1-{5'-O-Acetyl-2,3'-dideoxy-3,5'-ethano-7'-hydroxy-α,β-D-ribofuranosyl} thymine (36)

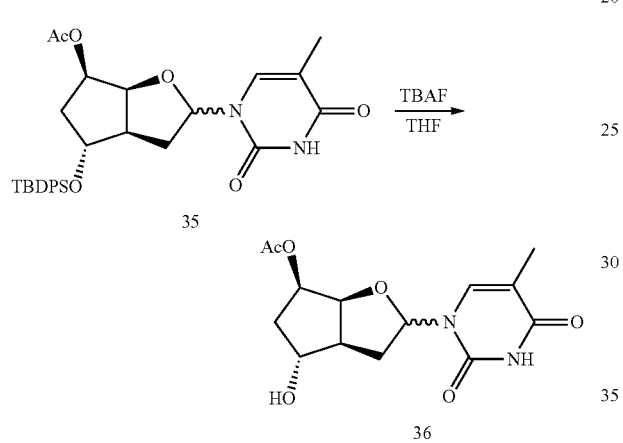

To a solution of the nucleoside 35 (924 mg, 1.68 mmol) in dry THF (10 mL) was added TBAF (1M in THF, 3.4 mL, 3.4 mmol) at rt. After stirring for 2 h at rt, the reaction mixture was diluted with satd NaHCO$_3$ (80 mL) and extracted with EtOAc (3×80 mL) and DCM (2×80 mL). The combined organic phases were dried over MgSO$_4$, filtered and evaporated. The crude product was purified by CC (5% MeOH in DCM) to yield an anomeric mixture of 36 (391 mg, 75%).

Data for 36: R$_f$=0.24 (7% MeOH in DCM);

$^1$H NMR (400 MHz, CDCl$_3$) δ 9.66 (br, 0.15H, H—N(3)), 9.63 (br, 0.85H, H—N(3)), 7.27 (d, J=1.0 Hz, 0.15H, H—C(6)), 7.06 (d, J=1.0 Hz, 0.85H, H—C(6)), 6.00 (t, J=6.1 Hz, 0.85H, H—C(1')), 5.91 (dd, J=8.8, 5.5 Hz, 0.15H, H—C(1')), 5.26-5.10 (m, 1H, H—C(5')), 4.92 (dd, J=6.5, 5.3 Hz, 0.85H, H—C(4')), 4.65 (dd, J=6.9, 5.7 Hz, 0.15H, H—C(4')), 4.19-4.03 (m, 1H, H—C(7')), 2.91-2.72 (m, 2H, H—C(3'), OH), 2.64 (ddd, J=13.3, 9.8, 5.5 Hz, 0.15H, H—C(2')), 2.25-2.15 (m, 1.70H, H—C(2')), 2.05 (s, 0.45H, MeCO$_2$), 2.04 (s, 2.55H, MeCO$_2$), 2.03-1.89 (m, 2H, H—C(6')), 1.88 (d, J=0.7 Hz, 0.45H, Me-C(5)), 1.85 (d, J=0.6 Hz, 2.55H, Me-C(5)), 1.42-1.28 (m, 0.15H, H—C(2')).

$^{13}$C NMR (101 MHz, CDCl$_3$) δ 170.87 (MeCO$_2$), 164.26 (C(4)), 150.66 (C(2)), 135.54 (C(6)), 111.22 (C(5)), 87.97 (C(1')), 82.97 (C(4')), 75.08 (C(7')), 74.52 (C(5')), 50.07 (C(3')), 37.81 (C(2')), 37.23 (C(6')), 21.02 (MeCO$_2$), 12.67 (Me-C(5)).

ESI$^+$-HRMS m/z calcd for C$_{14}$H$_{19}$O$_6$N$_2$ ([M+H]$^+$) 311.1238, found 311.1234.

Example 37

(3'S,5'R,7'R)-1-{5'-O-Acetyl-2',3'-dideoxy-3',5'-ethano-7'-O-[(4,4'-dimethoxytriphenyl)methyl]-α,β-D-ribofuranosyl} Thymine (37)

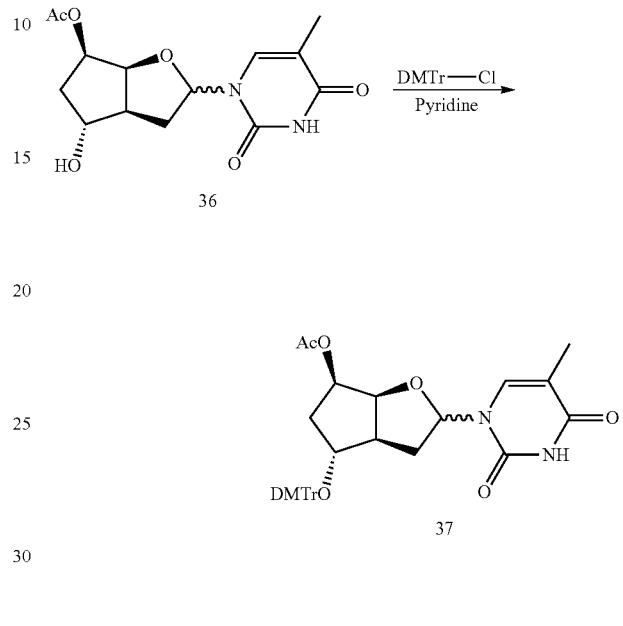

To a solution of the nucleoside 36 (364 mg, 1.17 mmol) in dry pyridine (7 mL) was added DMTr-Cl (1.19 g, 3.51 mmol) at rt. The solution was stirred for 1 day and then was diluted with satd NaHCO$_3$ (50 mL) and extracted with DCM (3×50 mL). The combined organic phases were dried over MgSO$_4$, filtered and evaporated. The crude product was purified by CC (EtOAc/hexane 2:1, +0.5% Et$_3$N) to yield an anomeric mixture of 37 (690 mg, 96%) as a yellow foam.

Data for 37: R$_f$=0.70 (8% MeOH in DCM);

$^1$H NMR (300 MHz, CDCl$_3$) δ 9.17 (br, 0.85H, H—N(3)), 8.56 (br, 0.15H, H—N(3)), 7.38-7.32 (m, 2H, H-arom), 7.29-7.15 (m, 7H, H-arom), 6.82 (d, J=1.1 Hz, 1H, H—C(6)), 6.76 (d, J=8.9 Hz, 4H, H-arom), 5.86 (t, J=6.0 Hz, 0.85H, H—C(1')), 5.71 (dd, J=8.9, 5.4 Hz, 0.15H, H—C(1')), 5.25 (dd, J=10.2, 5.6 Hz, 0.15H, H—C(5')), 5.21-5.11 (m, 0.85H, H—(C5')), 4.78 (dd, J=6.7, 4.8 Hz, 0.85H, H—C(4')), 4.49 (dd, J=7.1, 5.3 Hz, 0.15H, H—C(4')), 3.84 (br, 1H, H—C(7')), 3.72, 3.71 (2s, 6H, MeO), 2.34-2.23 (m, 1H, H—C(3')), 2.01, 1.99 (2s, 3H, MeCO$_2$), 1.82 (d, J=0.5 Hz, Me-C(5)), 1.80-1.56 (m, 4H, H—C(2'), H—C(6')).

$^{13}$C NMR (75 MHz, CDCl$_3$) δ 170.69 (MeCO$_2$), 163.91 (C(4)), 158.82 (MeO—C-arom), 150.33 (C(2)), 145.34, 136.64, 136.58 (C-arom), 135.00 (C(6)), 130.25, 128.39, 128.07, 127.15, 113.41 (CH-arom), 111.04 (C(5)), 87.70 (C(Ph)$_3$), 87.31 (C(1')), 83.15 (C(4')), 77.16 (C(7')), 74.96 (C(5')), 55.37 (MeO-DMTr), 49.12 (C(3')), 37.55 (C(2')), 36.82 (C(6')), 21.07 (MeCO$_2$), 12.66 (Me-C(5)).

ESI$^+$-HRMS m/z calcd for C$_{35}$H$_{36}$O$_8$N$_2$ ([M+H]$^+$) 612.2466, found 612.2453.

Example 38

(3'S,5'R,7'R)-1-{2',3'-Dideoxy-3',5'-ethano-7'-O-[(4,4'-dimethoxytriphenyl)methyl]-α-D-ribofuranosyl} thymine (38)

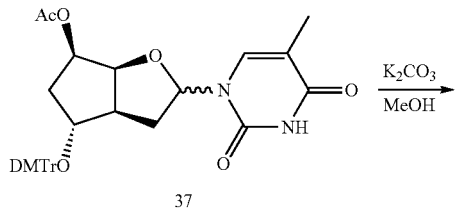

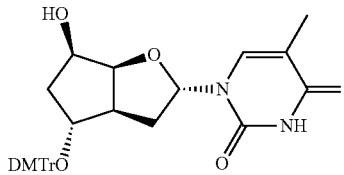

To a solution of the nucleoside 37 (690 mg, 1.12 mmol) in dry MeOH (10 mL) was added K$_2$CO$_3$ (467 mg, 3.36 mmol) at rt. The solution was stirred for 3 h and then diluted with satd NaCl (60 mL) and extracted with DCM (3×60 mL). The combined organic phases were dried over MgSO$_4$, filtered and evaporated. The crude product was purified by CC (3% isopropanol in Et$_2$O, +0.5% Et$_3$N) to yield the α-anomer 38 (550 mg, 86%) as a white solid.

Data for 38: $R_f$=0.39 (5% MeOH in DCM);

$^1$H NMR (400 MHz, CDCl$_3$) δ 9.37 (br, s, 1H, H—N(3)), 7.39-7.31 (m, 2H, H-arom), 7.25 (d, J=8.3 Hz, 4H, H-arom), 7.20 (t, J=7.7 Hz, 2H, H-arom), 7.16-7.08 (m, 1H, H-arom), 6.78 (d, J=1.1 Hz, 1H, H—C(6)), 6.74 (d, J=8.8 Hz, 4H, H-arom), 5.91 (dd, J=6.5, 4.9 Hz, 1H, H—C(1')), 4.57 (dd, J=7.2, 4.4 Hz, 1H, H—C(4')), 4.35-4.18 (m, 1H, H—C(5')), 3.86 (d, J=4.7 Hz, 1H, H—C(7')), 3.69 (s, 6H, MeO), 2.53 (br, 1H, OH), 2.22 (dd, J=15.3, 6.3 Hz, 1H, H—C(3')), 1.85-1.69 (m, 5H, Me-C(5), H—C(2'), H—C(6')), 1.66-1.49 (m, 2H, H—C(2'), H—C(6')).

$^{13}$C NMR (101 MHz, CDCl$_3$) δ 163.98 (C(4)), 158.67 (MeO—C-arom), 150.47 (C(2)), 145.48, 136.80, 136.75 (C-arom), 134.94 (C(6)), 130.19, 130.18, 128.35, 127.97, 127.01, 113.31 (CH-arom), 111.04 (C(5)), 87.82 (C(Ph)$_3$), 87.05 (C(1')), 85.74 (C(4')), 78.26 (C(7')), 73.33 (C(5')), 55.31 (MeO-DMTr), 48.81 (C(3')), 40.21 (C(6')), 37.68 (C(2')), 12.65 (Me-C(5)).

ESI$^+$-HRMS m/z calcd for C$_{33}$H$_{35}$O$_7$N$_2$ ([M+H]$^+$) 571.2439, found 571.2421.

Example 39

(3'S,5'R,7'R)-1-{5'-O-[(2-cyanoethoxy)-diisopropylaminophosphanyl]2',3'-Dideoxy-3',5'-ethano-7'-O-[(4,4'-dimethoxytriphenyl)methyl]-α-D-ribofuranosyl} Thymine (39)

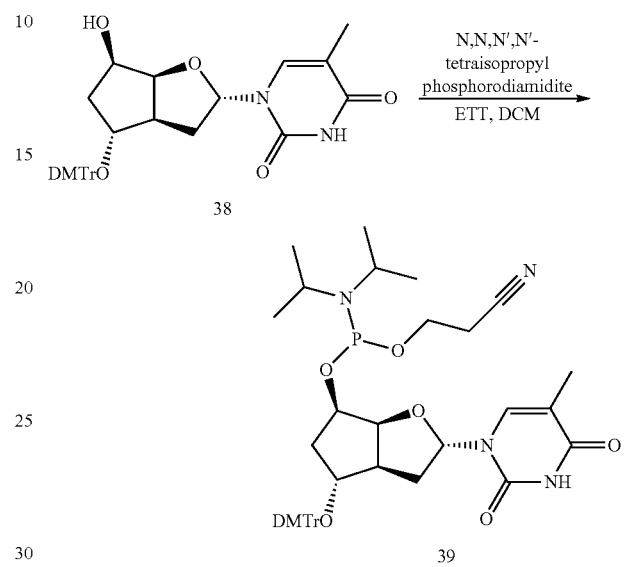

To a solution of the nucleoside 38 (200 mg, 0.350 mmol) and 5-(Ethylthio)-1H-tetrazole (59 mg, 0.46 mmol) in dry DCM (7 mL) was added dropwise 2-Cyanoethyl N,N,N',N'-tetraisopropylphosphordiamidite (0.17 mL, 0.53 mmol) at rt. After stirring for 1 h, the reaction mixture was diluted with DCM (50 mL) and washed with satd NaHCO$_3$ (2×25 mL) and satd NaCl (25 mL). Aqueous phases were combined and extracted with DCM (30 mL). The combined organic phases were dried over MgSO$_4$, filtered and evaporated. The crude product was purified by CC (2% MeOH in DCM, +0.5% Et$_3$N) to yield 39 (220 mg, mixture of two isomers, 81%) as a white solid.

Data for 39: $R_f$=0.44 (4% MeOH in DCM);

$^1$H NMR (300 MHz, CDCl$_3$) δ 9.03 (br, 1H, H—N(3)), 7.36 (d, J=8.1 Hz, 2H, H-arom), 7.30-7.07 (m, 7H, H-arom), 6.84 (s, 1H, H—C(6)), 6.80-6.69 (m, 4H, H-arom), 5.95, 5.88 (2dd, J=6.6, 4.8 Hz, 1H, H—C(1')), 4.70, 4.61 (2dd, J=7.3, 4.3 Hz, 1H, H—C(4')), 4.41-4.20 (m, 1H, H—C(5')), 3.94-3.82 (m, 1H, H—C(7')), 3.81-3.62 (m, 8H, MeO, OCH$_2$CH$_2$CN), 3.59-3.40 (m, 2H, (Me$_2$CH)$_2$N), 2.61-2.46 (m, 2H, OCH$_2$CH$_2$CN), 2.28 (ddd, J=14.1, 13.2, 7.3 Hz, 1H, H—C(3')), 1.91-1.73 (m, 5H, Me-C(5), H—C(6'), H—C(2')), 1.72-1.46 (m, 2H, H—C(6'), H—C(2')), 1.16-1.00 (m, 12H, (Me$_2$CH)$_2$N).

$^{13}$C NMR (75 MHz, CDCl$_3$) δ 164.01, 163.98 (C(4)), 158.70 (MeO—C-arom), 150.39, 150.17 (C(2)), 145.52, 136.84, 136.78 (C-arom), 135.44, 135.39 (C(6)), 130.21, 128.36, 128.32, 128.00, 127.03 (CH-arom), 118.02, 117.76 (OCH$_2$CH$_2$CN), 113.32 (CH-arom), 110.91, 110.59 (C(5)), 88.31, 88.06 (C(Ph)$_3$), 87.11, 87.06 (C(1')), 85.44, 85.39 ($J_{C,P}$=4.6, 3.1 Hz, C(4')), 78.25, 78.13 (C(7')), 74.70, 74.34 ($J_{C,P}$=13.5, 18.5 Hz, C(5')), 58.73, 58.47 ($J_{C,P}$=18.9, 20.1 Hz, (OCH$_2$CH$_2$CN)), 55.35, 55.32 (MeO-DMTr), 48.80, 48.64 (C(3')), 43.22, 43.06 ($J_{C,P}$=12.4, 11.0 Hz (Me$_2$CH)$_2$N), 39.68, 39.63 (C(6')), 38.06, 37.93 (C(2')), 24.81, 24.74, 24.71, 24.68, 24.65, 24.59 (6s, Me$_2$CH)$_2$N), 20.37, 20.35 (J$_{C,P}$=7.1, 6.8 Hz, OCH$_2$CH$_2$CN), 12.66 (Me-C(5)).

$^{31}$P NMR (122 MHz, CDCl$_3$) δ 148.18, 147.80.

ESI$^+$-HRMS m/z calcd for C$_{42}$H$_{52}$O$_8$N$_4$P ([M+H]$^+$) 771.3517, found 771.3517.

Example 40

(3'S,5'R,7'R)—N4-Benzoyl-1-{2',3'-dideoxy-3',5'-ethano-7'-O-[(4,4'-dimethoxytriphenyl)methyl]-α-D-ribofuranosyl}-5-methylcytosine (40)

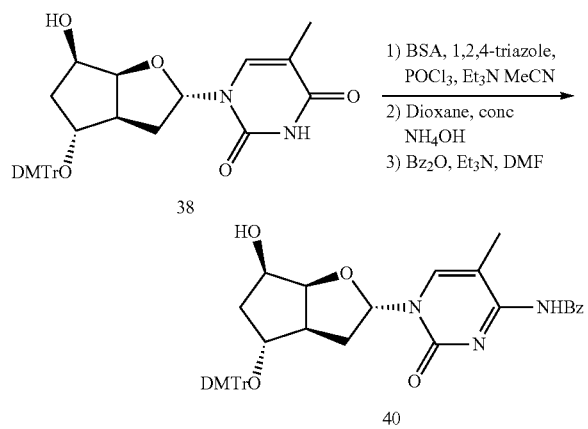

To a solution of the nucleoside 38 (268 mg, 0.470 mmol) in dry MeCN (5 mL) was added dropwise BSA (0.28 mL, 1.13 mmol) at 0°, and then the solution was stirred overnight at rt. In another flask, a suspension of 1,2,4-triazole (1.14 g, 16.5 mmol) in dry MeCN (50 mL) was cool down to 0° C. and POCl$_3$ (0.35 mL, 3.8 mmol) followed Et$_3$N (2.62 mL, 18.8 mmol) were added. The suspension was stirred for 30 min at 0° C., and then the previous prepared solution of the silylated compound 38 was added to the suspension and the mixture was further stirred for 7 h at rt. Reaction was quenched with addition satd NaHCO$_3$ (10 mL), MeCN removed under reduced pressure and the resulting mixture diluted with satd NaHCO$_3$ (30 mL) and extracted with DCM (3×30 mL). The combined organic phases were dried over MgSO$_4$, filtered and evaporated.

The crude product was then dissolved in a mixture of 1,4-dioxane (10 mL) and concd NH$_4$OH (10 mL). After stirring for 3 h at rt, the mixture was reduced to half of its volume in vacuo, diluted with satd NaHCO$_3$ (25 mL) and extracted with DCM (4×30 mL). The combined organic phases were dried over MgSO$_4$, filtered and evaporated.

The crude product was then dissolved in dry DMF (10 mL). Et$_3$N (80 μL, 0.56 mmol) followed by Bz$_2$O (266 mg, 1.18 mmol) were added at rt and the solution was stirred overnight. The resulting brownish solution was quenched by careful addition of satd NaHCO$_3$ (40 mL) and extracted with DCM (4×40 mL). The combined organic phases were dried over MgSO$_4$, filtered and evaporated. The crude product was purified by CC (EtOAc/hexane 1:1, +0.5% Et$_3$N) to yield 40 (263 mg, 83%) as a white foam.

Data for 40: R$_f$=0.53 (EtOAc/hexane 3:1);

$^1$H NMR (300 MHz, CDCl$_3$) δ 13.11 (br, 1H, NH), 8.30-8.10 (m, 2H, H-arom), 7.47-7.29 (m, 5H, H-arom), 7.28-7.06 (m, 7H, H-arom), 7.00 (d, J=0.8 Hz, 1H, H—C(6)), 6.74 (d, J=8.6 Hz, 4H, H-arom), 5.89 (dd, J=6.3, 4.6 Hz, 1H, H—C(1')), 4.61 (dd, J=7.2, 4.5 Hz, 1H, H—C(4')), 4.33-4.20 (m, 1H, H—C(5')), 3.87 (br, 1H, H—C(7')), 3.69 (s, 6H, MeO), 2.32-2.13 (m, 2H, H—C(3'), OH), 1.99 (s, 3H, Me-C(5)), 1.87-1.73 (m, 2H, H—C(2'), H—C(6')), 1.66-1.47 (m, 2H, H—C(2'), H—C(6')).

$^{13}$C NMR (75 MHz, CDCl$_3$) δ 179.61 (CONH), 159.76 (C(4)), 158.74 (MeO—C-arom), 147.87 (C(2)), 145.47 (C-arom), 137.17 (C(6)), 136.77, 136.68, 136.03 (C-arom), 132.55, 130.21, 129.98, 128.34, 128.21, 128.03, 127.07, 113.35 (CH-arom), 111.81 (C(5)), 88.74 (C(Ph)$_3$), 87.13 (C(1')), 86.12 (C(4')), 78.17 (C(7')), 73.31 (C(5')), 55.35 (MeO-DMTr), 48.63 (C(3')), 40.35 (C(6')), 38.06 (C(2')), 13.78 (Me-C(5)).

ESI$^+$-HRMS m/z calcd for C$_{40}$H$_{40}$O$_7$N$_3$ ([M+H]$^+$) 674.2861, found 674.2877.

Example 41

(3'S,5'R,7'R)—N4-Benzoyl-1-{5'-O-[(2-cyanoethoxy)-diisopropylaminophosphanyl]2',3'-dideoxy-3,5'-ethano-7'-O-[(4,4'-dimethoxytriphenyl)methyl]-α-D-ribofuranosyl}-5-methylcytosine (41)

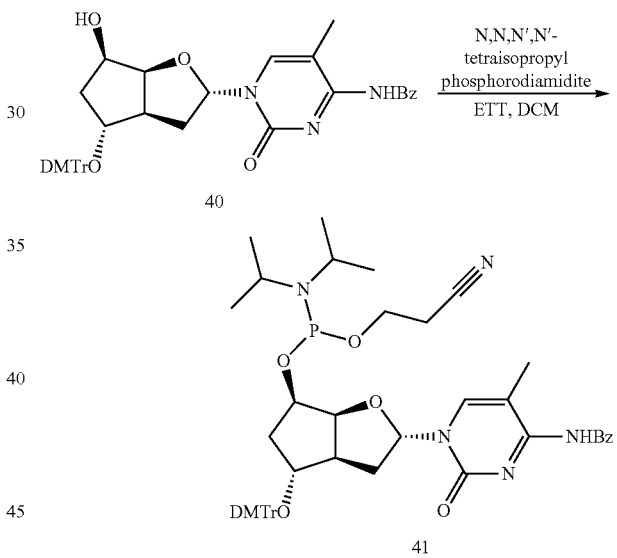

To a solution of the nucleoside 40 (250 mg, 0.371 mmol) and 5-(Ethylthio)-1H-tetrazole (73 mg, 0.56 mmol) in dry DCM (8 mL) was added dropwise 2-Cyanoethyl N,N,N',N'-tetraisopropylphosphordiamidite (0.20 mL, 0.63 mmol) at rt. After stirring for 30 min, the reaction mixture was diluted with DCM (30 mL) and washed with satd NaHCO$_3$ (2×20 mL) and satd NaCl (20 mL). Aqueous phases were combined and extracted with DCM (20 mL).

The combined organic phases were dried over MgSO$_4$, filtered and evaporated. The crude product was purified by CC (EtOAc/hexane 1:1, +0.5% Et$_3$N) to yield 41 (260 mg, mixture of two isomers, 80%) as a white foam.

Data for 41: R$_f$=0.57 (EtOAc/hexane 1:1);

$^1$H NMR (300 MHz, CDCl$_3$) δ 13.26 (br, 1H, NH), 8.32 (d, J=7.2 Hz, 2H, H-arom), 7.58-7.39 (m, 5H, H-arom), 7.38-7.14 (m, 8H, H-arom, H—C(6)), 6.88-6.77 (m, 4H, H-arom), 6.01, 5.96 (2dd, J=6.3, 4.6 Hz, 1H, H—C(1')), 4.82, 4.74 (2dd, J=7.3, 4.3 Hz, 1H, H—C(4')), 4.42 (td, J=10.6, 6.0 Hz, 1H, H—C(5')), 3.97 (br, 1H, H—C(7')), 3.91-3.68 (m, 8H, MeO, OCH$_2$CH$_2$CN), 3.59 (dtd, J=16.7, 6.7, 3.4 Hz, 2H, (Me$_2$CH)$_2$N)), 2.62 (dt, J=15.5, 6.4 Hz, 2H, OCH$_2$CH$_2$CN), 2.49-2.23 (m, 1H, H—C(3')), 2.11, 2.09 (2d, J=0.5 Hz, 3H, Me-C(5)), 2.00-1.82 (m, 2H, H—C(6'), H—C(2')), 1.82-1.55 (m, 2H, H—C(6'), H—C(2')), 1.17 (dd, J=16.3, 6.8 Hz, 12H, (Me$_2$CH)$_2$N).

$^{13}$C NMR (101 MHz, CDCl$_3$) δ 179.60 (CONH), 159.97 (C(4)), 158.76 (MeO—C-arom), 147.81, 147.70 (C(2)), 145.54 (C-arom), 137.34, 136.83 (C(6)), 136.77, 136.72, 136.65, 136.55 (C-arom), 132.45, 130.22, 130.20, 129.96, 128.34, 128.31, 128.18, 128.00, 127.04 (CH-arom), 117.89, 117.71 (OCH$_2$CH$_2$CN), 113.35 (CH-arom), 111.60, 111.36 (C(5)), 89.24, 89.01 (C(Ph)$_3$), 87.16, 87.12 (C(1')), 85.78, 85.62 (J$_{C,P}$=4.3, 3.2 Hz, C(4')), 78.20, 77.98 (C(7')), 74.68, 74.37 (J$_{C,P}$=13.4, 18.2 Hz, C(5')), 58.70, 58.44 (J$_{C,P}$=18.5, 20.0 Hz, (OCH$_2$CH$_2$CN)), 55.36, 55.33 (MeO-DMTr), 48.65, 48.44 (C(3')), 43.27, 43.14 (J$_{C,P}$=12.4, 12.3 Hz (Me$_2$CH)$_2$N), 39.87, 39.64 (J$_{C,P}$=3.4, 3.7 Hz (C(6')), 38.30, 38.22 (C(2')), 24.80, 24.72, 24.70, 24.67, 24.63 (Me$_2$CH)$_2$N), 20.39, 20.37 (J$_{C,P}$=7.2, 6.8 Hz, OCH$_2$CH$_2$CN), 13.72 (Me-C(5)).

$^{31}$P NMR (121 MHz, CDCl$_3$) δ 148.18, 147.96.

ESI$^+$-HRMS m/z calcd for C$_{49}$H$_{57}$O$_8$N$_5$P ([M+H]$^+$) 874.3939, found 874.3946.

Example 42

(3'R,5'R,7'R)—N6-Benzoyl-9-{7'-[(tert-butyldiphenylsilyl)oxy]-2',3'-dideoxy-3',5'-ethano-α-D-ribofuranosyl} adenine (42)

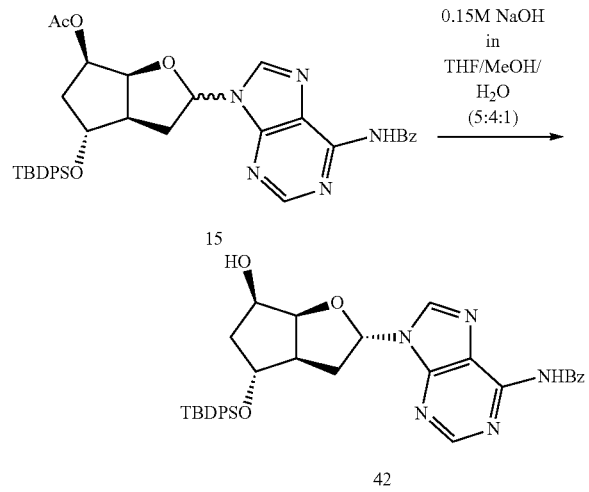

The nucleoside 15 (1.74 g, 2.64 mmol) was dissolved in 0.15 M NaOH in THF/methanol/H$_2$O (5:4:1, 80 mL) at 0° C. The reaction was stirred for 20 min and quenched by addition of NH$_4$Cl (1.06 g). Solvents were then removed under reduced pressure and the product purified by CC (5% isopropanol in DCM) to yield 42 (α-anomer, 836 mg, 51%) and 16 (β-anomer, 287 mg, 18%) as white foams.

Data for 42: R$_f$=0.35 (5% MeOH in DCM);

$^1$H NMR (300 MHz, CDCl$_3$) δ 9.34 (s, 1H, NH), 8.71 (s, 1H, H—C(2)), 8.02 (d, J=7.4 Hz, 2H, H-arom)), 7.92 (s, 1H, H—C(8)), 7.68-7.58 (m, 4H, H-arom), 7.58-7.31 (m, 9H, H-arom), 6.23 (dd, J=6.7, 2.4 Hz, 1H, H—C(1')), 4.74 (dd, J=6.6, 4.9 Hz, 1H, H—C(4')), 4.49 (dt, J=12.5, 6.3 Hz, 1H, H—C(5')), 4.10 (br, 1H, H—C(7')), 3.07 (d, J=6.7 Hz, 1H, OH), 2.92 (dd, J=15.4, 7.3 Hz, 1H, H—C(3')), 2.52-2.35 (m, 1H, H—C(2')), 2.10-1.97 (m, 1H, H—C(6')), 1.94-1.77 (m, 2H, H—C(2'), H—C(6')), 1.06 (s, 9H, (CH$_3$)$_3$—C—Si).

$^{13}$C NMR (75 MHz, CDCl$_3$) δ 164.98 (CONH), 152.65 (C(2)), 151.31 (C(4)), 149.69 (C(6)), 140.93 (C(8)), 135.74 (CH-arom), 133.82, 133.68, 133.39 (C-arom), 132.77, 130.02, 129.98, 128.76, 128.06, 127.87, 127.85 (CH-arom), 123.38 (C(5)), 87.16 (C(1')), 85.35 (C(4')), 77.40 (C(7')), 72.79 (C(5')), 50.63 (C(3')), 40.86 (C(6')), 37.25 (C(2')), 26.94 ((CH$_3$)$_3$—C—Si), 19.05 ((CH$_3$)$_3$—C—Si).

ESI$^+$-HRMS m/z calcd for C$_{35}$H$_{38}$O$_4$N$_5$Si ([M+H]$^+$) 620.2688, found 620.2671.

Example 43

(3'R,5'R,7'R)—N6-Benzoyl-9-{5'-O-acetyl-7'-[(tert-butyldiphenylsilyl)oxy]-2',3'-dideoxy-3',5'-ethano-α-D-ribofuranosyl} adenine (43)

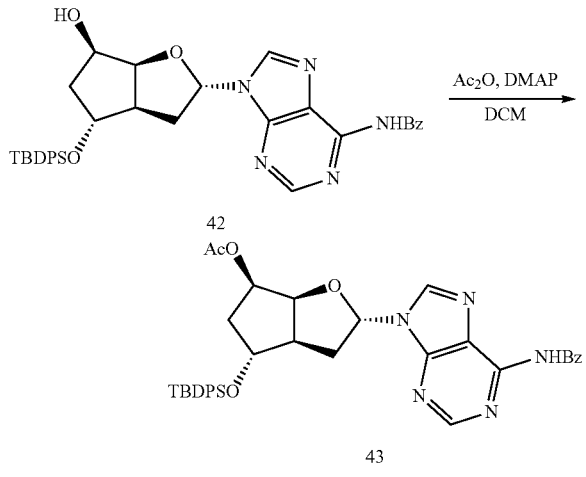

To a solution of the nucleoside 42 (1.09 g, 1.75 mmol) and 4-dimethylaminopyridine (321 mg, 2.63 mmol) in dry DCM (50 mL) was added acetic anhydride (0.83 mL, 8.8 mmol) at rt. After stirring overnight, the reaction was quenched by addition of satd NaHCO$_3$ (50 mL). The phases were separated and aqueous phase further extracted with DCM (2×80 mL). The combined organic phases were dried over MgSO$_4$, filtered and evaporated. The crude product was purified by CC (2.5% MeOH in DCM) to yield 43 (1.04 g, 90%) as white foams.

Data for 43: R$_f$=0.33 (EtOAc/hexane 4:1);

$^1$H NMR (300 MHz, CDCl$_3$) δ 8.99 (br, 1H, NH), 8.73 (s, 1H, H—C(2)), 8.09-7.99 (m, 2H, H-arom), 7.98 (s, 1H, H—C(8)), 7.70-7.58 (m, 5H, H-arom), 7.57-7.48 (m, 2H, H-arom), 7.47-7.34 (m, 6H, H-arom), 6.22 (dd, J=6.8, 3.2 Hz, 1H, H—C(1')), 5.45-5.35 (m, 1H, H—C(5')), 5.01 (dd, J=6.7, 5.0 Hz, 1H, H—C(4')), 4.09 (d, J=4.1 Hz, 1H, H—C(7')), 3.02 (dt, J=9.5, 6.5 Hz, 1H, H—C(3')), 2.55 (ddd, J=13.5, 10.0, 3.2 Hz, 1H, H—C(2')), 2.15 (dd, J=13.2, 6.2 Hz, 1H, H—C(6')), 2.09 (s, 3H, MeCO$_2$), 2.01 (dt, J=8.0, 3.5 Hz, 1H, H—C(2')), 1.88 (dt, J=13.6, 5.3 Hz, 1H, H—C(6')), 1.08 (s, 9H, (CH$_3$)$_3$—C—Si).

$^{13}$C NMR (101 MHz, CDCl$_3$) δ 170.61 (MeCO$_2$), 164.75 (CONH), 152.67 (C(2)), 151.37 (C(4)), 149.64 (C(6)), 141.41 (C(8)), 135.85 (CH-arom), 133.71, 133.38 (C-arom), 132.91, 130.15, 130.10, 128.99, 128.02, 127.99, 127.97 (CH-arom), 123.64 (C(5)), 87.37 (C(1')), 83.37 (C(4')), 76.63 (C(7')), 74.51 (C(5')), 51.19 (C(3')), 37.44 (C(2')), 37.32 (C(6')), 27.01 ((CH$_3$)$_3$—C—Si), 21.08 (MeCO$_2$), 19.14 ((CH$_3$)$_3$—C—Si).

ESI$^+$-HRMS m/z calcd for C$_{37}$H$_{40}$O$_5$N$_5$Si ([M+H]$^+$) 662.2793, found 662.2787.

Example 44

(3'S,5'R,7'R)—N6-Benzoyl-9-{5'-O-acetyl-2',3'-dideoxy-3',5'-ethano-7'-hydroxy-α-D-ribofuranosyl} adenine (44)

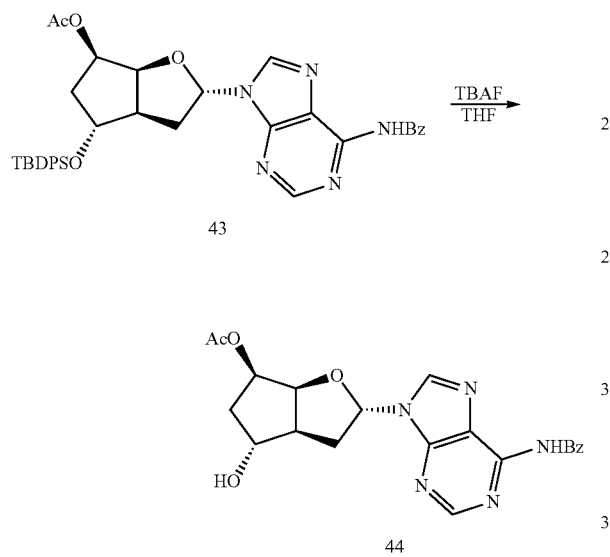

To a solution of the nucleoside 43 (990 mg, 1.50 mmol) in dry THF (50 mL) was added TBAF (1M in THF, 3.0 mL, 3.0 mmol) at rt. After stirring for 3.5 hours at rt, the solution was diluted with EtOAc (30 mL) and THF was removed under reduced pressure. The mixture was then diluted with satd NaHCO$_3$ (50 mL) and extracted with DCM (4×50 mL). The combined organic phases were dried over MgSO$_4$, filtered and evaporated. The crude product was purified by CC (6% MeOH in DCM) to yield 44 (570 mg, 90%) as a white foam, containing traces of TBAF.

Data for 44: R$_f$=0.33 (10% MeOH in DCM);

$^1$H NMR (400 MHz, CDCl$_3$) δ 9.60 (br, 1H, NH), 8.67 (s, 1H, H—C(2)), 8.09 (s, 1H, H—C(8)), 7.96 (d, J=7.4 Hz, 2H, H-arom), 7.51 (t, J=7.4 Hz, 1H, H-arom), 7.42 (t, J=7.5 Hz, 2H, H-arom), 6.33 (dd, J=6.7, 3.1 Hz, 1H, H—C(1')), 5.25 (ddd, J=9.7, 6.4, 5.3 Hz, 1H, H—C(5')), 4.92 (dd, J=6.4, 5.4 Hz, 1H, H—C(1')), 4.14 (br, 2H, H—C(7'), OH), 3.06 (dd, J=16.0, 6.6 Hz, 1H, H—C(3')), 2.87 (ddd, J=13.2, 9.9, 3.0 Hz, 1H, H—C(2')), 2.26-2.17 (m, 1H, H—C2')), 2.10-1.98 (m, 5H, H—C(6'), MeCO$_2$).

$^{13}$C NMR (75 MHz, CDCl$_3$) δ 170.64 (MeCO$_2$), 165.27 (CONH), 152.49 (C(2)), 151.26 (C(4)), 149.58 (C(6)), 141.64 (C(8)), 133.60 (C-arom), 132.82, 128.76, 128.06 (CH-arom), 123.30 (C(5)), 87.30 (C(1')), 83.17 (C(4')), 74.67 (C(7')), 74.20 (C(5')), 50.41 (C(3')), 37.43 (C(2')), 36.92 (C(6')), 20.96 (MeCO$_2$).

ESI$^+$-HRMS m/z calcd for C$_{21}$H$_{22}$O$_5$N$_5$ ([M+H]$^+$) 424.1615, found 424.1623.

Example 45

(3'S,5'R,7'R)—N6-Benzoyl-9-{5'-O-acetyl-2',3'-dideoxy-3',5'-ethano-7'-O-[(4,4'-dimethoxytriphenyl)methyl]-α-D-ribofuranosyl} Adenine (45)

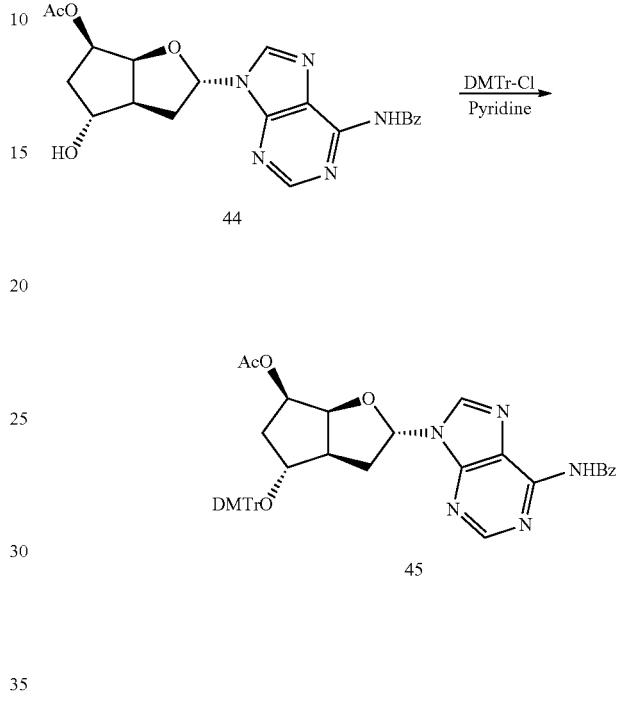

To a solution of nucleoside 44 (570 mg, 1.35 mmol) in dry pyridine (16 mL) was added DMTr-Cl (1.37 g, 4.04 mmol) at rt. The solution was stirred for 1 day and then was diluted with satd NaHCO$_3$ (100 mL) and extracted with DCM (3×80 mL). The combined organic phases were dried over MgSO$_4$, filtered and evaporated. The crude product was purified by CC (2% MeOH in DCM, +0.5% Et$_3$N) to yield 45 (876 mg, 89%) as a yellow foam.

Data for 45: R$_f$=0.81 (5% MeOH in DCM);

$^1$H NMR (300 MHz, CDCl$_3$) δ 9.42 (d, J=14.6 Hz, 1H, NH), 8.73 (s, 1H, H—C(2)), 8.03 (d, J=7.6 Hz, 2H, H-arom), 7.93 (s, 1H, H—C(8)), 7.66-7.55 (m, 1H, H-arom), 7.55-7.45 (m, 4H, H-arom), 7.45-7.22 (m, 7H, H-arom), 6.87 (d, J=8.7 Hz, 4H, H-arom), 6.25 (dd, J=6.6, 2.4 Hz, 1H, H—C(1')), 5.47-5.33 (m, 1H, H—C(5')), 4.89 (dd, J=6.7, 4.9 Hz, 1H, H—C(4')), 4.02 (d, J=2.5 Hz, 1H, H—C(7')), 3.79 (s, 6H, MeO), 2.58 (dd, J=16.0, 6.9 Hz, 1H, H—C(3')), 2.38 (ddd, J=12.7, 10.0, 2.4 Hz, 1H, H—C(2')), 2.11 (s, 3H, MeCO$_2$), 2.09-1.87 (m, 3H, H—C(2'), H—C(6')). $^{13}$C NMR (75 MHz, CDCl$_3$) δ 170.40 (MeCO$_2$), 164.84 (CONH), 158.66 (MeO—C-arom), 152.45 (C(2)), 151.22 (C(4)), 149.51 (C(6)), 145.23 (C-arom), 141.23 (C(8)), 136.51, 133.65 (C-arom), 132.68, 130.12, 128.75, 128.33, 127.95, 127.90, 127.03 (CH-arom), 123.55 (C(5)), 113.27 (CH-arom), 87.19 (C(Ph)$_3$), 87.12 (C(1')), 83.25 (C(4')), 77.16 (C(7')), 74.41 (C(5')), 55.23 (MeO-DMTr), 49.23 (C(3')), 37.61 (C(2')), 36.22 (C(6')), 20.98 (MeCO$_2$).

ESI$^+$-HRMS m/z calcd for C$_{42}$H$_{40}$O$_7$N$_5$ ([M+H]$^+$) 726.2922, found 726.2905.

Example 46

(3'S,5'R,7'R)—N6-benzoyl-9-{2',3'-dideoxy-3',5'-ethano-7'-O-[(4,4'-dimethoxytriphenyl)methyl]-α-D-ribofuranosyl} Adenine (46)

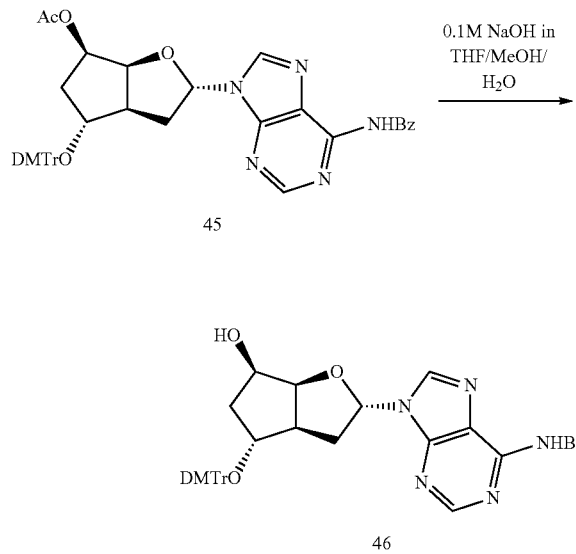

The nucleoside 45 (870 mg, 1.20 mmol) was dissolved in 0.1 M NaOH in THF/methanol/H₂O (5:4:1, 50 mL) at 0° C. The reaction was stirred for 30 min at 0° C. and then quenched by addition of NH₄Cl (321 mg). The solution was diluted with satd NaHCO₃ (100 mL) and extracted with DCM (4×80 mL). The combined organic phases were dried over MgSO₄, filtered and evaporated. The crude product was purified by CC (3% MeOH in DCM, +0.5% Et₃N) to yield 46 (777 mg, 94%) as white foams.

Data for 46: $R_f$=0.26 (5% MeOH in DCM);

$^1$H NMR (300 MHz, CDCl₃) δ 9.39 (s, 1H, NH), 8.61 (s, 1H, H—C(2)), 7.93 (d, J=7.4 Hz, 2H, H-arom), 7.75 (s, 1H, H—C(8)), 7.46 (t, J=7.3 Hz, 1H, H-arom), 7.40-7.31 (m, 4H, H-arom), 7.29-7.16 (m, 6H, H-arom), 7.11 (t, J=7.2 Hz, 1H, H-arom), 6.73 (d, J=8.7 Hz, 4H, H-arom), 6.12 (dd, J=6.5, 1.9 Hz, 1H, H—C(1')), 4.53 (dd, J=7.5, 4.5 Hz, 1H, H—C(4')), 4.32 (br, 1H, H—C(5')), 3.90 (t, J=4.5 Hz, 1H, H—C(7')), 3.66, 3.65 (2s, 6H, MeO), 3.31 (br, 1H, OH), 2.36 (dd, J=16.5, 8.1 Hz, 1H, H—C(3')), 2.04 (ddd, J=12.0, 9.9, 2.0 Hz, 1H, H—C(2')), 1.92-1.69 (m, 3H, H—C(2'), H—C(6')).

$^{13}$C NMR (75 MHz, CDCl₃) δ 164.92 (CONH), 158.64 (MeO—C-arom), 152.60 (C(2)), 151.28 (C(4)), 149.61 (C(6)), 145.44 (C-arom), 140.71 (C(8)), 136.77, 133.65 (C-arom), 132.72, 130.15, 130.12, 128.73, 128.39, 128.04, 127.96, 127.02 (CH-arom), 123.27 (C(5)), 113.28 (CH-arom), 87.11 (C(1')), 87.01 (C(Ph)₃), 85.60 (C(4')), 78.16 (C(7')), 72.72 (C(5')), 55.28 (MeO-DMTr), 48.89 (C(3')), 39.93 (C(6')), 37.55 (C(2')).

ESI⁺-HRMS m/z calcd for $C_{40}H_{38}O_6N_5$ ([M+H]⁺) 684.2817, found 684.2800.

Example 47

(3'S,5'R,7'R)—N6-Benzoyl-9-{5'-O-[(2-cyanoethoxy)-diisopropylaminophosphanyl]-2',3'-dideoxy-3',5'-ethano-7'-O-[(4,4'-dimethoxytriphenyl)methyl]-α-D-ribofuranosyl} Adenine (47)

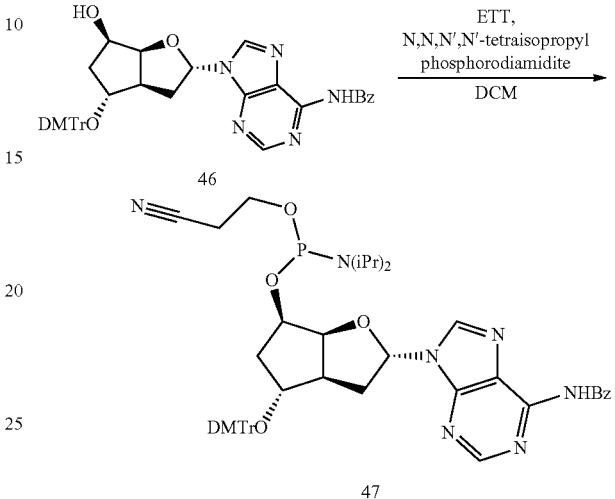

To a solution of the nucleoside 46 (199 mg, 0.290 mmol) and 5-(Ethylthio)-1H-tetrazole (57 mg, 0.44 mmol) in dry DCM (7 mL) was added dropwise 2-Cyanoethyl N,N,N',N'-tetraisopropylphosphordiamidite (0.16 mL, 0.49 mmol) at rt. After stirring for 60 min, the reaction mixture was diluted with satd NaHCO₃ (20 mL) and extracted with DCM (3×20 mL). The combined organic phases were dried over MgSO₄, filtered and evaporated. The crude product was purified by CC (EtOAc, +0.5% Et₃N) to yield 47 (197 mg, mixture of two isomers, 77%) as a white foam.

Data for 47: $R_f$=0.75 (5% MeOH in DCM);

$^1$H NMR (300 MHz, CDCl₃) δ 8.98 (br, 1H, NH), 8.68, 8.67 (2s, 1H, C(2)), 7.94 (d, J=7.6 Hz, 2H, H-arom), 7.90, 7.84 (2s, 1H, C(8)), 7.56-7.49 (m, 1H, H-arom), 7.48-7.34 (m, 4H, H-arom), 7.30-7.10 (m, 7H, H-arom), 6.80-6.69 (m, 4H, Harom), 6.21, 6.15 (2dd, J=6.8, 2.2 Hz, 1H, H—C(1')), 4.69, 4.59 (2dd, J=7.3, 4.5 Hz, 1H, H—C(4')), 4.44 (tt, J=12.3, 6.3 Hz, 1H, H—C(5')), 3.90 (dd, J=9.0, 3.8 Hz, 1H, H—C(5')), 3.82-3.63 (m, 8H, MeO, OCH₂CH₂CN), 3.59-3.43 (m, 2H, (Me₂CH)₂N), 2.61-2.49 (m, 2H, OCH₂CH₂CN), 2.47-2.07 (m, 2H, H—C(3'), H—C(2')), 1.98-1.66 (m, 3H, H—C(2'), H—C(6')), 1.15-1.03 (m, 12H, (Me₂CH)₂N).

$^{13}$C NMR (101 MHz, CDCl₃) δ 164.67 (CONH), 158.77 (MeO—C-arom), 152.58 (C(2)), 151.34, 151.29 (C(4)), 149.46 (C(6)), 145.55, 145.54 (C-arom), 141.58, 141.50 (C(8)), 136.87, 136.85, 136.84, 133.85 (C-arom), 132.85, 130.26, 130.23, 130.20, 128.97, 128.47, 128.43, 128.02, 127.96, 127.08 (CH-arom), 123.62, 123.58 (C(5)), 117.91, 117.70 (OCH₂CH₂CN), 113.37 (CH-arom), 87.80, 87.67 (C(1')), 87.20, 87.14 (C(Ph)₃), 85.29, 85.22 (($J_{C,P}$=4.2, 3.1 Hz, C(4')), 78.16, 77.96 (C(7')), 74.28, 73.98 ($J_{C,P}$=14.8, 18.4 Hz, C(5')), 58.80, 58.61 ($J_{C,P}$=16.2, 17.3 Hz OCH₂CH₂CN), 55.37, 55.35 (MeO-DMTr), 49.02, 48.91 (C(3')), 43.29, 43.16 ($J_{C,P}$=8.9, 9.0 Hz, ((Me₂CH)₂N), 39.09 (C(6')), 37.99, 37.95 (C(2')), 24.82, 24.77, 24.74, 24.70, 24.64 ((Me₂CH)₂N), 20.43, 20.42 ($J_{C,P}$=1.4, 1.9 Hz, OCH₂CH₂CN).

$^{31}$P NMR (121 MHz, CDCl$_3$) δ 148.14, 148.11.

ESI$^+$-HRMS m/z calcd for C$_{45}$H$_{56}$O$_7$N$_8$P ([M+H]$^+$) 884.3895, found 884.3904.

Example 48

(3'R,5'R,7'R)-2-Amino-6-chloro-9-{7'-[(tert-butyldiphenylsilyl)oxy]-2',3'-dideoxy-3,5'-ethano-α-D-ribofuranosyl} purine (48)

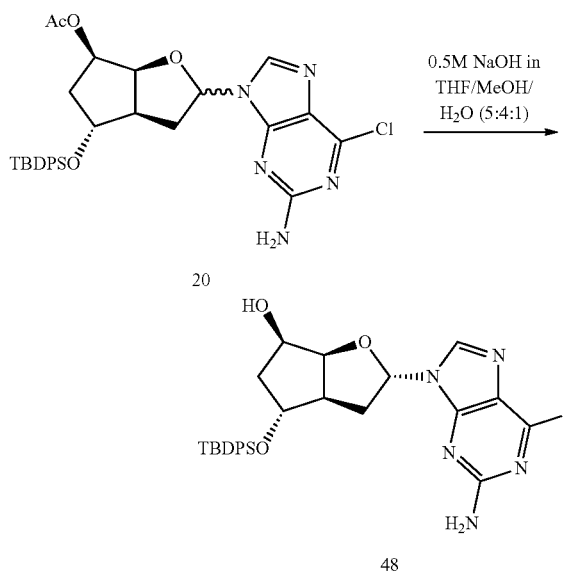

48

The nucleoside 20 (1.78 g, 3.01 mmol) was dissolved in 0.5 M NaOH in THF/methanol/H$_2$O (5:4:1, 15 mL) at 0° C. The reaction was stirred for 20 min at 0° C. and was quenched by addition of NH$_4$Cl (484 mg). The suspension was then diluted with satd NaHCO$_3$ (100 mL) and extracted with DCM (4×75 mL). The combined organic phases were dried over MgSO$_4$, filtered and evaporated. The crude product was purified by CC (3% MeOH in DCM) to yield 48 (α-anomer, 992 mg, 60%) and 21 (β-anomer, 428 mg, 25%) as white foams.

Data for 48: R$_f$=0.34 (5% MeOH in DCM);

$^1$H NMR (400 MHz, CDCl$_3$) δ 7.71-7.60 (m, 5H, H-arom, H—C(8)), 7.49-7.34 (m, 6H, H-arom), 6.08 (dd, J=6.9, 2.6 Hz, 1H, H—C(1')), 5.26 (s, 2H, NH$_2$), 4.70 (dd, J=7.5, 4.8 Hz, 1H, H—C(4')), 4.47 (dt, J=10.0, 5.1 Hz, 1H, H—C(5')), 4.11 (t, J=3.3 Hz, 1H, H—C(7')), 2.87 (dd, J=16.5, 7.7 Hz, 1H, H—C(3')), 2.57 (br, 1H, OH), 2.27 (ddd, J=14.0, 9.9, 2.6 Hz, 1H, H—C(2')), 2.10-2.01 (m, 1H, H—C(6')), 1.92-1.76 (m, 2H, H—C(2'), H—C(6')), 1.06 (s, 9H, (CH$_3$)$_3$—C—Si).

$^{13}$C NMR (75 MHz, CDCl$_3$) δ 159.09 (C(2)), 153.05 (C(4)), 151.46 (C(6)), 139.91 (C(8)), 135.71 (CH-arom), 133.96, 133.27 (C-arom), 130.00, 129.96, 127.86, 127.83 (CH-arom), 125.52 (C(5)), 86.46 (C(1')), 84.92 (C(4')), 77.40 (C(7')), 72.63 (C(5')), 50.55 (C(3')), 40.92 (C(6')), 36.78 (C(2')), 26.88 ((CH$_3$)$_3$—C—Si), 19.01 ((CH$_3$)$_3$—C—Si).

ESI$^+$-HRMS m/z calcd for C$_{28}$H$_{33}$O$_3$N$_5$ClSi ([M+H]$^+$) 550.2036, found 550.2019.

Example 49

(3'R,5'R,7'R)-9-{7'-[(tert-butyldiphenylsilyl)oxy]-2',3'-dideoxy-3',5'-ethano-α-D-ribofuranosyl} guanine (49)

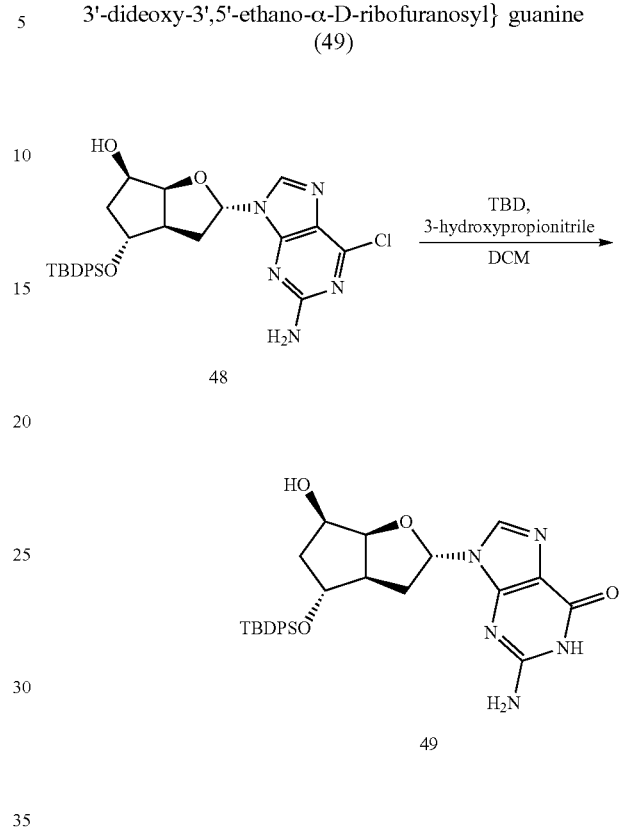

To a solution of the nucleoside 48 (610 mg, 1.03 mmol) in dry DCM (15 mL) were added 3-hydroxypropionitrile (0.28 mL, 4.12 mmol) followed by 1,5,7-Triazabicyclo[4.4.0]dec-5-ene (287 mg, 2.06 mmol) at rt. After 4 hours of stirring at rt, a second portion of 3-hydroxypropionitrile (0.28 mL, 3.23 mmol) followed by 1,5,7-Triazabicyclo[4.4.0]dec-5-ene (287 mg, 2.06 mmol) were added. The reaction was further stirred for 2 days and then was directly purified by CC (10% MeOH in DCM) to yield 49 (500 mg, 87%) as white foam.

Data for 49: R$_f$=0.30 (10% MeOH in DCM);

$^1$H NMR (400 MHz, MeOD) δ 7.73-7.61 (m, 5H, H-arom, H—C(8)), 7.53-7.32 (m, 6H, H-arom), 6.06 (dd, J=6.9, 3.7 Hz, 1H, H—C(1')), 4.74 (dd, J=7.0, 4.6 Hz, 1H, H—C(4')), 4.46-4.36 (m, 1H, H—C(5')), 4.11 (br, 1H, H—C(7')), 2.91 (dd, J=16.2, 6.6 Hz, 1H, H—C(3')), 2.31 (ddd, J=13.8, 10.0, 3.7 Hz, 1H, H—C(2')), 1.98-1.78 (m, 3H, H—C(2'), H—C(3')), 1.07 (s, 9H, (CH$_3$)$_3$—C—Si).

$^{13}$C NMR (101 MHz, MeOD) δ 159.30 (C(2)), 155.14 (C(6)), 152.38 (C(4)), 137.28 (C(8)), 136.93, 136.88 (CH-arom), 135.13, 134.78 (C-arom), 131.07, 131.06, 128.91, 128.89 (CH-arom), 117.98 (C(5)), 87.72 (C(1')), 86.25 (C(4')), 79.21, (C(7')) 73.87 (C(5')), 52.13 (C(3')), 41.44 (C(6')), 38.35 (C(2')), 27.42 ((CH$_3$)$_3$—C—Si), 19.82 ((CH$_3$)$_3$—C—Si)).

ESI$^+$-HRMS m/z calcd for C$_{28}$H$_{34}$O$_4$N$_5$Si ([M+H]$^+$) 532.2386, found 532.2367.

Example 50

(3'R,5'R,7'R)— N2-Acetyl-9-{5'-O-acetyl-7'-[(tert-butyldiphenylsilyl)oxy]-2',3'-dideoxy-3',5'-ethano-α-D-ribofuranosyl} guanine (50)

Example 51

(3'S,5'R,7'R)— N2-Acetyl-9-{5'-O-acetyl-2',3'-dideoxy-3',5'-ethano-7'-hydroxy-α-D-ribofuranosyl} guanine (51)

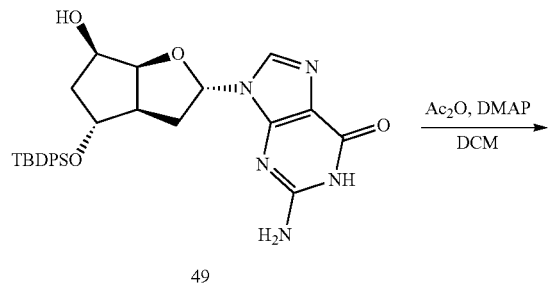

49

Ac₂O, DMAP
DCM
→

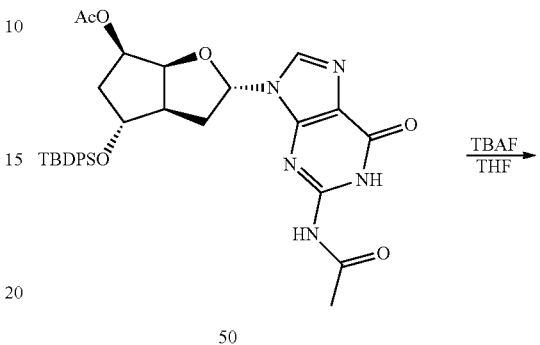

50

TBAF
THF
→

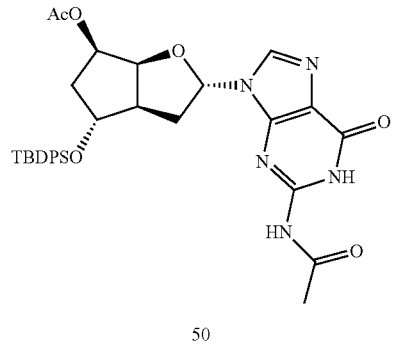

50

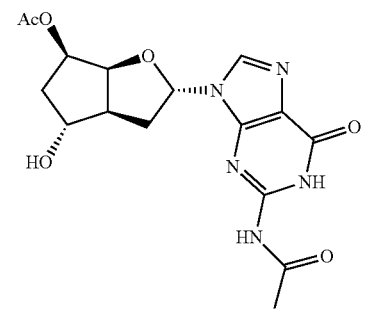

51

To a solution of nucleoside 49 (500 mg, 0.940 mmol) and 4-Dimethylaminopyridine (276 mg, 2.4 mmol) in dry DCM (15 mL) was added acetic anhydride (1.0 mL, 10.3 mmol) at rt. After stirring for 2 days, reaction was quenched by addition of satd NaHCO₃ (30 mL). The mixture was then extracted with DCM (3×30 mL). The combined organic phases were dried over MgSO₄, filtered and evaporated. The crude product was purified by CC (3.5% MeOH in DCM) to yield 50 (441 mg, 76%) as white foam.

Data for 50: $R_f$=0.62 (10% MeOH in DCM);

$^1$H NMR (300 MHz, CDCl₃) δ 12.11 (br, 1H, NH—C(4)), 9.94 (br, 1H, H—N(1)), 7.62 (d, J=6.7 Hz, 5H, H-arom, H—C(8)), 7.46-7.31 (m, 6H, H-arom), 6.03 (dd, J=6.7, 2.7 Hz, 1H, H—C(1')), 5.31 (dt, J=10.3, 5.2 Hz, 1H, H—(C5')), 4.99-4.81 (m, 1H, H—C(4')), 4.02 (d, J=3.8 Hz, 1H, H—C(7')), 2.88 (dd, J=16.0, 6.6 Hz, 1H, H—C(3')), 2.44-2.20 (m, 4H, MeCONH, H—C(2')), 2.12-1.73 (m, 6H, MeCO₂, H—C(6'), H—C(2')), 1.04 (s, 9H, (CH₃)₃—C—Si).

$^{13}$C NMR (75 MHz, CDCl₃) δ 172.73 (MeCONH), 170.46 (MeCO₂), 155.87 (C(6)), 148.09 (C(4)), 147.47 (C(2)), 137.13 (C(8)), 135.74 (CH-arom), 133.62, 133.29 (C-arom), 130.13, 130.09, 127.96, 127.93 (CH-arom), 121.54 (C(5)), 86.47 (C(1')), 82.81 (C(4')), 76.60 (C(7')), 74.37 (C(5')), 51.23 (C(3')), 37.04, 37.01, (C(2'), C(6')) 26.92 ((CH₃)₃—C—Si), 24.46 (MeCONH), 21.00 (MeCO₂), 19.05 ((CH₃)₃—C—Si).

ESI⁺-HRMS m/z calcd for C₃₂H₃₈O₆N₅Si ([M+H]⁺) 616.2586, found 616.2580.

To a solution of nucleoside 50 (440 mg, 0.714 mmol) in dry THF (5 mL) was added TBAF (1M in THF, 1.1 mL, 1.1 mmol) at rt. The solution was stirred for 4 hours at rt and then was directly purified by CC (13% MeOH in DCM) to yield 51 (235 mg, 87%) as white foam. Crystals suitable for X-ray analysis were obtained by recrystallization in a mixture of H₂O/MeOH.

Data for 51: $R_f$=0.25 (13% MeOH in DCM);

$^1$H NMR (300 MHz, MeOD) δ 8.03 (s, 1H, H—C(8)), 6.28 (dd, J=7.0, 3.8 Hz, 1H, H—C(1')), 5.21 (ddd, J=9.2, 6.8, 5.1 Hz, 1H, H—C(5')), 4.98 (dd, J=6.7, 5.0 Hz, 1H, H-(4')), 4.13-4.05 (m, 1H, H—C(7')), 3.17-3.05 (m, 1H, H—C(3')), 2.86 (ddd, J=13.8, 10.0, 3.8 Hz, 1H, H—C(2')), 2.39-2.27 (m, 1H, H—C(2')), 2.24 (s, 3H, MeCONH), 2.16-2.00 (m, 5H, MeCO₂, H—C(6')).

$^{13}$C NMR (101 MHz, MeOD) δ 174.95 (MeCONH), 172.32 (MeCO₂), 157.50 (C(6)), 149.96 (C(4)), 149.38 (C(2)), 139.66 (C(8)), 121.76 (C(5)), 88.23 (C(1')), 84.23 (C(4')), 75.83 (C(5'), C(7')), 51.65 (C(3')), 38.04, 37.93 (C(2'), C(6')), 23.83 (MeCONH), 20.71 (MeCO₂).

ESI⁺-HRMS m/z calcd for C₁₆H₂₀O₆N₅ ([M+H]⁺) 378.1408, found 378.1419.

Example 52

(3'S,5'R,7'R)— N2-Acetyl-9-{5'-O-acetyl-2',3'-dideoxy-3',5'-ethano-7'-O-[(4,4'-dimethoxytriphenyl)methyl]-α-D-ribofuranosyl} Guanine (52)

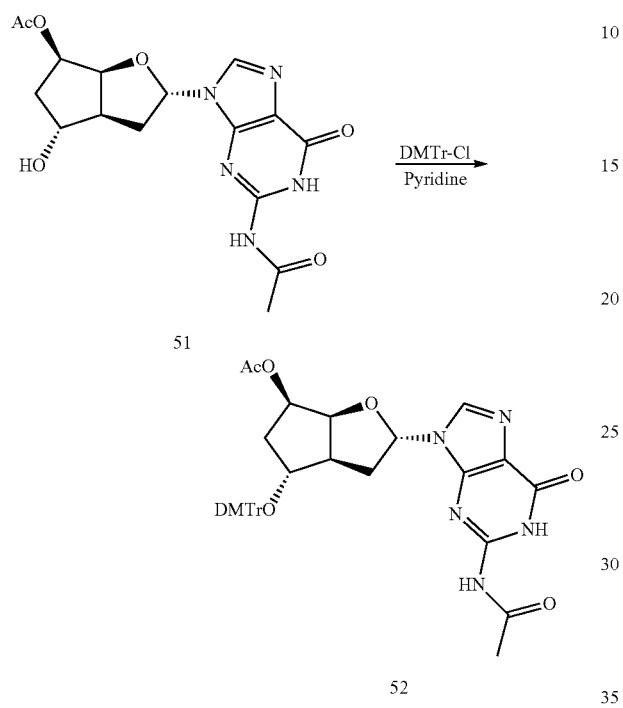

To a solution of the nucleoside 51 (186 mg, 0.492 mmol) in dry pyridine (10 mL) was added DMTr-Cl (501 mg, 1.48 mmol) at rt. The solution was stirred for 2 days and then was diluted with satd NaHCO$_3$ (40 mL) and extracted with DCM (3×30 mL). The combined organic phases were dried over MgSO$_4$, filtered and evaporated. The crude product was purified by CC (3% MeOH in DCM, +0.5% Et$_3$N) to yield 52 (333 mg, 99%) as a yellow foam.

Data for 52: R$_f$=0.56 (10% MeOH in DCM);

$^1$H NMR (300 MHz, CDCl$_3$) δ 12.05 (br, 1H, NH—C(4)), 9.90 (br, 1H, H—N(1)), 7.40 (s, 1H, H—C(8)), 7.38-7.31 (m, 2H, H-arom), 7.28-7.08 (m, 7H, H-arom), 6.75 (dd, J=9.0, 2.7 Hz, 4H, H-arom), 5.95-5.85 (m, 1H, H—C(1')), 5.30-5.10 (m, 1H, H—C(5')), 4.70-4.58 (m, 1H, H—C(4')), 3.81 (br, 1H, H—C(7')), 3.68, 3.68 (2s, 6H, MeO), 2.25-2.07 (m, 5H, MeCONH, H—C(3'), H—C(2')), 1.96-1.79 (m, 5H, MeCO$_2$, H—C(2'), H—C(6')), 1.74-1.59 (m, 1H, H—C(6')).

$^{13}$C NMR (75 MHz, CDCl$_3$) δ 172.65 (MeCONH), 170.42 (MeCO$_2$), 158.73, 158.70 (MeO—C-arom), 155.86 (C(6)), 147.96 (C(4)), 147.43 (C(2)), 145.31 (C-arom), 137.17 (C(8)), 136.69, 136.44 (C-arom), 130.32, 130.21, 128.29, 128.05, 127.09 (CH-arom), 121.53 (C(5)), 113.38, 113.35 (CH-arom), 87.25 (C(Ph)$_3$), 86.73 (C(1')), 82.77 (C(4')), 77.19 (C(7')), 74.37 (C(5')), 55.38 (MeO-DMTr), 49.28 (C(3')), 37.25 (C(2')), 36.06 (C(6')), 24.40 (MeCONH), 21.01 (MeCO$_2$).

ESI$^+$-HRMS m/z calcd for C$_{37}$H$_{38}$O$_8$N$_5$ ([M+H]$^+$) 680.2715, found 680.2718.

Example 53

(3'S,5'R,7'R)—N2-(N,N-Dimethylformamidino)-9-{2',3'-dideoxy-3',5'-ethano-7'-O-[(4,4'-dimethoxytriphenyl)methyl]-α-D-ribofuranosyl} guanine (53)

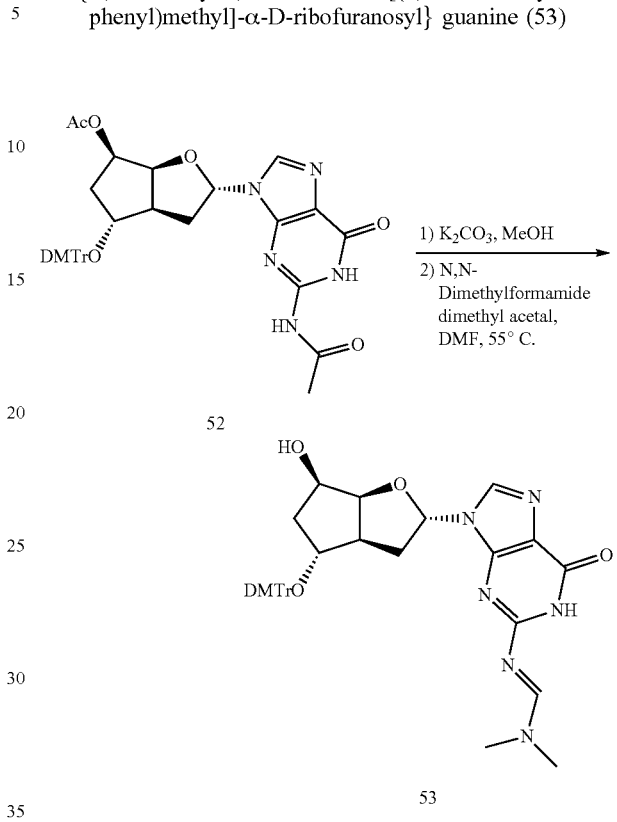

To a solution of the nucleoside 52 (333 mg, 0.490 mmol) in dry MeOH (10 mL) was added K$_2$CO$_3$ (305 mg, 2.20 mmol) at rt. The suspension was stirred for 7 h at rt, then NH$_4$Cl (78 mg, 1.46 mmol) was added and the resulting mixture was filtered through a short pad of SiO$_2$. The SiO$_2$ was washed with additional MeOH and then solvent was evaporated.

The crude product was dissolved in dry DMF (10 mL) and N,N-Dimethylformamide dimethyl acetal (0.33 mL, 2.5 mmol) was added. The solution was stirred for 2 hours at 55° C. and then the solvents were removed under reduced pressure. The crude product was purified by CC (7% MeOH in DCM, +0.5% Et$_3$N) to yield 53 (245 mg, 77%) as white foam containing traces of Et$_3$N.

Data for 53: R$_f$=0.32 (12% MeOH in DCM);

$^1$H NMR (300 MHz, CDCl$_3$) δ 9.75 (br, 1H, H—N(1)), 8.25 (s, 1H, NCHN(CH$_3$)$_2$), 7.37 (d, J=7.3 Hz, 2H, H-arom), 7.29-7.08 (m, 8H, H-arom, H—C(8)), 6.74 (d, J=8.1 Hz, 4H, H-arom), 6.03 (dd, J=6.7, 2.8 Hz, 1H, H—C(1')), 4.57 (dd, J=7.5, 4.6 Hz, 1H, H—C(4')), 4.37-4.26 (m, 1H, H—C(5')), 3.89 (t, J=3.9 Hz, 1H, H—C(7')), 3.67, 3.67 (2s, 6H, MeO), 3.24 (br, 1H, OH), 2.94 (s, 3H, NCHN(CH$_3$)$_2$), 2.87 (s, 3H, NCHN(CH$_3$)$_2$), 2.35 (dd, J=15.9, 7.6 Hz, 1H, H—C(3')), 1.94-1.68 (m, 4H, H—C(2'), H—C(6')).

$^{13}$C NMR (75 MHz, CDCl$_3$) δ 158.61 (MeO—C-arom), 158.28 (C(2)), 157.92 (NCHN(CH$_3$)$_2$), 156.69 (C(6)), 149.90 (C(4)), 145.52, 136.86, 136.77 (C-arom), 135.50 (C(8)), 130.15, 128.32, 127.92, 126.95 (CH-arom), 120.27 (C(5)), 113.24 (CH-arom), 86.92 (C(Ph)$_3$), 85.57 (C(1')), 85.12 (C(4')), 78.31 (C(7')), 72.69 (C(5')), 55.28 (MeO- DMTr), 49.28 (C(3')), 41.38 (NCHN(CH$_3$)$_2$), 39.77 (C(6')), 37.58 (C(2')), 35.04 (NCHN(CH$_3$)$_2$).

ESI$^+$-HRMS m/z calcd for C$_{36}$H$_{39}$O$_6$N$_6$ ([M+H]$^+$) 651.2926, found 651.2921.

Example 54

(3'S,5'R,7'R)—N2-(N,N-Dimethylformamidino)-9-{5'-O-[(2-cyanoethoxy)-diisopropylaminophosphanyl]-2',3'-dideoxy-3',5'-ethano-7'-O-[(4,4'-dimethoxytriphenyl)methyl]-α-D-ribofuranosyl} guanine (54)

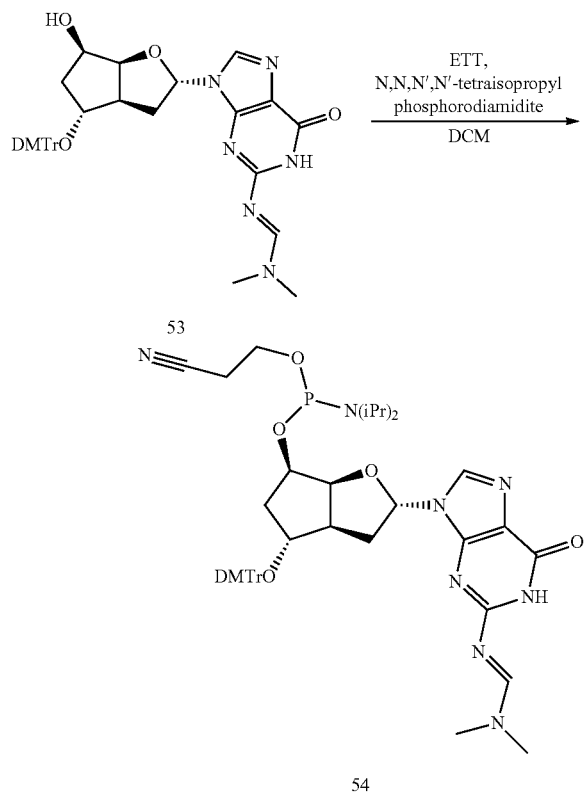

To a solution of the nucleoside 53 (245 mg, 0.377 mmol) and 5-(Ethylthio)-1H-tetrazole (74 mg, 0.57 mmol) in dry DCM (15 mL) was added dropwise 2-Cyanoethyl N,N,N',N'-tetraisopropylphosphordiamidite (0.20 mL, 0.64 mmol) at rt. After stirring for 50 min, the reaction mixture was diluted with satd NaHCO$_3$ (25 mL) and extracted with DCM (3×25 mL). The combined organic phases were dried over MgSO$_4$, filtered and evaporated. The crude product was purified by CC (3% MeOH in DCM, +0.5% Et$_3$N) to yield 54 (212 mg, mixture of two isomers, 67%) as a white foam.

Data for 54: R$_f$=0.42 (7% MeOH in DCM);

$^1$H NMR (300 MHz, CDCl$_3$) δ 9.35 (br, 1H, H—N(1)), 8.51, 8.49 (2s, 1H, NCHN(CH$_3$)$_2$), 7.41-7.10 (m, 10H, H-arom, H—C(8)), 6.83-6.70 (m, 4H, H-arom), 6.15-6.00 (m, 1H, H—C(1')), 4.64-4.36 (m, 2H, H—C(4'), H—C(5')), 3.90-3.82 (m, 1H, H—C(7')), 3.80-3.62 (m, 8H, MeO, OCH$_2$CH$_2$CN), 3.59-3.43 (m, 2H, (Me$_2$CH)$_2$N), 3.04, 3.02 (2s, 6H, NCHN(CH$_3$)$_2$), 2.67-2.48 (m, 2H, OCH$_2$CH$_2$CN), 2.32 (ddd, J=24.1, 15.1, 6.7 Hz, 1H, H—C(3')), 2.02-1.63 (m, 4H, H—C(2'), H—C(6')), 1.14-1.03 (m, 12H, (Me$_2$CH)$_2$N).

$^{13}$C NMR (101 MHz, CDCl$_3$) δ 158.76 (MeO—C-arom), 158.17, 158.12 (C(2)), 158.03 (NCHN(CH$_3$)$_2$), 156.66, 156.59 (C(6)), 149.85, 149.79 (C(4)), 145.51, 145.49, 136.84, 136.77, 136.73, 136.71 (C-arom), 135.76, 135.59 (C(8)), 130.24, 130.20, 128.41, 128.33, 128.02, 127.10, 127.08 (CH-arom), 120.74, 120.70 (C(5)), 117.98, 117.72 (OCH$_2$CH$_2$CN), 113.34 (CH-arom), 87.16, 87.10 (C(Ph)$_3$), 86.00, 85.72 (C(1')), 84.13, 84.10 (J$_{C,P}$=3.6, 2.5 Hz, C(4')), 78.02, 77.67 (C(7')), 74.15, 73.74 (=15.3, 18.7 Hz, C(5')), 58.90, 58.67 (J$_{C,P}$=18.7, 19.7 Hz OCH$_2$CH$_2$CN), 55.38, 55.36 (MeO-DMTr), 49.20, 49.09 (C(3')), 43.20, 43.15 (J$_{C,P}$=12.4, 12.6 Hz, ((Me$_2$CH)$_2$N), 41.42, 41.38 (NCHN(CH$_3$)$_2$), 38.68, 38.65 (C(6')), 37.97, 37.84 (C(2')), 35.25 (NCHN(CH$_3$)$_2$), 24.83, 24.75, 24.68, 24.60, 24.53 ((Me$_2$CH)$_2$N), 20.35, 20.28 (OCH$_2$CH$_2$CN).

$^{31}$P NMR (121 MHz, CDCl$_3$) δ 148.21, 148.01.

ESI$^+$-HRMS m/z calcd for C$_{45}$H$_{56}$O$_7$N$_8$P ([M+H]$^+$) 851.4004, found 851.4013.

Example 55

(3aR,4R,6R,6aS)-4-((Tert-butyldiphenylsilyl)oxy)-2-methoxyhexahydro-2H-cyclopenta[b]furan-6-yl (4-nitrobenzoate) (55)

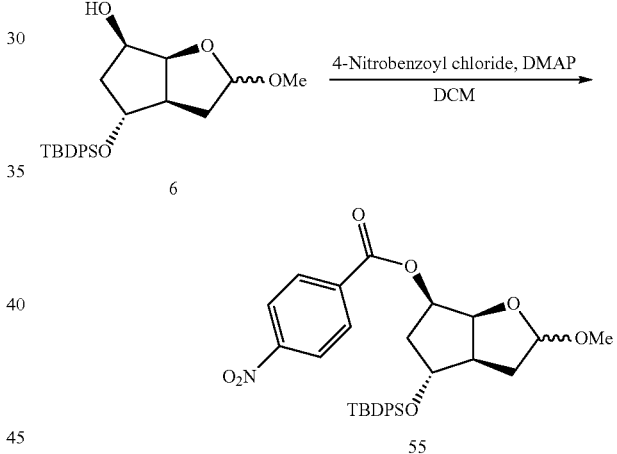

To a solution of the sugar 6 (195 mg, 0.437 mmol) and 4-Dimethylaminopyridine (70 mg, 0.568 mmol) in dry DCM (10 mL) was added 4-Nitrobenzoyl chloride (158 mg, 0.850 mmol) at rt. After stirring overnight, reaction was quenched by slow addition of satd NaHCO$_3$ (3 mL). The mixture was then diluted with satd NaHCO$_3$ (15 mL) and extracted with DCM (3×15 mL). The combined organic phases were dried over MgSO$_4$, filtered and evaporated. The crude product was purified by CC (EtOAc/hexanne 1:5) to yield a mixture of 55 (260 mg, 98%) in an anomeric ratio α/β≈4:1 as a white solid.

Data for 55: R$_f$=0.62 (EtOAc/hexane 1:2);

$^1$H NMR (300 MHz, CDCl$_3$) δ 8.33-8.17 (m, 4H, H-arom), 7.72-7.61 (m, 4H, H-arom), 7.51-7.32 (m, 6H, H-arom), 5.65-5.47 (m, 1H, H—C(6)), 4.97 (dd, J=9.2, 5.6 Hz, 1H, H—C(2)), 4.87 (t, J=5.8 Hz, 1H, H—C(6a)), 4.18 (d, J=5.0 Hz, 0.2H, H—C(4)), 3.98 (d, J=3.5 Hz, 0.8H, H—C(4)), 3.21 (d, J=15.1 Hz, 3H, MeO), 2.88 (dd, J=16.6, 7.9 Hz, 0.8H, H—C(3a)), 2.75-2.62 (m, 0.2H, H—C(3a)), 2.49-2.34 (m, 0.2H, H—C(5)), 2.24-1.83 (m, 2.8H, H-(5), H—C(3)), 1.28 (ddd, J=13.0, 7.9, 4.9 Hz, 1H, H—C(3)), 1.09 (s, 9H, (CH₃)₃—C—Si).

$^{13}$C NMR (75 MHz, CDCl₃) δ 164.46, 164.41 (CO₂R), 150.63 (O₂N—C-arom), 135.87, 135.82 (CH-arom), 134.07, 133.75, 133.69 (CH-arom), 130.98, 130.89, 129.98, 129.96, 129.91, 127.89, 127.87, 127.85, 123.59 (CH-arom), 106.49, 106.39 (C(2)), 83.21, 79.87 (C(6a)), 76.54 (C(4)), 76.09 (C(6)), 54.55, 54.47 (MeO), 51.69, 50.30 (C(3a), 38.07 (C(3)), 37.17, 36.65 (C(5)), 27.04, 26.99 90 ((CH₃)₃—C—Si), 19.14 ((CH₃)₃—C—Si).

ESI⁺-HRMS m/z calcd for C₃₁H₃₅O₇NaSi ([M+Na]⁺) 584.2075, found 584.2085.

Example 56

(3'R,5'R,7'R)-1-{7'-[(tert-butyldiphenylsilyl)oxy]-2, 3'-dideoxy-3,5'-ethano-5'-O-(4-nitrobenzoate)-α,β-D-ribofuranosyl} Thymine (56)

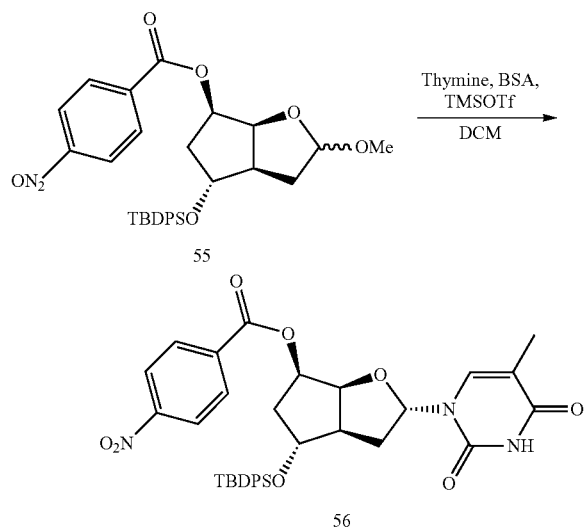

To a solution of the sugar 55 (260 mg, 0.463 mmol) and thymine (84 mg, 0.695 mmol) in dry MeCN (3 mL) was added dropwise BSA (0.34 mL, 1.4 mmol) at rt. After stirring for 30 min at rt, the solution was cooled down to 0° C. and TMSOTf (0.10 mL, 1.3 mmol) was added dropwise. After further stirring for 2 h at 0° C. and for 18 h at rt, the reaction mixture was diluted with satd NaHCO₃ (30 mL) and extracted with DCM (4×40 mL). The combined organic phases were dried over MgSO₄, filtered and evaporated. The crude product was purified by CC (2% MeOH in DCM) to yield a mixture of 56 (240 mg, 79%) in an anomeric ratio α/β≈88:12 as white foam.

Data for 56: $R_f$=0.56 (DCM+3% MeOH);

$^1$H NMR (300 MHz, CDCl₃) δ 9.38 (br, 1H, (s, 1H, H—N(3)), 8.32-8.23 (m, 2H, H-arom), 8.22-8.11 (m, 2H, H-arom), 7.65 (dd, J=7.7, 1.5 Hz, 4H, H-arom), 7.50-7.36 (m, 6H, H-arom), 6.95 (d, J=0.9 Hz, 1H, H—C(6)), 5.96 (t, J=6.3 Hz, 1H, H—C(1')), 5.55 (dt, J=9.9, 6.0 Hz, 1H, H—C(5')), 5.13 (dd, J=6.4, 5.4 Hz, 1H, H—C(4')), 4.20-4.05 (m, 1H, H—C(7')), 2.94-2.78 (m, 1H, H—C(3')), 2.22 (dd, J=13.3, 6.4 Hz, 1H, H—C(6')), 2.09-1.73 (m, 6H, H—C(2'), Me-C(5)), 1.09 (s, 9H, (CH₃)₃—C—Si).

$^{13}$C NMR (75 MHz, CDCl₃) δ 164.32, 163.79 (C(4), CO₂R), 150.65, 150.39 (O₂N—C-arom, C(2)), 135.70, 135.68 (CH-arom), 135.13 (C-arom), 134.83 (C(6)), 133.46, 133.10 (C-arom), 130.91, 130.73, 130.11, 127.93, 123.60 (CH-arom), 111.30 (C(5)), 87.26 (C(1')), 82.44 (C(4')), 76.40 (C(7')), 76.07 (C(5')), 50.76 (C(3')), 37.94 (C(6')), 36.68 (C(2')), 26.89 ((CH₃)₃—C—Si), 19.03 ((CH₃)₃—C—Si), 12.62 (Me-C(5)).

ESI⁺-HRMS m/z calcd for C₃₅H₃₇O₈N₃NaSi ([M+Na]⁺) 678.2242, found 678.2254.

Example 57

(3'R,5'R,7'R)-1-{2',3'-dideoxy-3',5'-ethano-7'-hydroxy-5'-O-(4-nitrobenzoate)-α,β-D-ribofuranosyl} thymine (57)

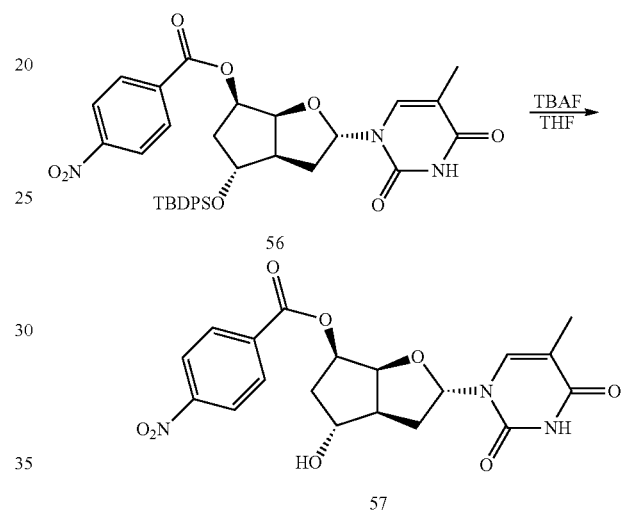

To a solution of the nucleoside 56 (220 mg, 0.335 mmol) in dry THF (2 mL) was added TBAF (1M in THF, 0.84 mL, 0.84 mmol) at rt. After stirring for 4 h at rt, the reaction mixture was diluted with satd NaHCO₃ (20 mL) and extracted with EtOAc (3×20 mL) and DCM (2×80 mL). The combined organic phases were dried over MgSO₄, filtered and evaporated. The crude product was purified by CC (5% MeOH in DCM) to yield an anomeric mixture of 57 (101 mg, 72%). Crystals suitable for X-ray analysis were obtained by recrystallization in EtOAc.

Data for 57: $R_f$=0.50 (DCM+7% MeOH);

$^1$H NMR (300 MHz, CDCl₃) δ 8.96 (br, 1H, H—N(3)), 8.34-8.17 (m, 4H, H-arom), 7.07 (d, J=1.1 Hz, 1H, H—C(6)), 6.11 (t, J=6.3 Hz, 1H, H—C(1')), 5.57-5.45 (m, 1H, H—C(5')), 5.15 (dd, J=6.6, 5.4 Hz, 1H, H—C(4')), 4.38-4.23 (m, 1H, H—C(7')), 2.96 (dd, J=13.5, 6.9 Hz, 1H, H—C(3')), 2.26 (ddd, J=13.1, 10.3, 5.4 Hz, 4H, H—C(2'), H—C(6')), 1.91 (d, J=0.9 Hz, 3H, Me-C(5)).

ESI⁺-HRMS m/z calcd for C₁₉H₁₉O₈N₃Na ([M+Na]⁺) 440.1064, found 440.1072.

Example 58

Design and Synthesis of Oligomers of Alpha Anomeric Monomers

Figure 4:
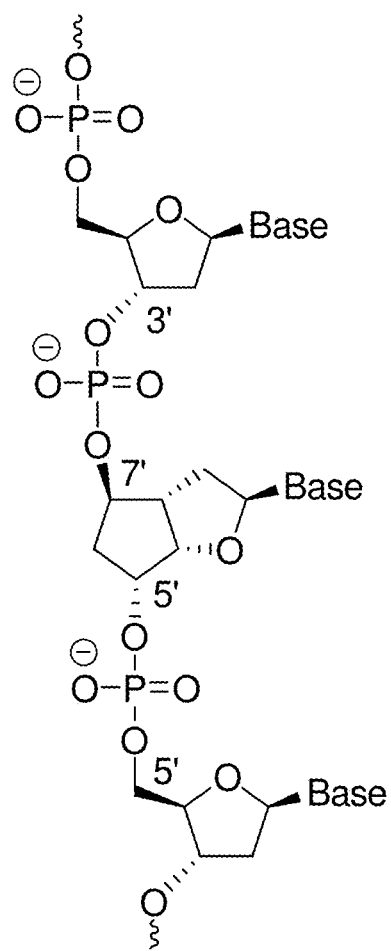
FIG. 4: Insertion of 7',5'-α-bc-DNA with polarity reversal inside β-DNA.

To assess the accommodation of the modification inside natural β-DNA strand, five oligodeoxynucleotides (ON16-20) with single or multiple insertions of the thymidine building block 6 were prepared. In order to fit the geometry of β-DNA, the modification was inserted with polarity reversal, resulting in 3'-7' and 5'-'5 nucleosidic linkages (see FIGS. 1 and 4). To test the pairing properties of this new system with natural nucleic acid, but also toward itself, the fully modified ON21 containing all four nucleobases, as well as its antiparallel (ON22) and parallel (ON23) fully modified complements were prepared. Finally, a fully modified strand with phosphorothioate linkage was synthesized (ON24), with the aim to test its potential antisense properties. The syntheses were performed using classical automated phosphoramidite chemistry. Fully modified strands were synthesized in a 5'→7' direction. As a consequence, complete cleavage of the DMTr protecting group from the 7' position required a solution of 5% dichloroacetic acid in dichloroethane. In these conditions, coupling yield were >98% based on trityl assay. Fully modified strands could be completely cleaved from universal solid support by a smooth treatment in concentrated ammonia at 55° C. overnight (for further synthetic and analytical details see below).

Process of Alpha Anomeric Oligonucleotide Synthesis, Deprotection and Purification Oligonucleotides syntheses were performed on a Pharmaci-Gene-Assembler-Plus DNA synthesizer on a 1.3 μmol scale. Natural DNA phosphoramidites (dT, dC4bz, dG2DMF, dA6Bz) and solid support (dA-Q-CPG 500, dmf-dG-Q-CPG 500, Glen Unysupport 500) were purchased from Glen Research. Natural DNA phosphoramidites were prepared as a 0.1 M solution in MeCN and were coupled using a 4 min step. 7',5'-α-bc-DNA phosphoramidites were prepared as a 0.1 M solution in 1,2-dichloroethane and were coupled using an extended 12 min step. 5-(Ethylthio)-1H-tetrazole (0.25 M in MeCN) was used as coupling agent. Detritylation of modified nucleoside was performed with a solution of 5% dichloroacetic acid in dichloroethane. Sulfurization was performed with a solution of 0.2 M phenylacetyl disulfide in MeCN/pyridine (1:1) and with a reaction time of 3.5 min Capping and oxidation were performed with standard conditions. Cleavage from solid support and deprotection of oligonucleotides was achieved by treatment with concentrated ammonia at 55° C. for 16 h. After centrifugation, the supernatant were collected, the beads further washed with $H_2O$ (0.5 mL×2) and the resulting solutions were evaporated to dryness. Crude oligonucleotides were purified by ion-exchange HPLC (Dionex-DNAPac PA200). Buffer solutions of 25 mM Trizma in $H_2O$, pH 8.0, was used as the mobile phase "A" and 25 mM Trizma, 1.25 M NaCl in $H_2O$, pH 8.0, was used as the mobile phase "B". For the phosphorothioate strand, a buffer solution of 10 mM NaOH in $H_2O$, pH 12.0, was used as the mobile phase "A" and 10 mM NaOH, 2.50 M NaCl in $H_2O$, pH 12.0, was used as the mobile phase "B". The purified oligonucleotides were then desalted with Sep-pack C-18 cartridges. Concentrations were determined by measuring the absorbance at 260 nm with a Nanodrop spectrophotometer, using the extinction coefficient of the corresponding natural DNA oligonucleotides. Characterizations of oligonucleotides were performed by ESI⁻ mass spectrometry or by LC-MS.

Example 59

Pairing Properties of Modified Oligodeoxynucleotides Synthesized of Alpha Anomeric Monomers with Complementary DNA and RNA The duplex's stability of oligonucleotides was assessed by UV melting curves at 260 nm, and their $T_m$s were compared to their natural DNA analogs (Table 1). Oligonucleotides ON16-17 with a single incorporation resulted in a strong destabilization with DNA complements and slightly lower destabilization with RNA. This penalty appears to be cumulative and ON18, with the two previous positions modified, further decreased the $T_m$s. However, when two or five modifications were introduced consecutively (ON19-20), the destabilization per modification is reduced to approximately −3° C. versus DNA and −1.3° C. versus RNA. These data suggests that a junction between the DNA and 7',5'-α-bc-DNA induces a strong destabilization, with a depreciation of $T_m$ between −4 and −9° C., depending on the sequence context. Such destabilizations by heterobackbone junctions have already been observed for α-DNA (Aramini et al., Nucleic Acids Res 1998, 26, 5644, Aramini et al., Biochemistry 1997, 36, 9715) and for α-LNA (Nielsen et al., Chemistry—A European Journal 2002, 8, 712). This destabilization could be compensated by inserting the modifications as a block.

TABLE 1

$T_m$ and $\Delta T_m$/mod data from UV-melting curves (260 nm) of ON16-20 in duplex with complementary DNA and RNA.

| Entry | Sequence[a,b,c] | $T_m$ (° C.) vs DNA | $\Delta T_m$/mod (° C.) | $T_m$ (° C.) vs RNA | $\Delta T_m$/mod (° C.) |
|---|---|---|---|---|---|
| ON16 | 5'-d(GGA TGT TCt CGA)-3' (SEQ ID NO: 16) | 40.0 | −9.1 | 42.6 | −6.8 |
| ON17 | 5'-d(GGA t GT TCT CGA)-3' (SEQ ID NO: 17) | 43.0 | −6.1 | 45.8 | −3.6 |
| ON18 | 5'-d(GGA tGT TCt CGA)-3' (SEQ ID NO: 18) | 32.8 | −8.1 | 38.0 | −5.7 |
| ON19 | 5'-d(GGA TGt tCT CGA)-3' (SEQ ID NO: 19) | 42.9 | −3.1 | 47.0 | −1.2 |
| ON20 | 5'-d(GCA ttt ttA CCG)-3'[d] (SEQ ID NO: 20) | 34.0 | −2.7 | 37.2 | −1.4 |

[a]total strand conc. 2 μM in 10 mM $NaH_2PO_4$, 150 mM NaCl, pH 7.0.
[b]A, G, T, C denote natural 2'-deoxynucleosides; t (bold type) corresponds to modified nucleosides.
[c]$T_m$ of unmodified duplexes, DNA/DNA: 49.1° C., DNA/RNA: 49.4° C.
[d]$T_m$ of unmodified duplexes, DNA/DNA: 47.5° C., DNA/RNA: 44.0° C.

Example 60

Pairing Properties of Fully Modified Oligonucleotides Synthesized of Alpha Anomeric Monomers As expected, all three fully modified sequences ON21-23 exhibit a cooperative and reversible melting behavior with their parallel DNA and RNA complements (FIG. 5), but not with their antiparallel complements. The resulting 7',5'-α-bc-DNA/DNA duplexes are slightly less stable than their natural counterparts, with a destabilization between −0.1 and −0.5° C. per modification (Table 2). Surprisingly, it has been found that ON21-23 form very stable duplexes with RNA, resulting in a great stabilization between 1.3 and 1.5° C. per modification. A quite astonishing difference exists on the stabilizing effect between the fully modified strands and natural oligodeoxynucleotides strands with single or multiple incorporations. This stresses the importance of synthesizing fully modified strands in order to characterize a new pairing system.

TABLE 2

$T_m$ and $\Delta T_m$/mod data from UV-melting curves (260 nm) of ON21-24 in duplex with complementary parallel DNA and RNA.

| Entry | Sequence[a,b] | $T_m$(° C.) vs parallel DNA | $\Delta T_m$/mod (° C.) | $T_m$(° C.) vs parallel RNA | $\Delta T_m$/mod (° C.) |
|---|---|---|---|---|---|
| ON21 | 5'-d(agc tct tgt agg)-7'[c] (SEQ ID NO: 21) | 43.2 | −0.5 | 65.0 | 1.3 |
| ON22 | 5'-d(cct aca aga gct)-7'[d] (SEQ ID NO: 22) | 43.8 | −0.4 | 58.6 | 1.3 |
| ON23 | 5'-d(tcg aga aca tcc)-7'[e] (SEQ ID NO: 23) | 47.7 | −0.1 | 61.6 | 1.5 |
| ON24 | 5'-d(t*c*c*a*t*t*c*g*g*c*t*c*c*a*a*)-7'[f] (SEQ ID NO: 24) | 43.2 | −1.3 | 77.0 | 0.6 |

[a] total strand conc. 2 µM in 10 mM NaH₂PO₄, 150 mM NaCl, pH 7.0.
[b] a, g, t, c corresponds to modified adenine, guanine, thymine and methylcytosine respectively, * denotes a phosphorothioate linkage.
[c] $T_m$ of unmodified duplexes, DNA/DNA: 49.1° C., DNA/RNA: 49.4° C.
[d] $T_m$ of unmodified duplexes, DNA/RNA: 43.0° C.
[e] $T_m$ of unmodified duplexes, DNA/DNA: 49.0° C., DNA/RNA: 43.3° C.
[f] $T_m$ of unmodified duplexes, DNA/DNA: 62.0° C., DNA/RNA: 67.4° C.

To test the mismatches discrimination, UV melting experiments were performed with ON21 and its parallel DNA complements possessing all three alternative nucleobases at the position 4 (Table 3). Such mispairing has a strong destabilizing effect and reduce the $T_m$s by −9.6 to −14.3° C. When compared to its natural counterpart, 7',5'-α-bc-DNA has a better mismatch discrimination ability with the $T_m$s further reduced by −1.0 to −2.4° C. Increasing the mismatch discrimination should reduce the potential off-target effects and therefore represents an appealing property for an antisense candidate. Modification with a phosphorothioate linkage is well accommodated in the context of 7',5'-α-bc-DNA and the destabilizing effect is in the range of the −0.5° C. per nucleotide reported for this modification (Kurreck, J. European journal of biochemistry/FEBS 2003, 270, 1628). ON24 maintains a good affinity toward RNA with a stabilizing effect of 0.6° C. when compared with natural DNA.

TABLE 3

$T_m$ values from UV-melting curves (260 nm) of ON21 and DNA1 in duplex with complementary DNA incorporating one mismatch.

| Entry | Duplex[a] | X = A | X = T | X = G | X = C |
|---|---|---|---|---|---|
| ON21 | 5'-d(agc tct tgt agg)-7' (SEQ ID NO: 21) | 43.2 | 30.0 | 33.5 | 28.9 |
| DNA-X | 5'-d(TCG XGA ACA TCC)-3' (SEQ ID NO: 25) | | | | |

TABLE 3-continued $T_m$ values from UV-melting curves (260 nm) of ON21 and DNA1 in duplex with complementary DNA incorporating one mismatch.

| Entry | Duplex[a] | X = A | X = T | X = G | X = C |
|---|---|---|---|---|---|
| DNA1 | 5'-d(GGA TGT TCT CGA)-3'<br>(SEQ ID NO: 26) | 49.1 | 38.3 | 40.5 | 36.7 |
| DNA-X | 5'-d(TCG XGA ACA TCC)-3'<br>(SEQ ID NO: 25) | | | | |

Experimental conditions: total strand conc. 2 µM in 10 mM NaH$_2$PO$_4$, 150 mM NaCl, pH 7.0
[a] A, G, T, C denote natural 2'-deoxynucleosides; a, g, t, c corresponds to modified adenine, guanine, thymine and methylcytosine respectively.

Figure 5:
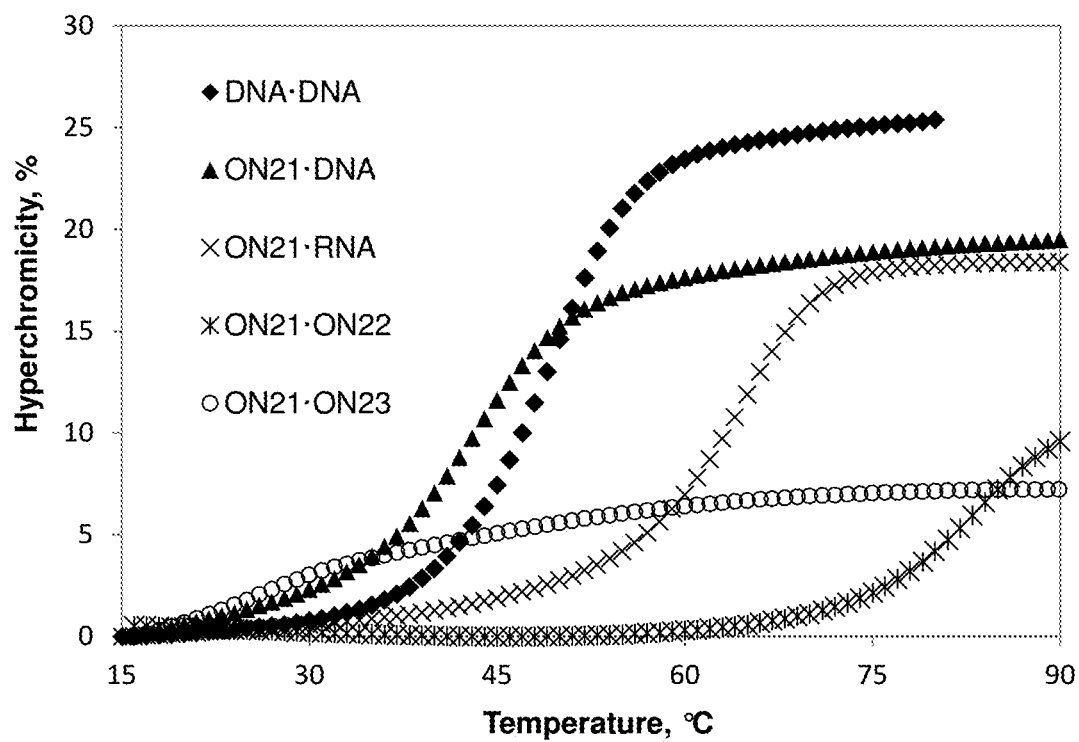
FIG. 5: UV-melting curves (260 nm) of oligonucleotide ON21 (SEQ ID NO: 21) with fully modified parallel (oligonucleotide ON22; SEQ ID NO: 22) and antiparallel (oligonucleotide ON23; SEQ ID NO: 23) complement, parallel DNA and parallel RNA, in comparison with the corresponding natural DNA duplex. Total strand concentration: 2 µM in 10 mM $NaH_2PO_4$, 150 mM NaCl, pH 7.0.

In its own series, ON21 formed a very stable duplex toward its antiparallel complement ON22, resulting in an unexpected $T_m$ of 83.6° C. Due to this high $T_m$, the complete classical sigmoidal transition could be observed only in the absence of sodium chloride, decreasing the $T_m$ to 68.6° C. (Table 4). Interestingly, the formation of duplex resulted in a low hypochromicity of only 10% (FIG. 5). This is an indication of a base stacking differing from classical helix and therefore, formation of duplex with a geometry deviating from canonical A or B-duplexes could be expected. On the other hand, no sigmoidal melting transition has been observed between ON21 and its parallel complement ON23 (FIG. 5). The change in hypochromicity occurring does not differ from the UV melting experiments performed on the two single strand separately, which was associated with a base stacking occurring inside the single strands. To test the ability of 7',5'-α-bc-DNA to fit inside A-like helix, a melting experiment was performed toward tricyclo-DNA (tc-DNA), a conformationally constrained mimic of RNA (Renneberg et al., Journal of the American Chemical Society 2002, 124, 5993.). When ON21 is mixed with complementary parallel tc-DNA strand (Tc1), a surprisingly high Tm of 81° C. was observed, demonstrating the ability of 7',5'-α-bc-DNA to adapt to this helix geometry.

Example 61

Thermodynamic Data of Duplex Formation of Alpha Anomeric Oligomers

The thermodynamic data for duplexes formations of ON21 with DNA and RNA and their natural counterpart have been extracted by curves fitting to the experimental melting curves, following an established methodology (Petersheim et al., Biochemistry 1983, 22, 256) (Table 5). As expected, the free energy ΔG at 25° C. follows the same trend as the $T_m$ data, with ON21.RNA being the most favored duplex. With respect to natural system, ON21 binds with natural nucleic acids with a lower enthalpy. However, this destabilization is compensated by an entropic gain. This behavior is typical in the bc-DNA series and arises from the conformational rigidity added by the ethylene bridge. Interestingly, the selectivity of 7',5'-α-bc-DNA for RNA over DNA is mostly enthalpically driven.

TABLE 4

$T_m$ values from UV-melting curves (260 nm) of ON22-23 and Tc1 in duplex with ON21.

| Entry | Sequence[a,b] | NaCl concentration [m/M] | ΔT$_m$ (° C.) VS ON21 |
|---|---|---|---|
| ON22 | 5'-d(cct aca aga gct)-7'<br>(SEQ ID NO: 22) | 150 | 83.6 |
| ON22 | 5'-d(cct aca aga gct)-7'<br>(SEQ ID NO: 22) | 50 | 79.6 |
| ON22 | 5'-d(cct aca aga gct)-7'<br>(SEQ ID NO: 22) | 0 | 68.6 |
| ON23 | 5'-d(tcg aga aca tcc)-7'<br>(SEQ ID NO: 23) | 150 | <10 |
| Tc1 | 5'-d(tcg aga aca tcc)-3'<br>(SEQ ID NO: 27) | 150 | 81.0 |

[a] total strand conc. 2 µM in 10 mM NaH$_2$PO$_4$, pH 7.0.
[b] a, g, t, c corresponds to modified adenine, guanine, thymine and methylcytosine respectively, a, g, t, c corresponds to tricyclo-DNA adenine, guanine, thymine and methylcytosine respectively

TABLE 5

Thermodynamic data of duplex formation.

| Duplex | Sequences[a] | $\Delta H$ [kcal mol$^{-1}$] | $\Delta S$ [cal mol$^{-1}$ K$^{-1}$] | $\Delta G 25°$ C. [kcal mol$^{-1}$] |
|---|---|---|---|---|
| DNA•DNA | 5'-GGA TGT TCT CGA-3' (SEQ ID NO: 26) 3'-CCT ACA AGA GCT-5' (SEQ ID NO: 29) \ | −91.7 | −257.9 | −14.8 |
| DNA•RNA | 5'-GGA TGT TCT CGA-3' (SEQ ID NO: 26) 3'-CCU ACA AGA GCU-5' (SEQ ID NO: 28) | −92.1 | −258.3 | −15.0 |
| ON21•DNA | 7'-gga tgt tct cga-5' (SEQ ID NO: 21) 3'-CCT ACA AGA GCT-5' (SEQ ID NO: 29) | −79.7 | −224.2 | −12.9 |
| ON21•RNA | 7'-gga tgt tct cga-5' (SEQ ID NO: 21) 3'-CCU ACA AGA GCU-5' (SEQ ID NO: 28), | −83.9 | −222.0 | −17.7 |

[a] A, G, T, U, C denote nucleosides; a, g, t, c corresponds to modified adenine, guanine, thymine and methylcytosine respectively

Example 62

CD-Spectroscopy of Alpha Anomeric Oligomer

Figure 6:
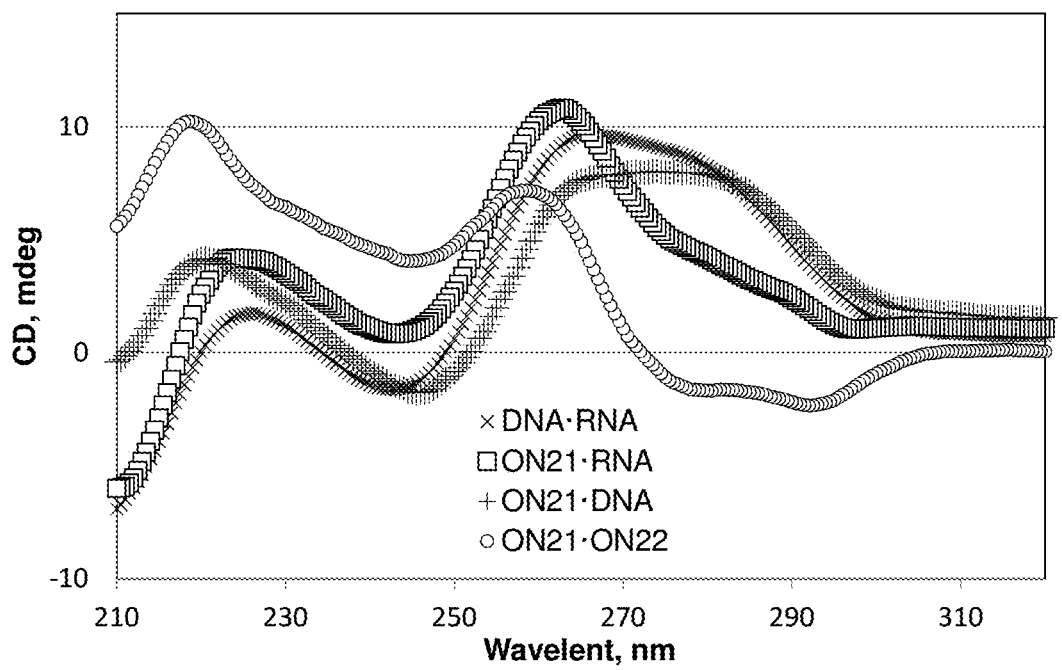
FIG. 6: CD-spectra of duplexes a) DNA.RNA, b) ON21.RNA and c) ON21.DNA d) ON21.ON22 at 20° C. Experimental conditions: Total strand conc. 2 µM in 10 mM NaH2PO4, 150 mM NaCl, pH 7.0.

The CD-spectra of ON21 in duplex with DNA, RNA or ON22 have been measured and compared with the corresponding natural DNA/RNA duplex (FIG. 6). Both duplexes of ON21 with DNA or RNA have a CD signature relatively close the natural A/B-helix. However, the ON21/DNA duplex does not display a negative signal at 210 nm and has the ellipticity at 226 nm blue shifted by 5 nm and associated with a gain in amplitude. The ON21/RNA duplex also has a peak of higher positive amplitude at 226 nm, and the positive ellipticity at 266 is blue shifted by 4 nm and formed a sharper peak. On the other hand, the modified homo duplex has a very atypical CD signature, characterized by a broad negative ellipticity between 275 and 300 nm of small amplitude and two positive peaks at 259 nm and 218 nm. In agreement with low hypochromicity change upon duplex formation, the CD spectra of the homo duplex indicate the formation of a structure deviating from conventional helix.

Example 63

Biological Stability of Alpha Anomeric Oligomers

Figure 7:
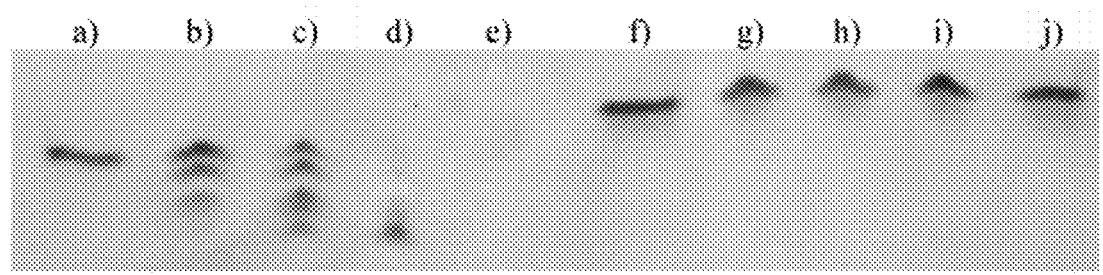
FIG. 7: Cropped picture of a gel. a) DNA control experiment. DNA digestion reaction after b) 1 hour c) 2 hours d) 4 hours e) 24 hours; f) control experiment with oligonucleotide ON21; ON21 digestion reaction after g) 1 hour h) 2 hours i) 4 hours j) 24 hours.

The biostability of the fully modified oligonucleotide ON21 was studied under simulated physiological conditions in comparison with its corresponding natural oligonucleotide. Oligonucleotides were incubated in a 1:1 mixture of H$_2$O and human serum at 37° C. and reaction outcome were analyzed by 20% denaturing PAGE. In detail, ON21 and its corresponding natural oligonucleotide were diluted to 10 µM in a 1:1 mixture of H$_2$O and human serum (from human male AB plasma, USA origin, sterile-filtered (Sigma)). The reactions were performed at a 20 µL scale and were incubated at 37° C. Control reactions (a, were performed by incubating the oligonucleotides at 10 µM in H$_2$O at 37° C. for 24 hours. The reactions were stopped at specific times by addition of formamide (20 µL). The resulting mixtures were stored at −20° C. before being heat denaturated for 5 min at 90° C. and then analyzed by 20% denaturing PAGE. Visualization was performed with a stains-all solution. The experiment showed complete digestion of natural DNA strand already after 4 hours (d), where the modified oligonucleotide remained completely stable even after 24 hours (j) (FIG. 7). The 7',5'-α-bc-DNA modification appears to confer a significantly improved biostability.

Example 64

Complement C3 Activation by Alpha Anomeric Oligomers

Complement activation represents an important toxic response often associated with the in vivo use of antisense ONs. Moreover, in vivo tests performed with tc-DNA induced occasionally such an acute toxicity, limiting consequently their use. In this context, it is of particular interest to test the complement activation of 7',5'-α-bc-DNA, containing phosphorothioate nucleosidic linkages, and compare it with well-characterized modified or natural ONs. Experiments were carried by incubating mouse serum samples with 4 mg/ml of the tested ONs at 37° C. for 45 min. Mouse C3 complement activation was then analyzed by ELISA using PanSpecific C3 reagent followed by SC5b-9 kit.

Figure 8:
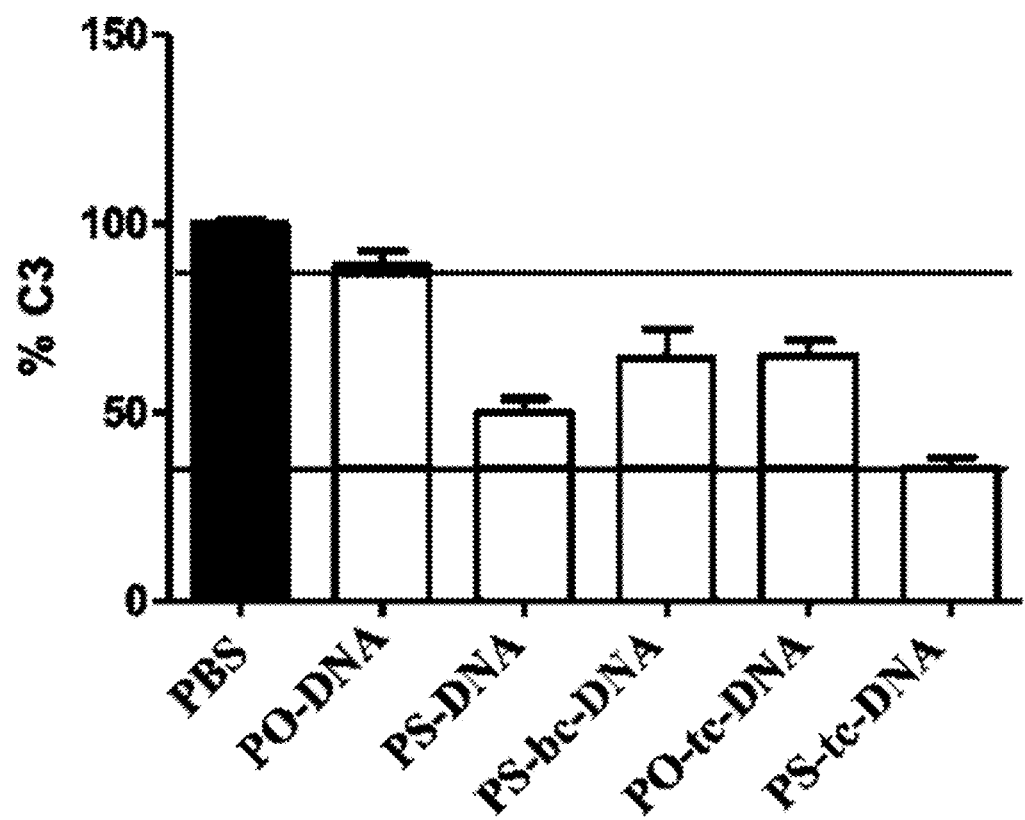
FIG. 8: Results of C3 complement activation; PO denotes phosphate nucleosidic linkages, PS denotes phosphorothioate nucleosidic linkages, bc-DNA denotes the 7',5'-α-bc-DNA scaffold, tc-DNA denotes the tricyclo scaffold. Each measurement has been repeated at least 3 times. The sequence is similar for the 5 ONs.

Incubation with ON24 (PS-7',5'-α-bc-DNA scaffold) resulted in level of C3 complement protein lower than with natural DNA, but higher than with PS-DNA (FIG. 8). The protein level is similar than with non-toxic PO-tc-DNA. These promising results indicate that ON24 does not activate the complement significantly.

Example 65

Antisense Activity

Duchenne muscular dystrophy (DMD) is a lethal muscle degenerative disease that arises from mutations in the DMD gene resulting in out-of-frame dystrophin transcripts and ultimately in the lack of functional dystrophin protein. In DMD, aberrant disease-related pre-mRNA transcripts can be functionally restored by antisense oligonucleotides (AO). Such AOs can change the slice pattern and can correct aberrant out of frame dystrophin transcripts via the exclusion of specific dystrophin exons. Thereby the open reading frame is restored and a shortened but functional dystrophin protein product is generated (Yang et al., PloS one 2013, 8, e61584). The ability of the 7',5'-α-bc-DNA scaffold to induce exon skipping was assessed in vitro by transfecting myoblasts from mdx mice—a murine model for Duchenne muscular dystrophy—with ON24 using lipofectamine LTX. Mdx myoblasts were incubated with 7',5'-α-bc-DNA, and RNA was isolated, amplified by nested RT-PCR and analyzed by gels (PAGE).

Figure 9:
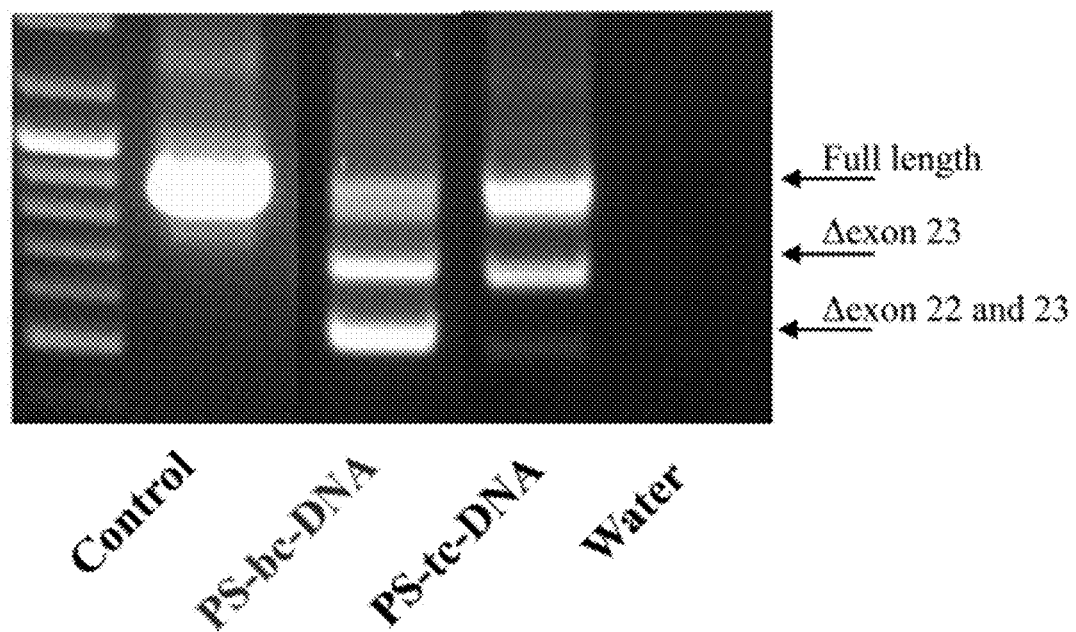
FIG. 9: Comparison of the mRNA expression level after incubation with PS-α-bc-DNA or PS-tc-DNA. Sequence is similar for the two ONs. Abbreviations as mentioned in FIG. 8.

The results indicate a high level of exon 23 skipping, as well as a significant level of a double skip of exons 22 and 23 (FIG. 9). This double exons skipping is often encountered for compounds efficient in restoring disrupted reading frames (Mann et al., Proceedings of the National Academy of Sciences of the United States of America 2001, 98, 42; Mann et al., The journal of gene medicine 2002, 4, 644; Yin et al., J. Molecular therapy. Nucleic acids 2013, 2, e124; Yang et al., PloS one 2013, 8, e61584) and testifies to the potency of ON24 for therapeutic exon skipping in muscular dystrophies. Moreover, 7',5'-α-bc-DNA induced a higher level of exon skipping than tc-DNA, a modification known to have a significant therapeutic effect in mice (Goyenvalle et al., Nat Med 2015, 21, 270). Therefore, the 7',5'-α-bc-DNA scaffold meets the prerequisites to induce a strong effect in therapeutic exon skipping.

Example 66

X-Ray Crystal Structure Determination of Alpha-Anomers

Figure 3:
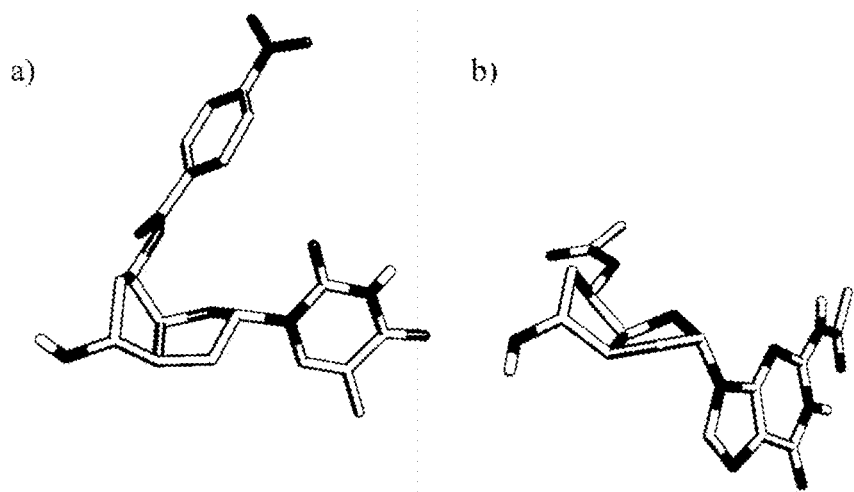
FIG. 3: X-ray structure of a) 5'-O-p-nitrobenzoyl-7',5'-α-bc-T, b) 5'-O-acetyl-7',5'-α-bc-GAc. Non-polar hydrogen atoms are omitted for clarity.

Crystals of the monomers were obtained, mainly to confirm the relative configuration of the 7',5'-α-bc-DNA series, but also to compare this structure with the minimum found by ab initio calculations. To obtain crystals for the thymidine and the guanosine monomers, a p-nitrobenzoate was introduced at O3' to be able to crystalize the T monomers (compound 57). This molecule co-crystallized with EtOAc giving rise to crystals of low quality. The resulting structure (FIG. 3a) adopts a C1'-endo, O4'-exo sugar pucker and a C6'-endo conformation in the carbocyclic ring. This conformation orients the C5' substituent in a pseudoequatorial position and the C7' hydroxyl group in a pseudoaxial position. This structure deviates in the sugar pucker from the minima predicted by ab initio calculations. However, further analysis demonstrated that the p-nitrobenzoate substituent disturbed the sugar conformation. The protected guanosine 51 gave rise to crystals of good quality. In this case (FIG. 3b), the furanose adopts an almost perfect C1'-exo conformation, while the carbocyclic ring adopts a geometry as described above. This time, the structure matches perfectly with one of the minimal conformers predicted by ab initio calculation.

Compound 57:

A colorless transparent crystal of $[C_{19}H_{19}N_3O_8]_2[0.5(C_4H_8O_2)]$ was mounted in air and used for X-ray structure determination at ambient conditions. All measurements were made on an Oxford Diffraction SuperNova area-detector diffractometer (Dupradeau et al., Nucleic Acids Res 2008, 36, D360) using mirror optics monochromated Mo Kα radiation (λ=0.71073 Å) and Al filtered (Lu et al., Nature protocols 2008, 3, 1213). The unit cell constants and an orientation matrix for data collection were obtained from a least-squares refinement of the setting angles of reflections in the range 1.7°<θ<28.07°. A total of 440 frames were collected using ω scans, with 15+15 seconds exposure time, a rotation angle of 1° per frame, a crystal-detector distance of 65.1 mm, at T=223(2) K. Data reduction was performed using the CrysAlisPro program (Dupradeau et al., Nucleic Acids Res 2008, 36, D360). The intensities were corrected for Lorentz and polarization effects, and an absorption correction based on the multi-scan method using SCALE3 ABSPACK in CrysAlisPro was applied. Data collection and refinement parameters are given in Table 6. The structure was solved by direct methods using SHELXT, which revealed the positions of all non-hydrogen atoms of the title compound. The non-hydrogen atoms were refined anisotropically. All H-atoms were placed in geometrically calculated positions and refined using a riding model where each H-atom was assigned a fixed isotropic displacement parameter with a value equal to 1.2 Ueq of its parent atom. Refinement of the structure was carried out on $F^2$ using full-matrix least-squares procedures, which minimized the function $\Sigma w(F_o^2-F_c^2)^2$. The weighting scheme was based on counting statistics and included a factor to downweight the intense reflections. All calculations were performed using the SHELXL-2014/7 program. The compound crystallizes in the monoclinic space group C 2, with a monoclinic angle very close to 90 degrees, which implies an easy pseudo-merohedral twinning that cannot be easily deconvoluted. Moreover, the p-NO$_2$-benzoate group of the main molecule is disordered over two conformation and the co-crystallized acetate solvent is disordered about a twofold axis. For all these reasons, the structure determination and refinement was somewhat complicated, some short intermolecular contacts are calculated, and the absolute configuration cannot be determined (Flack parameter being unrealistic), but it is assigned according to the reaction sequence.

TABLE 6

| Crystal data and structure refinement for compound 57 | | |
|---|---|---|
| Identification code | shelx | |
| Empirical formula | C21 H23 N3 O9 | |
| Formula weight | 461.42 | |
| Temperature | 223(2) K | |
| Wavelength | 0.71073 Å | |
| Crystal system | Monoclinic | |
| Space group | C 2 | |
| Unit cell dimensions | a = 22.6224(5) Å | a = 90° |
| | b = 7.9610(2) Å | b = 90.172(2)° |
| | c = 12.0447(3) Å | g = 90° |
| Volume | 2169.20(9) Å3 | |
| Z | 4 | |
| Density (calculated) | 1.413 Mg/m$^3$ | |
| Absorption coefficient | 0.112 mm$^{-1}$ | |
| F(000) | 968 | |
| Crystal size | 0.344 × 0.265 × 0.072 mm$^3$ | |
| Theta range for data collection | 1.691 to 28.071°. | |
| Index ranges | −28 <= h <= 28, −9 <= k <= 10, −15 <= l <= 15 | |
| Reflections collected | 7292 | |
| Independent reflections | 4360 [R(int) = 0.0206] | |
| Completeness to theta = 25.242° | 100.0% | |
| Absorption correction | Gaussian | |
| Max. and min. transmission | 0.994 and 0.979 | |
| Refinement method | Full-matrix least-squares on F2 | |

TABLE 6-continued

Crystal data and structure refinement for compound 57

| | |
|---|---|
| Data/restraints/parameters | 4360/319/405 |
| Goodness-of-fit on F2 | 1.027 |
| Final R indices [I > 2sigma(I)] | R1 = 0.0541, wR2 = 0.1280 |
| R indices (all data) | R1 = 0.0694, wR2 = 0.1414 |
| Absolute structure parameter | 1.7(6) |
| Extinction coefficient | n/a |
| Largest diff. peak and hole | 0.329 and −0.208 e.Å−3 |

Compound 51:

A colorless transparent crystal of [C16H19N5O6].(CH4O) was mounted in air and used for X-ray structure determination at ambient conditions. All measurements were made on an Oxford Diffraction SuperNova area-detector diffractometer (Dupradeau et al., Nucleic Acids Res 2008, 36, D360) using mirror optics monochromated Mo Kα radiation (λ=0.71073 Å) and Al filtered. The unit cell constants and an orientation matrix for data collection were obtained from a least-squares refinement of the setting angles of reflections in the range 1.5°<θ<27.2°. A total of 970 frames were collected using w scans, with 45+45 seconds exposure time, a rotation angle of 1° per frame, a crystal-detector distance of 65.1 mm, at T=123(2) K. Data reduction was performed using the CrysAlisPro program. The intensities were corrected for Lorentz and polarization effects, and an absorption correction based on the multi-scan method using SCALES ABSPACK in CrysAlisPro was applied. Data collection and refinement parameters are given in Table 7. The structure was solved by direct methods using SHELXS-97, which revealed the positions of all non-hydrogen atoms of the title compound. The non-hydrogen atoms were refined anisotropically. All H-atoms were placed in geometrically calculated positions and refined using a riding model where each H-atom was assigned a fixed isotropic displacement parameter with a value equal to 1.2 Ueq of its parent atom. Refinement of the structure was carried out on F² using full-matrix least-squares procedures, which minimized the function $\Sigma w(F_o^2-F_c^2)^2$. The weighting scheme was based on counting statistics and included a factor to downweight the intense reflections. All calculations were performed using the SHELXL-97 program (Lu et al., Nature protocols 2008, 3, 1213).

TABLE 7

Crystal data and structure refinement for compound 51

| | | |
|---|---|---|
| Empirical formula | C17H23N5O7 | |
| Formula weight | 409.40 | |
| Temperature | 123(2) K | |
| Wavelength | 0.71073 Å | |
| Crystal system | Monoclinic | |
| Space group | P 21 | |
| Unit cell dimensions | a = 4.83370(10) Å | a = 90° |
| | b = 25.1367(4) Å | b = 92.4850(10)° |
| | c = 15.2979(2) Å | g = 90° |
| Volume | 1857.00(5) Å3 | |
| Z | 4 | |
| Density (calculated) | 1.464 Mg/m³ | |
| Absorption coefficient | 0.115 mm−1 | |
| F(000) | 864 | |
| Crystal size | 0.4678 × 0.1255 × 0.0405 mm³ | |
| Theta range for data collection | 1.559 to 27.205° | |

TABLE 7-continued

Crystal data and structure refinement for compound 51

| | |
|---|---|
| Index ranges | −6 <= h <= 6, −31 <= k <= 32, −19 <= l <= 19 |
| Reflections collected | 25075 |
| Independent reflections | 7480 [R(int) = 0.0452] |
| Completeness to theta = 25.000° | 100.0% |
| Absorption correction | Gaussian |
| Max. and min. transmission | 0.996 and 0.97 |
| Refinement method | Full-matrix least-squares on F2 |
| Data/restraints/parameters | 7480/1/533 |
| Goodness-of-fit on F2 | 1.058 |
| Final R indices [I > 2sigma(I)] | R1 = 0.0579, wR2 = 0.1456 |
| R indices (all data) | R1 = 0.0657, wR2 = 0.1518 |
| Absolute structure parameter | 0.7(4) |
| Extinction coefficient | n/a |
| Largest diff. peak and hole | 1.403 and −0.492 e.Å−3 |

Example 67

Design and Synthesis of Oligomers of Beta Anomeric Monomers

A series of oligonucleotides with single and multiple incorporations of building blocks 12, 14, 19 and 25 as well as fully modified sequences were synthesized using classical automated phosphoramidite chemistry (for synthetic and analytical details see suppl. Inf.). Oligonucleotides with single and multiple incorporations were primarily prepared to determine the effect of the modifications on the $T_m$ when complexed with complementary DNA and RNA, as well as to determine the Watson-Crick base pairing selectivity. Fully modified oligonucleotides were synthesized to characterize the pairing behavior not only with natural DNA and RNA, but also to investigate the self-pairing of 7',5'-bc-DNA. The main interest here was to determine whether this novel structural DNA analogue is capable of forming an independent base-pairing system that could be of interest as an alternative genetic system.

Process of Beta Anomeric Oligonucleotide Synthesis, Deprotection and Purification Oligonucleotides syntheses were performed on a Pharmaci-Gene-Assembler-Plus DNA synthesizer on a 1.3 µmol scale. Natural DNA phosphoramidites (dT, dC$^{4bz}$, dG$^{2DMF}$, dA$^{6Bz}$) and solid support (dA-Q-CPG 500, dmf-dG-Q-CPG 500, Glen Unysupport 500) were purchased from Glen Research. Natural DNA phosphoramidites were prepared as a 0.1 M solution in MeCN and were coupled using a 4 min step. Bc-DNA phosphoramidites were prepared as a 0.1 M solution in 1,2-dichloroethane and were coupled using an extended 12 min step. 5-(Ethylthio)-1H-tetrazole (0.25 M in MeCN) was used as coupling agent. Capping, oxidation and detritylation were performed with standard conditions. Cleavage from solid support and deprotection of oligonucleotides was achieved by treatment with concentrated ammonia at 55° C. for 16 h. After centrifugation, the supernatant were collected, the beads further washed with H2O (0.5 mL×2) and the resulting solutions were evaporated to dryness. Fully modified sequences were further treated with NaOH (0.4 M in H2O/MeOH 1:1) for 1 h at rt to achieve complete cleavage from the universal support linker and were then filtrated using spin-columns (Amicon Ultra 0.5 mL centrifugal filters, MWCO 3 kDa). Crude oligonucleotides were purified by ion-exchange HPLC (Dionex-DNA-Pac PA200). Buffer solutions of 25 mM Trizma in $H_2O$, pH 8.0, was used as the mobile phase "A" and 25 mM Trizma, 1.25 M NaCl in $H_2O$, pH 8.0, was used as the mobile phase "B". The purified oligonucleotides were then desalted with Sep-pack C-18 cartridges. Concentrations were determined by measuring the absorbance at 260 nm with a Nanodrop spectrophotometer, using the extinction coefficient of the corresponding natural DNA oligonucleotides. Characterizations of oligonucleotides were performed by ESI⁻ mass spectrometry.

Example 68

Pairing Properties of Modified β-Oligodeoxynucleotides with Complementary DNA and RNA To determine the effect of single and multiple modifications on duplex stability modified oligodeoxynucleotides ON1-ON11 were prepared, represented in Table 8, and measured $T_m$ values of duplexes with complementary DNA and RNA by UV-melting curve analysis.

According to the $\Delta T_m$/mod data, the impact of single or double modifications on thermal duplex stability is relatively moderate. Purine modifications (ON6, 7) tend to destabilize duplexes with complementary DNA but show a slight increase in $T_m$ with complementary RNA. Within the pyrimidine series there is, however, more variability. Modified thymidine nucleosides (ON1-3) typically lead to a small depression of $T_m$ with RNA as complement while no clear trend with DNA is observed. Interestingly, both cytosine modifications (ON4, 5, 8-10) significantly stabilize duplexes with complementary DNA while having less effect on the $T_m$ with complementary RNA. The stabilizing effect is more pronounced for the 5-methyl cytosine nucleosides, pointing to its potential to reinforce stacking interactions with neighboring base-pairs.

To determine the base-pairing selectivity $T_m$s of ON2 in complex with complementary DNA having all three possible mismatched bases opposing the site of modification was measured (Table 9). The $T_m$s of the mismatched duplexes are lower by 5.1 to 13° C. with the GT wobble pair, as expected, being least destabilizing. These data compare well with the fully natural mismatched series, indicating no significant change in base pairing selectivity of the modification.

TABLE 8

$T_m$ and $\Delta T_m$/mod data from UV-melting curves (260 nm) of ON1-ON11 in duplex with complementary DNA and RNA.

| Entry | Sequence[a,b,c] | $T_m$ (° C.) vs DNA | $\Delta T_m$/mod (° C.) | $T_m$ (° C.) vs RNA | $\Delta T_m$/mod (° C.) |
|---|---|---|---|---|---|
| ON1 | d(GGATGTTCtCGA) (SEQ ID NO: 1) | 50.3 | 1.2 | 47.6 | -1.8 |
| ON2 | d(GGAtGTTCTCGA) (SEQ ID NO: 2) | 49.0 | -0.1 | 47.0 | -2.4 |
| ON3 | d(GGATGttCTCGA) (SEQ ID NO: 3) | 46.9 | -1.1 | 45.4 | -2.0 |
| ON4 | d(GGATGTTcTCGA) (SEQ ID NO: 4) | 52.2 | 3.1 | 50.4 | 1.0 |
| ON5 | d(GGATGTTCTcGA) (SEQ ID NO: 5) | 53.4 | 4.3 | 49.5 | 0.1 |
| ON6 | d(GGaTGTTCTCGA) (SEQ ID NO: 6) | 45.6 | -3.5 | 50.0 | 0.6 |
| ON7 | d(GGATgTTCTCGA) (SEQ ID NO: 7) | 46.3 | -2.8 | 50.0 | 0.6 |
| ON8 | d(GGATGTTcTCGA) (SEQ ID NO: 8) | 50.7 | 1.6 | 50.0 | 0.6 |
| ON9 | d(GGATGTTCTcGA) (SEQ ID NO: 9) | 51.8 | 2.8 | 49.2 | -0.2 |
| ON10 | d(GGATGTTcTcGA) (SEQ ID NO: 10) | 51.9 | 1.4 | 48.5 | -0.9 |
| ON11 | d(GCAttt ttACCG)[d] (SEQ ID NO: 11) | 33.2 | -2.9 | 27.9 | -3.2 |

[a]total strand conc. 2 μM in 10 mM $NaH_2PO_4$, 150 mM NaCl, pH 7.0.
[b]A, G, T, C denote natural 2'-deoxynucleosides; a, t, g, c corresponds to modified nucleosides,
cstands for the modified 5-methyl cytosine nucleoside.
[c]$T_m$ of unmodified duplexes, DNA/DNA: 49.1° C., DNA/RNA: 49.4° C.
[d]$T_m$ of unmodified duplexes, DNA/DNA: 47.5° C., DNA/RNA: 44.0° C.

TABLE 9

T$_m$ values from UV-melting curves (260 nm) of ON2 and DNA1
in duplex with complementary DNA incorporating one mismatch.

| Entry | Duplex | X = A | X = T | X = G | X = C |
|---|---|---|---|---|---|
| ON2 | 5'-d(GGA TGT TCt CGA)-3' (SEQ ID NO: 2) | 50.3 | 41.0 | 45.2 | 37.3 |
| DNA | 5'-d(TCG XGA ACA TCC)-3' (SEQ ID NO: 25) | | | | |
| DNA 1 | 5'-d(GGA TGT TCT CGA)-3' (SEQ ID NO: 26) | 49.1 | 38.3 | 40.5 | 36.7 |
| DNA | 5'-d(TCG XGA ACA TCC)-3' (SEQ ID NO: 25) | | | | |

Experimental conditions: total strand conc. 2 µM in 10 mM NaH$_2$PO$_4$, 150 mM NaCl, pH 7.0

Example 69

Pairing Properties of Fully Modified β-Oligonucleotides with Complementary DNA and RNA A fully modified nonamer consisting of pyrimidine bases only (ON12) as well as 3 dodecamers (ON13-15) containing all four bases were prepared to test their affinity to complementary DNA or RNA in either the antiparallel or parallel orientation. Form the corresponding T$_m$ data (Table 10) it becomes clear that binding is generally weak. Even under high salt (1 M NaCl) conditions, no melting transition could be observed for ON12 with the antiparallel DNA or RNA complement in the temperature range from 5-80° C., suggesting that no duplex was formed. However, with the longer dodecamers ON13-15, transitions were observed with complementary antiparallel DNA and RNA. The T$_m$s of these duplexes are roughly 30° C. lower as compared to the natural control duplexes, amounting to an average ΔT$_m$/mod of −2.5° C. This was not expected from the T$_m$ experiments of single incorporations (Table 8) and highlights the importance of fully modified oligonucleotides when characterizing novel pairing systems. Importantly, no signs of duplex formation were found with the corresponding parallel DNA and RNA complements. This clearly demonstrates that 7',5'-bc-DNA is still able to communicate with the natural nucleic acids via antiparallel duplex structures, albeit on a substantially lower affinity level.

Example 70

Self-pairing of 7',5'-β-bc-DNA

ON14 has been designed to be the antiparallel and ON15 to be the parallel complement to ON13. With this it was possible to investigate self-pairing of 7',5'-bc-DNA in both orientations. It turned out that the antiparallel duplex ON13.ON14 showed a classical sigmoidal melting behavior (FIG. 11) with a T$_m$ of 54.5° C. This is higher by 5.4° C. compared to the natural duplex of the same sequence. Interestingly the hyperchromicity at 260 nm of the 7',5'-bc-DNA duplex amounts to only 20% of that of the natural duplex. This indicates significantly different stacking arrangement of the bases in both duplex conformations. In the parallel orientation (ON13.ON15) no transition could be found demonstrating the inability of parallel duplex formation in 7',5'-bc-DNA.

Example 71

Thermodynamic Data of Duplex Formation of Beta Anomeric Oligomers

Transition enthalpies and entropies were determined for the duplex ON13.ON14 and the corresponding natural duplex by curve fitting to the experimental melting curves in analogy to known methods (Table 11) (Petersheim et al., Biochemistry 1983, 22, 256). These data suggest that the

TABLE 10

T$_m$ values from UV-melting curves (260 nm) of fully modified ON12-ON15 in duplex with complementary antiparallel or parallel DNA or RNA.

| Entry | Sequence | T$_m$(° C.) vs DNA antiparallel | T$_m$(° C.) vs RNA antiparallel | T$_m$(° C.) vs DNA parallel | T$_m$(° C.) vs RNA parallel |
|---|---|---|---|---|---|
| ON12 | 5'-(ttt tct cct)-7' | <10 | <10 | n.m.$^a$ | n.m.$^a$ |
| ON13 | 5'-(gga tgt tct cga)-7' | 18.9 | 18.6 | <10 | <10 |
| ON14 | 5'-(tcg aga aca tcc)-7' | 15.7 | n.d.$^a$ | <10 | <10 |
| ON15 | 5'-(cct aca aga gct)-7' | 13.1 | 13.0 | <10 | n.d.$^a$ |

Experimental conditions: total strand concentration: 2 µM in 10 mM NaH$_2$PO$_4$, 1M NaCl, pH 7.0.
$^a$n.m.: not measured.
$^b$n.d.: not detectable due to formation of a self-structure of the corresponding RNA strand with a T$_m$ of 28° C.

natural duplex is enthalpically stabilized while the 7',5'-bc-DNA duplex is entropically favored. This matches with previous findings in the bc-DNA series and hints to conformational restriction of the 7',5'-bc-DNA backbone as the origin of the entropic stabilization. The free enthalpies of duplex formation ($\Delta G$) are in line with the $T_m$ data which qualify them as a measure for thermodynamic duplex stability.

TABLE 11

Thermodynamic data of duplex formation.

| 5'-GGA TGT TCT CGA (SEQ ID NO: 26) CCT ACA AGA GCT-5' (SEQ ID NO: 29) | $\Delta H$ [kcal mol$^{-1}$] | $\Delta S$ [cal mol$^{-1}$ K$^{-1}$] | $\Delta G^{25°\ C.}$ [kcal mol$^{-1}$] |
|---|---|---|---|
| DNA·DNA (SEQ ID NOS: 26 and 29) | −91.7 | −257.9 | −14.8 |
| ON13·ON14 (SEQ ID NOS: 13 and 14) | −77.0 | −208.0 | −15.0 |

Example 72

CD-Spectroscopy of Beta Anomers of Beta Anomeric Oligomers

Figure 11:
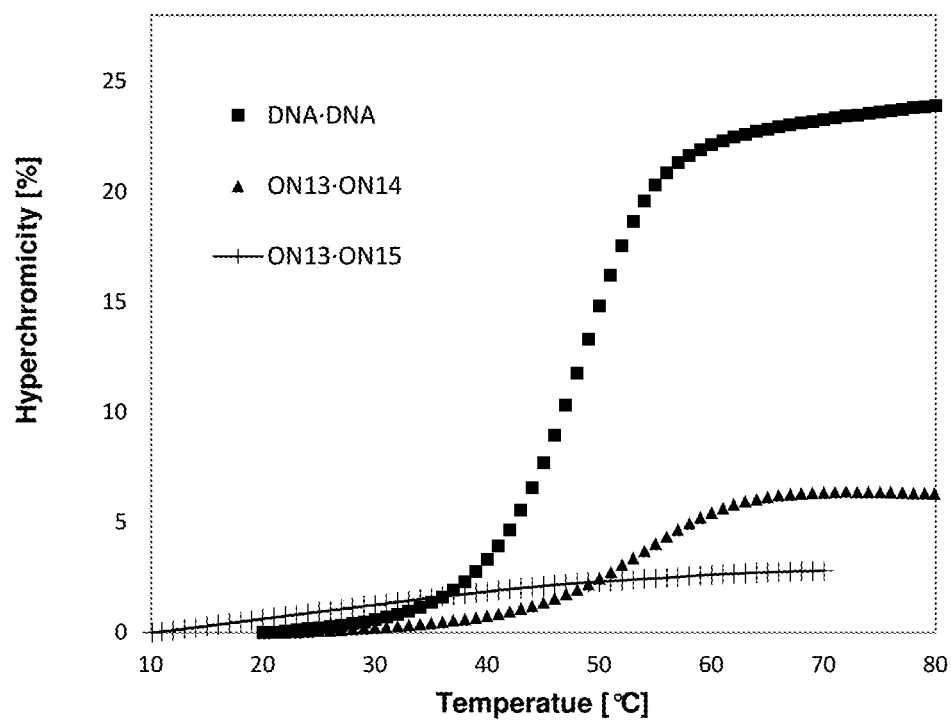
FIG. 11: UV-melting curves (260 nm) of the homo 7',5'-β-bc-DNA duplex in comparison with the corresponding natural DNA duplex. Total strand concentration: 2 μM in 10 mM NaH$_2$PO$_4$, 150 mM NaCl, pH 7.0.
Figure 12:
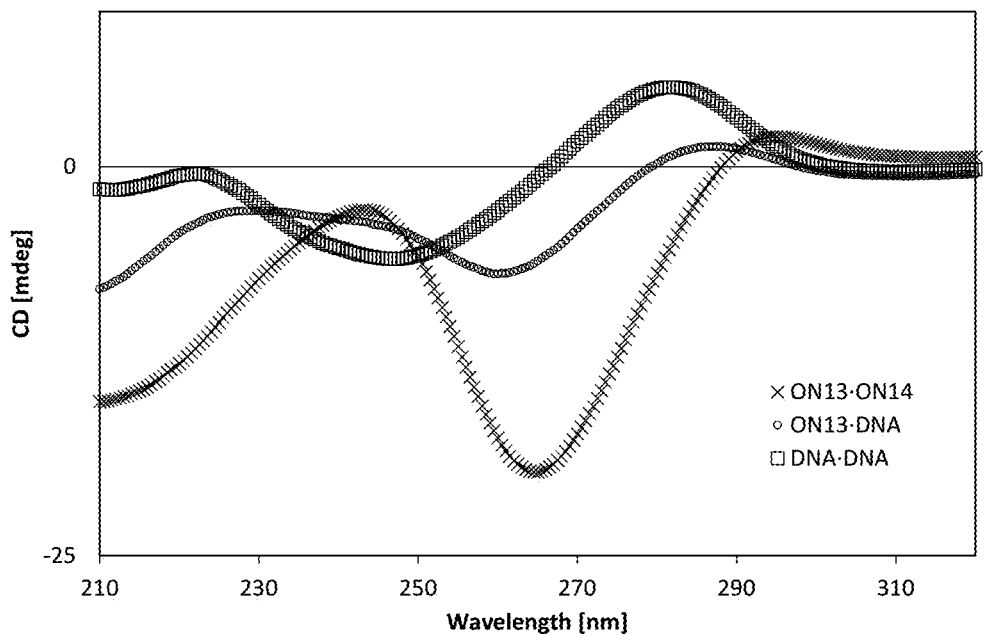
FIG. 12: CD-spectra of the three duplexes a) ON13.ON14, b) ON13.DNA and c) DNA.DNA at temperatures between 10 and 80° C. Experimental conditions: Total strand concentration 2 μM in 10 mM NaH$_2$PO$_4$, 1 M NaCl, pH 7.0, 10° C.

To gain insight into the structural properties of the homo 7',5'-bc-DNA duplex and the hybrid 7',5'-bc-DNA/DNA duplex CD-spectra were measured and compared with that of the corresponding natural DNA duplex (FIG. 12). As expected, the natural duplex shows the classical features of a B-DNA duplex. The homo 7',5'-bc-DNA duplex, however, has a CD signature that is significantly different from that of A- or B-type double helices. It is characterized by two minimum ellipticities around 215 and 265 nm with a maximum at 243 nm. The hybrid duplex carries a signature which is closer to that of the DNA duplex. Compared to B-DNA, the minimum ellipticity at 260 nm is red shifted by about 15 nm while the maximum ellipticity at 288 nm is red-shifted by about 7 nm and associated with a loss in amplitude. The differences in the three CD spectra thus indicate differential arrangements of the bases within the base-stack, induced by the change in backbone geometry of each strand. This is in agreement with the differential hyperchromicities of the two pairing systems in the corresponding UV-melting curves (FIG. 11).

Example 73

X-Ray Crystal Structure of a 7',5'-α-Bc-DNA Monomer

Figure 10:
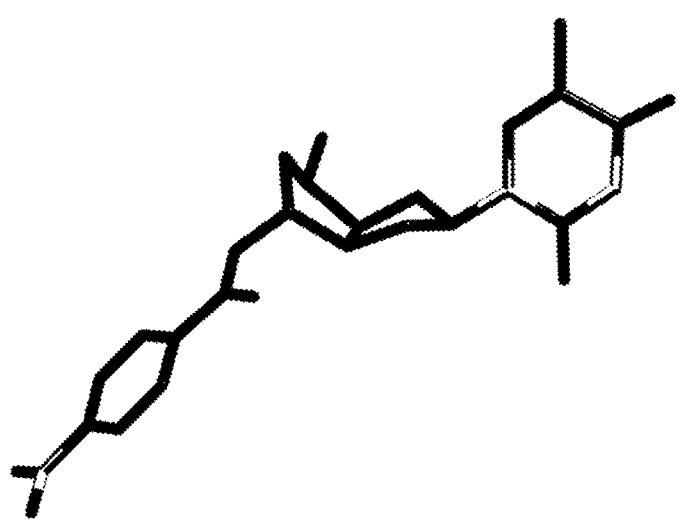
FIG. 10: X-ray structure of 7'-O-p-nitrobenzoyl-7',5'-β-bc-T. Hydrogen atoms are omitted for clarity.

A 7',5'-bc-T analogue was prepared, carrying a p-nitrobenzoate group at O7'. This compound could be crystallized and its structure solved (FIG. 10). Besides establishing final proof for the relative configuration of the 7',5'-bc-DNA series we also obtained information on the preferred conformation of the bicyclic sugar scaffold. It clearly emerges that the furanose part exists in a perfect 1'-exo conformation while the carbocyclic ring occurs in the 6'-endo configuration, thus placing the oxy-substituent at C7' in a pseudoaxial and the 5'OH group in a pseudoequatorial position. This structure matches exactly one of the two low energy conformers determined by ab initio calculations.

Compound 33:

A colorless transparent crystal of [$C_{19}H_{19}N_3O_8$] was mounted in air and used for X-ray structure determination at ambient conditions. All measurements were made on an Oxford Diffraction SuperNova area-detector diffractometer (Oxford Diffraction (2010)) using mirror optics monochromated Mo Kα radiation (λ=0.71073 Å) and Al filtered (Macchi et al., J. Appl. Cryst 2011, 44, 763.). The unit cell constants and an orientation matrix for data collection were obtained from a least-squares refinement of the setting angles of reflections in the range 2.°<θ<27.°. A total of 530 frames were collected using w scans, with 2.5+2.5 seconds exposure time, a rotation angle of 1° per frame, a crystal-detector distance of 65.1 mm, at T=173(2) K. Data reduction was performed using the CrysAlisPro (Version 1.171.34.44). Oxford Diffraction Ltd., Y., Oxfordshire, UK) program. The intensities were corrected for Lorentz and polarization effects, and an absorption correction based on the multi-scan method using SCALES ABSPACK in CrysAlisPro was applied. Data collection and refinement parameters are given in Table 12. The structure was solved by direct methods using SHELXS-97 (Sheldrick, Acta Cryst. 2008, A64, 112-122), which revealed the positions of all non-hydrogen atoms of the title compound. The non-hydrogen atoms were refined anisotropically. All H-atoms were placed in geometrically calculated positions and refined using a riding model where each H-atom was assigned a fixed isotropic displacement parameter with a value equal to 1.2 Ueq of its parent atom. Refinement of the structure was carried out on $F^2$ using full-matrix least-squares procedures, which minimized the function $\Sigma w(F_o^2-F_c^2)^2$. The weighting scheme was based on counting statistics and included a factor to down weight the intense reflections. All calculations were performed using the SHELXL-97 program (Macchi et al., J. Appl. Cryst 2011, 44, 763).

TABLE 12

Crystal data and structure refinement for compound 33.

| | |
|---|---|
| Identification code | shelx |
| Empirical formula | C19H19N3O8 |
| Formula weight | 417.37 |
| Temperature | 173(2) K |
| Wavelength | 0.71073 Å |
| Crystal system | Monoclinic |
| Space group | P 21 |
| Unit cell dimensions | a = 7.0712(2) Å    α = 90° |
| | b = 6.48123(16) Å    β = 98.062(3)° |
| | c = 20.4085(6) Å    γ = 90° |
| Volume | 926.08(4) Å3 |
| Z | 2 |
| Density (calculated) | 1.497 Mg/m$^3$ |
| Absorption coefficient | 0.119 mm$^{-1}$ |
| F(000) | 436 |
| Crystal size | 0.5326 × 0.308 × 0.1151 mm$^3$ |
| Theta range for data collection | 2.016 to 27.110° |
| Index ranges | −8 <= h <= 8, −7 <= k <= 8, −24 <= l <= 24 |
| Reflections collected | 6928 |
| Independent reflections | 3651 [R(int) = 0.0200] |
| Completeness to theta = 25.000° | 99.8% |
| Absorption correction | Gaussian |
| Max. and min. transmission | 0.987 and 0.963 |

TABLE 12-continued

Crystal data and structure refinement for compound 33.

| | |
|---|---|
| Refinement method | Full-matrix least-squares on $F^2$ |
| Data/restraints/parameters | 3651/1/274 |
| Goodness-of-fit on $F^2$ | 1.059 |
| Final R indices [I > 2sigma(I)] | R1 = 0.0344, wR2 = 0.0772 |
| R indices (all data) | R1 = 0.0387, wR2 = 0.0808 |
| Absolute structure parameter | −0.9(5) |
| Extinction coefficient | 0.009(2) |
| Largest diff. peak and hole | 0.212 and −0.236 e.Å$^{-3}$ |

What is claimed is:

1. A compound of formula (I):

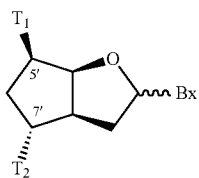

(I)

wherein $T_1$ and $T_2$ are each independently selected from the group consisting of $OR_1$ and $OR_2$;
and; wherein
$R_1$ is H or a hydroxyl protecting group, and
$R_2$ is a phosphorus moiety; and wherein
Bx is a nucleobase.

2. The compound of claim 1, having the structure of formula (II)

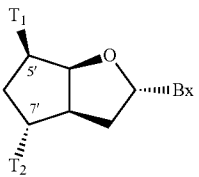

(II)

wherein $T_1$ and $T_2$ are each independently selected from the group consisting of $OR_1$ and $OR_2$.

3. The compound of claim 1, having the structure of formula (III)

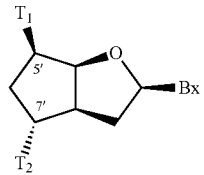

(III)

wherein $T_1$ and $T_2$ are each independently selected from the group consisting of $OR_1$ and $OR_2$.

4. The compound of claim 1, wherein said phosphorus moiety $R_2$ is selected from the group consisting of a phosphate moiety, a phosphoramidate moiety and a phosphoramidite moiety.

5. The compound of claim 1, having the structure selected from the group consisting of:

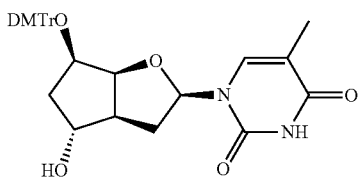

11

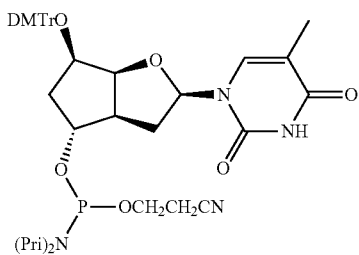

12

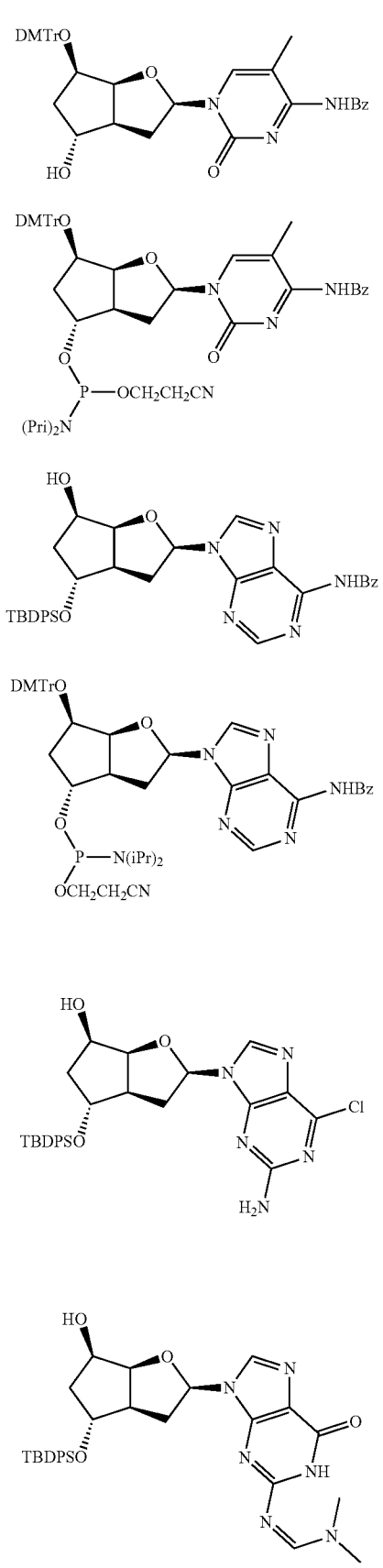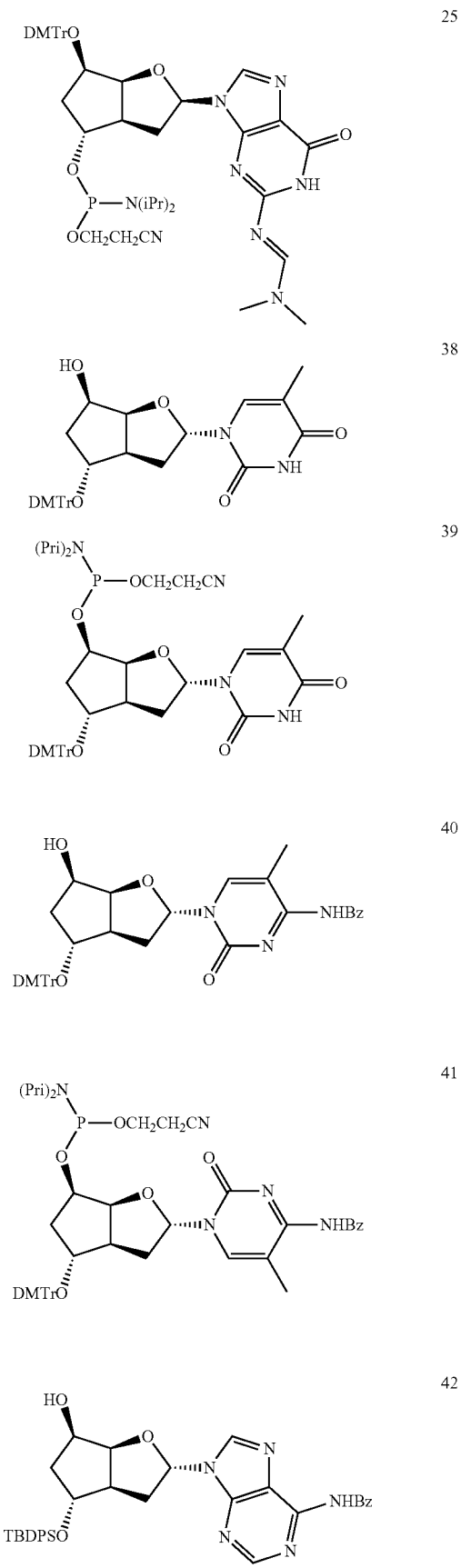

-continued

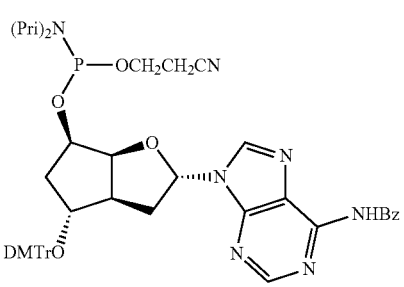
47

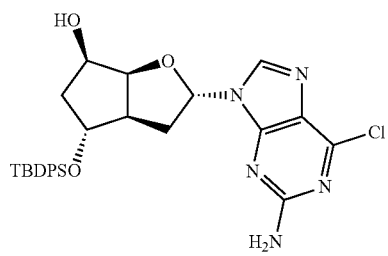
48

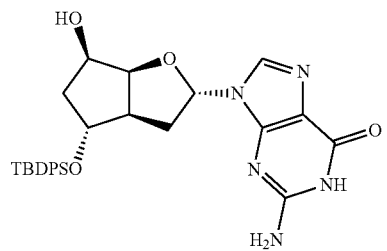
49

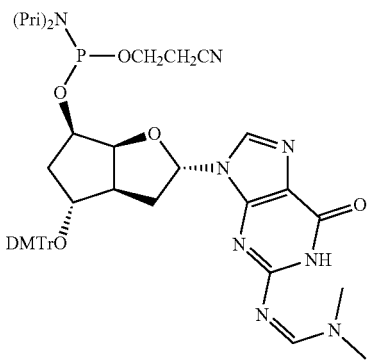
54

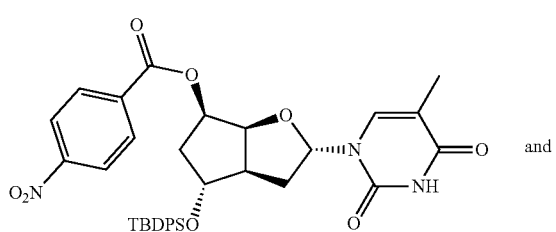
and
56

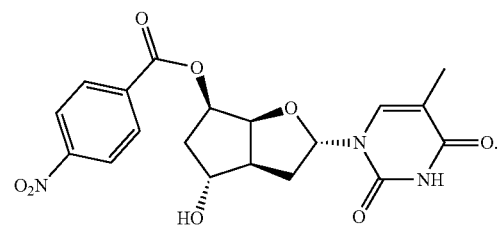
57

6. The compound of claim 1, wherein the nucleobase is selected from the group consisting of a purine base and a pyrimidine base.

7. An oligomer comprising at least one monomer subunit as a compound of formula (IV)

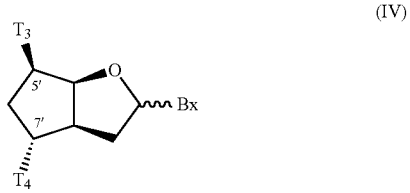

(IV)

wherein either $T_3$ or $T_4$ are independently a nucleosidic linkage group; and when $T_3$ is a nucleosidic linkage group;

$T_4$ is selected from the group consisting of $OR_1$, $OR_2$, a 5' terminal group, a 7' terminal group and a nucleosidic linkage group, and when $T_4$ is a nucleosidic linkage group;

$T_3$ is selected from the group consisting of $OR_1$, $OR_2$, a 5' terminal group, a 7' terminal group and a nucleosidic linkage group, and;

wherein $R_1$ is selected from H and a hydroxyl protecting group, and $R_2$ is a phosphorus moiety; and Bx is a nucleobase.

8. The oligomer of claim 7, having the structure of formula (V):

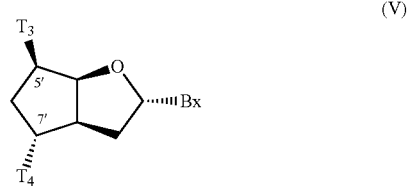

(V)

wherein:
(i) when $T_3$ is a nucleosidic linkage group, $T_4$ is selected from the group consisting of a 7' terminal group, $OR_1$, and $OR_2$; or
(ii) when $T_3$ is selected from the group consisting of a 5' terminal group, $OR_1$, and $OR_2$, $T_4$ is a nucleosidic linkage group; or
(iii) $T_3$ and $T_4$ are independently of each other a nucleosidic linkage group.

9. The oligomer of claim 7, having the structure of formula (VI):

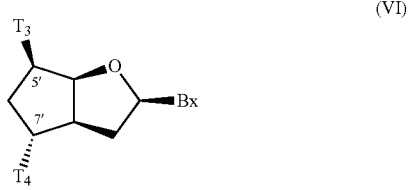

(VI)

wherein:
(i) when $T_3$ is a nucleosidic linkage group, $T_4$ is selected from the group consisting of a 7' terminal group, $OR_1$, and $OR_2$; or (ii) when $T_3$ is selected from the group consisting of a 5' terminal group, $OR_1$, and $OR_2$, $T_4$ is a nucleosidic linkage group; or (iii) $T_3$ and $T_4$ are independently of each other a nucleosidic linkage group.

10. The oligomer of claim 7, wherein each nucleosidic linkage group is independently selected from the group consisting of a phosphodiester linkage group, a phosphotriester linkage group, a phosphorothioate linkage group, a phosphorodithioate linkage group, a phosphonate linkage group, a phosphonothioate linkage group, a phosphinate linkage group, a phosphorthioamidate linkage and a phosphoramidate linkage group.

11. The oligomer of claim 10 wherein each nucleosidic linkage group is independently selected from the group consisting of a phosphodiester linkage group and a phosphorothioate linkage group.

12. The oligomer of claim 11 wherein each nucleosidic linkage group is a phosphorothioate linkage group.

13. The oligomer of claim 11, wherein each nucleosidic linkage group is a phosphodiester linkage group.

14. The oligomer of claim 7, comprising at least two contiguous monomer subunits of compounds of formula (IV), wherein each of the contiguous subunit of compound of formula (IV) is independently linked to the adjacent contiguous subunit of compound of formula (IV) by the nucleosidic linkage group, wherein the nucleosidic linkage group links a 5' terminus and a 7' terminus of the two contiguous subunits of compounds of formula (IV).

15. The oligomer of claim 7, wherein said oligomer comprises at least one nucleic acid sequence, wherein said nucleic acid sequence comprises said at least one monomer subunit of compound of formula (IV), and wherein said nucleic acid sequence is selected from the group consisting of the SEQ ID NO: 1 to 24.

16. The oligomer of claim 15, wherein the nucleic acid sequence is SEQ ID NO: 24.

17. The oligomer of claim 7, wherein the oligomer comprises a nucleic acid sequence, wherein said nucleic acid sequence consists of at least two contiguous monomer subunits of compounds of formula (V), wherein said nucleic acid sequence is flanked on its 5' terminus and on its 7' terminus by at least one nucleotide or nucleoside that is different from the compound of formula (IV), wherein the 5' terminus of said nucleic acid sequence is linked to a 5' terminus of the nucleotide or nucleoside that is different from the compound of formula (IV), and wherein the 7' terminus of said nucleic acid sequence is linked to a 3' terminus of the nucleotide or nucleoside that is different from the compound of formula (IV).

18. The oligomer of claim 7, wherein the oligomer comprises a nucleic acid sequence, wherein said nucleic acid sequence consists of at least two contiguous monomer subunits of compounds of formula (VI), wherein said nucleic acid sequence is flanked on its 5' terminus and on its 7' terminus each by at least one nucleotide or nucleoside that is different from the compound of formula (IV), wherein the 5' terminus of said nucleic acid sequence is linked to a 3' terminus of the nucleotide or nucleoside that is different from the compound of formula (IV), and wherein the 7' terminus of said nucleic acid sequence is linked to a 5' terminus of the nucleotide or nucleoside that is different from the compound of formula (IV).

19. The oligomer of claim 7, wherein said monomer subunit of compound of formula (IV) is selected from the group consisting of:

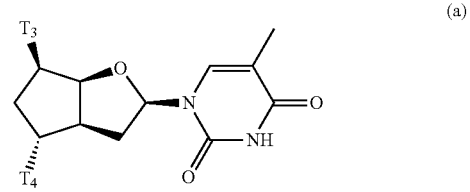

(a)

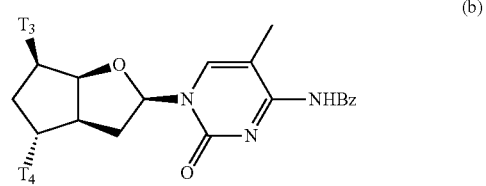

(b)

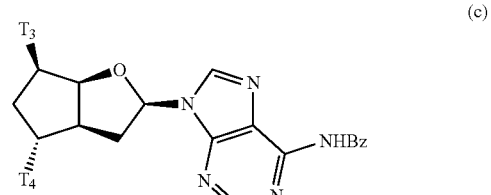

(c)

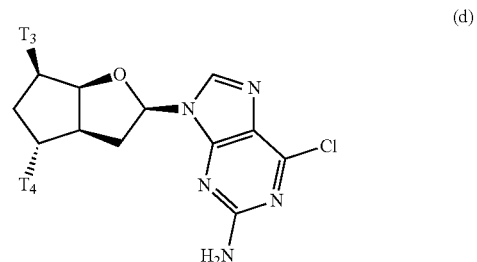

(d)

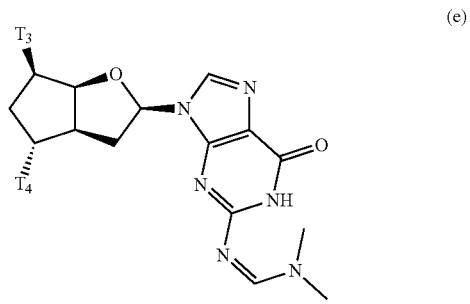

(e)

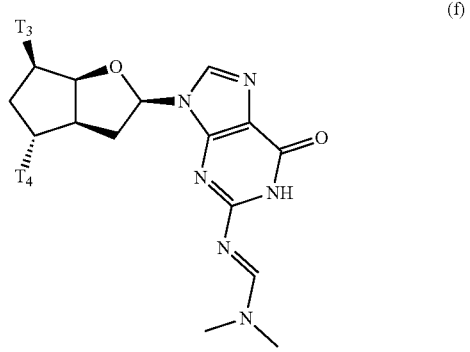

(f)

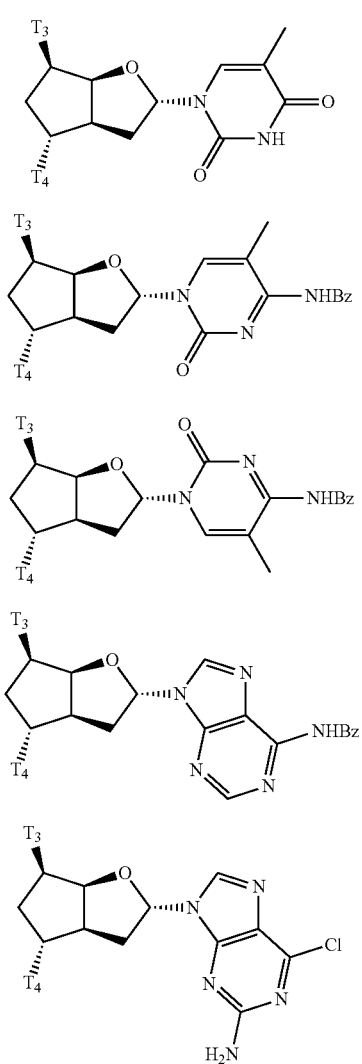
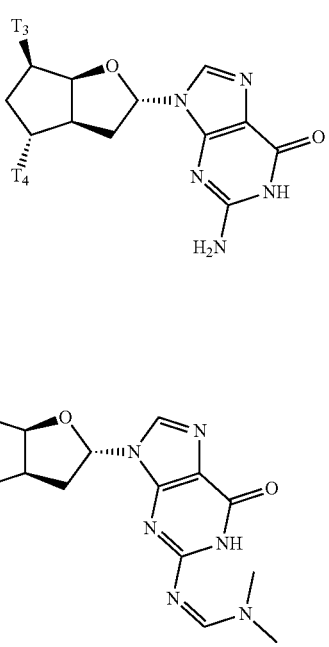
20. The oligomer of claim 7, wherein the nucleobase is selected from the group consisting of a purine base and a pyrimidine base.
* * * * *

UNITED STATES PATENT AND TRADEMARK OFFICE
CERTIFICATE OF CORRECTION

| | |
|---|---|
| PATENT NO. | : 11,028,117 B2 |
| APPLICATION NO. | : 16/465127 |
| DATED | : June 8, 2021 |
| INVENTOR(S) | : Christian Leumann and Eamien Evequoz |

It is certified that error appears in the above-identified patent and that said Letters Patent is hereby corrected as shown below:

In the Specification

In Column 2, Line 1, delete "(Marhère" and insert --(Marlière--.

In Column 6, Line 10, delete "trifiuoroacetyl," and insert --trifluoroacetyl,--.

In Column 7, Line 39, delete "HB⁻" and insert --$HB^+$--.

In Column 11, Line 57, delete "phosphoroamidite" and insert --phosphoramidite--.

In Column 13, Line 56, delete "—(CH₂)—NHC(O)CF₃" and insert -- —$(CH_2)_n$NHC(O)CF₃--.

In Column 14, Line 2, delete "pyrollidine," and insert --pyrrolidine,--.

In Column 14, Line 18, delete "Fri," and insert --Pri,--.

In Column 14, Line 24, delete "substitutents" and insert --substituents--.

In Column 17, Line 15, delete "Rig" and insert --$R_{12}$--.

In Column 17, Line 30, delete "Rig" and insert --$R_{18}$--.

In Column 17, Line 38, delete "Rig" and insert --$R_{19}$--.

In Column 20, Line 34, delete "thionoalkyl" and insert --thioalkyl--.

In Column 20, Line 37, delete "thionoalkyl" and insert --thioalkyl--.

In Column 20, Line 41, delete "thionoalkyl" and insert --thioalkyl--.

Signed and Sealed this
Twenty-first Day of February, 2023

Katherine Kelly Vidal
*Director of the United States Patent and Trademark Office*

CERTIFICATE OF CORRECTION (continued)
U.S. Pat. No. 11,028,117 B2

In Column 22, Line 4, delete "Bicylic" and insert --Bicyclic--.

In Column 22, Line 31, delete "deoxyribnucleosides," and insert --deoxyribonucleosides,--.

In Column 22, Line 32, delete "deoxyribnucleosides," and insert --deoxyribonucleosides,--.

In Column 24, Line 11, delete "McRaw-Hiff" and insert --McGraw-Hill--.

In Column 43, Line 45, delete "(Frog" and insert --(Prog--.

In Column 45, Line 12, delete "3505" and insert --350S--.

In Column 61, Line 41, delete "Hexanne" and insert --Hexane--.

In Column 68, Line 52, delete "Hexanne" and insert --Hexane--.

In Column 108, Line 56, delete "hexanne" and insert --hexane--.

In Columns 115-116, Line 58, after "respectively" insert --.--.

In Columns 117-118, Line 22, after "respectively" insert --.--.

In Column 117, Line 63, delete "(a," and insert --(a, f)--.

In Columns 123-124, Line 57, delete "$\underline{c}$stands" and insert --$\underline{c}$ stands--.

In Columns 125-126, Line 55, below "5'-(ttt tct cct)-7'" insert --(SEQ ID NO: 12)--.

In Columns 125-126, Line 57, below "5'-(gga tgt tct cga)-7'" insert --(SEQ ID NO: 13)--.

In Columns 125-126, Line 59, below "5'-(tcg aga aca tcc)-7'" insert --(SEQ ID NO: 14)--.

In Columns 125-126, Line 61, below "5'-(cct aca aga gct)-7'" insert --(SEQ ID NO: 15)--.

In the Claims

In Column 158, Claim 8, Line 45, delete "OR$_1$,and" and insert --OR$_1$, and--.

In Column 158, Claim 9, Line 67, delete "OR$_1$,and" and insert --OR$_1$, and--.